US012201594B2

(12) United States Patent
Campbell et al.

(10) Patent No.: US 12,201,594 B2
(45) Date of Patent: *Jan. 21, 2025

(54) METHODS AND COMPOSITIONS FOR TREATMENT OF PAIN USING CAPSAICIN

(71) Applicant: Centrexion Therapeutics Corporation, Boston, MA (US)

(72) Inventors: James N. Campbell, Baltimore, MD (US); Peter D. Hanson, Prides Crossing, MA (US); Randall Stevens, Rockport, MA (US)

(73) Assignee: Centrexion Therapeutics Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/339,414

(22) Filed: Jun. 4, 2021

(65) Prior Publication Data

US 2021/0299072 A1 Sep. 30, 2021

Related U.S. Application Data

(63) Continuation of application No. 16/984,384, filed on Aug. 4, 2020, now Pat. No. 11,026,903, which is a continuation of application No. 16/631,277, filed as application No. PCT/US2018/043094 on Jul. 20, 2018, now abandoned.

(60) Provisional application No. 62/535,003, filed on Jul. 20, 2017.

(51) Int. Cl.
| | |
|---|---|
| *A61K 31/167* | (2006.01) |
| *A61F 7/00* | (2006.01) |
| *A61F 7/10* | (2006.01) |
| *A61K 9/00* | (2006.01) |
| *A61P 19/02* | (2006.01) |

(52) U.S. Cl.
CPC ............. *A61K 31/167* (2013.01); *A61F 7/10* (2013.01); *A61K 9/0014* (2013.01); *A61K 9/0019* (2013.01); *A61P 19/02* (2018.01); *A61F 2007/0042* (2013.01)

(58) Field of Classification Search
CPC .. A61K 31/167; A61K 9/0019; A61K 9/0014; A61P 19/02; A61F 7/10; A61F 2007/0042
See application file for complete search history.

(56) References Cited

U.S. PATENT DOCUMENTS

| | | | |
|---|---|---|---|
| 4,599,342 A | 7/1986 | LaHann | |
| 5,021,450 A | 6/1991 | Blumberg | |
| 5,099,030 A | 3/1992 | Gardner et al. | |
| 5,318,960 A | 6/1994 | Toppo | |
| 5,431,914 A | 7/1995 | Adekunle et al. | |
| 5,962,532 A | 10/1999 | Campbell et al. | |
| 5,985,860 A | 11/1999 | Toppo | |
| 6,060,060 A | 5/2000 | Belgorod | |
| 6,248,788 B1 | 6/2001 | Robbins et al. | |
| 6,277,398 B1 | 8/2001 | Caruso | |
| 7,943,166 B2 | 5/2011 | Muhammad et al. | |
| 7,964,644 B2 | 6/2011 | Meyer | |
| 8,158,682 B2 | 4/2012 | Sangameswaran et al. | |
| 8,263,093 B2 | 9/2012 | Muhammad et al. | |
| 8,273,390 B2 | 9/2012 | Muhammad et al. | |
| 8,338,457 B2 | 12/2012 | Iadarola et al. | |
| 8,367,733 B2 | 2/2013 | Burch et al. | |
| 8,420,600 B2 | 4/2013 | Burch et al. | |
| 8,637,569 B2 | 1/2014 | Birbara | |
| 8,703,741 B2 | 4/2014 | Meyer | |
| 8,734,770 B2 | 5/2014 | Muhammad et al. | |
| 9,044,452 B2 | 6/2015 | Meyer | |
| 9,359,316 B1 | 6/2016 | Husfeld et al. | |
| 9,956,166 B2 | 5/2018 | Zucker et al. | |
| 9,956,190 B2 | 5/2018 | Birbara et al. | |
| 10,493,047 B2 | 12/2019 | Ostovic et al. | |

(Continued)

FOREIGN PATENT DOCUMENTS

| | | |
|---|---|---|
| CN | 101119713 A | 2/2008 |
| CN | 101507818 A | 8/2009 |

(Continued)

OTHER PUBLICATIONS

Burch Ronald, Carter Richard B, Lazar Jeff. Clarivate English Machine Translation of ES 2562025 T3. Mar. 2, 2016. p. 1-39 (Year: 2016).*
Hu (International Journal of Pharmaceutics 618 (2022) 121696 p. 1-13) (Year: 2022).*
U.S. Appl. No. 16/631,277, Methods and Compositions for Treatment of Pain Using Capsaicin, filed Jan. 15, 2020.
Akesson in "A comparison of two formulations of intradermal capsaicin as models of neuropathic pain in healthy volunteers" (2007) Master Thesis in Pharmacy; The University of Adelaide Australia.

(Continued)

*Primary Examiner* — Noble E Jarrell
*Assistant Examiner* — Richard Grant Peckham
(74) *Attorney, Agent, or Firm* — Dechert LLP

(57) ABSTRACT

The invention provides methods and compositions for treatment of pain, such as joint pain, using capsaicin in a procedure that attenuates transient burning sensation experienced by patients due to capsaicin administration. The methods desirably provide relief from joint pain, such as osteoarthritic knee joint pain, for an extended duration, such as at least about 3 months, 6 months, 9 months, or 1 year. To attenuate the adverse side effect of a transient burning sensation caused by capsaicin-induced neuronal excitation, the methods utilize a cooling article, such as a material wrap cooled via a circulating fluid, to reduce the temperature of tissue to be exposed to capsaicin to within a certain range for certain durations of time, optionally in combination with administering a local anesthetic agent, resulting in the substantial reduction or even elimination of transient burning sensation caused by capsaicin.

29 Claims, 14 Drawing Sheets

(56) References Cited

U.S. PATENT DOCUMENTS

| | | |
|---|---|---|
| 10,765,649 B2 | 9/2020 | Ostovic et al. |
| 10,772,853 B2 | 9/2020 | Ostovic et al. |
| 11,000,490 B2 | 5/2021 | Ostovic et al. |
| 11,026,903 B2 * | 6/2021 | Campbell .............. A61P 29/02 |
| 11,344,516 B2 | 5/2022 | Ostovic et al. |
| 2003/0104085 A1 | 6/2003 | Yeomans |
| 2005/0020690 A1 | 1/2005 | Burch et al. |
| 2006/0148903 A1 | 7/2006 | Burch et al. |
| 2006/0222690 A1 | 10/2006 | Bley |
| 2007/0021338 A1 | 1/2007 | Hansen et al. |
| 2010/0047181 A1 | 2/2010 | Meyer |
| 2010/0196281 A1 | 8/2010 | Meyer |
| 2010/0234470 A1 | 9/2010 | Sangameswaran et al. |
| 2011/0245708 A1 | 10/2011 | Finkel et al. |
| 2011/0311952 A1 | 12/2011 | Fairfield et al. |
| 2013/0157985 A1 | 6/2013 | Bucks et al. |
| 2013/0245729 A1 | 9/2013 | Edelman et al. |
| 2013/0252925 A1 | 9/2013 | Bucks et al. |
| 2013/0280176 A1 | 10/2013 | Diezi et al. |
| 2013/0280177 A1 | 10/2013 | Raman et al. |
| 2013/0303495 A1 | 11/2013 | Dhingra et al. |
| 2014/0017313 A1 | 1/2014 | Coulter et al. |
| 2014/0142073 A1 | 5/2014 | Birbara et al. |
| 2014/0161889 A1 | 6/2014 | Mikulasik et al. |
| 2015/0132374 A1 | 5/2015 | Coulter et al. |
| 2015/0132396 A1 | 5/2015 | Coulter et al. |
| 2015/0133561 A1 | 5/2015 | Birbara et al. |
| 2015/0306233 A1 | 10/2015 | Chiou et al. |
| 2016/0339105 A1 | 11/2016 | Shah et al. |
| 2016/0346241 A1 | 12/2016 | Amrutkar et al. |
| 2016/0354315 A1 | 12/2016 | Li |
| 2017/0239198 A1 | 8/2017 | Muzari |
| 2017/0266139 A1 | 9/2017 | Burch et al. |
| 2018/0169039 A1 | 6/2018 | Muhammad et al. |
| 2018/0311189 A1 | 11/2018 | Campbell et al. |
| 2019/0022036 A1 | 1/2019 | Campbell et al. |
| 2019/0038573 A1 | 2/2019 | Westphal et al. |
| 2020/0046656 A1 | 2/2020 | Ostovic et al. |
| 2020/0093765 A1 | 3/2020 | Ostovic et al. |
| 2020/0093766 A1 | 3/2020 | Ostovic et al. |
| 2020/0206166 A1 | 7/2020 | Campbell et al. |

FOREIGN PATENT DOCUMENTS

| | | |
|---|---|---|
| CN | 102205127 A | 10/2011 |
| CN | 105960230 A | 9/2016 |
| EP | 0646372 A1 | 4/1995 |
| EP | 3119794 B1 | 10/2017 |
| WO | WO-1996040079 A1 | 12/1996 |
| WO | WO-1998020867 A1 | 5/1998 |
| WO | WO-1998040070 A1 | 9/1998 |
| WO | WO-2002076444 A1 | 10/2002 |
| WO | WO-2004056305 A2 | 7/2004 |
| WO | WO-2004058286 A1 | 7/2004 |
| WO | WO-2006058140 A2 | 6/2006 |
| WO | WO-2008005802 A2 | 1/2008 |
| WO | WO-2014019095 A1 | 2/2014 |
| WO | WO-2014075084 A2 | 5/2014 |
| WO | WO-2014128233 A1 | 8/2014 |
| WO | WO-2015052510 A1 | 4/2015 |
| WO | WO-2015073577 A1 | 5/2015 |
| WO | WO-2015198059 A1 | 12/2015 |
| WO | WO-2015198350 A1 | 12/2015 |
| WO | WO-2016077749 A1 | 5/2016 |
| WO | WO-2016086063 A1 | 6/2016 |
| WO | WO-2016126540 A1 | 8/2016 |
| WO | WO-2017087803 A1 | 5/2017 |
| WO | WO-2017127628 A1 | 7/2017 |
| WO | WO-2017147146 A1 | 8/2017 |
| WO | WO-2017205534 A1 | 11/2017 |
| WO | WO-2018085476 A1 | 5/2018 |
| WO | WO-2018217937 A1 | 11/2018 |

OTHER PUBLICATIONS

Basith et al., "Harnessing the Therapeutic Potential of Capsaicin and its Analogues in Pain and Other Diseases," Molecules, pp. 1-28, (2016).

Botz in "The role of sensory neuropeptides in mouse models of neuropathy and immune arthritis" (year 2015) University PECS, Medical School.

Cantillon et al. in "Preliminary safety, tolerability and efficacy of ALGRX 4975 in Osteoarthritis (OA) of the knee" in *Journal of Pain* (2005) vol. 6(3), Supplement, p. S39.

Chen et al. in Arzneimittelforschung (2010) vol. 60(9), pp. 571-574 (Abstract only).

Clinicaltrials Publication: "Study to Evaluate the Safety and Efficacy of CNTX-4975 in Subjects With Chronic, Moderate to Severe Osteoarthritis Knee Pain," a clinical study description, available from clinicaltrials.gov online on Aug. 8, 2017.

Clinicaltrials Publication: "Study to Evaluate the Safety and Efficacy of CNTX-4975 in Subjects With Chronic, Moderate to Severe Osteoarthritis Knee Pain," a clinical study description, available from clinicaltrials.gov online on May 20, 2016.

Clinicaltrials Publication: "The Effect of Injection Site Cooling on Pain Experienced After the Administration of CNTX-4975-05 Into the Knee," a clinical study description, available from clinicaltrials.gov online on Mar. 29, 2018.

Clinicaltrials Publication: "A Study to Compare Levels of Capsaicin After Intra-Articular Injection and Topical Application in Patients With Painful Knee Osteoarthritis," a clinical study description, available from clinicaltrials.gov online on Jul. 17, 2018.

Clinicaltrials Publication for Study NCT02869867, available from clinicaltrials.gov online on Mar. 27, 2017.

Costanzo et al. in Cough (2014) 10:6; doi: 10.1186/1745-9974-10-6 (published Sep. 25, 2014).

Ezawa et al. in International Journal of Medicinal Chemistry (2016) Article ID 8723139, 9 pages.

Galano et al. in J. Phys. Chem. B (2012) vol. 116, pp. 1200-1208.

Gustafsson et al. in Br. J. Clin. Pharmacol. (2009) vol. 68(4), pp. 511-517.

Ha et al. in J. Pharm. Sci. (2002) vol. 91(10), pp. 2252-2264 (Abstract only).

Hanson et al. in "Safety and Tolerability of CNTX-4975 in Subjects with Chronic, Moderate to Severe Knee Pain Associated with Osteoarthritis (Oa): A Pilot Study," presented as a poster at the American Pain Society Annual Scientific Meeting on May 17-20, 2017.

International Search Report and Written Opinion of the International Searching Authority for PCT/US2018/043094 mailed Oct. 12, 2018 (12 pages).

Kadekawa et al. in Am. J. Physiol. Renal Physiol. (2017) vol. 313, F796-F804.

Kistner et al. in Sci. Rep. (2016) vol. 6, p. 28621.

Knolle et al., "Comparison of cooling and EMLA to reduce the burning pain during capsaicin 8% patch application: A randomized, double-blind, placebo-controlled study," Pain, vol. 154, pp. 2729-2736, (2013).

Kopec et al. in Cough (2008) 4:3 doi 10.1186/1745-9974-4-3 (published May 27, 2008).

Leffler et al., "The vanilloid receptor TRPV1 is activated and sensitized by local anesthetics in rodent sensory neurons," The Journal of Clinical Investigation, vol. 118, No. 2, pp. 763-776, (2008).

Med Device Online publication entitled "New Motorized Cold Therapy System Introduced" (published Jun. 14, 2005).

Pharma Ingredients & Services Technical Information by BASF (Mar. 2012).

Polar Care—Product Insert (available via the Internet in Jun. 2017).

Remadevi and Szallasi, "Adlea (ALGRX-4975), an injectable capsaicin (TRPV1 receptor agonist) formulation for long-lasting pain relief," IDrugs, vol. 11, pp. 120-132, (2008).

Shen et al. in Journal of Inclusion Phenomena and Macrocyclic Chemistry (2012) vol. 72, pp. 263-274.

Stevens et al. in "Efficacy and safety of CNTX-4975 in subjects with moderate to severe osteoarthritis knee pain: 24-week, randomized,

(56) References Cited

OTHER PUBLICATIONS double-blind, placebo-controlled, dose-ranging study," in Annals of the Rheumatic Diseases (2017) vol. 76, suppl. 2, p. 121 (Abstract).
Tateba et al. in Agric. Biol. Chem. (1991) vol. 55(3), pp. 873-874.
Turgut et al. in Environ. Sci. Pollut. Res. Int. (2004) vol. 11(1), pp. 7-10 (Abstract only).
Wong and Gavva, "Therapeutic potential of vanilloid receptor TRPV1 agonists and antagonists as analgesics: Recent advances and setbacks," Brain Research Reviews 60, pp. 267-277, (2009).
Zhang et al. in Journal of Pain Research (2014) vol. 7, pp. 547-554.
Zhao et al. in Pharm Biol. (2016) vol. 54(1), pp. 130-138 (Abstract only).
BASF Pharma Ingredients & Services: Technical Information Soluplus (Jul. 2010).
Chang, A. et al., "Capsaicin," *StatPearls Publishing, NCBI Bookshelf*, pp. 1-6 (2021).
LaMotte, R.H. et al., "Neurogenic Hyperalgesia: Psychophysical Studies of Underlying Mechanisms," *Journal of Neurophysiology*, vol. 66, No. 1, pp. 190-211 (1991).
Green, "Sensory interactions between capsaicin and temperature in the oral cavity," Chem Senses. 1986;11(3):371-82.
Warren et al., "Intra-articular Knee Temperature Changes: Ice Versus Cryotherapy Device," Am J Sports Med. 2004;32(2):441-5.

\* cited by examiner

METHODS AND COMPOSITIONS FOR TREATMENT OF PAIN USING CAPSAICIN

CROSS REFERENCE TO RELATED APPLICATIONS

This application is a continuation of U.S. patent application Ser. No. 16/984,384, filed Aug. 4, 2020, which is a continuation of U.S. patent application Ser. No. 16/631,277, filed Jan. 15, 2020, which is the national stage of International (PCT) Patent Application Serial No. PCT/US2018/043094, filed Jul. 20, 2018, which claims the benefit of and priority to U.S. Provisional Patent Application Ser. No. 62/535,003, filed Jul. 20, 2017, the contents of each of which are hereby incorporated by reference.

FIELD OF THE INVENTION

The invention provides methods and compositions for treatment of pain, such as joint pain, using capsaicin in a procedure that attenuates transient burning sensation experienced by patients due to capsaicin administrations, through use of controlled cooling to reduce the temperature of tissue to be exposed to capsaicin optionally in combination with use of a local anesthetic agent.

BACKGROUND

Pain can function as a protective mechanism that allows healthy human beings and animals to avoid tissue damage and/or prevent further damage to injured tissue. However, there are many instances in which pain persists beyond its usefulness. Such unnecessary suffering from pain can impair a subject's physical mobility, mental performance, and even contribute to depression.

Substantial resources have been devoted over the years to researching the causes of various types of pain and to the development of medicine to attenuate pain experienced by a patient. Exemplary classes of common pain-relief medications include opioids, non-steroidal anti-inflammatory agents, corticosteroids, and centrally acting agents such as anti-depressants, anti-epileptics, pregabalin, and gabapentin. Capsaicin has been described for use in treating pain. See, for example, U.S. Pat. Nos. 5,962,532; 8,420,600; 8,367,733; and 8,158,682. Certain commercial products containing capsaicin for pain relief formulate the capsaicin as a cream (e.g., Capzasin) or in a patch (e.g., a capsaicin-containing transdermal patch marketed under the trade name QUTENZA®) for topical application to the skin of a patient.

One challenging aspect of using capsaicin to treat pain, particularly when capsaicin is administered by injection, is that administration of capsaicin causes an initial neuronal excitation resulting in the adverse side effect of a transient burning sensation. This transient burning sensation can be substantial for some patients. Certain approaches for addressing the adverse side effect of transient burning sensation caused by capsaicin have been described in the literature, including approaches described in U.S. Pat. No. 5,962,532.

Due to the unmet need for additional treatment options to achieve relief from pain, particularly treatment options that do not suffer from the addiction problems associated with many opioid-based pain therapies, the need exists for new procedures for treating pain. The present invention addresses this need and provides other related advantages.

SUMMARY

The invention provides methods and compositions for treatment of pain, such as joint pain, using capsaicin in a procedure that attenuates transient burning sensation experienced by patients due to capsaicin administration. The methods desirably provide relief from joint pain, such as osteoarthritic knee joint pain, for an extended duration, such as at least about 3 months, 6 months, 9 months, or 1 year. Because administration of capsaicin causes initial neuronal excitation resulting in the adverse side effect of a transient burning sensation, the methods utilize a cooling article, such as a material wrap cooled via a circulating fluid, to reduce the temperature of tissue to be exposed to capsaicin for certain durations of time, optionally in combination with administering a local anesthetic agent, in order to attenuate the transient burning sensation experienced by patients, resulting in the substantial reduction or even elimination of transient burning sensation caused by capsaicin. The cooling article desirably has an exterior surface temperature in the range of from about 5° C. to about 15° C., and more desirably from about 5° C. to about 10° C., for application to the exterior surface of the patient's joint, such as a knee joint.

Because overcooling of skin tissue can cause the adverse effect of skin necrosis, while insufficient cooling can be inadequate to sufficiently reduce the transient burning sensation experienced by patients due to capsaicin administration, the methods desirably apply a cooling article having a particular temperature range (e.g., from about 5° C. to about 15° C., and more desirably from about 5° C. to about 10° C.) for particular durations of time both before and after administration of capsaicin. The therapeutic methods can be further characterized according to the temperature of tissue and/or fluid in the joint into which capsaicin is administered, and in certain embodiments, fluid in the intra-articular space of a joint, such as a knee joint, is cooled to a temperature in the range from about 26° C. to about 33° C., prior to administration of capsaicin, and then maintained at a temperature in the range from about 26° C. to about 33° C. for a duration of at least 30 minutes after administration of capsaicin.

The foregoing techniques for reducing transient burning sensation due to administration of capsaicin can be used to minimize procedure pain experienced by patients undergoing capsaicin therapy for pain due to a painful nerve, and provided herein are methods for treating pain due a painful nerve, such as an intermetatarsal neuroma. The methods utilize a cooling article, such as a material wrap cooled via a circulating fluid, to reduce the temperature of tissue to be exposed to capsaicin for certain durations of time, optionally in combination with administering a local anesthetic agent, in order to attenuate the transient burning sensation experienced by patients, resulting in the substantial reduction or even elimination of transient burning sensation caused by capsaicin.

Various aspects and embodiments of the invention are described in further detail below. Accordingly, one aspect of the invention provides a method of ameliorating osteoarthritic knee joint pain in a human patient, wherein the method comprises:

a. applying for a duration of about 15 minutes a cooling article to an exterior surface of a human patient's knee presenting with osteoarthritic knee joint pain, wherein the cooling article has an exterior surface temperature in the range of from about 5° C. to about 15° C. for application to the exterior surface of said knee; then
  b. administering by injection into the intra-articular space of the joint of said knee a pharmaceutical composition comprising a single pain-relief agent selected from the group consisting of lidocaine and a pharmaceutically acceptable salt thereof, in order to deliver a dose of lidocaine in an amount ranging from about 0.1 g to about 0.5 g; then c. applying for a duration of about 30 minutes a cooling article to an exterior surface of said knee, wherein the cooling article has an exterior surface temperature in the range of from about 5° C. to about 15° C. for application to the exterior surface of said knee; then d. administering by injection into the intra-articular space of the joint of said knee a pharmaceutical composition comprising capsaicin in order to deliver a dose of capsaicin in an amount of about 1 mg; and then e. applying a cooling article to an exterior surface of said knee for a duration of at least about 30 minutes, wherein the cooling article has an exterior surface temperature in the range of from about 5° C. to about 15° C. for application to the exterior surface of said knee;

to thereby ameliorate osteoarthritic knee joint pain in the human patient.

Another aspect of the invention provides a method of attenuating transient burning sensation due to injection of capsaicin into a human osteoarthritic knee joint, wherein the method comprises:

a. applying for a duration of about 15 minutes a cooling article to an exterior surface of a human patient's knee presenting with osteoarthritic knee joint pain, wherein the cooling article has an exterior surface temperature in the range of from about 5° C. to about 15° C. for application to the exterior surface of said knee; then b. administering by injection into the intra-articular space of the joint of said knee a pharmaceutical composition comprising a single pain-relief agent selected from the group consisting of lidocaine and a pharmaceutically acceptable salt thereof, in order to deliver a dose of lidocaine in an amount ranging from about 0.1 g to about 0.5 g; then c. applying for a duration of about 30 minutes a cooling article to an exterior surface of said knee, wherein the cooling article has an exterior surface temperature in the range of from about 5° C. to about 15° C. for application to the exterior surface of said knee; then d. administering by injection into the intra-articular space of the joint of said knee a pharmaceutical composition comprising capsaicin in order to deliver a dose of capsaicin in an amount of about 1 mg; and then e. applying a cooling article to an exterior surface of said knee for a duration of at least about 30 minutes, wherein the cooling article has an exterior surface temperature in the range of from about 5° C. to about 15° C. for application to the exterior surface of said knee;

to thereby attenuate transient burning sensation due to injection of capsaicin.

Another aspect of the invention provides a method of ameliorating osteoarthritic knee joint pain in a human patient, wherein the method comprises:

a. applying a cooling article to an exterior surface of a human patient's knee presenting with osteoarthritic knee joint pain; then b. administering by injection into the intra-articular space of the joint of said knee a pharmaceutical composition comprising a single pain-relief agent selected from the group consisting of lidocaine and a pharmaceutically acceptable salt thereof, in order to deliver a dose of lidocaine in an amount of about 0.1 g to about 0.5 g; then c. applying a cooling article to an exterior surface of said knee to achieve a temperature in the range of from about 26° C. to about 33° C. for fluid in the intra-articular space of the joint of said knee; then d. administering by injection into the intra-articular space of the joint of said knee a pharmaceutical composition comprising capsaicin in order to deliver a dose of capsaicin in an amount of about 1 mg; and then e. applying a cooling article to an exterior surface of said knee;

to thereby ameliorate osteoarthritic knee joint pain in the human patient.

Another aspect of the invention provides a method of attenuating transient burning sensation due to injection of capsaicin into a human osteoarthritic knee joint, wherein the method comprises:

a. applying a cooling article to an exterior surface of a human patient's knee presenting with osteoarthritic knee joint pain; then b. administering by injection into the intra-articular space of the joint of said knee a pharmaceutical composition comprising a single pain-relief agent selected from the group consisting of lidocaine and a pharmaceutically acceptable salt thereof, in order to deliver a dose of lidocaine in an amount of ranging from about 0.1 g to about 0.5 g; then c. applying a cooling article to an exterior surface of said knee to achieve a temperature in the range of from about 26° C. to about 33° C. for fluid in the intra-articular space of the joint of said knee; then d. administering by injection into the intra-articular space of the joint of said knee a pharmaceutical composition comprising capsaicin in order to deliver a dose of capsaicin in an amount of about 1 mg; and then e. applying a cooling article to an exterior surface of said knee;

to thereby attenuate transient burning sensation due to injection of capsaicin.

Another aspect of the invention provides a method of ameliorating joint pain in a human patient, wherein the method comprises:

a. optionally applying a cooling article to a human patient's skin in proximity to a joint in need of pain relief therapy; then b. optionally administering a local anesthetic agent into said joint; then c. applying for a duration of at least about 10 minutes a cooling article to the patient's skin in proximity to said joint, wherein the cooling article has an exterior surface temperature in the range of from about 1° C. to about 15° C. for application to the human patient's skin in proximity to said joint; then d. administering by injection into said joint a pharmaceutical composition comprising capsaicin in order to deliver a dose of capsaicin in an amount of from about 0.01 mg to about 4 mg; and then e. optionally applying for a duration of at least about 10 minutes a cooling article to the patient's skin in proximity to said joint, wherein the cooling article has an exterior surface temperature in the range of from about 1° C. to about 15° C. for application to the human patient's skin in proximity to said joint;

to thereby ameliorate joint pain in the human patient.

Another aspect of the invention provides a method of attenuating transient burning sensation due to injection of capsaicin into a joint in a human patient, wherein the method comprises:

a. optionally applying a cooling article to a human patient's skin in proximity to a joint in need of pain relief therapy;
b. optionally administering a local anesthetic agent into said joint;
c. applying for a duration of at least about 10 minutes a cooling article to the patient's skin in proximity to said joint, wherein the cooling article has an exterior surface temperature in the range of from about 1° C. to about 15° C. for application to the human patient's skin in proximity to said joint; then
d. administering by injection into said joint a pharmaceutical composition comprising capsaicin in order to deliver a dose of capsaicin in an amount of from about 0.01 mg to about 4 mg; and then
e. optionally applying for a duration of at least about 10 minutes a cooling article to the patient's skin in proximity to said joint, wherein the cooling article has an exterior surface temperature in the range of from about 1° C. to about 15° C. for application to the human patient's skin in proximity to said joint;
to thereby attenuate transient burning sensation due to injection of capsaicin.

Another aspect of the invention provides a method of ameliorating joint pain in a human patient, wherein the method comprises:
a. optionally applying a cooling article to a human patient's skin in proximity to a joint in need of pain relief therapy; then
b. optionally administering a local anesthetic agent into said joint; then
c. applying a cooling article to the patient's skin in proximity to said joint to achieve a temperature in the range of from about 20° C. to about 33° C. for tissue or fluid in the interior of the joint; then
d. administering by injection into said joint a pharmaceutical composition comprising capsaicin in order to deliver a dose of capsaicin in an amount of from about 0.01 mg to about 4 mg; and then
e. optionally applying a cooling article to the patient's skin in proximity to said joint; to thereby ameliorate joint pain in the human patient.

Another aspect of the invention provides a method of attenuating transient burning sensation due to injection of capsaicin into a joint in a human patient, wherein the method comprises:
a. optionally applying a cooling article to a human patient's skin in proximity to a joint in need of pain relief therapy;
b. optionally administering a local anesthetic agent into said joint;
c. applying a cooling article to the patient's skin in proximity to said joint to achieve a temperature in the range of from about 20° C. to about 33° C. for tissue or fluid in the interior of the joint; then
d. administering by injection into said joint a pharmaceutical composition comprising capsaicin in order to deliver a dose of capsaicin in an amount of from about 0.01 mg to about 4 mg; and then
e. optionally applying a cooling article to the patient's skin in proximity to said joint; to thereby attenuate transient burning sensation due to injection of capsaicin.

Another aspect of the invention provides a method of ameliorating pain due to an intermetatarsal neuroma in a human patient, wherein the method comprises:
a. applying for a duration of about 15 minutes a cooling article to a human patient's skin in proximity to an intermetatarsal neuroma in need of pain relief therapy, wherein the cooling article has an exterior surface temperature in the range of from about 5° C. to about 15° C. for application to the patient's foot; then
b. administering by injection into tissue adjacent to the intermetatarsal neuroma a pharmaceutical composition comprising a single pain-relief agent selected from the group consisting of lidocaine and a pharmaceutically acceptable salt thereof, in order to deliver a dose of lidocaine in an amount ranging from about 1 mg to about 50 mg;
c. applying for a duration of about 30 minutes a cooling article to the human patient's skin in proximity to the intermetatarsal neuroma in need of pain relief therapy, wherein the cooling article has an exterior surface temperature in the range of from about 5° C. to about 15° C. for application to the patient's foot; then
d. administering by injection into tissue adjacent to the intermetatarsal neuroma capsaicin in an amount of from about 100 µg to 300 µg; and then
e. applying for a duration of at least about 30 minutes a cooling article to the patient's skin in proximity to the intermetatarsal neuroma, wherein the cooling article has an exterior surface temperature in the range of from about 5° C. to about 15° C. for application to the patient's foot;
to thereby ameliorate pain due to the intermetatarsal neuroma in the human patient.

Another aspect of the invention provides a method of attenuating transient burning sensation due to injection of capsaicin into tissue adjacent to an intermetatarsal neuroma in a human patient, wherein the method comprises:
a. applying for a duration of about 15 minutes a cooling article to a human patient's skin in proximity to an intermetatarsal neuroma in need of pain relief therapy, wherein the cooling article has an exterior surface temperature in the range of from about 5° C. to about 15° C. for application to the patient's foot; then
b. administering by injection into tissue adjacent to the intermetatarsal neuroma a pharmaceutical composition comprising a single pain-relief agent selected from the group consisting of lidocaine and a pharmaceutically acceptable salt thereof, in order to deliver a dose of lidocaine in an amount ranging from about 1 mg to about 50 mg;
c. applying for a duration of about 30 minutes a cooling article to the human patient's skin in proximity to the intermetatarsal neuroma in need of pain relief therapy, wherein the cooling article has an exterior surface temperature in the range of from about 5° C. to about 15° C. for application to the patient's foot; then
d. administering by injection into tissue adjacent to the intermetatarsal neuroma capsaicin in an amount of from about 100 µg to 300 µg; and then
e. applying for a duration of at least about 30 minutes a cooling article to the patient's skin in proximity to the intermetatarsal neuroma, wherein the cooling article has an exterior surface temperature in the range of from about 5° C. to about 15° C. for application to the patient's foot;
to thereby attenuate transient burning sensation due to injection of capsaicin into tissue adjacent to an intermetatarsal neuroma in a human patient.

Another aspect of the invention provides a method of ameliorating pain due to an intermetatarsal neuroma in a human patient, wherein the method comprises:
   a. applying a cooling article to a human patient's skin in proximity to an intermetatarsal neuroma in need of pain relief therapy; then
   b. administering by injection into tissue adjacent to the intermetatarsal neuroma a pharmaceutical composition comprising a single pain-relief agent selected from the group consisting of lidocaine and a pharmaceutically acceptable salt thereof, in order to deliver a dose of lidocaine in an amount ranging from about 1 mg to about 50 mg;
   c. applying a cooling article to a human patient's skin in proximity to an intermetatarsal neuroma in need of pain relief therapy to achieve a temperature in the range of from about 26° C. to about 33° C. for tissue in proximity to the intermetatarsal neuroma;
   d. administering by injection into tissue adjacent to the intermetatarsal neuroma capsaicin in an amount of from about 100 μg to 300 μg; and then
   e. applying a cooling article to the human patient's skin in proximity to the intermetatarsal neuroma in need of pain relief therapy;
      to thereby ameliorate pain due to the intermetatarsal neuroma in the human patient.

Another aspect of the invention provides a method of attenuating transient burning sensation due to injection of capsaicin into tissue adjacent to an intermetatarsal neuroma, wherein the method comprises:
   a. applying a cooling article to a human patient's skin in proximity to an intermetatarsal neuroma in need of pain relief therapy; then
   b. administering by injection into tissue adjacent to the intermetatarsal neuroma a pharmaceutical composition comprising a single pain-relief agent selected from the group consisting of lidocaine and a pharmaceutically acceptable salt thereof, in order to deliver a dose of lidocaine in an amount ranging from about 1 mg to about 50 mg;
   c. applying a cooling article to a human patient's skin in proximity to an intermetatarsal neuroma in need of pain relief therapy to achieve a temperature in the range of from about 26° C. to about 33° C. for tissue in proximity to the intermetatarsal neuroma;
   d. administering by injection into tissue adjacent to the intermetatarsal neuroma capsaicin in an amount of from about 100 μg to 300 μg; and then
   e. applying a cooling article to the human patient's skin in proximity to the intermetatarsal neuroma in need of pain relief therapy;
      to thereby attenuate transient burning sensation due to injection of capsaicin into tissue in proximity to an intermetatarsal neuroma.

The foregoing therapeutic methods may be further characterized according to various features, such as the dose of lidocaine local anesthetic agent, dose of capsaicin, duration of reduction in pain, and features of the cooling article. These and other features are more fully described in the detailed description below.

DETAILED DESCRIPTION

Figure 1:
FIG. 1 is an illustration of a cooling article, that is a wrap-on pad, applied to a human knee.

The invention provides methods and compositions for treatment of pain, such as joint pain, using capsaicin in a procedure that attenuates transient burning sensation experienced by patients due to capsaicin administration. The methods desirably provide relief from joint pain, such as osteoarthritic knee joint pain, for an extended duration, such as at least about 3 months, 6 months, 9 months, or 1 year. Because administration of capsaicin causes initial neuronal excitation resulting in the adverse side effect of a transient burning sensation, the methods utilize a cooling article, such as a material wrap cooled via a circulating fluid, to reduce the temperature of tissue to be exposed to capsaicin for certain durations of time, optionally in combination with administering a local anesthetic agent, in order to attenuate the transient burning sensation experienced by patients, resulting in the substantial reduction or even elimination of transient burning sensation caused by capsaicin. The cooling article desirably has an exterior surface temperature in the range of from about 5° C. to about 15° C., and more desirably from about 5° C. to about 10° C., for application to the exterior surface of the patient's joint, such as a knee joint.

Because overcooling of skin tissue can cause the adverse effect of skin necrosis, while insufficient cooling can be inadequate to sufficiently reduce the transient burning sensation experienced by patients due to capsaicin administration, the methods desirably apply a cooling article having a particular temperature range (e.g., from about 5° C. to about 15° C., and more desirably from about 5° C. to about 10° C.) for particular durations of time both before and after administration of capsaicin. The therapeutic methods can be further characterized according to the temperature of tissue and/or fluid in the joint into which capsaicin is administered, and in certain embodiments, fluid in the intra-articular space of a joint, such as a knee joint, is cooled to a temperature in the range from about 26° C. to about 33° C., prior to administration of capsaicin, and then maintained at a temperature in the range from about 26° C. to about 33° C. for a duration of at least 30 minutes after administration of capsaicin.

Transient burning sensation due to capsaicin administration may manifest in patients in the form of a burning sensation, pain, and/or ache in the area in which capsaicin was administered. Techniques described herein are designed to reduce the magnitude of such transient burning sensation experienced by the patient.

The foregoing techniques for reducing transient burning sensation due to administration of capsaicin can be used to minimize procedure pain experienced by patients undergoing capsaicin therapy for pain due to painful nerve, and provided herein are methods for treating pain due a painful nerve, such as an intermetatarsal neuroma. The methods utilize a cooling article, such as a material wrap cooled via a circulating fluid, to reduce the temperature of tissue to be exposed to capsaicin for certain durations of time, optionally in combination with administering a local anesthetic agent, in order to attenuate the transient burning sensation experienced by patients, resulting in the substantial reduction or even elimination of transient burning sensation caused by capsaicin.

The practice of the present invention employs, unless otherwise indicated, conventional techniques of organic chemistry, pharmacology, cell biology, and biochemistry. Such techniques are explained in the literature, such as in "Comprehensive Organic Synthesis" (B. M. Trost & I. Fleming, eds., 1991-1992); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety. Various aspects of the invention are set forth below in sections; however, aspects of the invention described in one particular section are not to be limited to any particular section.

I. DEFINITIONS

To facilitate an understanding of the present invention, a number of terms and phrases are defined below.

The terms "a" and "an" as used herein mean "one or more" and include the plural unless the context is inappropriate.

The phrase "Injection Pain Scale" refers to a measure of pain experienced by a patient upon administration of capsaicin by injection, where the extent of pain experienced by the patient is rated by the patient as one of the following: (i) none, (ii) mild pain, (iii) moderate pain, or (iv) intense pain.

The abbreviation "NPRS" refers to Numerical Pain Rating Scale, as further described herein.

As used herein, the terms "subject" and "patient" refer to organisms to be treated by the methods of the present invention. Such organisms are preferably mammals (e.g., murines, simians, equines, bovines, porcines, canines, felines, and the like), and more preferably humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect (e.g., lessening, reducing, modulating, or eliminating) that results in the improvement of the condition, disease, disorder, and the like. The terms "ameliorate" and "ameliorating" refer to lessening, reducing, and/or eliminating the stated condition, such as pain. The terms "attenuate" and "attenuating" refer to lessening, reducing, and/or eliminating the stated condition, such as pain.

Compounds of the disclosure may contain a C—C double bond and, therefore, exist as geometric isomers. Individual geometric isomers of compounds of the present invention can be prepared synthetically from commercially available starting materials that contain a single geometric isomer in high purity and/or through separating a mixture of geometric isomers using chromatographic procedures known in the art. Substituents around a carbon-carbon double bond are designated as being in the "Z" or "E" configuration wherein the terms "Z" and "E" are used in accordance with IUPAC standards. Substituents around a carbon-carbon double bond alternatively can be referred to as "cis" or "trans," where "cis" represents substituents on the same side of the double bond and "trans" represents substituents on opposite sides of the double bond.

The compounds may be in amorphic or crystalline form, and the invention encompasses all such amorphic and crystalline forms.

As used herein, the term "pharmaceutical composition" refers to the combination of an active agent with a carrier, inert or active, making the composition especially suitable for therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

As used herein, the term "pharmaceutically acceptable salt" refers to any pharmaceutically acceptable salt (e.g., acid or base) of a compound of the present invention which, upon administration to a subject, is capable of providing a compound of this invention. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Unless specified otherwise, the term "about" refers to within ±10% of the stated value. The invention encompasses embodiments where the value is within ±9%, ±8%, ±7%, ±6%, ±5%, ±4%, ±3%, ±2%, or ±1% of the stated value.

The term "alkyl" as used herein refers to a saturated straight or branched hydrocarbon, such as a straight or branched group of 1-12, 1-10, or 1-6 carbon atoms, referred to herein as $C_1$-$C_{12}$alkyl, $C_1$-$C_{10}$alkyl, and $C_1$-$C_6$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "hydroxyalkyl" refers to an alkyl group substituted by 1 or 2 hydroxyl groups. In certain embodiments, the hydroxyalkyl is an alkyl group substituted by only 1 hydroxyl group.

The term "hydroxyalkanoic acid" refers to saturated straight or branched hydrocarbon that is substituted by (i) one —$CO_2H$ group, and (ii) one or two hydroxyl groups.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$alkenyl, $C_2$-$C_{10}$alkenyl, and $C_2$-$C_6$alkenyl, respectively. Exemplary alkenyl groups include vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, and the like.

The term "hydroxyalkenyl" refers to an alkenyl group substituted by 1 or 2 hydroxyl groups. In certain embodiments, the hydroxyalkenyl is an alkenyl group substituted by only 1 hydroxyl group.

The term "hydroxyalkenoic acid" refers to an unsaturated straight or branched hydrocarbon having one carbon-carbon double bond, wherein the hydrocarbon is substituted by (i) one —$CO_2H$ group, and (ii) one or two hydroxyl groups.

The term "polyethylene glycolyl" refers to a radical of polyethylene glycol. The polyethylene glycolyl is a chemical fragment that is part of a larger molecule. When the polyethylene glycolyl is bonded at one location to the remainder of the molecule, then the polyethylene glycolyl is a mono-radical, such as "—$(CH_2CH_2O)x$-H" where x is an integer greater than 1. When the polyethylene glycolyl is used as a component within a molecule connecting two fragments of the molecule, the polyethylene glycolyl is a diradical, having a point of attachment at each terminus of the polyethylene glycolyl, which may illustrated as "—$(CH_2CH_2O)x$-" where x is an integer greater than 1. In certain embodiments, x is an integer in the range of about 5 to about 100, about 5 to about 50, about 5 to about 25, about 5 to about 15, about 10 to about 50, about 10 to about 30, or about 10 to about 20. In certain embodiments, x is about 10, 11, 12, 13, 14, 15, 16, 17, 18, or 19. In certain preferred embodiments, x is about 15.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

II. THERAPEUTIC APPLICATIONS FOR JOINT PAIN

One aspect of the invention provides methods for treating joint pain using injectable capsaicin and procedures to attenuate transient burning sensation due to capsaicin administration. The methods desirably provide relief from joint pain for an extended duration, such as at least about 3 months, 6 months, 9 months, or 1 year. The methods utilize a cooling article, such as a material wrap cooled via a circulating fluid, to reduce the temperature of tissue to be exposed to capsaicin for certain durations of time, optionally in combination with administering a local anesthetic agent. In a preferred embodiment, the methods are used to ameliorate osteoarthritic knee joint pain in a human patient by administering capsaicin to the intra-articular space of the joint of the patient's knee via a protocol that applies a cooling article to an exterior surface of the patient's knee presenting with osteoarthritic knee joint pain before and after administration of capsaicin, such as where the cooling article has an exterior surface temperature in the range of from about 5° C. to about 15° C., and more preferably from about 5° C. to about 10° C., for application to the exterior surface of the patient's knee. Various aspects and embodiments of the methods are described below.

First Method

One aspect of the invention provides a method of ameliorating osteoarthritic knee joint pain in a human patient, wherein the method comprises:

a. applying for a duration of about 15 minutes a cooling article to an exterior surface of a human patient's knee presenting with osteoarthritic knee joint pain, wherein the cooling article has an exterior surface temperature in the range of from about 5° C. to about 15° C. for application to the exterior surface of said knee; then b. administering by injection into the intra-articular space of the joint of said knee a pharmaceutical composition comprising a single pain-relief agent selected from the group consisting of lidocaine and a pharmaceutically acceptable salt thereof, in order to deliver a dose of lidocaine in an amount ranging from about 0.1 g to about 0.5 g; then c. applying for a duration of about 30 minutes a cooling article to an exterior surface of said knee, wherein the cooling article has an exterior surface temperature in the range of from about 5° C. to about 15° C. for application to the exterior surface of said knee; then d. administering by injection into the intra-articular space of the joint of said knee a pharmaceutical composition comprising capsaicin in order to deliver a dose of capsaicin in an amount of about 1 mg; and then e. applying a cooling article to an exterior surface of said knee for a duration of at least about 30 minutes, wherein the cooling article has an exterior surface temperature in the range of from about 5° C. to about 15° C. for application to the exterior surface of said knee;

to thereby ameliorate osteoarthritic knee joint pain in the human patient.

Second Method

One aspect of the invention provides a method of ameliorating osteoarthritic knee joint pain in a human patient, wherein the method comprises:

a. applying for a duration of about 15 minutes a cooling article to an exterior surface of a human patient's knee presenting with osteoarthritic knee joint pain, wherein the cooling article has an exterior surface temperature in the range of from about 5° C. to about 15° C.; then b. administering by injection into the intra-articular space of the joint of said knee a pharmaceutical composition comprising a single pain-relief agent selected from the group consisting of lidocaine and a pharmaceutically acceptable salt thereof; then c. applying for a duration of about 30 minutes a cooling article to an exterior surface of said knee, wherein the cooling article has an exterior surface temperature in the range of from about 5° C. to about 15° C.; then d. administering by injection into the intra-articular space of the joint of said knee a pharmaceutical composition comprising capsaicin in order to deliver a dose of capsaicin in an amount of about 1 mg; and then e. optionally applying a cooling article to an exterior surface of said knee for a duration of at least about 30 minutes, wherein the cooling article has an exterior surface temperature in the range of from about 5° C. to about 15° C.;

to thereby ameliorate osteoarthritic knee joint pain in the human patient.

In certain embodiments, the method comprises step (e), which is applying a cooling article to an exterior surface of said knee for a duration of at least about 30 minutes, wherein the cooling article has an exterior surface temperature in the range of from about 5° C. to about 15° C.

Third Method

One aspect of the invention provides a method of attenuating transient burning sensation due to injection of capsaicin into a human osteoarthritic knee joint, wherein the method comprises:

a. applying for a duration of about 15 minutes a cooling article to an exterior surface of a human patient's knee presenting with osteoarthritic knee joint pain, wherein the cooling article has an exterior surface temperature in the range of from about 5° C. to about 15° C. for application to the exterior surface of said knee; then b. administering by injection into the intra-articular space of the joint of said knee a pharmaceutical composition comprising a single pain-relief agent selected from the group consisting of lidocaine and a pharmaceutically acceptable salt thereof, in order to deliver a dose of lidocaine in an amount ranging from about 0.1 g to about 0.5 g; then c. applying for a duration of about 30 minutes a cooling article to an exterior surface of said knee, wherein the cooling article has an exterior surface temperature in the range of from about 5° C. to about 15° C. for application to the exterior surface of said knee; then d. administering by injection into the intra-articular space of the joint of said knee a pharmaceutical composition comprising capsaicin in order to deliver a dose of capsaicin in an amount of about 1 mg; and then e. applying a cooling article to an exterior surface of said knee for a duration of at least about 30 minutes, wherein the cooling article has an exterior surface temperature in the range of from about 5° C. to about 15° C. for application to the exterior surface of said knee;

to thereby attenuate transient burning sensation due to injection of capsaicin.

Fourth Method

One aspect of the invention provides a method of attenuating transient burning sensation due to injection of capsaicin into a human osteoarthritic knee joint, wherein the method comprises:

a. applying for a duration of about 15 minutes a cooling article to an exterior surface of a human patient's knee presenting with osteoarthritic knee joint pain, wherein the cooling article has an exterior surface temperature in the range of from about 5° C. to about 15° C.; then b. administering by injection into the intra-articular space of the joint of said knee a pharmaceutical composition comprising a single pain-relief agent selected from the group consisting of lidocaine and a pharmaceutically acceptable salt thereof; then c. applying for a duration of about 30 minutes a cooling article to an exterior surface of said knee, wherein the cooling article has an exterior surface temperature in the range of from about 5° C. to about 15° C.; then d. administering by injection into the intra-articular space of the joint of said knee a pharmaceutical composition comprising capsaicin in order to deliver a dose of capsaicin in an amount of about 1 mg; and then e. optionally applying a cooling article to an exterior surface of said knee for a duration of at least about 30 minutes, wherein the cooling article has an exterior surface temperature in the range of from about 5° C. to about 15° C.;

to thereby attenuate transient burning sensation due to injection of capsaicin.

In certain embodiments, the method comprises step (e), which is applying a cooling article to an exterior surface of said knee for a duration of at least about 30 minutes, wherein the cooling article has an exterior surface temperature in the range of from about 5° C. to about 15° C.

Fifth Method

One aspect of the invention provides a method of ameliorating osteoarthritic knee joint pain in a human patient, wherein the method comprises:

a. applying a cooling article to an exterior surface of a human patient's knee presenting with osteoarthritic knee joint pain; then b. administering by injection into the intra-articular space of the joint of said knee a pharmaceutical composition comprising a single pain-relief agent selected from the group consisting of lidocaine and a pharmaceutically acceptable salt thereof, in order to deliver a dose of lidocaine in an amount of about 0.1 g to about 0.5 g; then
c. applying a cooling article to an exterior surface of said knee to achieve a temperature in the range of from about 26° C. to about 33° C. for fluid in the intra-articular space of the joint of said knee; then
d. administering by injection into the intra-articular space of the joint of said knee a pharmaceutical composition comprising capsaicin in order to deliver a dose of capsaicin in an amount of about 1 mg; and then
e. applying a cooling article to an exterior surface of said knee;
to thereby ameliorate osteoarthritic knee joint pain in the human patient.

Sixth Method

One aspect of the invention provides a method of ameliorating osteoarthritic knee joint pain in a human patient, wherein the method comprises:
a. applying a cooling article to an exterior surface of a human patient's knee presenting with osteoarthritic knee joint pain; then
b. administering by injection into the intra-articular space of the joint of said knee a pharmaceutical composition comprising a single pain-relief agent selected from the group consisting of lidocaine and a pharmaceutically acceptable salt thereof; then
c. applying a cooling article to an exterior surface of said knee to achieve a temperature in the range of from about 26° C. to about 33° C. for fluid in the intra-articular space of the joint of said knee; then
d. administering by injection into the intra-articular space of the joint of said knee a pharmaceutical composition comprising capsaicin in order to deliver a dose of capsaicin in an amount of about 1 mg; and then
e. optionally applying a cooling article to an exterior surface of said knee;
to thereby ameliorate osteoarthritic knee joint pain in the human patient.

In certain embodiments, the method comprises step (e), which is applying a cooling article to an exterior surface of said knee.

Seventh Method

One aspect of the invention provides a method of attenuating transient burning sensation due to injection of capsaicin into a human osteoarthritic knee joint, wherein the method comprises:
a. applying a cooling article to an exterior surface of a human patient's knee presenting with osteoarthritic knee joint pain; then
b. administering by injection into the intra-articular space of the joint of said knee a pharmaceutical composition comprising a single pain-relief agent selected from the group consisting of lidocaine and a pharmaceutically acceptable salt thereof, in order to deliver a dose of lidocaine in an amount of ranging from about 0.1 g to about 0.5 g; then
c. applying a cooling article to an exterior surface of said knee to achieve a temperature in the range of from about 26° C. to about 33° C. for fluid in the intra-articular space of the joint of said knee; then
d. administering by injection into the intra-articular space of the joint of said knee a pharmaceutical composition comprising capsaicin in order to deliver a dose of capsaicin in an amount of about 1 mg; and then
e. applying a cooling article to an exterior surface of said knee;
to thereby attenuate transient burning sensation due to injection of capsaicin.

Eighth Method

One aspect of the invention provides a method of attenuating transient burning sensation due to injection of capsaicin into a human osteoarthritic knee joint, wherein the method comprises:
a. applying a cooling article to an exterior surface of a human patient's knee presenting with osteoarthritic knee joint pain; then
b. administering by injection into the intra-articular space of the joint of said knee a pharmaceutical composition comprising a single pain-relief agent selected from the group consisting of lidocaine and a pharmaceutically acceptable salt thereof; then
c. applying a cooling article to an exterior surface of said knee to achieve a temperature in the range of from about 26° C. to about 33° C. for fluid in the intra-articular space of the joint of said knee; then
d. administering by injection into the intra-articular space of the joint of said knee a pharmaceutical composition comprising capsaicin in order to deliver a dose of capsaicin in an amount of about 1 mg; and then
e. optionally applying a cooling article to an exterior surface of said knee; to thereby attenuate transient burning sensation due to injection of capsaicin.

In certain embodiments, the method comprises step (e), which is applying a cooling article to an exterior surface of said knee.

Exemplary Features of the First, Second, Third, and Fourth Methods

The above First, Second, Third, and Fourth Methods may be further characterized by additional features, such as a step comprising flexing the knee, characterization of the temperature of the cooling article surface for application to the exterior surface of the knee, dose of lidocaine, characterization of the pharmaceutical composition comprising a single pain-relief agent, and the like. A more thorough description of such features is provided below. The invention embraces all permutations and combinations of these features.

Flexing the Knee

The methods may be further characterized according to the presence or absence of a step that involves flexing the knee that received capsaicin. For example, in certain embodiments, after administration of the pharmaceutical composition comprising capsaicin in step (d) but prior to step (e) said knee is flexed. In certain embodiments, after administration of the pharmaceutical composition comprising capsaicin in step (d) but prior to step (e) said knee is flexed about 5 times. In certain embodiments, after administration of the pharmaceutical composition comprising capsaicin in step (d) but prior to step (e) said knee is flexed about 5 times over a period of about 1 minute. In certain embodiments, after administration of the pharmaceutical composition comprising capsaicin in step (d) but prior to step (e) said knee is flexed and extended. In certain embodiments, after administration of the pharmaceutical composition comprising capsaicin in step (d) but prior to step (e) said knee is flexed and extended about 5 times. In certain embodiments, after administration of the pharmaceutical composition comprising capsaicin in step (d) but prior to step (e) said knee is flexed and extended about 5 times over a period of about 1 minute.

Temperature of the Cooling Article Surface for Application to Exterior Surface of the Knee The methods may be further characterized according to temperature of the cooling article surface for application to the exterior surface of the knee. For example, in certain embodiments, the cooling article has an exterior surface temperature in the range of from about 6° C. to about 13° C. for application to the exterior surface of said knee. In certain embodiments, the cooling article has an exterior surface temperature in the range of from about 7° C. to about 13° C. for application to the exterior surface of said knee. In certain embodiments, the cooling article has an exterior surface temperature in the range of from about 7° C. to about 10° C. for application to the exterior surface of said knee. In certain embodiments, the cooling article has an exterior surface temperature in the range of from about 5° C. to about 10° C. for application to the exterior surface of said knee. In certain embodiments, the cooling article has an exterior surface temperature in the range of from about 8° C. to about 10° C. for application to the exterior surface of said knee. In certain embodiments, the cooling article has an exterior surface temperature in the range of from about 6° C. to about 8° C. for application to the exterior surface of said knee. In certain embodiments, the cooling article has an exterior surface temperature in the range of from about 5° C. to about 8° C. for application to the exterior surface of said knee. In certain embodiments, the cooling article has an exterior surface temperature in the range of from about 5° C. to about 7° C. for application to the exterior surface of said knee.

In certain embodiments, the cooling article has an exterior surface temperature of about 12° C. for application to the exterior surface of said knee. In certain embodiments, the cooling article has an exterior surface temperature of about 11° C. for application to the exterior surface of said knee. In certain embodiments, the cooling article has an exterior surface temperature of about 10° C. for application to the exterior surface of said knee. In certain embodiments, the cooling article has an exterior surface temperature of about 9° C. for application to the exterior surface of said knee. In certain embodiments, the cooling article has an exterior surface temperature of about 8° C. for application to the exterior surface of said knee. In certain embodiments, the cooling article has an exterior surface temperature of about 7° C. for application to the exterior surface of said knee. In certain embodiments, the cooling article has an exterior surface temperature of about 6° C. for application to the exterior surface of said knee. In certain embodiments, the cooling article has an exterior surface temperature of about 5° C. for application to the exterior surface of said knee.

Temperature of Fluid in the Intra-Articular Space of the Joint of Said Knee

The methods may be further characterized according to the temperature of fluid in the intra-articular space of the joint of the knee to receive or has received capsaicin according to the method. For example, in certain embodiments, in step (e) fluid in the intra-articular space of the joint of said knee is maintained at a temperature in the range of from 26° C. to about 33° C. for a duration of at least 30 minutes. In certain embodiments, in step (e) fluid in the intra-articular space of the joint of said knee is maintained at a temperature in the range of from 26° C. to about 33° C. for a duration of from about 30 minutes to about 90 minutes. In certain embodiments, in step (e) fluid in the intra-articular space of the joint of said knee is maintained at a temperature in the range of from 26° C. to about 28° C. for a duration of at least 30 minutes. In certain embodiments, in step (e) fluid in the intra-articular space of the joint of said knee is maintained at a temperature in the range of from 26° C. to about 28° C. for a duration of from about 30) minutes to about 90 minutes. In certain embodiments, in step (e) fluid in the intra-articular space of the joint of said knee is maintained at a temperature in the range of from 28° C. to about 30° C. for a duration of at least 30 minutes. In certain embodiments, in step (e) fluid in the intra-articular space of the joint of said knee is maintained at a temperature in the range of from 28° C. to about 30° C. for a duration of from about 30 minutes to about 90 minutes. In certain embodiments, in step (e) fluid in the intra-articular space of the joint of said knee is maintained at a temperature in the range of from 30° C. to about 32° C. for a duration of at least 30 minutes. In certain embodiments, in step (e) fluid in the intra-articular space of the joint of said knee is maintained at a temperature in the range of from 30° C. to about 32° C. for a duration of from about 30 minutes to about 90 minutes. In certain embodiments, in step (e) fluid in the intra-articular space of the joint of said knee is maintained at a temperature of about 26° C. for a duration of at least 30 minutes. In certain embodiments, in step (e) fluid in the intra-articular space of the joint of said knee is maintained at a temperature of about 26° C. for a duration of from about 30 minutes to about 90 minutes. In certain embodiments, in step (e) fluid in the intra-articular space of the joint of said knee is maintained at a temperature of about 27° C. for a duration of at least 30 minutes. In certain embodiments, in step (e) fluid in the intra-articular space of the joint of said knee is maintained at a temperature of about 27° C. for a duration of from about 30 minutes to about 90 minutes. In certain embodiments, in step (e) fluid in the intra-articular space of the joint of said knee is maintained at a temperature of about 28° C. for a duration of at least 30 minutes. In certain embodiments, in step (e) fluid in the intra-articular space of the joint of said knee is maintained at a temperature of about 28° C. for a duration of from about 30 minutes to about 90 minutes. In certain embodiments, in step (e) fluid in the intra-articular space of the joint of said knee is maintained at a temperature of about 29° C. for a duration of at least 30 minutes. In certain embodiments, in step (e) fluid in the intra-articular space of the joint of said knee is maintained at a temperature of about 29° C. for a duration of from about 30 minutes to about 90 minutes. In certain embodiments, in step (e) fluid in the intra-articular space of the joint of said knee is maintained at a temperature of about 30° C. for a duration of at least 30 minutes. In certain embodiments, in step (e) fluid in the intra-articular space of the joint of said knee is maintained at a temperature of about 30° C. for a duration of from about 30 minutes to about 90 minutes. In certain embodiments, in step (e) fluid in the intra-articular space of the joint of said knee is maintained at a temperature of about 31° C. for a duration of at least 30 minutes. In certain embodiments, in step (e) fluid in the intra-articular space of the joint of said knee is maintained at a temperature of about 31° C. for a duration of from about 30 minutes to about 90 minutes. In certain embodiments, in step (e) fluid in the intra-articular space of the joint of said knee is maintained at a temperature of about 32° C. for a duration of at least 30 minutes. In certain embodiments, in step (e) fluid in the intra-articular space of the joint of said knee is maintained at a temperature of about 32° C. for a duration of from about 30 minutes to about 90 minutes. In certain embodiments, in step (e) fluid in the intra-articular space of the joint of said knee is maintained at a temperature of about 33° C. for a duration of at least 30 minutes. In certain embodiments, in step (e) fluid in the intra-articular space of the joint of said knee is maintained at a temperature of about 33° C. for a duration of from about 30) minutes to about 90 minutes.

In certain embodiments, step (c) comprises cooling fluid in the intra-articular space of the joint of said knee to a temperature in the range of from about 26° C. to about 28° C. In certain embodiments, step (c) comprises cooling fluid in the intra-articular space of the joint of said knee to a temperature in the range of from about 28° C. to about 30° C. In certain embodiments, step (c) comprises cooling fluid in the intra-articular space of the joint of said knee to a temperature in the range of from about 30° C. to about 32° C. In certain embodiments, step (c) comprises cooling fluid in the intra-articular space of the joint of said knee to a temperature of about 26° C. In certain embodiments, step (c) comprises cooling fluid in the intra-articular space of the joint of said knee to a temperature of about 27° C. In certain embodiments, step (c) comprises cooling fluid in the intra-articular space of the joint of said knee to a temperature of about 28° C. In certain embodiments, step (c) comprises cooling fluid in the intra-articular space of the joint of said knee to a temperature of about 29° C. In certain embodiments, step (c) comprises cooling fluid in the intra-articular space of the joint of said knee to a temperature of about 30° C. In certain embodiments, step (c) comprises cooling fluid in the intra-articular space of the joint of said knee to a temperature of about 31° C. In certain embodiments, step (c) comprises cooling fluid in the intra-articular space of the joint of said knee to a temperature of about 32° C. In certain embodiments, step (c) comprises cooling fluid in the intra-articular space of the joint of said knee to a temperature of about 33° C. In certain embodiments, in step (c) comprises cooling fluid in the intra-articular space of the joint of said knee to a temperature of about 29° C.

Dose of Lidocaine

The methods may be further characterized according to dose of lidocaine administered to the patient. For example, in certain embodiments, in step (b) the dose of lidocaine is about 0.3 g. In certain embodiments, in step (b) the dose of lidocaine is 0.3 g. In yet other embodiments, in step (b), the dose of lidocaine is about 0.1 g. about 0.2 g. about 0.4 g. or about 0.5 g. In yet other embodiments, in step (b), the dose of lidocaine is about 0.15 g.

Pharmaceutical Composition Comprising a Single Pain-Relief Agent

The methods may be further characterized according to features of the pharmaceutical composition comprising a single pain-relief agent. For example, in certain embodiments, the pharmaceutical composition comprising a single pain-relief agent is an aqueous mixture that contains lidocaine at a concentration of about 2% w/w. In certain embodiments, the pharmaceutical composition comprising a single pain-relief agent is an aqueous mixture that contains lidocaine at a concentration of about 1% w/w. In certain embodiments, the pharmaceutical composition comprising a single pain-relief agent further comprises sodium chloride. In certain embodiments, the pharmaceutical composition comprising a single pain-relief agent further comprises sodium chloride at a concentration ranging from about 4 mg/mL to about 8 mg/mL. In certain embodiments, the pharmaceutical composition comprising a single pain-relief agent has a volume in the range of from about 13 mL to about 17 mL. In certain embodiments, the pharmaceutical composition comprising a single pain-relief agent has a volume of about 15 mL. In certain embodiments, the pharmaceutical composition comprising a single pain-relief agent has a volume of about 15 mL. In yet other embodiments, the pharmaceutical composition comprising a single pain-relief agent has a volume in the range of from about 1 mL to about 3 mL, about 3 mL to about 5 mL, about 5 mL to about 7 mL, about 7 mL to about 9 mL, about 9 mL to about 11 mL, about 11 mL to about 13 mL, about 13 mL to about 15 mL, or about 17 mL to about 19 mL. In yet other embodiments, the pharmaceutical composition comprising a single pain-relief agent has a volume of about 1, 2, 3, 4, 5, 6, 7, 8, 9, 10, 11, 12, 13, 14, 15, 16, 17, 18, or 19 mL.

The methods may be further characterized according to the temperature of the pharmaceutical composition comprising a single pain-relief agent, which is to be administered to the patient. For example, in certain embodiments, the pharmaceutical composition comprising a single pain-relief agent has a temperature in the range of from about 1° C. to about 5° C., about 5° C. to about 10° C., about 10° C. to about 15° C., about 15° C. to about 20° C., about 20° C. to about 25° C., or about 22° C. to about 24° C. In certain embodiments, the pharmaceutical composition comprising a single pain-relief agent has a temperature of about 23° C.

Pharmaceutical Composition Comprising Capsaicin

The methods may be further characterized according to features of the pharmaceutical composition comprising capsaicin. For example, in certain embodiments, the pharmaceutical composition comprising capsaicin is an aqueous mixture containing capsaicin. In certain embodiments, the pharmaceutical composition comprising capsaicin has a volume of about 4 mL. In certain embodiments, the pharmaceutical composition comprising capsaicin has a volume of about 2 mL. In certain embodiments, the pharmaceutical composition comprising capsaicin has a volume of about 0.05 mL, 0.1 mL, 0.125 mL, 0.2 mL, 0.5 mL, 0.75 mL, 1.0 mL, 1.25 mL, 1.5 mL, 1.75 mL, 2.0 mL, 2.25 mL, 2.5 mL, 2.75 mL, 3.0 mL, 3.25 mL, 3.5 mL, 3.75 mL, or 4.0 mL. In certain embodiments, the pharmaceutical composition comprising capsaicin has a volume in the range of from about 0.01 mL to about 0.1 mL, about 0.1 mL to about 0.2 mL, about 0.2 mL to about 0.5 mL, about 0.5 mL to about 0.75 mL, about 0.75 mL to about 1.0 mL, about 1.0 mL to about 1.5 mL, about 1.5 mL to about 2.0 mL, about 2.0 mL to about 2.5 mL, about 2.5 mL to about 3.0 mL, about 3.0 mL to about 3.5 mL, about 3.5 mL to about 4.0 mL, about 4.0 mL to about 5.0 mL, about 5.0 mL to about 6.0 mL, about 6.0 mL to about 9 mL, or about 9) mL to about 12 mL.

Duration of Cooling in Step (e)

The methods may be further characterized according to the duration of cooling in step (e). In certain embodiments, the duration in step (e) is from about 30 minutes to about 90 minutes. In certain embodiments, the duration in step (e) is from about 30 minutes to about 60) minutes. In certain embodiments, the duration in step (e) is from about 60 minutes to about 90 minutes. In certain embodiments, unless it would conflict with a minimum duration of time already specified in step (e), the duration in step (e) is from about 30 minutes to about 60 minutes, from about 60) minutes to about 90 minutes, from about 90 minutes to about 120 minutes, or from about 120 minutes to about 180) minutes.

Dose of Capsaicin

The methods may be further characterized according to the dose of capsaicin. In certain embodiments, the dose of capsaicin is 1 mg.

Exemplary Features of the Fifth, Sixth, Seventh, and Eighth Methods

The above Fifth, Sixth, Seventh, and Eighth Methods may be further characterized by additional features, such as a step comprising flexing the knee, characterization of the temperature of fluid in the intra-articular space of the joint of the knee to receive or has received capsaicin according to the method, characterization of the temperature of the cooling article surface for application to the exterior surface of the knee, the duration of cooling step (a), the dose of lidocaine, characterization of the pharmaceutical composition comprising a single pain-relief agent, and the like. A more thorough description of such features is provided below. The invention embraces all permutations and combinations of these features.

Flexing the Knee

The methods may be further characterized according to the presence or absence of a step that involves flexing the knee that received capsaicin. For example, in certain embodiments, after administration of the pharmaceutical composition comprising capsaicin in step (d) but prior to step (e) said knee is flexed. In certain embodiments, after administration of the pharmaceutical composition comprising capsaicin in step (d) but prior to step (e) said knee is flexed about 5 times. In certain embodiments, after administration of the pharmaceutical composition comprising capsaicin in step (d) but prior to step (e) said knee is flexed about 5 times over a period of about 1 minute. In certain embodiments, after administration of the pharmaceutical composition comprising capsaicin in step (d) but prior to step (e) said knee is flexed and extended. In certain embodiments, after administration of the pharmaceutical composition comprising capsaicin in step (d) but prior to step (e) said knee is flexed and extended about 5 times. In certain embodiments, after administration of the pharmaceutical composition comprising capsaicin in step (d) but prior to step (e) said knee is flexed and extended about 5 times over a period of about 1 minute.

Temperature of Fluid in the Intra-Articular Space of the Joint of Said Knee

The methods may be further characterized according to the temperature of fluid in the intra-articular space of the joint of the knee to receive or has received capsaicin according to the method. For example, in certain embodiments, in step (e) fluid in the intra-articular space of the joint of said knee is maintained at a temperature in the range of from 26° C. to about 33° C. for a duration of at least 30 minutes. In certain embodiments, in step (e) fluid in the intra-articular space of the joint of said knee is maintained at a temperature in the range of from 26° C. to about 33° C. for a duration of from about 30 minutes to about 90 minutes. In certain embodiments, in step (e) fluid in the intra-articular space of the joint of said knee is maintained at a temperature in the range of from 26° C. to about 28° C. for a duration of at least 30 minutes. In certain embodiments, in step (e) fluid in the intra-articular space of the joint of said knee is maintained at a temperature in the range of from 26° C. to about 28° C. for a duration of from about 30) minutes to about 90 minutes. In certain embodiments, in step (e) fluid in the intra-articular space of the joint of said knee is maintained at a temperature in the range of from 28° C. to about 30° C. for a duration of at least 30 minutes. In certain embodiments, in step (e) fluid in the intra-articular space of the joint of said knee is maintained at a temperature in the range of from 28° C. to about 30° C. for a duration of from about 30 minutes to about 90 minutes. In certain embodiments, in step (e) fluid in the intra-articular space of the joint of said knee is maintained at a temperature in the range of from 30° C. to about 32° C. for a duration of at least 30 minutes. In certain embodiments, in step (e) fluid in the intra-articular space of the joint of said knee is maintained at a temperature in the range of from 30° C. to about 32° C. for a duration of from about 30 minutes to about 90 minutes. In certain embodiments, in step (e) fluid in the intra-articular space of the joint of said knee is maintained at a temperature of about 26° C. for a duration of at least 30 minutes. In certain embodiments, in step (e) fluid in the intra-articular space of the joint of said knee is maintained at a temperature of about 26° C. for a duration of from about 30 minutes to about 90 minutes. In certain embodiments, in step (e) fluid in the intra-articular space of the joint of said knee is maintained at a temperature of about 27° C. for a duration of at least 30 minutes. In certain embodiments, in step (e) fluid in the intra-articular space of the joint of said knee is maintained at a temperature of about 27° C. for a duration of from about 30 minutes to about 90 minutes. In certain embodiments, in step (e) fluid in the intra-articular space of the joint of said knee is maintained at a temperature of about 28° C. for a duration of at least 30 minutes. In certain embodiments, in step (e) fluid in the intra-articular space of the joint of said knee is maintained at a temperature of about 28° C. for a duration of from about 30 minutes to about 90 minutes. In certain embodiments, in step (e) fluid in the intra-articular space of the joint of said knee is maintained at a temperature of about 29° C. for a duration of at least 30 minutes. In certain embodiments, in step (e) fluid in the intra-articular space of the joint of said knee is maintained at a temperature of about 29° C. for a duration of from about 30 minutes to about 90 minutes. In certain embodiments, in step (e) fluid in the intra-articular space of the joint of said knee is maintained at a temperature of about 30° C. for a duration of at least 30 minutes. In certain embodiments, in step (e) fluid in the intra-articular space of the joint of said knee is maintained at a temperature of about 30° C. for a duration of from about 30 minutes to about 90 minutes. In certain embodiments, in step (e) fluid in the intra-articular space of the joint of said knee is maintained at a temperature of about 31° C. for a duration of at least 30 minutes. In certain embodiments, in step (e) fluid in the intra-articular space of the joint of said knee is maintained at a temperature of about 31° C. for a duration of from about 30) minutes to about 90) minutes. In certain embodiments, in step (e) fluid in the intra-articular space of the joint of said knee is maintained at a temperature of about 32° C. for a duration of at least 30 minutes. In certain embodiments, in step (e) fluid in the intra-articular space of the joint of said knee is maintained at a temperature of about 32° C. for a duration of from about 30 minutes to about 90 minutes. In certain embodiments, in step (e) fluid in the intra-articular space of the joint of said knee is maintained at a temperature of about 33° C. for a duration of at least 30 minutes. In certain embodiments, in step (e) fluid in the intra-articular space of the joint of said knee is maintained at a temperature of about 33° C. for a duration of from about 30) minutes to about 90) minutes.

In certain embodiments, step (c) comprises applying a cooling article to an exterior surface of the knee to achieve a temperature in the range of from about 26° C. to about 28°

C. for fluid in the intra-articular space of the joint of said knee. In certain embodiments, step (c) comprises applying a cooling article to an exterior surface of the knee to achieve a temperature in the range of from about 28° C. to about 30° C. for fluid in the intra-articular space of the joint of said knee. In certain embodiments, step (c) comprises applying a cooling article to an exterior surface of the knee to achieve a temperature in the range of from about 30° C. to about 32° C. for fluid in the intra-articular space of the joint of said knee. In certain embodiments, step (c) comprises applying a cooling article to an exterior surface of the knee to achieve a temperature of about 26° C. for fluid in the intra-articular space of the joint of said knee. In certain embodiments, step (c) comprises applying a cooling article to an exterior surface of the knee to achieve a temperature of about 27° C. for fluid in the intra-articular space of the joint of said knee. In certain embodiments, step (c) comprises applying a cooling article to an exterior surface of the knee to achieve a temperature of about 28° C. for fluid in the intra-articular space of the joint of said knee. In certain embodiments, step (c) comprises applying a cooling article to an exterior surface of the knee to achieve a temperature of about 29° C. for fluid in the intra-articular space of the joint of said knee. In certain embodiments, step (c) comprises applying a cooling article to an exterior surface of the knee to achieve a temperature of about 30° C. for fluid in the intra-articular space of the joint of said knee. In certain embodiments, step (c) comprises applying a cooling article to an exterior surface of the knee to achieve a temperature of about 31° C. for fluid in the intra-articular space of the joint of said knee. In certain embodiments, step (c) comprises applying a cooling article to an exterior surface of the knee to achieve a temperature of about 32° C. for fluid in the intra-articular space of the joint of said knee. In certain embodiments, step (c) comprises applying a cooling article to an exterior surface of the knee to achieve a temperature of about 33° C. for fluid in the intra-articular space of the joint of said knee. In certain embodiments, in step (c) comprises applying a cooling article to an exterior surface of the knee to achieve a temperature of about 29° C. for fluid in the intra-articular space of the joint of said knee.

Temperature of the Cooling Article Surface for Application to Exterior Surface of the Knee The methods may be further characterized according to the temperature of the cooling article surface for application to the exterior surface of the knee to receive capsaicin. In certain embodiments, the cooling article has an exterior surface temperature in the range of from about 6° C. to about 13° C. for application to the exterior surface of said knee. In certain embodiments, the cooling article has an exterior surface temperature in the range of from about 7° C. to about 13° C. for application to the exterior surface of said knee. In certain embodiments, the cooling article has an exterior surface temperature in the range of from about 7° C. to about 10° C. for application to the exterior surface of said knee. In certain embodiments, the cooling article has an exterior surface temperature in the range of from about 5° C. to about 10° C. for application to the exterior surface of said knee. In certain embodiments, the cooling article has an exterior surface temperature in the range of from about 8° C. to about 10° C. for application to the exterior surface of said knee. In certain embodiments, the cooling article has an exterior surface temperature in the range of from about 6° C. to about 8° C. for application to the exterior surface of said knee. In certain embodiments, the cooling article has an exterior surface temperature in the range of from about 5° C. to about 8° C. for application to the exterior surface of said knee. In certain embodiments, the cooling article has an exterior surface temperature in the range of from about 5° C. to about 7° C. for application to the exterior surface of said knee. In certain embodiments, the cooling article has an exterior surface temperature of about 12° C. for application to the exterior surface of said knee. In certain embodiments, the cooling article has an exterior surface temperature of about 11° C. for application to the exterior surface of said knee. In certain embodiments, the cooling article has an exterior surface temperature of about 10° C. for application to the exterior surface of said knee. In certain embodiments, the cooling article has an exterior surface temperature of about 9° C. for application to the exterior surface of said knee. In certain embodiments, the cooling article has an exterior surface temperature of about 8° C. for application to the exterior surface of said knee. In certain embodiments, the cooling article has an exterior surface temperature of about 7° C. for application to the exterior surface of said knee. In certain embodiments, the cooling article has an exterior surface temperature of about 6° C. for application to the exterior surface of said knee. In certain embodiments, the cooling article has an exterior surface temperature of about 5° C. for application to the exterior surface of said knee.

Duration in Step (a)

The methods may be further characterized according to the duration of cooling step (a). For example, in certain embodiments, in step (a) the cooling article is applied for a duration of from about 5 minutes to about 30 minutes to the exterior surface of the patient's knee presenting with osteoarthritic knee joint pain. In certain embodiments, in step (a) the cooling article is applied for a duration of from about 5 minutes to about 15 minutes to the exterior surface of the patient's knee presenting with osteoarthritic knee joint pain. In certain embodiments, in step (a) the cooling article is applied for a duration of about 5, 6, 7, 8, 9, 10, 11, 12, 13, 14, 15, 16, 17, 18, 19, or 20 minutes to the exterior surface of the patient's knee presenting with osteoarthritic knee joint pain. In certain embodiments, in step (a) the cooling article is applied for a duration of about 15 minutes to the exterior surface of the patient's knee presenting with osteoarthritic knee joint pain.

Dose of Lidocaine

The methods may be further characterized according to the dose of lidocaine administered to the patient. For example, in certain embodiments, in step (b) the dose of lidocaine is about 0.3 g. In certain embodiments, in step (b) the dose of lidocaine is 0.3 g. In yet other embodiments, in step (b), the dose of lidocaine is about 0.1 g, about 0.2 g, about 0.4 g. or about 0.5 g. In yet other embodiments, in step (b), the dose of lidocaine is about 0.15 g. In yet other embodiments, in step (b), the dose of lidocaine is less than about 0.1 g, 0.2 g, 0.3 g, 0.4 g, 0.5 g, 0.6 g, 0.7 g, 0.8 g, 0.9 g, or 1.0 g.

Pharmaceutical Composition Comprising a Single Pain-Relief Agent

The methods may be further characterized according to features of the pharmaceutical composition comprising a single pain-relief agent. In certain embodiments, the pharmaceutical composition comprising a single pain-relief agent is an aqueous mixture containing lidocaine at a concentration of about 2% w/w. In certain embodiments, the pharmaceutical composition comprising a single pain-relief agent further comprises sodium chloride. In certain embodiments, the pharmaceutical composition comprising a single pain-relief agent further comprises sodium chloride at a concentration ranging from about 4 mg/ml to about 8 mg/mL. In certain embodiments, the pharmaceutical composition comprising a single pain-relief agent has a volume in the range of from about 13 mL to about 17 mL. In certain embodiments, the pharmaceutical composition comprising a single pain-relief agent has a volume of about 15 mL. In yet other embodiments, the pharmaceutical composition comprising a single pain-relief agent has a volume in the range of from about 1 mL to about 3 mL, about 3 mL to about 5 mL, about 5 mL to about 7 mL, about 7 mL to about 9 mL, about 9) mL to about 11 mL, about 11 mL to about 13 mL, about 13 mL to about 15 mL, or about 17 mL to about 19 mL. In yet other embodiments, the pharmaceutical composition comprising a single pain-relief agent has a volume of about 1, 2, 3, 4, 5, 6, 7, 8, 9, 10, 11, 12, 13, 14, 15, 16, 17, 18, or 19 mL.

The methods may be further characterized according to the temperature of the pharmaceutical composition comprising a single pain-relief agent, which is to be administered to the patient. For example, in certain embodiments, the pharmaceutical composition comprising a single pain-relief agent has a temperature in the range of from about 1° C. to about 5° C., about 5° C. to about 10° C., about 10° C. to about 15° C., about 15° C. to about 20° C., about 20° C. to about 25° C., or about 22° C. to about 24° C. In certain embodiments, the pharmaceutical composition comprising a single pain-relief agent has a temperature of about 23° C.

Pharmaceutical Composition Comprising Capsaicin

The methods may be further characterized according to features of the pharmaceutical composition comprising capsaicin. For example, in certain embodiments, the pharmaceutical composition comprising capsaicin is an aqueous mixture containing capsaicin. In certain embodiments, the pharmaceutical composition comprising capsaicin has a volume of about 4 mL. In certain embodiments, the pharmaceutical composition comprising capsaicin has a volume of about 2 mL. In certain embodiments, the pharmaceutical composition comprising capsaicin has a volume of about 0.05 mL, 0.1 mL, 0.125 mL, 0.2 mL, 0.5 mL, 0.75 mL, 1.0) mL, 1.25 mL, 1.5 mL, 1.75 mL, 2.0 mL, 2.25 mL, 2.5 mL, 2.75 mL, 3.0 mL, 3.25 mL, 3.5 mL, 3.75 mL, or 4.0 mL. In certain embodiments, the pharmaceutical composition comprising capsaicin has a volume in the range of from about 0.01 mL to about 0.1 mL, about 0.1 mL to about 0.2 mL, about 0.2 mL to about 0.5 mL, about 0.5 mL to about 0.75 mL, about 0.75 mL to about 1.0 mL, about 1.0 mL to about 1.5 mL, about 1.5 mL to about 2.0 mL, about 2.0 mL to about 2.5 mL, about 2.5 mL to about 3.0 mL, about 3.0 mL to about 3.5 mL, about 3.5 mL to about 4.0 mL, about 4.0 mL to about 5.0 mL, about 5.0 mL to about 6.0 mL, about 6.0 mL to about 9 mL, or about 9 mL to about 12 mL.

Duration of Cooling

The methods may be further characterized according to the duration of cooling. For example, in certain embodiments, in step (a) the cooling article is applied for a duration of from about 5 minutes to about 20 minutes to the exterior surface of said knee. In certain embodiments, in step (a) the cooling article is applied for a duration of about 10 minutes to the exterior surface of said knee. In certain embodiments, in step (c) the cooling article is applied for a duration of from about 15 minutes to about 45 minutes to the exterior surface of said knee. In certain embodiments, in step (c) the cooling article is applied for a duration of about 45 minutes to the exterior surface of said knee. In certain embodiments, in step (c) the cooling article is applied for a duration of about 30 minutes to the exterior surface of said knee. In certain embodiments, in step (e) the cooling article is applied for a duration of at least about 10 minutes, at least about 20 minutes, or at least about 30 minutes to the exterior surface of said knee. In certain embodiments, in step (e) the cooling article is applied for a duration of about 10 minutes, about 20) minutes, or about 30 minutes to the exterior surface of said knee. In certain embodiments, in step (e) the cooling article is applied for a duration of from about 15 minutes to about 90 minutes to the exterior surface of said knee. In certain embodiments, in step (e) the cooling article is applied for a duration of from about 30 minutes to about 90 minutes to the exterior surface of said knee. In certain embodiments, in step (e) the cooling article is applied for a duration of from about 30 minutes to about 60 minutes to the exterior surface of said knee. In certain embodiments, in step (e) the cooling article is applied for a duration of from about 60) minutes to about 90 minutes to the exterior surface of said knee. In certain embodiments, in step (e), the duration in step (e) is from about 15 minutes to about 30 minutes, from about 30 minutes to about 60) minutes, from about 60) minutes to about 90) minutes, from about 90) minutes to about 120) minutes, or from about 120 minutes to about 180 minutes.

Exemplary Features of the First Through the Eighth Methods

The above First, Second, Third, Fourth, Fifth, Sixth, Seventh, and Eighth Methods may be further characterized by additional features, such as the presence or absence of additional procedures to reduce transient burning sensation caused by capsaicin, magnitude of the transient burning sensation due to capsaicin, duration of reduction in osteoarthritic knee joint pain, and the like. A more thorough description of such features is provided below. The invention embraces all permutations and combinations of these features Additional Procedure to Reduce Transient Burning Sensation and/or Treat Osteoarthritic Knee Joint Pain The methods may be further characterized according to the presence or absence of additional procedures to reduce transient burning sensation caused by capsaicin. For example, in certain embodiments, other than the procedures set forth in steps (a), (b), (c), (d), (e), and optionally flexing said knee, the method does not contain any procedure that reduces transient burning sensation experienced by the patient due to administration of capsaicin. In certain embodiments, other than the procedures set forth in steps (a), (b), (c), (d), (e), and optionally flexing said knee, the method does not contain any procedure that reduces osteoarthritic knee joint pain. In certain embodiments, other administration of (i) the pharmaceutical composition comprising lidocaine and (ii) the pharmaceutical composition comprising capsaicin, the patient does not receive any other pain-relief medicine. In certain embodiments, other than the procedures set forth in steps (a), (b), (c), (d), (e), and optionally flexing and extending said knee, the method does not contain any procedure that reduces transient burning sensation experienced by the patient due to administration of capsaicin. In certain embodiments, other than the procedures set forth in steps (a), (b), (c), (d), (e), and optionally flexing and extending said knee, the method does not contain any procedure that reduces osteoarthritic knee joint pain.

Magnitude of Transient Burning Sensation Due to Capsaicin

The methods may be further characterized according to the magnitude of the transient burning sensation due to capsaicin. For example, in certain embodiments, the patient experiences transient burning sensation no greater than level one on a visual analog scale ranging from zero to four (i.e., (0) none. (1) mild, (2) moderate. (3) moderately severe, and (4) severe), due to administering the pharmaceutical composition comprising capsaicin. In certain embodiments, the patient experiences transient burning sensation no greater than level two on a visual analog scale ranging from zero to four (i.e., (0)) none. (1) mild, (2) moderate. (3) moderately severe, and (4) severe), due to administering the pharmaceutical composition comprising capsaicin. In certain embodiments, transient burning sensation is evaluated at about 10 minutes after administration of the pharmaceutical composition comprising capsaicin. In certain embodiments, transient burning sensation is evaluated at about 30 minutes after administration of the pharmaceutical composition comprising capsaicin. In certain embodiments, transient burning sensation is evaluated at about 60 minutes after administration of the pharmaceutical composition comprising capsaicin. In certain embodiments, transient burning sensation is evaluated at about 120 minutes after administration of the pharmaceutical composition comprising capsaicin.

Duration of Reduction in Osteoarthritic Knee Joint Pain

The methods may be further characterized according to the duration of reduction in osteoarthritic knee joint pain. In certain embodiments, the method is characterized by achieving a reduction in osteoarthritic knee joint pain for a duration of at least 3 months. In certain embodiments, the method is characterized by achieving a reduction in osteoarthritic knee joint pain for a duration of at least 4 months. In certain embodiments, the method is characterized by achieving a reduction in osteoarthritic knee joint pain for a duration of at least 5 months. In certain embodiments, the method is characterized by achieving a reduction in osteoarthritic knee joint pain for a duration of at least 6 months. In certain embodiments, the method is characterized by achieving a reduction in osteoarthritic knee joint pain for a duration of at least 7 months. In certain embodiments, the method is characterized by achieving a reduction in osteoarthritic knee joint pain for a duration of at least 8 months. In certain embodiments, the method is characterized by achieving a reduction in osteoarthritic knee joint pain for a duration of at least 9 months. In certain embodiments, the method is characterized by achieving a reduction in osteoarthritic knee joint pain for a duration of at least 10 months. In certain embodiments, the method is characterized by achieving a reduction in osteoarthritic knee joint pain for a duration of at least 11 months. In certain embodiments, the method is characterized by achieving a reduction in osteoarthritic knee joint pain for a duration of at least 12 months. In certain embodiments, the method is characterized by achieving a reduction in osteoarthritic knee joint pain for a duration of 4 months to 6 months. In certain embodiments, the method is characterized by achieving a reduction in osteoarthritic knee joint pain for a duration of 6 months to 9 months. In certain embodiments, the method is characterized by achieving a reduction in osteoarthritic knee joint pain for a duration of 6 months to 12 months. In certain embodiments, the method is characterized by achieving a reduction in osteoarthritic knee joint pain for a duration of 9 months to 12 months. In certain embodiments, the method is characterized by achieving a reduction in osteoarthritic knee joint pain for a duration of 12 months to 18 months.

Characterization of the Cooling Article

The methods may be further characterized according to features of the cooling article. In certain embodiments, the cooling article is a material wrap cooled via a circulating fluid. In certain embodiments, the cooling article is a textile wrap cooled via a circulating fluid. In certain embodiments, the cooling article covers at least 10%, 20%, 30%, 40%, 50%, 60%, 70%, 80%, or 90% of the external surface of said patient's knee. In certain embodiments, the cooling article covers at least 70% of the external surface of said patient's knee. In certain embodiments, the cooling article covers at least 80% of the external surface of said patient's knee. In certain embodiments, the cooling article covers at least 90% of the external surface of said patient's knee. In certain embodiments, the cooling article covers at least 95% of the external surface of said patient's knee.

In certain embodiments, the cooling article is a wrap-on cooled pad sold by Breg, Inc. Exemplary wrap-on pads sold by Breg, Inc. use circulating ice-water to achieve cooling, and include the Breg Knee WrapOn Polar Pad. FIG. 1 herein is an illustration of a cooling article, that is a wrap-on pad, applied to a human knee.

In certain embodiments, the cooling article is an at least partially frozen gel pack.

In certain embodiments, the cooling article is an Elasto-Gel All Purpose Therapy Wrap, such as one that measures 6 inches by 24 inches in size. The Elasto-Gel All Purpose Therapy Wrap may be characterized as one that is removed from a freezer (approximately 0° F.) just prior to application to a patient.

Ninth Method

One aspect of the invention provides a method of ameliorating joint pain in a human patient, comprising:
a. optionally applying a cooling article to a human patient's skin in proximity to a joint in need of pain relief therapy; then
b. optionally administering a local anesthetic agent into said joint; then
c. applying for a duration of at least about 10 minutes a cooling article to the patient's skin in proximity to said joint, wherein the cooling article has an exterior surface temperature in the range of from about 1° C. to about 15° C. for application to the human patient's skin in proximity to said joint; then
d. administering by injection into said joint a pharmaceutical composition comprising capsaicin in order to deliver a dose of capsaicin in an amount of from about 0.01 mg to about 4 mg; and then
e. optionally applying for a duration of at least about 10 minutes a cooling article to the patient's skin in proximity to said joint, wherein the cooling article has an exterior surface temperature in the range of from about 1° C. to about 15° C. for application to the human patient's skin in proximity to said joint;
to thereby ameliorate joint pain in the human patient.

In certain embodiments, the method comprises step (e) which is applying for a duration of at least about 10 minutes a cooling article to the patient's skin in proximity to said joint, wherein the cooling article has an exterior surface temperature in the range of from about 1° C. to about 15° C. for application to the human patient's skin in proximity to said joint.

In certain embodiments, step (c) comprises applying for a duration of at least about 45 minutes a cooling article to the patient's skin in proximity to said joint.

Tenth Method

One aspect of the invention provides a method of ameliorating joint pain in a human patient, comprising:
a. optionally applying a cooling article to a human patient's skin in proximity to a joint in need of pain relief therapy; then b. optionally administering a local anesthetic agent into said joint; then
c. applying a cooling article to the patient's skin in proximity to said joint, wherein the cooling article has an exterior surface temperature in the range of from about 0° C. to about 18° C.; then
d. administering by injection into said joint a pharmaceutical composition comprising a therapeutically effective amount of capsaicin; and then
e. optionally applying for a duration of at least about 10 minutes a cooling article to the patient's skin in proximity to said joint, wherein the cooling article has an exterior surface temperature in the range of from about 0° C. to about 18° C.;
to thereby ameliorate joint pain in the human patient.

In certain embodiments, the method comprises step (e) which is applying for a duration of at least about 10 minutes a cooling article to the patient's skin in proximity to said joint, wherein the cooling article has an exterior surface temperature in the range of from about 0° C. to about 18° C.

Eleventh Method

One aspect of the invention provides a method of attenuating transient burning sensation due to injection of capsaicin into a joint in a human patient, comprising:
a. optionally applying a cooling article to a human patient's skin in proximity to a joint in need of pain relief therapy; then
b. optionally administering a local anesthetic agent into said joint; then
c. applying for a duration of at least about 10 minutes a cooling article to the patient's skin in proximity to said joint, wherein the cooling article has an exterior surface temperature in the range of from about 1° C. to about 15° C. for application to the human patient's skin in proximity to said joint; then
d. administering by injection into said joint a pharmaceutical composition comprising capsaicin in order to deliver a dose of capsaicin in an amount of from about 0.01 mg to about 4 mg; and then
e. optionally applying for a duration of at least about 10 minutes a cooling article to the patient's skin in proximity to said joint, wherein the cooling article has an exterior surface temperature in the range of from about 1° C. to about 15° C. for application to the human patient's skin in proximity to said joint;
to thereby attenuate transient burning sensation due to injection of capsaicin.

In certain embodiments, the method comprises step (e) which is applying for a duration of at least about 10 minutes a cooling article to the patient's skin in proximity to said joint, wherein the cooling article has an exterior surface temperature in the range of from about 1° C. to about 15° C. for application to the human patient's skin in proximity to said joint.

Twelfth Method

One aspect of the invention provides a method of ameliorating joint pain in a human patient, comprising:
a. optionally applying a cooling article to a human patient's skin in proximity to a joint in need of pain relief therapy; then
b. optionally administering a local anesthetic agent into said joint; then
c. applying a cooling article to the patient's skin in proximity to said joint to achieve a temperature in the range of from about 20° C. to about 33° C. for tissue or fluid in the interior of the joint; then
d. administering by injection into said joint a pharmaceutical composition comprising capsaicin in order to deliver a dose of capsaicin in an amount of from about 0.01 mg to about 4 mg; and then
e. optionally applying a cooling article to the patient's skin in proximity to said joint; to thereby ameliorate joint pain in the human patient.

In certain embodiments, the method comprises step (e) which is applying a cooling article to the patient's skin in proximity to said joint.

Thirteenth Method

One aspect of the invention provides a method of attenuating transient burning sensation due to injection of capsaicin into a joint in a human patient, comprising:
a. optionally applying a cooling article to a human patient's skin in proximity to a joint in need of pain relief therapy; then
b. optionally administering a local anesthetic agent into said joint; then
c. applying a cooling article to the patient's skin in proximity to said joint to achieve a temperature in the range of from about 20° C. to about 33° C. for tissue or fluid in the interior of the joint; then
d. administering by injection into said joint a pharmaceutical composition comprising capsaicin in order to deliver a dose of capsaicin in an amount of from about 0.01 mg to about 4 mg; and then
e. optionally applying a cooling article to the patient's skin in proximity to said joint; to thereby attenuate transient burning sensation due to injection of capsaicin.

In certain embodiments, the method comprises step (e) which is applying a cooling article to the patient's skin in proximity to said joint.

Exemplary Features of the Twelfth and Thirteenth Methods

The above Twelfth Method and Thirteenth Method may be further characterized by additional features, such as the temperature of tissue or fluid in the interior of the joint to receive or which has received capsaicin according to the method, and the like. A more thorough description of such features is provided below. The invention embraces all permutations and combinations of these features.

Temperature of Tissue or Fluid in the Interior of the Joint

The methods may be further characterized according to the temperature of tissue or fluid in the interior of the joint to receive or which has received capsaicin according to the method. For example, in certain embodiments, step (c) comprises applying a cooling article to the patient's skin in proximity to the joint to achieve a temperature in the range of from about 20° C. to about 22° C. for tissue or fluid in the interior of the joint. In certain embodiments, step (c) comprises applying a cooling article to the patient's skin in proximity to the joint to achieve a temperature in the range of from about 22° C. to about 24° C. for tissue or fluid in the interior of the joint. In certain embodiments, step (c) comprises applying a cooling article to the patient's skin in proximity to the joint to achieve a temperature in the range of from about 24° C. to about 26° C. for tissue or fluid in the interior of the joint. In certain embodiments, step (c) comprises applying a cooling article to the patient's skin in proximity to the joint to achieve a temperature in the range of from about 26° C. to about 28° C. for tissue or fluid in the interior of the joint. In certain embodiments, step (c) comprises applying a cooling article to the patient's skin in proximity to the joint to achieve a temperature in the range of from about 28° C. to about 30° C. for tissue or fluid in the interior of the joint. In certain embodiments, step (c) comprises applying a cooling article to the patient's skin in proximity to the joint to achieve a temperature in the range of from about 30° C. to about 32° C. for tissue or fluid in the interior of the joint. In certain embodiments, step (c) comprises applying a cooling article to the patient's skin in proximity to the joint to achieve a temperature in the range of from about 25° C. to about 31° C. for tissue or fluid in the interior of the joint.

In certain embodiments, step (c) comprises applying a cooling article to the patient's skin in proximity to the joint to achieve a temperature of about 20° C. for tissue or fluid in the interior of the joint. In certain embodiments, step (c) comprises applying a cooling article to the patient's skin in proximity to the joint to achieve a temperature of about 21° C. for tissue or fluid in the interior of the joint. In certain embodiments, step (c) comprises applying a cooling article to the patient's skin in proximity to the joint to achieve a temperature of about 22° C. for tissue or fluid in the interior of the joint. In certain embodiments, step (c) comprises applying a cooling article to the patient's skin in proximity to the joint to achieve a temperature of about 23° C. for tissue or fluid in the interior of the joint. In certain embodiments, step (c) comprises applying a cooling article to the patient's skin in proximity to the joint to achieve a temperature of about 24° C. for tissue or fluid in the interior of the joint. In certain embodiments, step (c) comprises applying a cooling article to the patient's skin in proximity to the joint to achieve a temperature of about 25° C. for tissue or fluid in the interior of the joint. In certain embodiments, step (c) comprises applying a cooling article to the patient's skin in proximity to the joint to achieve a temperature of about 26° C. for tissue or fluid in the interior of the joint. In certain embodiments, step (c) comprises applying a cooling article to the patient's skin in proximity to the joint to achieve a temperature of about 27° C. for tissue or fluid in the interior of the joint. In certain embodiments, step (c) comprises applying a cooling article to the patient's skin in proximity to the joint to achieve a temperature of about 28° C. for tissue or fluid in the interior of the joint. In certain embodiments, step (c) comprises applying a cooling article to the patient's skin in proximity to the joint to achieve a temperature of about 29° C. for tissue or fluid in the interior of the joint. In certain embodiments, step (c) comprises applying a cooling article to the patient's skin in proximity to the joint to achieve a temperature of about 30° C. for tissue or fluid in the interior of the joint. In certain embodiments, step (c) comprises applying a cooling article to the patient's skin in proximity to the joint to achieve a temperature of about 31° C. for tissue or fluid in the interior of the joint. In certain embodiments, step (c) comprises applying a cooling article to the patient's skin in proximity to the joint to achieve a temperature of about 32° C. for tissue or fluid in the interior of the joint. In certain embodiments, step (c) comprises applying a cooling article to the patient's skin in proximity to the joint to achieve a temperature of about 33° C. for tissue or fluid in the interior of the joint.

Fourteenth Method

One aspect of the invention provides a method of attenuating transient burning sensation due to injection of capsaicin into a joint in a human patient, comprising:
  a. optionally applying a cooling article to a human patient's skin in proximity to a joint in need of pain relief therapy; then
  b. optionally administering a local anesthetic agent into said joint; then
  c. applying a cooling article to the patient's skin in proximity to said joint to achieve a temperature in the range of from about 5° C. to about 30° C. for said skin; then
  d. administering by injection into said joint a pharmaceutical composition comprising capsaicin in order to deliver a dose of capsaicin in an amount of from about 0.01 mg to about 4 mg; and then
  e. optionally applying a cooling article to the patient's skin in proximity to said joint; to thereby attenuate transient burning sensation due to injection of capsaicin.

In certain embodiments, the method comprises step (a) which is applying a cooling article to a human patient's skin in proximity to a joint in need of pain relief therapy. In certain embodiments, the method comprises step (b) which is administering a local anesthetic agent into said joint. In certain embodiments, the method comprises step (e) which is applying a cooling article to the patient's skin in proximity to said joint. In certain embodiments, the method comprises (i) step (a) which is applying a cooling article to a human patient's skin in proximity to a joint in need of pain relief therapy, (ii) step (b) which is administering a local anesthetic agent into said joint, and step (e) which is applying a cooling article to the patient's skin in proximity to said joint.

Fifteenth Method

One aspect of the invention provides a method of attenuating transient burning sensation due to injection of capsaicin into a joint in a human patient, comprising:
  a. optionally applying a cooling article to a human patient's skin in proximity to a joint in need of pain relief therapy; then
  b. optionally administering a local anesthetic agent into said joint; then
  c. applying a cooling article to the patient's skin in proximity to said joint to achieve a temperature in the range of from about 5° C. to about 30° C. for said skin; then
  d. administering by injection into said joint a pharmaceutical composition comprising capsaicin in order to deliver a dose of capsaicin in an amount of from about 0.01 mg to about 4 mg; and then
  e. optionally applying a cooling article to the patient's skin in proximity to said joint; to thereby attenuate transient burning sensation due to injection of capsaicin.

In certain embodiments, the method comprises step (a) which is applying a cooling article to a human patient's skin in proximity to a joint in need of pain relief therapy. In certain embodiments, the method comprises step (b) which is administering a local anesthetic agent into said joint. In certain embodiments, the method comprises step (e) which is applying a cooling article to the patient's skin in proximity to said joint. In certain embodiments, the method comprises (i) step (a) which is applying a cooling article to a human patient's skin in proximity to a joint in need of pain relief therapy, (ii) step (b) which is administering a local anesthetic agent into said joint, and step (e) which is applying a cooling article to the patient's skin in proximity to said joint.

Exemplary Features of the Fourteenth and Fifteenth Methods

The above Fourteenth Method and Fifteen Method may be further characterized by additional features, such as the temperature of the patient's skin in proximity to the joint to receive or which has received capsaicin according to the method, and the like. A more thorough description of such features is provided below. The invention embraces all permutations and combinations of these features.

Temperature of the Patient's Skin in Proximity to the Joint

The methods may be further characterized according to the temperature of the patient's skin in proximity to the joint to receive or which has received capsaicin according to the method. For example, in certain embodiments, step (c) comprises applying a cooling article to the patient's skin in proximity to said joint to achieve a temperature in the range of from about 5° C. to about 7° C. for said skin. In certain embodiments, step (c) comprises applying a cooling article to the patient's skin in proximity to said joint to achieve a temperature in the range of from about 7° C. to about 9° C. for said skin. In certain embodiments, step (c) comprises applying a cooling article to the patient's skin in proximity to said joint to achieve a temperature in the range of from about 9° C. to about 11° C. for said skin. In certain embodiments, step (c) comprises applying a cooling article to the patient's skin in proximity to said joint to achieve a temperature in the range of from about 11° C. to about 13° C. for said skin. In certain embodiments, step (c) comprises applying a cooling article to the patient's skin in proximity to said joint to achieve a temperature in the range of from about 13° C. to about 15° C. for said skin. In certain embodiments, step (c) comprises applying a cooling article to the patient's skin in proximity to said joint to achieve a temperature in the range of from about 15° C. to about 17° C. for said skin. In certain embodiments, step (c) comprises applying a cooling article to the patient's skin in proximity to said joint to achieve a temperature in the range of from about 17° C. to about 19° C. for said skin. In certain embodiments, step (c) comprises applying a cooling article to the patient's skin in proximity to said joint to achieve a temperature in the range of from about 19° C. to about 21° C. for said skin. In certain embodiments, step (c) comprises applying a cooling article to the patient's skin in proximity to said joint to achieve a temperature in the range of from about 21° C. to about 23° C. for said skin. In certain embodiments, step (c) comprises applying a cooling article to the patient's skin in proximity to said joint to achieve a temperature in the range of from about 23° C. to about 25° C. for said skin. In certain embodiments, step (c) comprises applying a cooling article to the patient's skin in proximity to said joint to achieve a temperature in the range of from about 25° C. to about 27° C. for said skin. In certain embodiments, step (c) comprises applying a cooling article to the patient's skin in proximity to said joint to achieve a temperature in the range of from about 27° C. to about 29° C. for said skin. In certain embodiments, step (c) comprises applying a cooling article to the patient's skin in proximity to said joint to achieve a temperature in the range of from about 29° C. to about 30° C. for said skin.

In certain embodiments, step (c) comprises applying a cooling article to the patient's skin in proximity to said joint to achieve a temperature of about 7° C. for said skin. In certain embodiments, step (c) comprises applying a cooling article to the patient's skin in proximity to said joint to achieve a temperature of about 8° C. for said skin. In certain embodiments, step (c) comprises applying a cooling article to the patient's skin in proximity to said joint to achieve a temperature of about 9° C. for said skin. In certain embodiments, step (c) comprises applying a cooling article to the patient's skin in proximity to said joint to achieve a temperature of about 10° C. for said skin. In certain embodiments, step (c) comprises applying a cooling article to the patient's skin in proximity to said joint to achieve a temperature of about 11° C. for said skin. In certain embodiments, step (c) comprises applying a cooling article to the patient's skin in proximity to said joint to achieve a temperature of about 12° C. for said skin. In certain embodiments, step (c) comprises applying a cooling article to the patient's skin in proximity to said joint to achieve a temperature of about 13° C. for said skin. In certain embodiments, step (c) comprises applying a cooling article to the patient's skin in proximity to said joint to achieve a temperature of about 14° C. for said skin. In certain embodiments, step (c) comprises applying a cooling article to the patient's skin in proximity to said joint to achieve a temperature of about 15° C. for said skin. In certain embodiments, step (c) comprises applying a cooling article to the patient's skin in proximity to said joint to achieve a temperature of about 16° C. for said skin. In certain embodiments, step (c) comprises applying a cooling article to the patient's skin in proximity to said joint to achieve a temperature of about 17° C. for said skin. In certain embodiments, step (c) comprises applying a cooling article to the patient's skin in proximity to said joint to achieve a temperature of about 18° C. for said skin. In certain embodiments, step (c) comprises applying a cooling article to the patient's skin in proximity to said joint to achieve a temperature of about 19° C. for said skin. In certain embodiments, step (c) comprises applying a cooling article to the patient's skin in proximity to said joint to achieve a temperature of about 20° C. for said skin. In certain embodiments, step (c) comprises applying a cooling article to the patient's skin in proximity to said joint to achieve a temperature of about 21° C. for said skin. In certain embodiments, step (c) comprises applying a cooling article to the patient's skin in proximity to said joint to achieve a temperature of about 22° C. for said skin. In certain embodiments, step (c) comprises applying a cooling article to the patient's skin in proximity to said joint to achieve a temperature of about 23° C. for said skin. In certain embodiments, step (c) comprises applying a cooling article to the patient's skin in proximity to said joint to achieve a temperature of about 24° C. for said skin. In certain embodiments, step (c) comprises applying a cooling article to the patient's skin in proximity to said joint to achieve a temperature of about 25° C. for said skin. In certain embodiments, step (c) comprises applying a cooling article to the patient's skin in proximity to said joint to achieve a temperature of about 25° C. for said skin. In certain embodiments, step (c) comprises applying a cooling article to the patient's skin in proximity to said joint to achieve a temperature of about 26° C. for said skin. In certain embodiments, step (c) comprises applying a cooling article to the patient's skin in proximity to said joint to achieve a temperature of about 28° C. for said skin. In certain embodiments, step (c) comprises applying a cooling article to the patient's skin in proximity to said joint to achieve a temperature of about 29° C. for said skin. In certain embodiments, step (c) comprises applying a cooling article to the patient's skin in proximity to said joint to achieve a temperature of about 30° C. for said skin.

Further, in certain embodiments, the method comprises step (e) wherein a cooling article is applied to the patient's skin in proximity to said joint to achieve a temperature in the range of from about 5° C. to about 30° C. for said skin for a duration of at least 30 minutes. In certain embodiments, the method comprises step (e) wherein a cooling article is applied to the patient's skin in proximity to said joint to achieve a temperature in the range of from about 5° C. to about 7° C. for said skin for a duration of at least 30 minutes. In certain embodiments, the method comprises step (e) wherein a cooling article is applied to the patient's skin in proximity to said joint to achieve a temperature in the range of from about 7° C. to about 9° C. for said skin for a duration of at least 30 minutes. In certain embodiments, the method comprises step (e) wherein a cooling article is applied to the patient's skin in proximity to said joint to achieve a temperature in the range of from about 9° C. to about 11° C. for said skin for a duration of at least 30 minutes. In certain embodiments, the method comprises step (e) wherein a cooling article is applied to the patient's skin in proximity to said joint to achieve a temperature in the range of from about 11° C. to about 13° C. for said skin for a duration of at least 30 minutes. In certain embodiments, the method comprises step (e) wherein a cooling article is applied to the patient's skin in proximity to said joint to achieve a temperature in the range of from about 13° C. to about 15° C. for said skin for a duration of at least 30 minutes. In certain embodiments, the method comprises step (e) wherein a cooling article is applied to the patient's skin in proximity to said joint to achieve a temperature in the range of from about 15° C. to about 17° C. for said skin for a duration of at least 30 minutes. In certain embodiments, the method comprises step (e) wherein a cooling article is applied to the patient's skin in proximity to said joint to achieve a temperature in the range of from about 17° C. to about 19° C. for said skin for a duration of at least 30 minutes. In certain embodiments, the method comprises step (e) wherein a cooling article is applied to the patient's skin in proximity to said joint to achieve a temperature in the range of from about 19° C. to about 21° C. for said skin for a duration of at least 30 minutes. In certain embodiments, the method comprises step (e) wherein a cooling article is applied to the patient's skin in proximity to said joint to achieve a temperature in the range of from about 21° C. to about 23° C. for said skin for a duration of at least 30 minutes. In certain embodiments, the method comprises step (e) wherein a cooling article is applied to the patient's skin in proximity to said joint to achieve a temperature in the range of from about 23° C. to about 25° C. for said skin for a duration of at least 30 minutes. In certain embodiments, the method comprises step (e) wherein a cooling article is applied to the patient's skin in proximity to said joint to achieve a temperature in the range of from about 25° C. to about 27° C. for said skin for a duration of at least 30 minutes. In certain embodiments, the method comprises step (e) wherein a cooling article is applied to the patient's skin in proximity to said joint to achieve a temperature in the range of from about 27° C. to about 29° C. for said skin for a duration of at least 30 minutes. In certain embodiments, the method comprises step (e) wherein a cooling article is applied to the patient's skin in proximity to said joint to achieve a temperature of about 5° C. for said skin for a duration of at least 30 minutes. In certain embodiments, the method comprises step (e) wherein a cooling article is applied to the patient's skin in proximity to said joint to achieve a temperature of about 6° C. for said skin for a duration of at least 30 minutes. In certain embodiments, the method comprises step (e) wherein a cooling article is applied to the patient's skin in proximity to said joint to achieve a temperature of about 7° C. for said skin for a duration of at least 30 minutes. In certain embodiments, the method comprises step (e) wherein a cooling article is applied to the patient's skin in proximity to said joint to achieve a temperature of about 8° C. for said skin for a duration of at least 30 minutes. In certain embodiments, the method comprises step (e) wherein a cooling article is applied to the patient's skin in proximity to said joint to achieve a temperature of about 9° C. for said skin for a duration of at least 30 minutes. In certain embodiments, the method comprises step (e) wherein a cooling article is applied to the patient's skin in proximity to said joint to achieve a temperature of about 10° C. for said skin for a duration of at least 30 minutes. In certain embodiments, the method comprises step (e) wherein a cooling article is applied to the patient's skin in proximity to said joint to achieve a temperature of about 11° C. for said skin for a duration of at least 30 minutes. In certain embodiments, the method comprises step (e) wherein a cooling article is applied to the patient's skin in proximity to said joint to achieve a temperature of about 12° C. for said skin for a duration of at least 30 minutes. In certain embodiments, the method comprises step (e) wherein a cooling article is applied to the patient's skin in proximity to said joint to achieve a temperature of about 13° C. for said skin for a duration of at least 30 minutes. In certain embodiments, the method comprises step (e) wherein a cooling article is applied to the patient's skin in proximity to said joint to achieve a temperature of about 14° C. for said skin for a duration of at least 30 minutes. In certain embodiments, the method comprises step (e) wherein a cooling article is applied to the patient's skin in proximity to said joint to achieve a temperature of about 15° C. for said skin for a duration of at least 30 minutes. In certain embodiments, the method comprises step (e) wherein a cooling article is applied to the patient's skin in proximity to said joint to achieve a temperature of about 16° C. for said skin for a duration of at least 30 minutes. In certain embodiments, the method comprises step (e) wherein a cooling article is applied to the patient's skin in proximity to said joint to achieve a temperature of about 17° C. for said skin for a duration of at least 30 minutes. In certain embodiments, the method comprises step (e) wherein a cooling article is applied to the patient's skin in proximity to said joint to achieve a temperature of about 18° C. for said skin for a duration of at least 30 minutes. In certain embodiments, the method comprises step (e) wherein a cooling article is applied to the patient's skin in proximity to said joint to achieve a temperature of about 19° C. for said skin for a duration of at least 30 minutes. In certain embodiments, the method comprises step (e) wherein a cooling article is applied to the patient's skin in proximity to said joint to achieve a temperature of about 20° C. for said skin for a duration of at least 30 minutes. In certain embodiments, the method comprises step (e) wherein a cooling article is applied to the patient's skin in proximity to said joint to achieve a temperature of about 21° C. for said skin for a duration of at least 30 minutes. In certain embodiments, the method comprises step (e) wherein a cooling article is applied to the patient's skin in proximity to said joint to achieve a temperature of about 22° C. for said skin for a duration of at least 30 minutes. In certain embodiments, the method comprises step (e) wherein a cooling article is applied to the patient's skin in proximity to said joint to achieve a temperature of about 23° C. for said skin for a duration of at least 30 minutes. In certain embodiments, the method comprises step (e) wherein a cooling article is applied to the patient's skin in proximity to said joint to achieve a temperature of about 24° C. for said skin for a duration of at least 30 minutes. In certain embodiments, the method comprises step (e) wherein a cooling article is applied to the patient's skin in proximity to said joint to achieve a temperature of about 25° C. for said skin for a duration of at least 30 minutes. In certain embodiments, the method comprises step (e) wherein a cooling article is applied to the patient's skin in proximity to said joint to achieve a temperature of about 26° C. for said skin for a duration of at least 30 minutes. In certain embodiments, the method comprises step (e) wherein a cooling article is applied to the patient's skin in proximity to said joint to achieve a temperature of about 27° C. for said skin for a duration of at least 30 minutes. In certain embodiments, the method comprises step (e) wherein a cooling article is applied to the patient's skin in proximity to said joint to achieve a temperature of about 28° C. for said skin for a duration of at least 30 minutes. In certain embodiments, the method comprises step (e) wherein a cooling article is applied to the patient's skin in proximity to said joint to achieve a temperature of about 29° C. for said skin for a duration of at least 30 minutes.

In certain embodiments, said duration is from about 30 minutes to about 60 minutes. In certain embodiments, said duration is from about 30 minutes to about 90 minutes. In certain embodiments, said duration is from about 60 minutes to about 90 minutes.

Exemplary More Specific Embodiments

In another aspect, the methods pertain to the following more specific embodiments.

Embodiment No. 1. A method of ameliorating osteoarthritic knee joint pain in a human patient, comprising:
  a. applying for a duration of about 15 minutes a cooling article to an exterior surface of a human patient's knee presenting with osteoarthritic knee joint pain; then
  b. administering by injection into the intra-articular space of the joint of said knee a pharmaceutical composition comprising a single pain-relief agent selected from the group consisting of lidocaine and a pharmaceutically acceptable salt thereof, in order to deliver a dose of lidocaine in an amount ranging from about 0.1 g to about 0.5 g; then
  c. applying for a duration of about 30 minutes a cooling article to an exterior surface of said knee to achieve a temperature in the range of from about 7° C. to about 30° C. for skin in contact with the cooling article; then
  d. administering by injection into the intra-articular space of the joint of said knee a pharmaceutical composition comprising capsaicin in order to deliver a dose of capsaicin in an amount of about 1 mg; and then
  e. applying a cooling article to an exterior surface of said knee to achieve a temperature in the range of from about 7° C. to about 30° C. for skin in contact with the cooling article for a duration of at least about 30 minutes:
    to thereby ameliorate osteoarthritic knee joint pain in the human patient.

Embodiment No. 2. A method of attenuating transient burning sensation due to injection of capsaicin into a human osteoarthritic knee joint, comprising:
  a. applying for a duration of about 15 minutes a cooling article to an exterior surface of a human patient's knee presenting with osteoarthritic knee joint pain; then
  b. administering by injection into the intra-articular space of the joint of said knee a pharmaceutical composition comprising a single pain-relief agent selected from the group consisting of lidocaine and a pharmaceutically acceptable salt thereof, in order to deliver a dose of lidocaine in an amount ranging from about 0.1 g to about 0.5 g; then
  c. applying for a duration of about 30 minutes a cooling article to an exterior surface of said knee to achieve a temperature in the range of from about 7° C. to about 30° C. for skin in contact with the cooling article; then
  d. administering by injection into the intra-articular space of the joint of said knee a pharmaceutical composition comprising capsaicin in order to deliver a dose of capsaicin in an amount of about 1 mg; and then
  e. applying a cooling article to an exterior surface of said knee to achieve a temperature in the range of from about 7° C. to about 30° C. for skin in contact with the cooling article for a duration of at least about 30 minutes:
    to thereby attenuate transient burning sensation due to injection of capsaicin.

Embodiment No. 3. The method of embodiment 1 or 2, wherein said temperature in steps (c) and (e) is from about 7° C. to about 9° C.

Embodiment No. 4. The method of embodiment 1 or 2, wherein said temperature in steps (c) and (e) is from about 9° C. to about 11° C.

Embodiment No. 5. The method of embodiment 1 or 2, wherein said temperature in steps (c) and (e) is from about 11° C. to about 13° C.

Embodiment No. 6. The method of embodiment 1 or 2, wherein said temperature in steps (c) and (e) is from about 13° C. to about 15° C.

Embodiment No. 7. The method of embodiment 1 or 2, wherein said temperature in steps (c) and (e) is from about 15° C. to about 17° C.

Embodiment No. 8. The method of embodiment 1 or 2, wherein said temperature in steps (c) and (e) is from about 17° C. to about 19° C.

Embodiment No. 9. The method of any one of embodiments 1-8, wherein the cooling article has an exterior surface temperature in the range of from about 5° C. to about 15° C. for application to the exterior surface of said knee.

Embodiment No. 10. The method of any one of embodiments 1-8, wherein the cooling article has an exterior surface temperature in the range of from about 5° C. to about 7° C. for application to the exterior surface of said knee.

Embodiment No. 11. The method of any one of embodiments 1-8, wherein the cooling article has an exterior surface temperature in the range of from about 7° C. to about 9° C. for application to the exterior surface of said knee.

Embodiment No. 12. The method of any one of embodiments 1-8, wherein the cooling article has an exterior surface temperature in the range of from about 9° C. to about 11° C. for application to the exterior surface of said knee.

Embodiment No. 13. The method of any one of embodiments 1-8, wherein the cooling article has an exterior surface temperature in the range of from about 9° C. to about 11° C. for application to the exterior surface of said knee.

Embodiment No. 14. The method of any one of embodiments 1-8, wherein the cooling article has an exterior surface temperature in the range of from about 13° C. to about 15° C. for application to the exterior surface of said knee.

Embodiment No. 15. The method of any one of embodiments 1-14, wherein after administration of the pharmaceutical composition comprising capsaicin in step (d) but prior to step (e) said knee is flexed.

Embodiment No. 16. The method of any one of embodiments 1-14, wherein after administration of the pharmaceutical composition comprising capsaicin in step (d) but prior to step (e) said knee is flexed about 5 times.

Embodiment No. 17. The method of any one of embodiments 1-16, wherein in step (b) the dose of lidocaine is about 0.3 g.

Embodiment No. 18. The method of any one of embodiments 1-16, wherein in step (b) the dose of lidocaine is 0.3 g.

Embodiment No. 19. The method of any one of embodiments 1-18, wherein the pharmaceutical composition comprising a single pain-relief agent is an aqueous mixture that contains lidocaine at a concentration of about 2% w/w.

Embodiment No. 20. The method of any one of embodiments 1-19, wherein the pharmaceutical composition comprising a single pain-relief agent further comprises sodium chloride.

Embodiment No. 21. The method of any one of embodiments 1-19, wherein the pharmaceutical composition comprising a single pain-relief agent further comprises sodium chloride at a concentration ranging from about 4 mg/mL to about 8 mg/mL.

Embodiment No. 22. The method of any one of embodiments 1-21, wherein the pharmaceutical composition comprising a single pain-relief agent has a volume in the range of from about 13 mL to about 17 mL.

Embodiment No. 23. The method of any one of embodiments 1-21, wherein the pharmaceutical composition comprising a single pain-relief agent has a volume of about 15 mL.

Embodiment No. 24. The method of any one of embodiments 1-23, wherein the pharmaceutical composition comprising capsaicin is an aqueous mixture containing capsaicin.

Embodiment No. 25. The method of any one of embodiments 1-24, wherein the pharmaceutical composition comprising capsaicin has a volume of about 4 mL.

Embodiment No. 26. The method of any one of embodiments 1-24, wherein the pharmaceutical composition comprising capsaicin has a volume of about 2 mL.

Embodiment No. 27. The method of any one of embodiments 1-26, wherein the duration in step (e) is from about 30 minutes to about 90 minutes.

Embodiment No. 28. The method of any one of embodiments 1-26, wherein the duration in step (e) is from about 30 minutes to about 60 minutes.

Embodiment No. 29. The method of any one of embodiments 1-28, wherein the dose of capsaicin is 1 mg.

In another aspect, the methods pertain to the following more specific embodiments.

Embodiment No. 1. A method of ameliorating joint pain in a human patient, comprising:
a. optionally applying a cooling article to a human patient's skin in proximity to a joint in need of pain relief therapy; then
b. optionally administering a local anesthetic agent into said joint; then
c. applying for a duration of at least about 10 minutes a cooling article to the patient's skin in proximity to said joint, wherein the cooling article has an exterior surface temperature in the range of from about 1° C. to about 15° C. for application to the human patient's skin in proximity to said joint; then
d. administering by injection into said joint a pharmaceutical composition comprising capsaicin in order to deliver a dose of capsaicin in an amount of about 1 mg; and then
e. optionally applying for a duration of at least about 10 minutes a cooling article to the patient's skin in proximity to said joint, wherein the cooling article has an exterior surface temperature in the range of from about 1° C. to about 15° C. for application to the human patient's skin in proximity to said joint;
to thereby ameliorate joint pain in the human patient, wherein the joint pain is osteoarthritic joint pain, and the joint is a knee joint.

Embodiment No. 2. A method of attenuating transient burning sensation due to injection of capsaicin into a joint in a human patient, comprising:
a. optionally applying a cooling article to a human patient's skin in proximity to a joint in need of pain relief therapy;
b. optionally administering a local anesthetic agent into said joint;
c. applying for a duration of at least about 10 minutes a cooling article to the patient's skin in proximity to said joint, wherein the cooling article has an exterior surface temperature in the range of from about 1° C. to about 15° C. for application to the human patient's skin in proximity to said joint; then
d. administering by injection into said joint a pharmaceutical composition comprising capsaicin in order to deliver a dose of capsaicin in an amount of about 1 mg; and then
e. optionally applying for a duration of at least about 10 minutes a cooling article to the patient's skin in proximity to said joint, wherein the cooling article has an exterior surface temperature in the range of from about 1° C. to about 15° C. for application to the human patient's skin in proximity to said joint;
to thereby attenuate transient burning sensation due to injection of capsaicin, wherein the joint pain is osteoarthritic joint pain, and the joint is a knee joint.

Embodiment No. 3. A method of ameliorating joint pain in a human patient, comprising:
a. optionally applying a cooling article to a human patient's skin in proximity to a joint in need of pain relief therapy; then
b. optionally administering a local anesthetic agent into said joint; then
c. applying a cooling article to the patient's skin in proximity to said joint to achieve a temperature in the range of from about 20° C. to about 33° C. for tissue or fluid in the interior of the joint; then
   d. administering by injection into said joint a pharmaceutical composition comprising capsaicin in order to deliver a dose of capsaicin in an amount of about 1 mg; and then
   e. optionally applying a cooling article to the patient's skin in proximity to said joint; to thereby ameliorate joint pain in the human patient, wherein the joint pain is osteoarthritic joint pain, and the joint is a knee joint.

Embodiment No. 4. A method of attenuating transient burning sensation due to injection of capsaicin into a joint in a human patient, comprising:
   a. optionally applying a cooling article to a human patient's skin in proximity to a joint in need of pain relief therapy;
   b. optionally administering a local anesthetic agent into said joint;
   c. applying a cooling article to the patient's skin in proximity to said joint to achieve a temperature in the range of from about 20° C. to about 33° C. for tissue or fluid in the interior of the joint; then
   d. administering by injection into said joint a pharmaceutical composition comprising capsaicin in order to deliver a dose of capsaicin in an amount of about 1 mg; and then
   e. optionally applying a cooling article to the patient's skin in proximity to said joint; to thereby attenuate transient burning sensation due to injection of capsaicin, wherein the joint pain is osteoarthritic joint pain, and the joint is a knee joint.

Embodiment No. 5. The method of embodiment 3 or 4, wherein step (c) comprises applying a cooling article to the patient's skin in proximity to the joint to achieve a temperature in the range of from about 24° C. to about 26° C. for tissue or fluid in the interior of the joint.

Embodiment No. 6. The method of embodiment 3 or 4, wherein step (c) comprises applying a cooling article to the patient's skin in proximity to the joint to achieve a temperature in the range of from about 26° C. to about 28° C. for tissue or fluid in the interior of the joint.

Embodiment No. 7. The method of embodiment 3 or 4, wherein step (c) comprises applying a cooling article to the patient's skin in proximity to the joint to achieve a temperature in the range of from about 28° C. to about 30° C. for tissue or fluid in the interior of the joint.

Embodiment No. 8. The method of embodiment 3 or 4, wherein step (c) comprises applying a cooling article to the patient's skin in proximity to the joint to achieve a temperature in the range of from about 30° C. to about 32° C. for tissue or fluid in the interior of the joint.

Embodiment No. 9. The method of embodiment 3 or 4, wherein step (c) comprises applying a cooling article to the patient's skin in proximity to the joint to achieve a temperature of about 27° C. for tissue or fluid in the interior of the joint.

Embodiment No. 10. The method of embodiment 3 or 4, wherein step (c) comprises applying a cooling article to the patient's skin in proximity to the joint to achieve a temperature of about 28° C. for tissue or fluid in the interior of the joint.

Embodiment No. 11. The method of embodiment 3 or 4, wherein step (c) comprises applying a cooling article to the patient's skin in proximity to the joint to achieve a temperature of about 29° C. for tissue or fluid in the interior of the joint.

Embodiment No. 12. The method of embodiment 3 or 4, wherein step (c) comprises applying a cooling article to the patient's skin in proximity to the joint to achieve a temperature of about 30° C. for tissue or fluid in the interior of the joint.

Embodiment No. 13. The method of embodiment 3 or 4, wherein step (c) comprises applying a cooling article to the patient's skin in proximity to the joint to achieve a temperature of about 31° C. for tissue or fluid in the interior of the joint.

Embodiment No. 14. The method of embodiment 3 or 4, wherein step (c) comprises applying a cooling article to the patient's skin in proximity to the joint to achieve a temperature of about 32° C. for tissue or fluid in the interior of the joint.

Embodiment No. 15. The method of any one of embodiments 1-14, wherein the method comprises step (e) in which a cooling article is applied for a duration of at least about 10 minutes to the patient's skin in proximity to said joint, wherein the cooling article has an exterior surface temperature in the range of from about 1° C. to about 15° C. for application to the exterior surface of the human patient's skin in proximity to said joint.

Embodiment No. 16. The method of any one of embodiments 1-14, wherein the method comprises step (e) in which a cooling article is applied to the patient's skin in proximity to the joint to achieve a temperature in the range of from about 24° C. to about 26° C. for tissue or fluid in the interior of the joint for a duration of at least 15 minutes.

Embodiment No. 17. The method of any one of embodiments 1-14, wherein the method comprises step (e) in which a cooling article is applied to the patient's skin in proximity to the joint to achieve a temperature in the range of from about 26° C. to about 28° C. for tissue or fluid in the interior of the joint for a duration of at least 15 minutes.

Embodiment No. 18. The method of any one of embodiments 1-14, wherein the method comprises step (e) in which a cooling article is applied to the patient's skin in proximity to the joint to achieve a temperature in the range of from about 28° C. to about 30° C. for tissue or fluid in the interior of the joint for a duration of at least 15 minutes.

Embodiment No. 19. The method of any one of embodiments 1-14, wherein the method comprises step (e) in which a cooling article is applied to the patient's skin in proximity to the joint to achieve a temperature in the range of from about 30° C. to about 32° C. for tissue or fluid in the interior of the joint for a duration of at least 15 minutes.

Embodiment No. 20. The method of any one of embodiments 15-19, wherein said duration in step (e) is at least 20 minutes.

Embodiment No. 21. The method of any one of embodiments 15-19, wherein said duration in step (e) is at least 30 minutes.

Embodiment No. 22. The method of any one of embodiments 15-19, wherein said duration is step (e) from about 30 minutes to about 90 minutes.

Embodiment No. 23. The method of any one of embodiments 15-19, wherein said duration is step (e) from about 30 minutes to about 60 minutes.

Embodiment No. 24. The method of any one of embodiments 1-23, wherein the method comprises step (a) in which for a duration of from about 5 minutes to about 30 minutes a cooling article is applied to a human patient's skin in proximity to a joint in need of pain relief therapy.

Embodiment No. 25. The method of any one of embodiments 1-23, wherein the method comprises step (a) in which for a duration of about 15 minutes a cooling article is applied to a human patient's skin in proximity to a joint in need of pain relief therapy.

Embodiment No. 26. The method of any one of embodiments 1-23, wherein the method does not contain step (a).

Embodiment No. 27. The method of any one of embodiments 1-26, wherein the method comprises step (b) of administering by injection into the joint a pharmaceutical composition comprising lidocaine in order to deliver a dose of lidocaine in an amount of about 0.1 g to about 0.5 g.

Embodiment No. 28. The method of any one embodiments 1-26, wherein the method comprises step (b) of administering by injection into the joint a pharmaceutical composition comprising a single pain-relief agent selected from the group consisting of lidocaine and a pharmaceutically acceptable salt thereof, in order to deliver a dose of lidocaine in an amount ranging from about 0.1 g to about 0.5 g.

Embodiment No. 29. The method of any one of embodiments 1-26, wherein the method comprises the following additional step that is performed between steps (c) and (d): administering into said joint a pharmaceutical composition comprising a single pain-relief agent selected from the group consisting of lidocaine and a pharmaceutically acceptable salt thereof, in order to deliver a dose of lidocaine in an amount ranging from about 0.1 g to about 0.5 g.

Embodiment No. 30. The method of embodiment 29, wherein the method does not contain step (b).

Embodiment No. 31. The method of any one of embodiments 27-30, wherein the dose of lidocaine is about 0.3 g.

Embodiment No. 32. The method of any one of embodiments 27-30, wherein the dose of lidocaine is about 0.15 g.

Embodiment No. 33. The method of any one of embodiments 27-31, wherein the pharmaceutical composition comprising lidocaine is an aqueous mixture containing lidocaine at a concentration of about 2% w/w.

Embodiment No. 34. The method of any one of embodiments 27-30 or 32, wherein the pharmaceutical composition comprising lidocaine is an aqueous mixture containing lidocaine at a concentration of about 1% w/w.

Embodiment No. 35. The method of any one of embodiments 27-31, wherein the pharmaceutical composition comprising lidocaine has a volume in the range of from about 13 mL to about 17 mL.

Embodiment No. 36. The method of any one of embodiments 27-31, wherein the pharmaceutical composition comprising lidocaine has a volume of about 15 mL.

Embodiment No. 37. The method of any one of embodiments 1-36, wherein step (c) comprises applying for a duration of about 20 minutes the cooling article to an exterior surface of said knee.

Embodiment No. 38. The method of any one of embodiments 1-36, wherein step (c) comprises applying for a duration of about 30 minutes the cooling article to an exterior surface of said knee.

Embodiment No. 39. The method of any one of embodiments 1-38, wherein after administration of the pharmaceutical composition comprising capsaicin in step (d) but prior to step (e) said joint is flexed.

Embodiment No. 40. The method of any one of embodiments 1-38, wherein after administration of the pharmaceutical composition comprising capsaicin in step (d) but prior to step (e) said joint is flexed about 5 times.

Embodiment No. 41. The method of any one of embodiments 1-40, wherein the pharmaceutical composition comprising capsaicin is an aqueous mixture containing capsaicin.

Embodiment No. 42. The method of any one of embodiments 1-40, wherein the pharmaceutical composition comprising capsaicin has a volume of about 2 mL.

Embodiment No. 43. The method of any one of embodiments 1-40, wherein the pharmaceutical composition comprising capsaicin has a volume of about 1 mL.

Embodiment No. 44. The method of any one of embodiments 1-40, wherein the cooling article has an exterior surface temperature in the range of from about 5° C. to about 15° C. for application to the human patient's skin in proximity to said joint.

Embodiment No. 45. The method of any one of embodiments 1-40, wherein the cooling article has an exterior surface temperature in the range of from about 7° C. to about 13° C. for application to the human patient's skin in proximity to said joint.

Embodiment No. 46. The method of any one of embodiments 1-40, wherein the cooling article has an exterior surface temperature in the range of from about 8° C. to about 10° C. for application to the human patient's skin in proximity to said joint.

Embodiment No. 47. The method of any one of embodiments 1-40, wherein the cooling article has an exterior surface temperature in the range of from about 5° C. to about 7° C. for application to the human patient's skin in proximity to said joint.

Embodiment No. 48. The method of any one of embodiments 1-40, wherein the cooling article has an exterior surface temperature in the range of from about 7° C. to about 9° C. for application to the human patient's skin in proximity to said joint.

Embodiment No. 49. The method of any one of embodiments 1-40, wherein the cooling article has an exterior surface temperature in the range of from about 9° C. to about 11° C. for application to the human patient's skin in proximity to said joint.

Embodiment No. 50. The method of any one of embodiments 1-40, wherein the cooling article has an exterior surface temperature in the range of from about 11° C. to about 13° C. for application to the human patient's skin in proximity to said joint.

Embodiment No. 51. The method of any one of embodiments 1-40, wherein the cooling article has an exterior surface temperature in the range of from about 13° C. to about 15° C. for application to the human patient's skin in proximity to said joint.

Embodiment No. 52. The method of any one of embodiments 1-40, wherein the cooling article has an exterior surface temperature of about 8° C. for application to the human patient's skin in proximity to said joint.

Embodiment No. 53. The method of any one of embodiments 1-40, wherein the cooling article has an exterior surface temperature of about 9° C. for application to the human patient's skin in proximity to said joint.

Embodiment No. 54. The method of any one of embodiments 1-40, wherein the cooling article has an exterior surface temperature of about 10° C. for application to the human patient's skin in proximity to said joint.

Embodiment No. 55. The method of any one of embodiments 1-40, wherein the cooling article has an exterior surface temperature of about 11° C. for application to the human patient's skin in proximity to said joint.

Embodiment No. 56. The method of any one of embodiments 1-40, wherein the cooling article has an exterior surface temperature of about 12° C. for application to the human patient's skin in proximity to said joint.

Additional Exemplary More Specific Embodiments

In another aspect, the invention provides a method of ameliorating osteoarthritic knee joint pain in a human patient, wherein the method comprises:
- a. applying for a duration of about 15 minutes a cooling article to an exterior surface of a human patient's knee presenting with osteoarthritic knee joint pain, wherein the cooling article has an exterior surface temperature in the range of from about 7° C. to about 13° C. for application to the exterior surface of said knee; then
- b. administering by injection into the intra-articular space of the joint of said knee a pharmaceutical composition comprising a single pain-relief agent selected from the group consisting of lidocaine and a pharmaceutically acceptable salt thereof, in order to deliver a dose of lidocaine in an amount ranging from about 0.1 g to about 0.5 g; then
- c. applying for a duration of about 30 minutes a cooling article to an exterior surface of said knee, wherein the cooling article has an exterior surface temperature in the range of from about 7° C. to about 13° C. for application to the exterior surface of said knee; then
- d. administering by injection into the intra-articular space of the joint of said knee a pharmaceutical composition comprising capsaicin in order to deliver a dose of capsaicin in an amount of about 1 mg; and then
- e. applying a cooling article to an exterior surface of said knee for a duration of at least about 30 minutes, wherein the cooling article has an exterior surface temperature in the range of from about 7° C. to about 13° C. for application to the exterior surface of said knee;

to thereby ameliorate osteoarthritic knee joint pain in the human patient.

In another aspect, the invention provides a method of ameliorating osteoarthritic knee joint pain in a human patient, wherein the method comprises:
- a. applying for a duration of about 30 to 45 minutes a cooling article to an exterior surface of a human patient's knee presenting with osteoarthritic knee joint pain, wherein the cooling article has an exterior surface temperature in the range of from about 7° C. to about 13° C. for application to the exterior surface of said knee; then
- b. administering by injection into the intra-articular space of the joint of said knee a pharmaceutical composition comprising a single pain-relief agent selected from the group consisting of lidocaine and a pharmaceutically acceptable salt thereof, in order to deliver a dose of lidocaine in an amount ranging from about 0.1 g to about 0.5 g; then
- c. administering by injection into the intra-articular space of the joint of said knee a pharmaceutical composition comprising capsaicin in order to deliver a dose of capsaicin in an amount of about 1 mg; and then
- d. applying a cooling article to an exterior surface of said knee for a duration of at least about 30 minutes, wherein the cooling article has an exterior surface temperature in the range of from about 7° C. to about 13° C. for application to the exterior surface of said knee;

to thereby ameliorate osteoarthritic knee joint pain in the human patient.

In another aspect, the invention provides a method of ameliorating osteoarthritic knee joint pain in a human patient, wherein the method comprises:
- a. administering by injection into the intra-articular space of the joint of said knee a pharmaceutical composition comprising a single pain-relief agent selected from the group consisting of lidocaine and a pharmaceutically acceptable salt thereof, in order to deliver a dose of lidocaine in an amount ranging from about 0.1 g to about 0.5 g; then
- b. applying for a duration of about 30 minutes a cooling article to an exterior surface of said knee, wherein the cooling article has an exterior surface temperature in the range of from about 7° C. to about 13° C. for application to the exterior surface of said knee; then
- c. administering by injection into the intra-articular space of the joint of said knee a pharmaceutical composition comprising capsaicin in order to deliver a dose of capsaicin in an amount of about 1 mg; and then
- d. applying a cooling article to an exterior surface of said knee for a duration of at least about 30 minutes, wherein the cooling article has an exterior surface temperature in the range of from about 7° C. to about 13° C. for application to the exterior surface of said knee;

to thereby ameliorate osteoarthritic knee joint pain in the human patient.

In another aspect, the invention provides a method of ameliorating osteoarthritic knee joint pain in a human patient, wherein the method comprises:
- a. applying for a duration of about 30 minutes a cooling article to an exterior surface of said knee, wherein the cooling article has an exterior surface temperature in the range of from about 7° C. to about 13° C. for application to the exterior surface of said knee; then
- b. administering by injection into the intra-articular space of the joint of said knee a pharmaceutical composition comprising a single pain-relief agent selected from the group consisting of lidocaine and a pharmaceutically acceptable salt thereof, in order to deliver a dose of lidocaine in an amount ranging from about 0.1 g to about 0.5 g; then
- c. administering by injection into the intra-articular space of the joint of said knee a pharmaceutical composition comprising capsaicin in order to deliver a dose of capsaicin in an amount of about 1 mg; and then
- d. applying a cooling article to an exterior surface of said knee for a duration of at least about 30 minutes, wherein the cooling article has an exterior surface temperature in the range of from about 7° C. to about 13° C. for application to the exterior surface of said knee;

to thereby ameliorate osteoarthritic knee joint pain in the human patient.

In another aspect, the invention provides a method of ameliorating osteoarthritic knee joint pain in a human patient, wherein the method comprises:
  a. applying for a duration of about 15 minutes a cooling article to an exterior surface of a human patient's knee presenting with osteoarthritic knee joint pain, wherein the cooling article has an exterior surface temperature in the range of from about 7° C. to about 13° C. for application to the exterior surface of said knee; then
  b. administering by injection into the intra-articular space of the joint of said knee a pharmaceutical composition comprising a single pain-relief agent selected from the group consisting of lidocaine and a pharmaceutically acceptable salt thereof, in order to deliver a dose of lidocaine in an amount ranging from about 0.1 g to about 0.5 g; then
  c. applying for a duration of about 20 minutes a cooling article to an exterior surface of said knee, wherein the cooling article has an exterior surface temperature in the range of from about 7° C. to about 13° C. for application to the exterior surface of said knee; then
  d. administering by injection into the intra-articular space of the joint of said knee a pharmaceutical composition comprising capsaicin in order to deliver a dose of capsaicin in an amount of about 1 mg; and then
  e. applying a cooling article to an exterior surface of said knee for a duration of at least about 20 minutes, wherein the cooling article has an exterior surface temperature in the range of from about 7° C. to about 13° C. for application to the exterior surface of said knee;
to thereby ameliorate osteoarthritic knee joint pain in the human patient.

In another aspect, the invention provides a method of ameliorating osteoarthritic knee joint pain in a human patient, wherein the method comprises:
  a. applying for a duration of about 20 to 30 minutes a cooling article to an exterior surface of a human patient's knee presenting with osteoarthritic knee joint pain, wherein the cooling article has an exterior surface temperature in the range of from about 7° C. to about 13° C. for application to the exterior surface of said knee; then
  b. administering by injection into the intra-articular space of the joint of said knee a pharmaceutical composition comprising a single pain-relief agent selected from the group consisting of lidocaine and a pharmaceutically acceptable salt thereof, in order to deliver a dose of lidocaine in an amount ranging from about 0.1 g to about 0.5 g; then
  c. administering by injection into the intra-articular space of the joint of said knee a pharmaceutical composition comprising capsaicin in order to deliver a dose of capsaicin in an amount of about 1 mg; and then
  d. applying a cooling article to an exterior surface of said knee for a duration of at least about 20 minutes, wherein the cooling article has an exterior surface temperature in the range of from about 7° C. to about 13° C. for application to the exterior surface of said knee;
to thereby ameliorate osteoarthritic knee joint pain in the human patient.

In another aspect, the invention provides a method of ameliorating osteoarthritic knee joint pain in a human patient, wherein the method comprises:
  a. administering by injection into the intra-articular space of the joint of said knee a pharmaceutical composition comprising a single pain-relief agent selected from the group consisting of lidocaine and a pharmaceutically acceptable salt thereof, in order to deliver a dose of lidocaine in an amount ranging from about 0.1 g to about 0.5 g; then
  b. applying for a duration of about 20 minutes a cooling article to an exterior surface of said knee, wherein the cooling article has an exterior surface temperature in the range of from about 7° C. to about 13° C. for application to the exterior surface of said knee; then
  c. administering by injection into the intra-articular space of the joint of said knee a pharmaceutical composition comprising capsaicin in order to deliver a dose of capsaicin in an amount of about 1 mg; and then
  d. applying a cooling article to an exterior surface of said knee for a duration of at least about 20 minutes, wherein the cooling article has an exterior surface temperature in the range of from about 7° C. to about 13° C. for application to the exterior surface of said knee;
to thereby ameliorate osteoarthritic knee joint pain in the human patient.

In another aspect, the invention provides a method of ameliorating osteoarthritic knee joint pain in a human patient, wherein the method comprises:
  a. applying for a duration of about 20 minutes a cooling article to an exterior surface of said knee, wherein the cooling article has an exterior surface temperature in the range of from about 7° C. to about 13° C. for application to the exterior surface of said knee; then
  b. administering by injection into the intra-articular space of the joint of said knee a pharmaceutical composition comprising a single pain-relief agent selected from the group consisting of lidocaine and a pharmaceutically acceptable salt thereof, in order to deliver a dose of lidocaine in an amount ranging from about 0.1 g to about 0.5 g; then
  c. administering by injection into the intra-articular space of the joint of said knee a pharmaceutical composition comprising capsaicin in order to deliver a dose of capsaicin in an amount of about 1 mg; and then
  d. applying a cooling article to an exterior surface of said knee for a duration of at least about 20 minutes, wherein the cooling article has an exterior surface temperature in the range of from about 7° C. to about 13° C. for application to the exterior surface of said knee;
to thereby ameliorate osteoarthritic knee joint pain in the human patient.

Exemplary Features of the Ninth, Tenth, Eleventh, Twelfth, Thirteenth, Fourteenth and Fifteenth Methods The above Ninth Method, Tenth Method, Eleventh Method, Twelfth Method, Thirteenth Method, Fourteenth Method, and Fifteenth Method may be further characterized by additional features, such as the temperature and duration of cooling in step (e), features of step (a), presence or absence of administering a local anesthetic agent and features thereof, and the like. A more thorough description of such features is provided below. The invention embraces all permutations and combinations of these features.

Temperature and Duration of Cooling in Step (e)

The methods may be further characterized according to the temperature and duration of cooling in step (e). For example, in certain embodiments, the method comprises step (e) in which a cooling article is applied for a duration of at least about 10 minutes to the patient's skin in proximity to said joint, wherein the cooling article has an exterior surface temperature in the range of from about 1° C. to about 15° C. for application to the exterior surface of the human patient's skin in proximity to said joint. In certain embodiments, the method comprises step (e) in which a cooling article is applied to the patient's skin in proximity to the joint to achieve a temperature in the range of from about 20° C. to about 22° C. for tissue or fluid in the interior of the joint for a duration of at least 15 minutes. In certain embodiments, the method comprises step (e) in which a cooling article is applied to the patient's skin in proximity to the joint to achieve a temperature in the range of from about 22° C. to about 24° C. for tissue or fluid in the interior of the joint for a duration of at least 15 minutes. In certain embodiments, the method comprises step (e) in which a cooling article is applied to the patient's skin in proximity to the joint to achieve a temperature in the range of from about 24° C. to about 26° C. for tissue or fluid in the interior of the joint for a duration of at least 15 minutes. In certain embodiments, the method comprises step (e) in which a cooling article is applied to the patient's skin in proximity to the joint to achieve a temperature in the range of from about 26° C. to about 28° C. for tissue or fluid in the interior of the joint for a duration of at least 15 minutes. In certain embodiments, the method comprises step (e) in which a cooling article is applied to the patient's skin in proximity to the joint to achieve a temperature in the range of from about 28° C. to about 30° C. for tissue or fluid in the interior of the joint for a duration of at least 15 minutes. In certain embodiments, the method comprises step (e) in which a cooling article is applied to the patient's skin in proximity to the joint to achieve a temperature in the range of from about 30° C. to about 32° C. for tissue or fluid in the interior of the joint for a duration of at least 15 minutes. In certain embodiments, the method comprises step (e) in which a cooling article is applied to the patient's skin in proximity to the joint to achieve a temperature in the range of from about 25° C. to about 31° C. for tissue or fluid in the interior of the joint for a duration of at least 15 minutes. In certain embodiments, the method comprises step (e) in which a cooling article is applied to the patient's skin in proximity to the joint to achieve a temperature in the range of from about 24° C. to about 26° C. for tissue or fluid in the interior of the joint for a duration of at least 10 minutes. In certain embodiments, the method comprises step (e) in which a cooling article is applied to the patient's skin in proximity to the joint to achieve a temperature in the range of from about 26° C. to about 28° C. for tissue or fluid in the interior of the joint for a duration of at least 10 minutes. In certain embodiments, the method comprises step (e) in which a cooling article is applied to the patient's skin in proximity to the joint to achieve a temperature in the range of from about 28° C. to about 30° C. for tissue or fluid in the interior of the joint for a duration of at least 10 minutes. In certain embodiments, the method comprises step (e) in which a cooling article is applied to the patient's skin in proximity to the joint to achieve a temperature in the range of from about 30° C. to about 32° C. for tissue or fluid in the interior of the joint for a duration of at least 10 minutes.

In certain embodiments, said duration is at least 30 minutes. In certain embodiments, said duration is from about 30 minutes to about 90 minutes. In certain embodiments, said duration is from about 30 minutes to about 60 minutes. In certain embodiments, said duration is from about 60) minutes to about 90 minutes.

The term proximity is understood from the perspective of physicians knowledgeable in the art, and may be, for example, tissue within 2 mm, 3 mm, 4 mm, 5 mm, 6 mm, 7 mm, 8 mm, 9 mm, 1 cm, 1.5 cm, or 2 cm of the joint.

In certain embodiments, the method comprises step (e) in which a cooling article is applied to the patient's skin in proximity to the joint to achieve a temperature in the range of from about 25° C. to about 31° C. for tissue or fluid in the interior of the joint for a duration of at least 30 minutes. In certain embodiments, the method comprises step (e) in which a cooling article is applied to the patient's skin in proximity to the joint to achieve a temperature in the range of from about 25° C. to about 31° C. for tissue or fluid in the interior of the joint for a duration of from about 30 minutes to about 90 minutes.

Characterization of Step (a)

The methods may be further characterized according to features of step (a). For example, in certain embodiments, the method comprises step (a) in which a cooling article is applied to a human patient's skin in proximity to a joint in need of pain relief therapy.

In certain embodiments, the method comprises step (a) in which for a duration of from about 5 minutes to about 30 minutes a cooling article is applied to a human patient's skin in proximity to a joint in need of pain relief therapy. In certain embodiments, the method comprises step (a) in which the cooling article is applied for a duration of from about 5 minutes to about 30 minutes to the exterior surface of the patient's knee presenting with osteoarthritic knee joint pain. In certain embodiments, the method comprises step (a) in which the cooling article is applied for a duration of from about 5 minutes to about 15 minutes to the exterior surface of the patient's knee presenting with osteoarthritic knee joint pain. In certain embodiments, the method comprises step (a) in which the cooling article is applied for a duration of about 5, 6, 7, 8, 9, 10, 11, 12, 13, 14, 15, 16, 17, 18, 19, or 20 minutes to the exterior surface of the patient's knee presenting with osteoarthritic knee joint pain. In certain embodiments, the method comprises step (a) in which the cooling article is applied for a duration of about 15 minutes to the exterior surface of the patient's knee presenting with osteoarthritic knee joint pain.

Administering a Local Anesthetic Agent

The methods may be further characterized according to the presence or absence of administering a local anesthetic agent and features thereof. For example, in certain embodiments, the method comprises step (b) of administering a local anesthetic agent into said joint. In certain embodiments, the local anesthetic agent is a caine analagesic. In certain embodiments, the local anesthetic agent is lidocaine, dibucaine, bupivacaine, ropivacaine, etidocaine, tetracaine, procaine, chlorocaine, prilocaine, mepivacaine, xylocaine, 2-chloroprocaine, a pharmaceutically acceptable salt thereof, or a combination of one or more of the foregoing. In certain embodiments, the local anesthetic agent is lidocaine or a pharmaceutically acceptable salt thereof. In certain embodiments, the local anesthetic agent is lidocaine hydrochloride. In certain embodiments, the method comprises step (b) of administering by injection into the joint a pharmaceutical composition comprising lidocaine in order to deliver a dose of lidocaine in an amount of about 0.1 g to about 0.5 g. In certain embodiments, the dose of lidocaine is about 0.3 g. In certain embodiments, the dose of lidocaine is about 0.15 g. In certain embodiments, the dose of lidocaine is about 0.1 g, 0.2, 0.3 g, 0.4 g, or 0.5 g. In certain embodiments, the pharmaceutical composition comprising lidocaine is an aqueous mixture containing lidocaine at a concentration of about 2% w/w. In certain embodiments, the pharmaceutical composition comprising lidocaine is an aqueous mixture containing lidocaine at a concentration of about 1% w/w.

The local anesthetic agent may be administered as part of a pharmaceutical composition. The method may be further characterized according to the temperature of the pharmaceutical composition comprising the local anesthetic agent, which is to be administered to the patient. For example, in certain embodiments, the pharmaceutical composition comprising the local anesthetic agent has a temperature in the range of from about 1° C. to about 5° C., about 5° C. to about 10° C., about 10° C. to about 15° C., about 15° C. to about 20° C., about 20° C. to about 25° C., or about 22° C. to about 24° C. In certain embodiments, the pharmaceutical composition comprising the local anesthetic agent has a temperature of about 23° C.

Flexing the Joint

The methods may be further characterized according to presence or absence of a step involving flexing the joint that received capsaicin. For example, in certain embodiments, after administration of the pharmaceutical composition comprising capsaicin in step (d) but prior to step (e) said joint is flexed. In certain embodiments, after administration of the pharmaceutical composition comprising capsaicin in step (d) but prior to step (e) said joint is flexed about 5 times. In certain embodiments, after administration of the pharmaceutical composition comprising capsaicin in step (d) but prior to step (e) said knee is flexed about 5 times over a period of about 1 minute. In certain embodiments, after administration of the pharmaceutical composition comprising capsaicin in step (d) but prior to step (e) said joint is flexed and extended. In certain embodiments, after administration of the pharmaceutical composition comprising capsaicin in step (d) but prior to step (e) said joint is flexed and extended about 5 times. In certain embodiments, after administration of the pharmaceutical composition comprising capsaicin in step (d) but prior to step (e) said knee is flexed and extended about 5 times over a period of about 1 minute.

Pharmaceutical Composition Comprising Capsaicin

The methods may be further characterized according to features of the pharmaceutical composition comprising capsaicin. For example, in certain embodiments, the pharmaceutical composition comprising capsaicin is an aqueous mixture containing capsaicin. In certain embodiments, the pharmaceutical composition comprising capsaicin has a volume of about 4 mL. In certain embodiments, the pharmaceutical composition comprising capsaicin has a volume of about 2 mL. In certain embodiments, the pharmaceutical composition comprising capsaicin has a volume of about 1 mL. In certain embodiments, the pharmaceutical composition comprising capsaicin has a volume of about 0.5 mL.

Joint and Type of Joint Pain

The methods may be further characterized according to the identity of the joint and type of joint pain. For example, in certain embodiments, the joint is a knee joint, hip joint, shoulder joint, elbow joint, ankle joint, carpal joint, tarsal joint, or metatarsal joint. In certain embodiments, the joint is a knee joint. In certain embodiments, the joint is a thumb joint. In certain embodiments, the joint is a hip joint. The joint may be further characterized according to whether the joint has, or does not have, a synovial membrane. In certain embodiments, the joint has an intra-articular space surrounded by a synovial membrane. In embodiments where the joint has an intra-articular space surrounded by a synovial membrane, the local anesthetic agent and the pharmaceutical composition comprising capsaicin are administered to the intra-articular space by injection.

In certain embodiments, the joint pain is arthritic joint pain. In certain embodiments, the joint pain is osteoarthritic joint pain. In certain embodiments, the joint pain is rheumatoid arthritic joint pain. In yet other embodiments, the joint pain is due to trauma to the joint. In yet other embodiments, the joint pain is due to aging of the patient. In yet other embodiments, the joint pain is due to an inflammatory disease affecting the joint. In yet other embodiments, the joint pain is due to a non-inflammatory disease affecting the joint. In yet other embodiments, the joint pain is due to psoriatic arthritis. In yet other embodiments, the joint pain is due to ankylosing spondylitis.

In certain embodiments, the joint is a knee joint presenting with pain. In certain embodiments, the joint is an osteoarthritic knee joint. In certain embodiments, the joint is a knee joint afflicted with rheumatoid arthritis.

In certain embodiments, the joint is a knee joint that afflicted by one or more of rheumatoid arthritis, trauma to the joint, an inflammatory disease, or a non-inflammatory disease. In yet other embodiments, the joint is a knee joint, and the joint pain is due to aging of the patient.

Temperature of the Cooling Article Surface

The methods may be further characterized according to the temperature of the cooling article surface. For example, in certain embodiments, the cooling article has an exterior surface temperature in the range of from about 1° C. to about 3° C. for application to the human patient's skin in proximity to said joint. In certain embodiments, the cooling article has an exterior surface temperature in the range of from about 3° C. to about 5° C. for application to the human patient's skin in proximity to said joint. In certain embodiments, the cooling article has an exterior surface temperature in the range of from about 5° C. to about 7° C. for application to the human patient's skin in proximity to said joint. In certain embodiments, the cooling article has an exterior surface temperature in the range of from about 7° C. to about 9° C. for application to the human patient's skin in proximity to said joint. In certain embodiments, the cooling article has an exterior surface temperature in the range of from about 9° C. to about 11° C. for application to the human patient's skin in proximity to said joint. In certain embodiments, the cooling article has an exterior surface temperature in the range of from about 11° C. to about 13° C. for application to the human patient's skin in proximity to said joint. In certain embodiments, the cooling article has an exterior surface temperature in the range of from about 13° C. to about 15° C. for application to the human patient's skin in proximity to said joint.

In certain embodiments, the cooling article has an exterior surface temperature of about 1° C. for application to the human patient's skin in proximity to said joint. In certain embodiments, the cooling article has an exterior surface temperature of about 2° C. for application to the human patient's skin in proximity to said joint. In certain embodiments, the cooling article has an exterior surface temperature of about 3° C. for application to the human patient's skin in proximity to said joint. In certain embodiments, the cooling article has an exterior surface temperature of about 4° C. for application to the human patient's skin in proximity to said joint. In certain embodiments, the cooling article has an exterior surface temperature of about 5° C. for application to the human patient's skin in proximity to said joint. In certain embodiments, the cooling article has an exterior surface temperature of about 6° C. for application to the human patient's skin in proximity to said joint. In certain embodiments, the cooling article has an exterior surface temperature of about 7° C. for application to the human patient's skin in proximity to said joint. In certain embodiments, the cooling article has an exterior surface temperature of about 8° C. for application to the human patient's skin in proximity to said joint. In certain embodiments, the cooling article has an exterior surface temperature of about 9° C. for application to the human patient's skin in proximity to said joint. In certain embodiments, the cooling article has an exterior surface temperature of about 10° C. for application to the human patient's skin in proximity to said joint. In certain embodiments, the cooling article has an exterior surface temperature of about 11° C. for application to the human patient's skin in proximity to said joint. In certain embodiments, the cooling article has an exterior surface temperature of about 12° C. for application to the human patient's skin in proximity to said joint. In certain embodiments, the cooling article has an exterior surface temperature of about 13° C. for application to the human patient's skin in proximity to said joint. In certain embodiments, the cooling article has an exterior surface temperature of about 14° C. for application to the human patient's skin in proximity to said joint. In certain embodiments, the cooling article has an exterior surface temperature of about 15° C. for application to the human patient's skin in proximity to said joint.

Dose of Capsaicin

The methods may be further characterized according to the dose of capsaicin administered. For example, in certain embodiments, the dose of capsaicin is from about 0.01 mg to about 0.1 mg. In certain embodiments, the dose of capsaicin is from about 0.1 mg to about 0.5 mg. In certain embodiments, the dose of capsaicin is from about 0.5 mg to about 1.0 mg. In certain embodiments, the dose of capsaicin is from about 1 mg to about 1.5 mg. In certain embodiments, the dose of capsaicin is from about 1.5 mg to about 2.0 mg. In certain embodiments, the dose of capsaicin is from about 2.0 mg to about 4.0 mg. In certain embodiments, the dose of capsaicin is about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3 mg, 3.5 mg, 4.0 mg, 4.5 mg, 5.0 mg, 6 mg, or 7 mg. In certain embodiments, the dose of capsaicin is about 1 mg. In certain embodiments, the dose of capsaicin is 1 mg.

Additional Procedure to Reduce Transient Burning Sensation

The methods may be further characterized according to the presence or absence of an additional procedure to reduce transient burning sensation due to the capsaicin. For example, in certain embodiments, other than the procedures set forth in steps (a). (b). (c). (d), (e), and optionally flexing said joint, the method does not contain any procedure that reduces transient burning sensation experienced by the patient due to administration of capsaicin. In certain embodiments, other than the procedures set forth in steps (a), (b), (c), (d), (e), and optionally flexing said joint, the method does not contain any procedure that reduces joint pain. In certain embodiments, other than administration of (i) the local anesthetic agent and (ii) the pharmaceutical composition comprising capsaicin, the patient does not receive any other pain-relief medicine. In certain embodiments, other than the procedures set forth in steps (a), (b), (c), (d), (e), and optionally flexing and extending said joint, the method does not contain any procedure that reduces transient burning sensation experienced by the patient due to administration of capsaicin. In certain embodiments, other than the procedures set forth in steps (a), (b), (c), (d), (e), and optionally flexing and extending said joint, the method does not contain any procedure that reduces joint pain.

Magnitude of Transient Burning Sensation Due to Capsaicin

The methods may be further characterized according to the magnitude of the transient burning sensation due to capsaicin. For example, in certain embodiments, the patient experiences transient burning sensation no greater than level one on a visual analog scale ranging from zero to four (i.e., (0)) none, (1) mild, (2) moderate, (3) moderately severe, and (4) severe), due to administering the pharmaceutical composition comprising capsaicin. In certain embodiments, the patient experiences transient burning sensation no greater than level two on a visual analog scale ranging from zero to four (i.e., (0)) none, (1) mild, (2) moderate, (3) moderately severe, and (4) severe), due to administering the pharmaceutical composition comprising capsaicin. In certain embodiments, transient burning sensation is evaluated at about 10 minutes after administration of the pharmaceutical composition comprising capsaicin. In certain embodiments, transient burning sensation is evaluated at about 30 minutes after administration of the pharmaceutical composition comprising capsaicin. In certain embodiments, transient burning sensation is evaluated at about 60 minutes after administration of the pharmaceutical composition comprising capsaicin. In certain embodiments, transient burning sensation is evaluated at about 120 minutes after administration of the pharmaceutical composition comprising capsaicin.

Duration of Reduction in Joint Pain

The methods may be further characterized according to the duration of reduction in joint pain. For example, in certain embodiments, the method is characterized by achieving a reduction in joint pain for a duration of at least 3 months. In certain embodiments, the method is characterized by achieving a reduction in joint pain for a duration of at least 4 months. In certain embodiments, the method is characterized by achieving a reduction in joint pain for a duration of at least 5 months. In certain embodiments, the method is characterized by achieving a reduction in joint pain for a duration of at least 6 months. In certain embodiments, the method is characterized by achieving a reduction in joint pain for a duration of at least 7 months. In certain embodiments, the method is characterized by achieving a reduction in joint pain for a duration of at least 8 months. In certain embodiments, the method is characterized by achieving a reduction in joint pain for a duration of at least 9 months. In certain embodiments, the method is characterized by achieving a reduction in joint pain for a duration of at least 10 months. In certain embodiments, the method is characterized by achieving a reduction in joint pain for a duration of at least 11 months. In certain embodiments, the method is characterized by achieving a reduction in joint pain for a duration of at least 12 months. In certain embodiments, the method is characterized by achieving a reduction in joint pain for a duration of 4 months to 6 months. In certain embodiments, the method is characterized by achieving a reduction in joint pain for a duration of 6 months to 9 months. In certain embodiments, the method is characterized by achieving a reduction in joint pain for a duration of 6 months to 12 months. In certain embodiments, the method is characterized by achieving a reduction in joint pain for a duration of 9 months to 12 months. In certain embodiments, the method is characterized by achieving a reduction in joint pain for a duration of 12 months to 18 months.

Characterization of the Cooling Article

The methods may be further characterized according to features of the cooling article. For example, in certain embodiments, the cooling article is a material wrap cooled via a circulating fluid. In certain embodiments, the cooling article is a textile wrap cooled via a circulating fluid. In certain embodiments, the cooling article is an at least partially frozen gel pack. In certain embodiments, the cooling article covers at least 10%, 20%, 30%, 40%, 50%, 60%, 70%, 80%, or 90% of the external surface of said joint. In certain embodiments, the cooling article covers at least 70% of the external surface of said joint. In certain embodiments, the cooling article covers at least 80% of the external surface of said joint. In certain embodiments, the cooling article covers at least 90% of the external surface of said joint. In certain embodiments, the cooling article covers at least 95% of the external surface of said joint.

Exemplary Features of the First Through Fifteenth Methods

The above First through Fifteenth Methods may be further characterized by additional features, such as isomeric purity of the capsaicin, chemical purity of the capsaicin, avoidance of heat to the area exposed to capsaicin, and the like. A more thorough description of such features is provided below. The invention embraces all permutations and combinations of these features.

Isomeric Purity of Capsaicin

The methods may be further characterized according to the isomeric purity of capsaicin. For example, in certain embodiments, the capsaicin is a mixture of cis-capsaicin and trans-capsaicin that contains at least 98% by weight trans-capsaicin. In certain embodiments, the capsaicin is a mixture of cis-capsaicin and trans-capsaicin that contains at least 99% by weight trans-capsaicin.

Chemical Purity of Capsaicin

The methods may be further characterized according to the chemical purity of capsaicin. For example, in certain embodiments, the capsaicin has a chemical purity of at least 98% by weight (which means the presence of a component other than capsaicin is ≤2% by weight). In certain embodiments, the capsaicin has a chemical purity of at least 99% by weight (which means the presence of a component other than capsaicin is ≤1% by weight). In certain embodiments, the capsaicin has a chemical purity of at least 99.5% by weight (which means the presence of a component other than capsaicin is ≤0.5% by weight). In certain embodiments, the capsaicin has a chemical purity of at least 99.8% by weight (which means the presence of a component other than capsaicin is ≤0.2% by weight).

Avoidance of Heat

The methods may be further characterized according to the presence or absence of a step of avoiding heat for certain durations of time after administration of capsaicin. For example, in certain embodiments, the patient does not expose area receiving a capsaicin dose to heat for a duration of at least 12 hours after administration of capsaicin. In certain embodiments, the patient does not expose area receiving a capsaicin dose to heat for a duration of at least 24 hours after administration of capsaicin.

Procedures to Evaluate Reduction in Pain

Reduction in pain experienced by the patient can be evaluated using procedures described in the literature, such as Patient Global Impression of Change (PGIC; change vs baseline in index knee on 7-point scale; 1=very much improved; 7=very much worse, with scores of 1 or 2 indicating significant improvement), Patient-specific Functional Scale (PSFS; rate≤3 important activities difficult to perform due to index knee pain on 0-10 scale; 0=able to perform; 10=unable to perform), and the Western Ontario and McMaster Universities Osteoarthritis Index (WOMAC) B stiffness subscale and WOMAC C function subscale.

Duration of Time Between Steps

The methods may be further characterized according to the duration of time that elapses between performing individual steps of the method, such as the duration of time between completion of step (a) and start of step (b). In certain embodiments, the method is characterized by one or more of (i) the duration of time between completion of step (a) and start of step (b), (ii) the duration of time between completion of step (b) and start of step (c), (iii) the duration of time between completion of step (c) and start of step (d), and (iv) the duration of time between completion of step (d) and start of step (e). In certain embodiments, the duration of time between sequential steps is as soon as reasonably achievable according to standard medical procedure. In certain embodiments, the duration of time between sequential steps is less than 30 minutes, 20) minutes, 15 minutes, 10) minutes, 5 minutes, 3 minutes, or 1 minute. In a preferred embodiment, the duration of time between sequential steps is less than 20) minutes.

The methods can be further characterized according to the duration of time between completion of step (b) and the start of step (d). In certain embodiments, the duration of time between completion of step (b) and the start of step (d) is from about 30 minutes to about 60 minutes. In certain embodiments, the duration of time between completion of step (b) and the start of step (d) is from about 40) minutes to about 60) minutes. In certain embodiments, the duration of time between completion of step (b) and the start of step (d) is from about 50 minutes to about 60 minutes. In certain embodiments, the duration of time between completion of step (b) and the start of step (d) is from about 30 minutes to about 50 minutes. In certain embodiments, the duration of time between completion of step (b) and the start of step (d) is from about 30 minutes to about 45 minutes.

Reducing Effusion Volume in Joints with Effusion

For patients in which the joint to receive capsaicin is a joint that suffers from effusion, in certain embodiments, the volume of intra-articular fluid in the joint presenting with joint effusion is reduced prior to administration of a local anesthetic agent (e.g., the pharmaceutical composition comprising a single pain-relief agent) and/or capsaicin. In certain embodiments, the volume of intra-articular fluid in the joint presenting with joint effusion is reduced prior to administering a local anesthetic agent. In certain embodiments, the volume of intra-articular fluid in the joint presenting with joint effusion is reduced to achieve a volume of intra-articular fluid that is within about 5%, 10% or 20% of that of a healthy patient of similar height, weight, and age.

Temperature of the Patient's Skin in Proximity to the Joint

The methods may be further characterized according to the temperature of the patient's skin in proximity to the joint to receive or which has received capsaicin according to the method. For example, in certain embodiments, in step (c) applying a cooling article to the patient's skin in proximity to said joint achieves a temperature in the range of from about 5° C. to about 7° C. for said skin. In certain embodiments, in step (c) applying a cooling article to the patient's skin in proximity to said joint achieves a temperature in the range of from about 7° C. to about 9° C. for said skin. In certain embodiments, in step (c) applying a cooling article to the patient's skin in proximity to said joint achieves a temperature in the range of from about 9° C. to about 11° C. for said skin. In certain embodiments, in step (c) applying a cooling article to the patient's skin in proximity to said joint achieves a temperature in the range of from about 11° C. to about 13° C. for said skin. In certain embodiments, in step (c) applying a cooling article to the patient's skin in proximity to said joint achieves a temperature in the range of from about 13° C. to about 15° C. for said skin. In certain embodiments, in step (c) applying a cooling article to the patient's skin in proximity to said joint achieves a temperature in the range of from about 15° C. to about 17° C. for said skin. In certain embodiments, in step (c) applying a cooling article to the patient's skin in proximity to said joint achieves a temperature in the range of from about 17° C. to about 19° C. for said skin. In certain embodiments, in step (c) applying a cooling article to the patient's skin in proximity to said joint achieves a temperature in the range of from about 19° C. to about 21° C. for said skin. In certain embodiments, in step (c) applying a cooling article to the patient's skin in proximity to said joint achieves a temperature in the range of from about 21° C. to about 23° C. for said skin. In certain embodiments, in step (c) applying a cooling article to the patient's skin in proximity to said joint achieves a temperature in the range of from about 23° C. to about 25° C. for said skin. In certain embodiments, in step (c) applying a cooling article to the patient's skin in proximity to said joint achieves a temperature in the range of from about 25° C. to about 27° C. for said skin. In certain embodiments, in step (c) applying a cooling article to the patient's skin in proximity to said joint achieves a temperature in the range of from about 27° C. to about 29° C. for said skin. In certain embodiments, in step (c) applying a cooling article to the patient's skin in proximity to said joint achieves a temperature in the range of from about 29° C. to about 30° C. for said skin.

In certain embodiments, in step (c) applying a cooling article to the patient's skin in proximity to said joint achieves a temperature of about 7° C. for said skin. In certain embodiments, in step (c) applying a cooling article to the patient's skin in proximity to said joint achieves a temperature of about 8° C. for said skin. In certain embodiments, in step (c) applying a cooling article to the patient's skin in proximity to said joint achieves a temperature of about 9° C. for said skin. In certain embodiments, in step (c) applying a cooling article to the patient's skin in proximity to said joint achieves a temperature of about 10° C. for said skin. In certain embodiments, in step (c) applying a cooling article to the patient's skin in proximity to said joint achieves a temperature of about 11° C. for said skin. In certain embodiments, in step (c) applying a cooling article to the patient's skin in proximity to said joint achieves a temperature of about 12° C. for said skin. In certain embodiments, in step (c) applying a cooling article to the patient's skin in proximity to said joint achieves a temperature of about 13° C. for said skin. In certain embodiments, in step (c) applying a cooling article to the patient's skin in proximity to said joint achieves a temperature of about 14° C. for said skin. In certain embodiments, in step (c) applying a cooling article to the patient's skin in proximity to said joint achieves a temperature of about 15° C. for said skin. In certain embodiments, in step (c) applying a cooling article to the patient's skin in proximity to said joint achieves a temperature of about 16° C. for said skin. In certain embodiments, in step (c) applying a cooling article to the patient's skin in proximity to said joint achieves a temperature of about 17° C. for said skin. In certain embodiments, in step (c) applying a cooling article to the patient's skin in proximity to said joint achieves a temperature of about 18° C. for said skin. In certain embodiments, in step (c) applying a cooling article to the patient's skin in proximity to said joint achieves a temperature of about 19° C. for said skin. In certain embodiments, in step (c) applying a cooling article to the patient's skin in proximity to said joint achieves a temperature of about 20° C. for said skin. In certain embodiments, in step (c) applying a cooling article to the patient's skin in proximity to said joint achieves a temperature of about 21° C. for said skin. In certain embodiments, in step (c) applying a cooling article to the patient's skin in proximity to said joint achieves a temperature of about 22° C. for said skin. In certain embodiments, in step (c) applying a cooling article to the patient's skin in proximity to said joint achieves a temperature of about 23° C. for said skin. In certain embodiments, in step (c) applying a cooling article to the patient's skin in proximity to said joint achieves a temperature of about 24° C. for said skin. In certain embodiments, in step (c) applying a cooling article to the patient's skin in proximity to said joint achieves a temperature of about 25° C. for said skin. In certain embodiments, in step (c) applying a cooling article to the patient's skin in proximity to said joint achieves a temperature of about 25° C. for said skin. In certain embodiments, in step (c) applying a cooling article to the patient's skin in proximity to said joint achieves a temperature of about 26° C. for said skin. In certain embodiments, in step (c) applying a cooling article to the patient's skin in proximity to said joint achieves a temperature of about 28° C. for said skin. In certain embodiments, in step (c) applying a cooling article to the patient's skin in proximity to said joint achieves a temperature of about 29° C. for said skin. In certain embodiments, in step (c) applying a cooling article to the patient's skin in proximity to said joint achieves a temperature of about 30° C. for said skin.

Further, in certain embodiments, the method comprises step (e) wherein a cooling article is applied to the patient's skin in proximity to said joint and achieves a temperature in the range of from about 5° C. to about 30° C. for said skin for a duration of at least 30 minutes. In certain embodiments, the method comprises step (e) wherein a cooling article is applied to the patient's skin in proximity to said joint and achieves a temperature in the range of from about 5° C. to about 7° C. for said skin for a duration of at least 30 minutes. In certain embodiments, the method comprises step (e) wherein a cooling article is applied to the patient's skin in proximity to said joint and achieves a temperature in the range of from about 7° C. to about 9° C. for said skin for a duration of at least 30 minutes. In certain embodiments, the method comprises step (e) wherein a cooling article is applied to the patient's skin in proximity to said joint and achieves a temperature in the range of from about 9° C. to about 11° C. for said skin for a duration of at least 30 minutes. In certain embodiments, the method comprises step (e) wherein a cooling article is applied to the patient's skin in proximity to said joint and achieves a temperature in the range of from about 11° C. to about 13° C. for said skin for a duration of at least 30 minutes. In certain embodiments, the method comprises step (e) wherein a cooling article is applied to the patient's skin in proximity to said joint and achieves a temperature in the range of from about 13° C. to about 15° C. for said skin for a duration of at least 30 minutes. In certain embodiments, the method comprises step (e) wherein a cooling article is applied to the patient's skin in proximity to said joint and achieves a temperature in the range of from about 15° C. to about 17° C. for said skin for a duration of at least 30 minutes. In certain embodiments, the method comprises step (e) wherein a cooling article is applied to the patient's skin in proximity to said joint and achieves a temperature in the range of from about 17° C. to about 19° C. for said skin for a duration of at least 30 minutes. In certain embodiments, the method comprises step (e) wherein a cooling article is applied to the patient's skin in proximity to said joint and achieves a temperature in the range of from about 19° C. to about 21° C. for said skin for a duration of at least 30 minutes. In certain embodiments, the method comprises step (e) wherein a cooling article is applied to the patient's skin in proximity to said joint and achieves a temperature in the range of from about 21° C. to about 23° C. for said skin for a duration of at least 30 minutes. In certain embodiments, the method comprises step (e) wherein a cooling article is applied to the patient's skin in proximity to said joint and achieves a temperature in the range of from about 23° C. to about 25° C. for said skin for a duration of at least 30 minutes. In certain embodiments, the method comprises step (e) wherein a cooling article is applied to the patient's skin in proximity to said joint and achieves a temperature in the range of from about 25° C. to about 27° C. for said skin for a duration of at least 30 minutes. In certain embodiments, the method comprises step (e) wherein a cooling article is applied to the patient's skin in proximity to said joint and achieves a temperature in the range of from about 27° C. to about 29° C. for said skin for a duration of at least 30 minutes. In certain embodiments, the method comprises step (e) wherein a cooling article is applied to the patient's skin in proximity to said joint and achieves a temperature of about 5° C. for said skin for a duration of at least 30 minutes. In certain embodiments, the method comprises step (e) wherein a cooling article is applied to the patient's skin in proximity to said joint and achieves a temperature of about 6° C. for said skin for a duration of at least 30 minutes. In certain embodiments, the method comprises step (e) wherein a cooling article is applied to the patient's skin in proximity to said joint and achieves a temperature of about 7° C. for said skin for a duration of at least 30 minutes. In certain embodiments, the method comprises step (e) wherein a cooling article is applied to the patient's skin in proximity to said joint and achieves a temperature of about 8° C. for said skin for a duration of at least 30 minutes. In certain embodiments, the method comprises step (e) wherein a cooling article is applied to the patient's skin in proximity to said joint and achieves a temperature of about 9° C. for said skin for a duration of at least 30 minutes. In certain embodiments, the method comprises step (e) wherein a cooling article is applied to the patient's skin in proximity to said joint and achieves a temperature of about 10° C. for said skin for a duration of at least 30 minutes. In certain embodiments, the method comprises step (e) wherein a cooling article is applied to the patient's skin in proximity to said joint and achieves a temperature of about 11° C. for said skin for a duration of at least 30 minutes. In certain embodiments, the method comprises step (e) wherein a cooling article is applied to the patient's skin in proximity to said joint and achieves a temperature of about 12° C. for said skin for a duration of at least 30 minutes. In certain embodiments, the method comprises step (e) wherein a cooling article is applied to the patient's skin in proximity to said joint and achieves a temperature of about 13° C. for said skin for a duration of at least 30 minutes. In certain embodiments, the method comprises step (e) wherein a cooling article is applied to the patient's skin in proximity to said joint and achieves a temperature of about 14° C. for said skin for a duration of at least 30 minutes. In certain embodiments, the method comprises step (e) wherein a cooling article is applied to the patient's skin in proximity to said joint and achieves a temperature of about 15° C. for said skin for a duration of at least 30 minutes. In certain embodiments, the method comprises step (e) wherein a cooling article is applied to the patient's skin in proximity to said joint and achieves a temperature of about 16° C. for said skin for a duration of at least 30 minutes. In certain embodiments, the method comprises step (e) wherein a cooling article is applied to the patient's skin in proximity to said joint and achieves a temperature of about 17° C. for said skin for a duration of at least 30 minutes. In certain embodiments, the method comprises step (e) wherein a cooling article is applied to the patient's skin in proximity to said joint and achieves a temperature of about 18° C. for said skin for a duration of at least 30 minutes. In certain embodiments, the method comprises step (e) wherein a cooling article is applied to the patient's skin in proximity to said joint and achieves a temperature of about 19° C. for said skin for a duration of at least 30 minutes. In certain embodiments, the method comprises step (e) wherein a cooling article is applied to the patient's skin in proximity to said joint and achieves a temperature of about 20° C. for said skin for a duration of at least 30 minutes. In certain embodiments, the method comprises step (e) wherein a cooling article is applied to the patient's skin in proximity to said joint and achieves a temperature of about 21° C. for said skin for a duration of at least 30 minutes. In certain embodiments, the method comprises step (e) wherein a cooling article is applied to the patient's skin in proximity to said joint and achieves a temperature of about 22° C. for said skin for a duration of at least 30 minutes. In certain embodiments, the method comprises step (e) wherein a cooling article is applied to the patient's skin in proximity to said joint and achieves a temperature of about 23° C. for said skin for a duration of at least 30 minutes. In certain embodiments, the method comprises step (e) wherein a cooling article is applied to the patient's skin in proximity to said joint and achieves a temperature of about 24° C. for said skin for a duration of at least 30 minutes. In certain embodiments, the method comprises step (e) wherein a cooling article is applied to the patient's skin in proximity to said joint and achieves a temperature of about 25° C. for said skin for a duration of at least 30 minutes. In certain embodiments, the method comprises step (e) wherein a cooling article is applied to the patient's skin in proximity to said joint and achieves a temperature of about 26° C. for said skin for a duration of at least 30 minutes. In certain embodiments, the method comprises step (e) wherein a cooling article is applied to the patient's skin in proximity to said joint and achieves a temperature of about 27° C. for said skin for a duration of at least 30 minutes. In certain embodiments, the method comprises step (e) wherein a cooling article is applied to the patient's skin in proximity to said joint and achieves a temperature of about 28° C. for said skin for a duration of at least 30 minutes. In certain embodiments, the method comprises step (e) wherein a cooling article is applied to the patient's skin in proximity to said joint and achieves a temperature of about 29° C. for said skin for a duration of at least 30 minutes.

In certain embodiments, said duration is from about 30 minutes to about 60 minutes. In certain embodiments, said duration is from about 30 minutes to about 90 minutes. In certain embodiments, said duration is from about 60 minutes to about 90 minutes.

Sixteenth Method

Methods described above involving capsaicin administration can be similarly used to administer to a patient a compound that is a vanilloid receptor agonist. Vanilloid receptor agonists, like capsaicin, often cause a transient burning sensation upon administration. Therefore, the cooling techniques and optional administration of a local anesthetic agent (e.g., lidocaine) offer benefits when administering a vanilloid receptor agonist to a patient. Accordingly, the invention includes a variation of the First through Fifteenth Methods described above in which capsaicin is the method is replaced with a vanilloid receptor agonist. Additionally, the further characterization of each of the First through Fifteenth Methods is reiterated here for the variation of the First through Fifteenth Methods described above in which capsaicin in the method is replaced with a vanilloid receptor agonist As an illustration of the foregoing, one aspect of the invention provides a method of ameliorating joint pain in a human patient, comprising:
a. optionally applying a cooling article to a human patient's skin in proximity to a joint in need of pain relief therapy; then
b. optionally administering a local anesthetic agent into said joint; then
c. applying for a duration of at least about 10 minutes a cooling article to the patient's skin in proximity to said joint, wherein the cooling article has an exterior surface temperature in the range of from about 1° C. to about 15° C. for application to the human patient's skin in proximity to said joint; then
d. administering by injection into said joint a therapeutically effective amount of a pharmaceutical composition comprising a vanilloid receptor agonist; and then
e. optionally applying for a duration of at least about 10 minutes a cooling article to the patient's skin in proximity to said joint, wherein the cooling article has an exterior surface temperature in the range of from about 1° C. to about 15° C. for application to the human patient's skin in proximity to said joint;
to thereby ameliorate joint pain in the human patient.

In certain embodiments, the method comprises step (a) which is applying a cooling article to a human patient's skin in proximity to a joint in need of pain relief therapy. In certain embodiments, the method comprises step (b) which is administering a local anesthetic agent into said joint. In certain embodiments, the method comprises step (e) which is applying for a duration of at least about 10 minutes a cooling article to the patient's skin in proximity to said joint, wherein the cooling article has an exterior surface temperature in the range of from about 1° C. to about 15° C. for application to the human patient's skin in proximity to said joint.

Further as an illustration of the foregoing, one aspect of the invention provides a method of ameliorating joint pain in a human patient, comprising:
a. optionally applying a cooling article to a human patient's skin in proximity to a joint in need of pain relief therapy; then
b. optionally administering a local anesthetic agent into said joint; then
c. applying a cooling article to the patient's skin in proximity to said joint to achieve a temperature in the range of from about 20° C. to about 33° C. for tissue or fluid in the interior of the joint; then
d. administering by injection into said joint a therapeutically effective amount of a pharmaceutical composition comprising a vanilloid receptor agonist; and then
e. optionally applying a cooling article to the patient's skin in proximity to said joint;
to thereby ameliorate joint pain in the human patient.

In certain embodiments, the method comprises step (a) which is applying a cooling article to a human patient's skin in proximity to a joint in need of pain relief therapy. In certain embodiments, the method comprises step (b) which is administering a local anesthetic agent into said joint. In certain embodiments, the method comprises step (e) which is applying a cooling article to the patient's skin in proximity to said joint.

Exemplary vanilloid receptor agonists include, for example, capsaicin, resiniferatoxin, N-vanillylnonanamides, N-vanillylsulfonamides, N-vanillylureas, N-vanillylcarbamates, N-[(substituted phenyl)methyl]alkylamides, methylene substituted N-[(substituted phenyl)methyl]alkanamides, N-[(substituted phenyl)methyl]-cis-monosaturated alkenamides, N-[(substituted phenyl)methyl]diunsaturated amides, 3-hydroxy acetanilide, hydroxyphenylacetamides, pseudocapsaicin, dihydrocapsaicin, nordihydrocapsaicin anandamide, piperine, zingerone, warburganal, polygodial, aframodial, cinnamodial, cinnamosmolide, cinnamolide, isovelleral, scalaradial, ancistrodial, beta-acaridial, merulidial, and scutigeral. In certain preferred embodiments, the vanilloid receptor agonist is resiniferatoxin.

III. THERAPEUTIC APPLICATIONS FOR PAIN DUE TO A PAINFUL NERVE

One aspect of the invention provides methods for treating pain due to an painful nerve, such as an intermetatarsal neuroma, using injectable capsaicin and procedures to attenuate transient burning sensation due to capsaicin administration. The methods desirably provide relief from pain due to the painful nerve for an extended duration, such as at least about 3 months, 6 months, 9 months, or 1 year. The methods utilize a cooling article, such as a material wrap cooled via a circulating fluid, to reduce the temperature of tissue to be exposed to capsaicin for certain durations of time, optionally in combination with administering a local anesthetic agent. In a preferred embodiment, the methods are used to ameliorate intermetatarsal neuroma pain in a human patient by administering capsaicin to tissue adjacent to the intermetatarsal neuroma via a protocol that applies a cooling article to an exterior surface of the patient's foot presenting with intermetatarsal neuroma pain before and after administration of capsaicin, such as where the cooling article has an exterior surface temperature in the range of from about 5° C. to about 15° C., and more preferably from about 5° C. to about 10° C., for application to the exterior surface of the patient's foot. Various aspects and embodiments of the methods are described below.

First Method

One aspect of the invention provides a method of ameliorating pain due to an intermetatarsal neuroma in a human patient, wherein the method comprises:
a. applying for a duration of about 15 minutes a cooling article to a human patient's skin in proximity to an intermetatarsal neuroma in need of pain relief therapy, wherein the cooling article has an exterior surface temperature in the range of from about 5° C. to about 15° C. for application to the patient's foot; then
b. administering by injection into tissue adjacent to the intermetatarsal neuroma a pharmaceutical composition comprising a single pain-relief agent selected from the group consisting of lidocaine and a pharmaceutically acceptable salt thereof, in order to deliver a dose of lidocaine in an amount ranging from about 1 mg to about 50 mg;
c. applying for a duration of about 30 minutes a cooling article to the human patient's skin in proximity to the intermetatarsal neuroma in need of pain relief therapy, wherein the cooling article has an exterior surface temperature in the range of from about 5° C. to about 15° C. for application to the patient's foot; then
d. administering by injection into tissue adjacent to the intermetatarsal neuroma capsaicin in an amount of from about 100 μg to 300 μg; and then
e. applying for a duration of at least about 30 minutes a cooling article to the patient's skin in proximity to the intermetatarsal neuroma, wherein the cooling article has an exterior surface temperature in the range of from about 5° C. to about 15° C. for application to the patient's foot;
   to thereby ameliorate pain due to an intermetatarsal neuroma in the human patient.

Second Method

One aspect of the invention provides a method of attenuating transient burning sensation due to injection of capsaicin into tissue adjacent to an intermetatarsal neuroma in a human patient, wherein the method comprises:
a. applying for a duration of about 15 minutes a cooling article to a human patient's skin in proximity to an intermetatarsal neuroma in need of pain relief therapy, wherein the cooling article has an exterior surface temperature in the range of from about 5° C. to about 15° C. for application to the patient's foot; then
b. administering by injection into tissue adjacent to the intermetatarsal neuroma a pharmaceutical composition comprising a single pain-relief agent selected from the group consisting of lidocaine and a pharmaceutically acceptable salt thereof, in order to deliver a dose of lidocaine in an amount ranging from about 1 mg to about 50 mg;
c. applying for a duration of about 30 minutes a cooling article to the human patient's skin in proximity to the intermetatarsal neuroma in need of pain relief therapy, wherein the cooling article has an exterior surface temperature in the range of from about 5° C. to about 15° C. for application to the patient's foot; then
d. administering by injection into tissue adjacent to the intermetatarsal neuroma capsaicin in an amount of from about 100 μg to 300 μg; and then
e. applying for a duration of at least about 30 minutes a cooling article to the patient's skin in proximity to the intermetatarsal neuroma, wherein the cooling article has an exterior surface temperature in the range of from about 5° C. to about 15° C. for application to the patient's foot;
   to thereby attenuate transient burning sensation due to injection of capsaicin into tissue adjacent to the intermetatarsal neuroma in the human patient.

Third Method

One aspect of the invention provides a method of ameliorating pain due to an intermetatarsal neuroma in a human patient, wherein the method comprises:
a. applying a cooling article to a human patient's skin in proximity to an intermetatarsal neuroma in need of pain relief therapy; then
b. administering by injection into tissue adjacent to the intermetatarsal neuroma a pharmaceutical composition comprising a single pain-relief agent selected from the group consisting of lidocaine and a pharmaceutically acceptable salt thereof, in order to deliver a dose of lidocaine in an amount ranging from about 1 mg to about 50 mg;
c. applying a cooling article to a human patient's skin in proximity to an intermetatarsal neuroma in need of pain relief therapy to achieve a temperature in the range of from about 26° C. to about 33° C. for tissue in proximity to the intermetatarsal neuroma;
d. administering by injection into tissue adjacent to the intermetatarsal neuroma capsaicin in an amount of from about 100 μg to 300 μg; and then
e. applying a cooling article to the human patient's skin in proximity to the intermetatarsal neuroma in need of pain relief therapy;
   to thereby ameliorate pain due to the intermetatarsal neuroma in the human patient.

Fourth Method

One aspect of the invention provides a method of attenuating transient burning sensation due to injection of capsaicin into tissue adjacent to an intermetatarsal neuroma, wherein the method comprises:
a. applying a cooling article to a human patient's skin in proximity to an intermetatarsal neuroma in need of pain relief therapy; then
b. administering by injection into tissue adjacent to the intermetatarsal neuroma a pharmaceutical composition comprising a single pain-relief agent selected from the group consisting of lidocaine and a pharmaceutically acceptable salt thereof, in order to deliver a dose of lidocaine in an amount ranging from about 1 mg to about 50 mg;
c. applying a cooling article to a human patient's skin in proximity to an intermetatarsal neuroma in need of pain relief therapy to achieve a temperature in the range of from about 26° C. to about 33° C. for tissue in proximity to the intermetatarsal neuroma;
d. administering by injection into tissue adjacent to the intermetatarsal neuroma capsaicin in an amount of from about 100 μg to 300 μg; and then
e. applying a cooling article to the human patient's skin in proximity to the intermetatarsal neuroma in need of pain relief therapy;
   to thereby attenuate transient burning sensation due to injection of capsaicin into tissue adjacent to an intermetatarsal neuroma.

Fifth Method

One aspect of the invention provides a method of ameliorating pain due to an intermetatarsal neuroma in a human patient, wherein the method comprises:
a. applying for a duration of at least about 10 minutes a cooling article to a human patient's skin in proximity to an intermetatarsal neuroma in need of pain relief therapy, wherein the cooling article has an exterior surface temperature in the range of from about 1° C. to about 15° C.; then
b. administering by injection into the intermetatarsal neuroma or tissue in proximity to the intermetatarsal neuroma a therapeutically effective amount of capsaicin; and then c. optionally applying for a duration of at least about 10 minutes a cooling article to the patient's skin in proximity to the intermetatarsal neuroma, wherein the cooling article has an exterior surface temperature in the range of from about 1° C. to about 15° C.;

to thereby ameliorate pain due intermetatarsal neuroma in the human patient.

Sixth Method

One aspect of the invention provides a method of attenuating transient burning sensation due to injection of capsaicin into tissue adjacent to an intermetatarsal neuroma in a human patient, wherein the method comprises:
a. applying for a duration of at least about 10 minutes a cooling article to a human patient's skin in proximity to an intermetatarsal neuroma in need of pain relief therapy, wherein the cooling article has an exterior surface temperature in the range of from about 1° C. to about 15° C.; then
b. administering by injection into tissue in proximity to the intermetatarsal neuroma a therapeutically effective amount of capsaicin; and then
c. optionally applying for a duration of at least about 10 minutes a cooling article to the patient's skin in proximity to the intermetatarsal neuroma, wherein the cooling article has an exterior surface temperature in the range of from about 1° C. to about 15° C.;
to thereby attenuate transient burning sensation due to injection of capsaicin into tissue in proximity to an intermetatarsal neuroma.

Seventh Method

One aspect of the invention provides a method of ameliorating pain due to an intermetatarsal neuroma in a human patient, wherein the method comprises:
a. applying a cooling article to a human patient's skin in proximity to an intermetatarsal neuroma in need of pain relief therapy to achieve a temperature in the range of from about 20° C. to about 33° C. for tissue in proximity to the intermetatarsal neuroma; then
b. administering by injection into tissue in proximity to the intermetatarsal neuroma a therapeutically effective amount of capsaicin; and then
c. optionally applying a cooling article to the patient's skin in proximity to the intermetatarsal neuroma;
to thereby ameliorate pain due to the intermetatarsal neuroma in the human patient.

Eighth Method

One aspect of the invention provides a method of attenuating transient burning sensation due to injection of capsaicin into tissue in proximity to an intermetatarsal neuroma, wherein the method comprises:
a. applying a cooling article to a human patient's skin in proximity to an intermetatarsal neuroma in need of pain relief therapy to achieve a temperature in the range of from about 20° C. to about 33° C. for tissue in proximity to the intermetatarsal neuroma; then
b. administering by injection into tissue in proximity to the intermetatarsal neuroma a therapeutically effective amount of capsaicin; and then
c. optionally applying a cooling article to the patient's skin in proximity to the intermetatarsal neuroma;

to thereby attenuate transient burning sensation due to injection of capsaicin into tissue in proximity to the intermetatarsal neuroma.

Exemplary Features of the First Through Eighth Methods Involving Use of Capsaicin in Connection with Treating an Intermetatarsal Neuroma The above First through Eighth Methods involving use of capsaicin in connection with treating an intermetatarsal neuroma may be further characterized by additional features, such dose of capsaicin, characterization of the temperature of the cooling article surface, dose of lidocaine, characterization of the pharmaceutical composition comprising a single pain-relief agent, and the like. A more thorough description of such features is provided below. The invention embraces all permutations and combinations of these features.

Dose of Capsaicin

The method may be further characterized according to the dose of capsaicin administered to the patient. For example, in certain embodiments, the dose of capsaicin is in an amount ranging from about 100 µg to about 300 µg of capsaicin. In certain embodiments, the dose of capsaicin is in an amount ranging from about 150 µg to about 250 µg of capsaicin. In certain embodiments, first dose of capsaicin is about 200 µg of capsaicin.

Total Number of Doses of Capsaicin

The methods may be further characterized according to the total number of doses of capsaicin administered to the patient. For example, in certain embodiments, over a duration of 1 year, the patient receives no more than four doses of capsaicin by injection into the patient's intermetatarsal space having an intermetatarsal neuroma. In certain embodiments, over a duration of 1 year, the patient receives no more than three doses of capsaicin by injection into the patient's intermetatarsal space having an intermetatarsal neuroma. In certain embodiments, over a duration of 1 year, the patient receives no more than two doses of capsaicin by injection into the patient's intermetatarsal space having an intermetatarsal neuroma.

The methods may also be characterized according to the number of additional doses of capsaicin administered to the patient subsequent to the second dose of capsaicin. For example, in certain embodiments, the patient receives at least 1, 2, 3, 4, 5, 6, 7, 8, 9, 10, 11, 12, 15, 20, 25, or 30 additional doses of capsaicin beyond the second dose of capsaicin. In certain embodiments, the patient receives from 1 to 3, 1 to 5, 1 to 10, 5 to 10, 5 to 15, 10 to 15, 10 to 20, 15 to 20, or 15 to 25 additional doses of capsaicin subsequent to the second dose of capsaicin. In certain preferred embodiments, the patient receives at least two additional doses of capsaicin subsequent to the second dose of capsaicin. In yet other embodiments, the patient receives at least four additional doses of capsaicin subsequent to the second dose of capsaicin. In yet other embodiments, the patient receives at least six additional doses of capsaicin subsequent to the second dose of capsaicin.

Patients may continue to receive capsaicin by injection to ameliorate pain due an intermetatarsal neuroma for many months and even multiple years so long as medically prudent, such as the pain relief therapy is well tolerated and sufficiently ameliorates the pain.

Duration of Pain Relief

The methods may be further characterized according to the duration over which pain due to the intermetatarsal neuroma is ameliorated. For example, in certain embodiments, the pain is ameliorated for a duration of at least 4 months. In certain embodiments, the pain is ameliorated for a duration of at least 5 months. In certain embodiments, the pain is ameliorated for a duration of at least 6 months. In certain embodiments, the pain is ameliorated for a duration of at least 7 months. In certain embodiments, the pain is ameliorated for a duration of at least 8 months. In certain embodiments, the pain is ameliorated for a duration of at least 9 months. In certain embodiments, the pain is ameliorated for a duration of at least 10 months. In certain embodiments, the pain is ameliorated for a duration of at least 11 months. In certain embodiments, the pain is ameliorated for a duration of at least 12 months. In yet other embodiments, the pain is ameliorated for a duration of from about 3 months to about 6 months, from about 3 months to about 9 months, from about 3 months to about 12 months, from about 3 months to about 24 months, from about 6 months to about 12 months, from about 6 months to about 24 months, or from about 12 months to about 24 months.

Temperature of the Cooling Article Surface for Application to the Patient's Foot The methods may be further characterized according to temperature of the cooling article surface for application to the patient's foot. For example, in certain embodiments, the cooling article has an exterior surface temperature in the range of from about 6° C. to about 13° C. for application to the patient's foot. In certain embodiments, the cooling article has an exterior surface temperature in the range of from about 7° C. to about 13° C. for application to the patient's foot. In certain embodiments, the cooling article has an exterior surface temperature in the range of from about 7° C. to about 10° C. for application to the patient's foot. In certain embodiments, the cooling article has an exterior surface temperature in the range of from about 5° C. to about 10° C. for application to the patient's foot. In certain embodiments, the cooling article has an exterior surface temperature in the range of from about 8° C. to about 10° C. for application to the patient's foot. In certain embodiments, the cooling article has an exterior surface temperature in the range of from about 6° C. to about 8° C. for application to the patient's foot. In certain embodiments, the cooling article has an exterior surface temperature in the range of from about 5° C. to about 8° C. for application to the patient's foot. In certain embodiments, the cooling article has an exterior surface temperature in the range of from about 5° C. to about 7° C. for application to the patient's foot.

In certain embodiments, the cooling article has an exterior surface temperature of about 12° C. for application to the patient's foot. In certain embodiments, the cooling article has an exterior surface temperature of about 11° C. for application to the patient's foot. In certain embodiments, the cooling article has an exterior surface temperature of about 10° C. for application to the patient's foot. In certain embodiments, the cooling article has an exterior surface temperature of about 9° C. for application to the patient's foot. In certain embodiments, the cooling article has an exterior surface temperature of about 8° C. for application to the patient's foot. In certain embodiments, the cooling article has an exterior surface temperature of about 7° C. for application to the patient's foot. In certain embodiments, the cooling article has an exterior surface temperature of about 6° C. for application to the patient's foot. In certain embodiments, the cooling article has an exterior surface temperature of about 5° C. for application to the patient's foot.

Temperature of Tissue in Proximity to the Intermetatarsal Neuroma

The methods may be further characterized according to the temperature of tissue in proximity to the intermetatarsal neuroma to receive or has received capsaicin according to the method. For example, in certain embodiments, in step (e) tissue in proximity to the intermetatarsal neuroma is maintained at a temperature in the range of from 26° C. to about 33° C. for a duration of at least 30 minutes. In certain embodiments, in step (e) tissue in proximity to the intermetatarsal neuroma is maintained at a temperature in the range of from 26° C. to about 33° C. for a duration of from about 30 minutes to about 90 minutes. In certain embodiments, in step (e) tissue in proximity to the intermetatarsal neuroma is maintained at a temperature in the range of from 26° C. to about 28° C. for a duration of at least 30 minutes. In certain embodiments, in step (e) tissue in proximity to the intermetatarsal neuroma is maintained at a temperature in the range of from 26° C. to about 28° C. for a duration of from about 30 minutes to about 90 minutes. In certain embodiments, in step (e) tissue in proximity to the intermetatarsal neuroma is maintained at a temperature in the range of from 28° C. to about 30° C. for a duration of at least 30 minutes. In certain embodiments, in step (e) tissue in proximity to the intermetatarsal neuroma is maintained at a temperature in the range of from 28° C. to about 30° C. for a duration of from about 30 minutes to about 90 minutes. In certain embodiments, in step (e) tissue in proximity to the intermetatarsal neuroma is maintained at a temperature in the range of from 30° C. to about 32° C. for a duration of at least 30 minutes. In certain embodiments, in step (e) tissue in proximity to the intermetatarsal neuroma is maintained at a temperature in the range of from 30° C. to about 32° C. for a duration of from about 30 minutes to about 90 minutes. In certain embodiments, in step (e) tissue in proximity to the intermetatarsal neuroma is maintained at a temperature of about 26° C. for a duration of at least 30 minutes. In certain embodiments, in step (e) tissue in proximity to the intermetatarsal neuroma is maintained at a temperature of about 26° C. for a duration of from about 30 minutes to about 90) minutes. In certain embodiments, in step (e) tissue in proximity to the intermetatarsal neuroma is maintained at a temperature of about 27° C. for a duration of at least 30 minutes. In certain embodiments, in step (e) tissue in proximity to the intermetatarsal neuroma is maintained at a temperature of about 27° C. for a duration of from about 30 minutes to about 90 minutes. In certain embodiments, in step (e) tissue in proximity to the intermetatarsal neuroma is maintained at a temperature of about 28° C. for a duration of at least 30 minutes. In certain embodiments, in step (e) tissue in proximity to the intermetatarsal neuroma is maintained at a temperature of about 28° C. for a duration of from about 30 minutes to about 90 minutes. In certain embodiments, in step (e) tissue in proximity to the intermetatarsal neuroma is maintained at a temperature of about 29° C. for a duration of at least 30 minutes. In certain embodiments, in step (e) tissue in proximity to the intermetatarsal neuroma is maintained at a temperature of about 29° C. for a duration of from about 30 minutes to about 90 minutes. In certain embodiments, in step (e) tissue in proximity to the intermetatarsal neuroma is maintained at a temperature of about 30° C. for a duration of at least 30 minutes. In certain embodiments, in step (e) tissue in proximity to the intermetatarsal neuroma is maintained at a temperature of about 30° C. for a duration of from about 30 minutes to about 90 minutes. In certain embodiments, in step (e) tissue in proximity to the intermetatarsal neuroma is maintained at a temperature of about 31° C. for a duration of at least 30 minutes. In certain embodiments, in step (e) tissue in proximity to the intermetatarsal neuroma is maintained at a temperature of about 31° C. for a duration of from about 30 minutes to about 90 minutes. In certain embodiments, in step (e) tissue in proximity to the intermetatarsal neuroma is maintained at a temperature of about 32° C. for a duration of at least 30 minutes. In certain embodiments, in step (e) tissue in proximity to the intermetatarsal neuroma is maintained at a temperature of about 32° C. for a duration of from about 30 minutes to about 90 minutes. In certain embodiments, in step (e) tissue in proximity to the intermetatarsal neuroma is maintained at a temperature of about 33° C. for a duration of at least 30 minutes. In certain embodiments, in step (e) tissue in proximity to the intermetatarsal neuroma is maintained at a temperature of about 33° C. for a duration of from about 30 minutes to about 90 minutes. The term proximity is understood from the perspective of physicians knowledgeable in the art, and may be, for example, tissue within 2 mm, 3 mm, 4 mm, 5 mm, 6 mm, or 7 mm of the intermetatarsal neuroma.

In certain embodiments, step (c) comprises cooling tissue in proximity to the intermetatarsal neuroma to a temperature in the range of from about 26° C. to about 28° C. In certain embodiments, step (c) comprises cooling tissue in proximity to the intermetatarsal neuroma to a temperature in the range of from about 28° C. to about 30° C. In certain embodiments, step (c) comprises cooling tissue in proximity to the intermetatarsal neuroma to a temperature in the range of from about 30° C. to about 32° C. In certain embodiments, step (c) comprises cooling tissue in proximity to the intermetatarsal neuroma to a temperature of about 26° C. In certain embodiments, step (c) comprises cooling tissue in proximity to the intermetatarsal neuroma to a temperature of about 27° C. In certain embodiments, step (c) comprises cooling tissue in proximity to the intermetatarsal neuroma to a temperature of about 28° C. In certain embodiments, step (c) comprises cooling tissue in proximity to the intermetatarsal neuroma to a temperature of about 29° C. In certain embodiments, step (c) comprises cooling tissue in proximity to the intermetatarsal neuroma to a temperature of about 30° C. In certain embodiments, step (c) comprises cooling tissue in proximity to the intermetatarsal neuroma to a temperature of about 31° C. In certain embodiments, step (c) comprises cooling tissue in proximity to the intermetatarsal neuroma to a temperature of about 32° C. In certain embodiments, step (c) comprises cooling tissue in proximity to the intermetatarsal neuroma to a temperature of about 33° C. In certain embodiments, in step (c) comprises cooling tissue in proximity to the intermetatarsal neuroma to a temperature of about 29° C.

Duration of Cooling in Step (e)

The methods may be further characterized according to the duration of cooling in step (e). For example, in certain embodiments, the duration in step (e) is from about 30) minutes to about 60) minutes. In certain embodiments, the duration in step (e) is from about 60) minutes to about 90) minutes. In certain embodiments, the duration in step (e) is from about 30) minutes to about 60) minutes, from about 60) minutes to about 90 minutes, from about 90) minutes to about 120 minutes, or from about 120 minutes to about 180) minutes.

Additional Procedure to Reduce Transient Burning Sensation

The methods may be further characterized according to the presence or absence of an additional procedure to reduce transient burning sensation due to the capsaicin. For example, in certain embodiments, other than the procedures set forth in steps (a), (b), (c), (d), and (e) the method does not contain any procedure that reduces transient burning sensation experienced by the patient due to administration of capsaicin. In certain embodiments, other than the procedures set forth in steps (a), (b), (c), (d), and (e), the method does not contain any procedure that reduces pain due to the intermetatarsal neuroma. In certain embodiments, other than administration of (i) the local anesthetic agent and (ii) the pharmaceutical composition comprising capsaicin, the patient does not receive any other pain-relief medicine.

Magnitude of Transient Burning Sensation Due to Capsaicin

The methods may be further characterized according to the magnitude of the transient burning sensation due to capsaicin. For example, in certain embodiments, the patient experiences transient burning sensation no greater than level one on a visual analog scale ranging from zero to four (i.e., (0)) none, (1) mild, (2) moderate, (3) moderately severe, and (4) severe), due to administering the pharmaceutical composition comprising capsaicin. In certain embodiments, the patient experiences transient burning sensation no greater than level two on a visual analog scale ranging from zero to four (i.e., (0) none, (1) mild, (2) moderate, (3) moderately severe, and (4) severe), due to administering the pharmaceutical composition comprising capsaicin. In certain embodiments, transient burning sensation is evaluated at about 10 minutes after administration of the pharmaceutical composition comprising capsaicin. In certain embodiments, transient burning sensation is evaluated at about 30 minutes after administration of the pharmaceutical composition comprising capsaicin. In certain embodiments, transient burning sensation is evaluated at about 60 minutes after administration of the pharmaceutical composition comprising capsaicin. In certain embodiments, transient burning sensation is evaluated at about 120 minutes after administration of the pharmaceutical composition comprising capsaicin.

Characterization of the Cooling Article

The methods may be further characterized according to features of the cooling article. For example, in certain embodiments, the cooling article is a material wrap cooled via a circulating fluid. In certain embodiments, the cooling article is a textile wrap cooled via a circulating fluid. In certain embodiments, the cooling article is an at least partially frozen gel pack. In certain embodiments, the cooling article covers at least 10% of the external surface of the patient's foot. In certain embodiments, the cooling article covers at least 20% of the external surface of the patient's foot. In certain embodiments, the cooling article covers at least 30% of the external surface of the patient's foot. In certain embodiments, the cooling article covers at least 50% of the external surface of the patient's foot. In certain embodiments, the cooling article covers at least 70% of the external surface of the patient's foot. In certain embodiments, the cooling article covers at least 80% of the external surface of the patient's foot. In certain embodiments, the cooling article covers at least 90% of the external surface of the patient's foot. In certain embodiments, the cooling article covers at least 95% of the external surface of the patient's foot.

Capsaicin

Capsaicin has the chemical name N-[(4-hydroxy-3-methoxyphenyl)methyl]-8-methylnon-6-enamide, and due to the presence of a C—C double bond can exist as a mixture of cis and trans isomers. The methods may be further characterized according to the isomeric purity of the capsaicin administered to the patient. For example, in certain embodiments, the capsaicin is a mixture of cis-capsaicin and trans-capsaicin that contains at least 95% by weight trans-capsaicin. In certain embodiments, the capsaicin is a mixture of cis-capsaicin and trans-capsaicin that contains at least 98% by weight trans-capsaicin. In certain embodiments, the capsaicin is a mixture of cis-capsaicin and trans-capsaicin that contains at least 99% by weight trans-capsaicin.

Formulations for Injection

The methods may be further characterized according to the formulation used to administer capsaicin to the patient. For example, in certain embodiments, the capsaicin is administered in the form of a liquid, injectable pharmaceutical formulation comprising a pharmaceutically acceptable carrier for injection into a patient. In certain embodiments, the liquid, injectable pharmaceutical formulation comprises water, capsaicin, and a poly(ethylene glycol). In certain other embodiments, the liquid, injectable pharmaceutical formulation consists essentially of water, capsaicin, and a poly(ethylene glycol).

The formulations may be further characterized according to the poly(ethylene glycol) used in the formulation, such as where the poly(ethylene glycol) has a number-average molecular weight of about 250 g/mol to about 350 g/mol. In certain embodiments, the poly(ethylene glycol) has a number-average molecular weight of about 300 g/mol.

The formulations may be further characterized according to the amount of poly(ethylene glycol) used in the formulation, such as where the poly(ethylene glycol) is present in an amount ranging from about 25% to about 35% by weight of the pharmaceutical formulation. In certain embodiments, the poly(ethylene glycol) is present in an amount of about 30% by weight of the pharmaceutical formulation.

Volume of Unit Dose Liquid Formulation Administered to the Patient

The methods may be further characterized according to amount of the formulation administered to the patient per injection. For example, in certain embodiments, the first dose of capsaicin, the second dose of capsaicin, and the any additional dose of capsaicin are individually a liquid, injectable pharmaceutical formulation having a volume in the range of about 1 to 3 mL. In other embodiments, the first dose of capsaicin, the second dose of capsaicin, and the any additional dose of capsaicin are individually a liquid, injectable pharmaceutical formulation having a volume of about 2 mL.

In certain other embodiments, the volume administered may be less, such as when administering to a pediatric patient. In certain embodiments, the first dose of capsaicin, the second dose of capsaicin, and the any additional dose of capsaicin are individually a liquid, injectable pharmaceutical formulation having a volume in the range of about 0.25 to 2 mL, 0.25 to 1 mL, 0.5 to 1 mL, or 0.5 to 1.5 mL.

Injection Procedure

The methods may be further characterized according to identity of tissue into which the capsaicin is injected. For example, in certain embodiments, any dose of capsaicin is injected into tissue adjacent to the intermetatarsal neuroma, whereby the medical instrument performing the injection does not penetrate into the intermetatarsal neuroma. It is understood that the injected capsaicin may diffuse through tissue adjacent to the intermetatarsal neuroma in order to reach the intermetatarsal neuroma. Ultrasound imaging may be used by medical personnel performing the injection to help guide the medical instrument (e.g., a syringe) used to administer the formulation containing capsaicin; this procedure helps ensure that the medical instrument performing the injection does not penetrate into the intermetatarsal neuroma but rather delivers capsaicin to tissue adjacent to the intermetatarsal neuroma so that the capsaicin may contact the intermetatarsal neuroma by diffusing through tissue adjacent to the intermetatarsal neuroma.

Avoidance of Heat

The methods may be further characterized according to activities to be avoided by the patient after being administered the capsaicin. For example, in certain embodiments, the patient does not expose area receiving a capsaicin dose to heat for a duration of at least 24 hours after administration of the capsaicin dose.

Identity of Local Anesthetic Agent

When the method recites administering a local anesthetic agent, the method may be further characterized according to the identity of the local anesthetic agent. If the method is silent on administering a local anesthetic agent, then a further embodiment of the invention pertains to an embodiment where a local anesthetic agent is administered to the patient immediately prior to injecting the capsaicin in order to ameliorate any pain experienced by the patient due to administering the capsaicin.

The local anesthetic agent may be, for example, a caine analagesic. Exemplary caine analgesics include, for example, lidocaine, dibucaine, bupivacaine, ropivacaine, etidocaine, tetracaine, procaine, chlorocaine, prilocaine, mepivacaine, xylocaine, 2-chloroprocaine, and pharmaceutically acceptable salts thereof. In certain embodiments, the local anesthetic agent is lidocaine or a pharmaceutically acceptable salt thereof.

The dose of local anesthetic will depend on the anesthetic being administered as well as the site where the local anesthetic is administered. For example, in embodiments where the local anesthetic is administered via a regional block (e.g., an ankle block), the dose of anesthetic may range from about 1 mL up to about 30 mL of a 1% solution of anesthetic agent (e.g., lidocaine). In other embodiments, a dose of up to 5 mg/kg of a solution containing 0.25% to 5% of anesthetic agent (e.g., lidocaine) may be administered as a nerve block, such as by administration to the site of pain or an area proximal to the site of pain. In yet other embodiments, the dose of local anesthetic may range from about 0.5 mL to about 60 mL of a 0.25% to 5% solution of anesthetic agent.

The methods may be further characterized according to the location in which the local anesthetic agent is administered. In certain embodiments, the local anesthetic agent is administered to tissue adjacent to the intermetatarsal neuroma. In certain embodiments, the local anesthetic agent is administered to the ankle attached to the patient's foot having the intermetatarsal neuroma.

Location of Intermetatarsal Neuroma

The methods may be further characterized according to the location of the intermetatarsal neuroma. In certain embodiments, the patient has an intermetatarsal neuroma in the third intermetatarsal space. In certain embodiments, the patient has an intermetatarsal neuroma in the second intermetatarsal space.

Characterization of the Intermetatarsal Neuroma

The methods may be further characterized according to features of the intermetatarsal neuroma, such as numbness in a toe of the foot having the intermetatarsal neuroma, paresthesia in a toe of the foot having the intermetatarsal neuroma, magnitude of pain experienced by the patient due to the intermetatarsal neuroma, and/or size of the intermetatarsal neuroma.

Accordingly, in certain embodiments, the method is further characterized by the feature that the patient experiences numbness in a toe or experiences paresthesia in a toe, each due to the intermetatarsal neuroma.

In certain embodiments, the method is characterized according to the magnitude of pain experienced by the patient due to the intermetatarsal neuroma. In certain embodiments, the patient experiences pain due to the intermetatarsal neuroma of at least a level 4 at some point during the twenty-four hour period prior to administering the first dose of capsaicin. In certain embodiments, the patient experiences pain due to the intermetatarsal neuroma of at least a level 5 at some point during the twenty-four hour period prior to administering the first dose of capsaicin. In certain embodiments, the patient experiences pain due to the intermetatarsal neuroma of at least a level 4 at some point during the twenty-four hour period prior to administering the capsaicin. In certain embodiments, the patient experiences pain due to the intermetatarsal neuroma of at least a level 5 at some point during the twenty-four hour period prior to administering the capsaicin.

Characterization of Pain Reduction Effect of Capsaicin Treatment

The methods may be further characterized according to reduction in pain provided by the capsaicin treatment. For example, in certain embodiments, the method is characterized by achieving a reduction in average walking foot pain due to the intermetatarsal neuroma for a certain duration of time. In certain embodiments, the method is characterized by achieving a reduction in average walking foot pain due to the intermetatarsal neuroma by at least 1 on the Numeric Pain Rating Scale (NPRS) for a duration of at least 3 months. In certain embodiments, the method is characterized by achieving a reduction in average walking foot pain due to the intermetatarsal neuroma by at least 1 on the Numeric Pain Rating Scale (NPRS) for a duration of at least 4 months. In certain embodiments, the method is characterized by achieving a reduction in average walking foot pain due to the intermetatarsal neuroma by at least 1 on the Numeric Pain Rating Scale (NPRS) for a duration of at least 5 months. In certain embodiments, the method is characterized by achieving a reduction in average walking foot pain due to the intermetatarsal neuroma by at least 1 on the Numeric Pain Rating Scale (NPRS) for a duration of at least 6 months. In certain embodiments, the method is characterized by achieving a reduction in average walking foot pain due to the intermetatarsal neuroma by at least 1 on the Numeric Pain Rating Scale (NPRS) for a duration of at least 7 months. In certain embodiments, the method is characterized by achieving a reduction in average walking foot pain due to the intermetatarsal neuroma by at least 1 on the Numeric Pain Rating Scale (NPRS) for a duration of at least 8 months. In certain embodiments, the method is characterized by achieving a reduction in average walking foot pain due to the intermetatarsal neuroma by at least 1 on the Numeric Pain Rating Scale (NPRS) for a duration of at least 9 months. In certain embodiments, the method is characterized by achieving a reduction in average walking foot pain due to the intermetatarsal neuroma by at least 1 on the Numeric Pain Rating Scale (NPRS) for a duration of at least 10 months. In certain embodiments, the method is characterized by achieving a reduction in average walking foot pain due to the intermetatarsal neuroma by at least 1 on the Numeric Pain Rating Scale (NPRS) for a duration of at least 11 months. In certain embodiments, the method is characterized by achieving a reduction in average walking foot pain due to the intermetatarsal neuroma by at least 1 on the Numeric Pain Rating Scale (NPRS) for a duration of at least 12 months. In certain embodiments, the method is characterized by achieving a reduction in average walking foot pain due to the intermetatarsal neuroma by at least 1 on the Numeric Pain Rating Scale (NPRS) for a duration of at least 12 months, where the patient features conditions where nerve growth is delayed in the area of the intermetatarsal neuroma, such as in diabetes mellitus.

In certain embodiments, the method is characterized by achieving a reduction in average walking foot pain due to the intermetatarsal neuroma by at least 2 on the Numeric Pain Rating Scale (NPRS) for a certain duration of time. In certain embodiments, the method is characterized by achieving a reduction in average walking foot pain due to the intermetatarsal neuroma by at least 2 on the Numeric Pain Rating Scale (NPRS) for a duration of at least 3 months. In certain embodiments, the method is characterized by achieving a reduction in average walking foot pain due to the intermetatarsal neuroma by at least 2 on the Numeric Pain Rating Scale (NPRS) for a duration of at least 4 months. In certain embodiments, wherein the method is characterized by achieving a reduction in average walking foot pain due to the intermetatarsal neuroma by at least 2 on the Numeric Pain Rating Scale (NPRS) for a duration of at least 5 months. In certain embodiments, wherein the method is characterized by achieving a reduction in average walking foot pain due to the intermetatarsal neuroma by at least 2 on the Numeric Pain Rating Scale (NPRS) for a duration of at least 6 months. In certain embodiments, wherein the method is characterized by achieving a reduction in average walking foot pain due to the intermetatarsal neuroma by at least 2 on the Numeric Pain Rating Scale (NPRS) for a duration of at least 7 months. In certain embodiments, wherein the method is characterized by achieving a reduction in average walking foot pain due to the intermetatarsal neuroma by at least 2 on the Numeric Pain Rating Scale (NPRS) for a duration of at least 8 months. In certain embodiments, wherein the method is characterized by achieving a reduction in average walking foot pain due to the intermetatarsal neuroma by at least 2 on the Numeric Pain Rating Scale (NPRS) for a duration of at least 9 months. In certain embodiments, wherein the method is characterized by achieving a reduction in average walking foot pain due to the intermetatarsal neuroma by at least 2 on the Numeric Pain Rating Scale (NPRS) for a duration of at least 10 months. In certain embodiments, wherein the method is characterized by achieving a reduction in average walking foot pain due to the intermetatarsal neuroma by at least 2 on the Numeric Pain Rating Scale (NPRS) for a duration of at least 11 months. In certain embodiments, wherein the method is characterized by achieving a reduction in average walking foot pain due to the intermetatarsal neuroma by at least 2 on the Numeric Pain Rating Scale (NPRS) for a duration of at least 12 months. In certain embodiments, wherein the method is characterized by achieving a reduction in average walking foot pain due to the intermetatarsal neuroma by at least 2 on the Numeric Pain Rating Scale (NPRS) for a duration of at least 12 months, where the patient features conditions where nerve growth is delayed in the area of the intermetatarsal neuroma, such as in diabetes mellitus.

The methods may be further characterized according to the maximal amount of pain experienced by the patient due to the intermetatarsal neuroma following administration of capsaicin. For example, in certain embodiments, the method is characterized by reducing the patient's average walking foot pain due to the intermetatarsal neuroma so that the patient's average walking foot pain due to the intermetatarsal neuroma is no greater than 1 on the Numeric Pain Rating Scale (NPRS) for certain durations of time, such as at least 1, 2, 3, 4, 5, 6, 7, 8, 9, 10, 11, or 12 months. Accordingly, in certain embodiments, the method is characterized by reducing the patient's average walking foot pain due to the intermetatarsal neuroma so that the patient's average walking foot pain due to the intermetatarsal neuroma is no greater than 1 on the Numeric Pain Rating Scale (NPRS) for a duration of at least 3 months. In certain embodiments, the method is characterized by reducing the patient's average walking foot pain due to the intermetatarsal neuroma so that the patient's average walking foot pain due to the intermetatarsal neuroma is no greater than 1 on the Numeric Pain Rating Scale (NPRS) for a duration of at least 4 months. In certain embodiments, the method is characterized by reducing the patient's average walking foot pain due to the intermetatarsal neuroma so that the patient's average walking foot pain due to the intermetatarsal neuroma is no greater than 1 on the Numeric Pain Rating Scale (NPRS) for a duration of at least 5 months. In certain embodiments, the method is characterized by reducing the patient's average walking foot pain due to the intermetatarsal neuroma so that the patient's average walking foot pain due to the intermetatarsal neuroma is no greater than 1 on the Numeric Pain Rating Scale (NPRS) for a duration of at least 6 months. In certain embodiments, the method is characterized by reducing the patient's average walking foot pain due to the intermetatarsal neuroma so that the patient's average walking foot pain due to the intermetatarsal neuroma is no greater than 1 on the Numeric Pain Rating Scale (NPRS) for a duration of at least 7 months. In certain embodiments, the method is characterized by reducing the patient's average walking foot pain due to the intermetatarsal neuroma so that the patient's average walking foot pain due to the intermetatarsal neuroma is no greater than 1 on the Numeric Pain Rating Scale (NPRS) for a duration of at least 8 months. In certain embodiments, the method is characterized by reducing the patient's average walking foot pain due to the intermetatarsal neuroma so that the patient's average walking foot pain due to the intermetatarsal neuroma is no greater than 1 on the Numeric Pain Rating Scale (NPRS) for a duration of at least 9 months. In certain embodiments, the method is characterized by reducing the patient's average walking foot pain due to the intermetatarsal neuroma so that the patient's average walking foot pain due to the intermetatarsal neuroma is no greater than 1 on the Numeric Pain Rating Scale (NPRS) for a duration of at least 10 months. In certain embodiments, the method is characterized by reducing the patient's average walking foot pain due to the intermetatarsal neuroma so that the patient's average walking foot pain due to the intermetatarsal neuroma is no greater than 1 on the Numeric Pain Rating Scale (NPRS) for a duration of at least 11 months. In certain embodiments, the method is characterized by reducing the patient's average walking foot pain due to the intermetatarsal neuroma so that the patient's average walking foot pain due to the intermetatarsal neuroma is no greater than 1 on the Numeric Pain Rating Scale (NPRS) for a duration of at least 12 months, where the patient features conditions where nerve growth is delayed in the area of the intermetatarsal neuroma, such as in diabetes mellitus. In yet other embodiments, the method is characterized by reducing the patient's average walking foot pain due to the intermetatarsal neuroma so that the patient's average walking foot pain due to the intermetatarsal neuroma is no greater than 2 on the Numeric Pain Rating Scale (NPRS) for certain durations of time, such as at least 1, 2, 3, 4, 5, 6, 7, 8, 9, 10, 11, or 12 months. In yet other embodiments, the method is characterized by reducing the patient's average walking foot pain due to the intermetatarsal neuroma so that the patient's average walking foot pain due to the intermetatarsal neuroma is no greater than 3 on the Numeric Pain Rating Scale (NPRS) for certain durations of time, such as at least 1, 2, 3, 4, 5, 6, 7, 8, 9, 10, 11, or 12 months. In yet other embodiments, the method is characterized by reducing the patient's average walking foot pain due to the intermetatarsal neuroma so that the patient's average walking foot pain due to the intermetatarsal neuroma is no greater than 4 on the Numeric Pain Rating Scale (NPRS) for certain durations of time, such as at least 1, 2, 3, 4, 5, 6, 7, 8, 9, 10, 11, or 12 months. In yet other embodiments, the method is characterized by reducing the patient's average walking foot pain due to the intermetatarsal neuroma so that the patient's average walking foot pain due to the intermetatarsal neuroma is no greater than 5 on the Numeric Pain Rating Scale (NPRS) for certain durations of time, such as at least 1, 2, 3, 4, 5, 6, 7, 8, 9, 10, 11, or 12 months.

The methods may be further characterized according to the reduction in pain experienced by the patient due to the intermetatarsal neuroma following administration of a first dose of capsaicin. Accordingly, in certain embodiments, the method is characterized by the feature that upon administration of the first dose of capsaicin, the patient experiences a reduction in average walking foot pain due to the intermetatarsal neuroma of at least 1 on the Numeric Pain Rating Scale (NPRS) within 2 weeks after administration of the first dose of capsaicin and lasting for a duration of at least 2 months. In certain embodiments, wherein upon administration of the first dose of capsaicin, the patient experiences a reduction in average walking foot pain due to the intermetatarsal neuroma of at least 2 on the Numeric Pain Rating Scale (NPRS) within 2 weeks after administration of the first dose of capsaicin and lasting for a duration of at least 2 months. In certain embodiments, wherein upon administration of the first dose of capsaicin, the patient experiences a reduction in average walking foot pain due to the intermetatarsal neuroma of at least 1 on the Numeric Pain Rating Scale (NPRS) within 2 weeks after administration of the first dose of capsaicin and lasting for a duration of at least 3 months. In certain embodiments, wherein upon administration of the first dose of capsaicin, the patient experiences a reduction in average walking foot pain due to the intermetatarsal neuroma of at least 2 on the Numeric Pain Rating Scale (NPRS) within 2 weeks after administration of the first dose of capsaicin and lasting for a duration of at least 3 months.

The methods may be further characterized according to ability to reduce the patient's worst neuroma foot pain due to the intermetatarsal neuroma so that the patient's worst neuroma foot pain due to the intermetatarsal neuroma is no greater than 1 on the Numeric Pain Rating Scale for certain duration of time, such as at least 1, 2, 3, 4, 5, 6, 7, 8, 9, 10, 11, or 12 months. In certain embodiments, the method is characterized by reducing the patient's worst neuroma foot pain due to the intermetatarsal neuroma so that the patient's worst neuroma foot pain due to the intermetatarsal neuroma is no greater than 1 on the Numeric Pain Rating Scale (NPRS) for a duration of at least 3 months. In certain embodiments, the method is characterized by reducing the patient's worst neuroma foot pain due to the intermetatarsal neuroma so that the patient's worst neuroma foot pain due to the intermetatarsal neuroma is no greater than 1 on the Numeric Pain Rating Scale (NPRS) for a duration of at least 4 months. In certain embodiments, the method is characterized by reducing the patient's worst neuroma foot pain due to the intermetatarsal neuroma so that the patient's worst neuroma foot pain due to the intermetatarsal neuroma is no greater than 1 on the Numeric Pain Rating Scale (NPRS) for a duration of at least 5 months. In certain embodiments, the method is characterized by reducing the patient's worst neuroma foot pain due to the intermetatarsal neuroma so that the patient's worst neuroma foot pain due to the intermetatarsal neuroma is no greater than 1 on the Numeric Pain Rating Scale (NPRS) for a duration of at least 6 months. In certain embodiments, the method is characterized by reducing the patient's worst neuroma foot pain due to the intermetatarsal neuroma so that the patient's worst neuroma foot pain due to the intermetatarsal neuroma is no greater than 1 on the Numeric Pain Rating Scale (NPRS) for a duration of at least 7 months. In certain embodiments, the method is characterized by reducing the patient's worst neuroma foot pain due to the intermetatarsal neuroma so that the patient's worst neuroma foot pain due to the intermetatarsal neuroma is no greater than 1 on the Numeric Pain Rating Scale (NPRS) for a duration of at least 8 months. In certain embodiments, the method is characterized by reducing the patient's worst neuroma foot pain due to the intermetatarsal neuroma so that the patient's worst neuroma foot pain due to the intermetatarsal neuroma is no greater than 1 on the Numeric Pain Rating Scale (NPRS) for a duration of at least 9 months. In certain embodiments, the method is characterized by reducing the patient's worst neuroma foot pain due to the intermetatarsal neuroma so that the patient's worst neuroma foot pain due to the intermetatarsal neuroma is no greater than 1 on the Numeric Pain Rating Scale (NPRS) for a duration of at least 10 months. In certain embodiments, the method is characterized by reducing the patient's worst neuroma foot pain due to the intermetatarsal neuroma so that the patient's worst neuroma foot pain due to the intermetatarsal neuroma is no greater than 1 on the Numeric Pain Rating Scale (NPRS) for a duration of at least 11 months. In certain embodiments, the method is characterized by reducing the patient's worst neuroma foot pain due to the intermetatarsal neuroma so that the patient's worst neuroma foot pain due to the intermetatarsal neuroma is no greater than 1 on the Numeric Pain Rating Scale (NPRS) for a duration of at least 12 months. In certain embodiments, the method is characterized by reducing the patient's worst neuroma foot pain due to the intermetatarsal neuroma so that the patient's worst neuroma foot pain due to the intermetatarsal neuroma is no greater than 1 on the Numeric Pain Rating Scale (NPRS) for a duration of at least 12 months, where the patient features conditions where nerve growth is delayed in the area of the intermetatarsal neuroma, such as in diabetes mellitus.

The methods may be further characterized according to ability to reduce the patient's worst neuroma foot pain due to the intermetatarsal neuroma so that the patient's worst neuroma foot pain due to the intermetatarsal neuroma is no greater than a certain threshold (e.g., 1 or 2) on the Numeric Pain Rating Scale for certain duration of time after administering the first dose of capsaicin, such as at least 1, 2, 3, 4, 5, 6, 7, 8, 9, 10, 11, or 12 months. In certain embodiments, upon administration of the first dose of capsaicin, the patient experiences a reduction in worst neuroma foot pain due to the intermetatarsal neuroma of at least 1 on the Numeric Pain Rating Scale (NPRS) within 2 weeks after administration of the first dose of capsaicin and lasting for a duration of at least 2 months. In certain embodiments, upon administration of a said dose of capsaicin, the patient experiences a reduction in worst neuroma foot pain due to the intermetatarsal neuroma of at least 2 on the Numeric Pain Rating Scale (NPRS) within 2 weeks after administration of the first dose of capsaicin and lasting for a duration of at least 2 months. In certain embodiments, upon administration of a said dose of capsaicin, the patient experiences a reduction in worst neuroma foot pain due to the intermetatarsal neuroma of at least 1 on the Numeric Pain Rating Scale (NPRS) within 2 weeks after administration of the first dose of capsaicin and lasting for a duration of at least 3 months. In certain embodiments, upon administration of a said dose of capsaicin, the patient experiences a reduction in worst neuroma foot pain due to the intermetatarsal neuroma of at least 2 on the Numeric Pain Rating Scale (NPRS) within 2 weeks after administration of the first dose of capsaicin and lasting for a duration of at least 3 months.

The methods may be further characterized according to ability to achieve an improvement in the patient's Revised Foot Function Index (FFI—R) score. Accordingly, in certain embodiments, upon administration of a first dose of capsaicin, the patient experiences an improvement in their Revised Foot Function Index (FFI—R) score of at least 1 within 2 weeks after administration of the dose of capsaicin and lasting for a duration of at least 2 months. In certain embodiments, upon administration of a said dose of capsaicin, the patient experiences an improvement in their Revised Foot Function Index (FFI—R) score of at least 2 within 2 weeks after administration of the dose of capsaicin and lasting for a duration of at least 2 months. In certain embodiments, upon administration of a said dose of capsaicin the patient experiences an improvement in their Revised Foot Function Index (FFI—R) score of at least 1 within 2 weeks after administration of the dose of capsaicin and lasting for a duration of at least 3 months. In certain embodiments, upon administration of a said dose of capsaicin, the patient experiences an improvement in their Revised Foot Function Index (FFI—R) score of at least 2 within 2 weeks after administration of the dose of capsaicin and lasting for a duration of at least 2 months. In certain embodiments, the method is characterized by the patient experiencing an improvement in their Revised Foot Function Index (FFI—R) score of at least 1 (or at least 2 or 3) for a duration of at least 2, 3, 4, 5, 6, 7, 8, 9, 10, 11, or 12 months.

The methods may be further characterized according to ability to achieve an improvement in the patient's Personalized Activity Rating Scale (PARS) score. In certain embodiments, upon administration of a said dose of capsaicin, the patient experiences an improvement in their Personalized Activity Rating Scale (PARS) score of at least 1 within 2 weeks after administration of the dose of capsaicin and lasting for a duration of at least 1 month. In certain embodiments, wherein upon administration of a said dose of capsaicin, the patient experiences an improvement in their Personalized Activity Rating Scale (PARS) score of at least 2 within 2 weeks after administration of the dose of capsaicin and lasting for a duration of at least 1 month. In certain embodiments, wherein upon administration of a said dose of capsaicin the patient experiences an improvement in their Personalized Activity Rating Scale (PARS) score of at least 1 within 2 weeks after administration of the dose of capsaicin and lasting for a duration of at least 2 months. In certain embodiments, wherein upon administration of a said dose of capsaicin, the patient experiences an improvement in their Personalized Activity Rating Scale (PARS) score of at least 2 within 2 weeks after administration of the dose of capsaicin and lasting for a duration of at least 2 months. In certain embodiments, the method is characterized by the patient experiencing an improvement in their Personalized Activity Rating Scale (PARS) score of at least 1 (or at least 2 or 3) for a duration of at least 2, 3, 4, 5, 6, 7, 8, 9, 10, 11, or 12 months.

The methods may be further characterized according to improvements in the patient's quality of life following administration of capsaicin to ameliorate pain due to the intermetatarsal neuroma. For example, in certain embodiments, the method is characterized by an improvement in the patient's Quality of Life score, such as an improvement on a EuroQol-5 Dimensions (EQ-5D-5L) scale.

Patient Populations for Treatment

The methods may be further characterized according to features of the patients to be treated. For example, in certain embodiments, during the 24 hour period prior to administration of the first dose of capsaicin, the patient suffers from one or more of the following: (a) an average walking foot pain due to the intermetatarsal neuroma of at least 4 on the Numeric Pain Rating Scale (NPRS); (b) a worst neuroma foot pain due to the intermetatarsal neuroma of at least 4 on the Numeric Pain Rating Scale (NPRS); or (c) a Revised Foot Function Index (FFI—R) score indicating the patient experiences at least two of the following: (i) moderate pain due to the intermetatarsal neuroma, (ii) moderate stiffness due to the intermetatarsal neuroma, and (iii) moderate difficulty in a physical activity due to the intermetatarsal neuroma. In certain other embodiments, during the 24 hour period prior to administration of the first dose of capsaicin, the patient suffers from one or more of the following: (a) an average walking foot pain due to the intermetatarsal neuroma of at least 6 on the Numeric Pain Rating Scale (NPRS); (b) a worst neuroma foot pain due to the intermetatarsal neuroma of at least 6 on the Numeric Pain Rating Scale (NPRS); or (c) a Revised Foot Function Index (FFI—R) score indicating the patient experiences at least two of the following: (i) severe pain due to the intermetatarsal neuroma, (ii) severe stiffness due to the intermetatarsal neuroma, and (iii) severe difficulty in a physical activity due to the intermetatarsal neuroma. In certain other embodiments, during the 24 hour period prior to administration of the first dose of capsaicin, the patient suffers from one or more of the following: (a) an average walking foot pain due to the intermetatarsal neuroma of at least 8 on the Numeric Pain Rating Scale (NPRS); (b) a worst neuroma foot pain due to the intermetatarsal neuroma of at least 8 on the Numeric Pain Rating Scale (NPRS); or (c) a Revised Foot Function Index (FFI—R) score indicating the patient experiences at all of the following: (i) severe pain due to the intermetatarsal neuroma, (ii) severe stiffness due to the intermetatarsal neuroma, and (iii) severe difficulty in a physical activity due to the intermetatarsal neuroma.

In certain embodiments, the patient is characterized according to one or more of: average walking foot pain due to the intermetatarsal neuroma, worst neuroma foot pain due to the intermetatarsal neuroma. Revised Foot Function Index (FFI—R) score, and Personalized Activity Rating Scale (PARS). Accordingly, in certain embodiments, during the 24 hour period prior to administration of the first dose of capsaicin, the patient suffers from one or more of the following: (a) an average walking foot pain due to the intermetatarsal neuroma of at least 4 on the Numeric Pain Rating Scale (NPRS); (b) a worst neuroma foot pain due to the intermetatarsal neuroma of at least 4 on the Numeric Pain Rating Scale (NPRS); (c) a Revised Foot Function Index (FFI—R) score indicating the patient experiences at least two of the following: (i) moderate pain due to the intermetatarsal neuroma, (ii) moderate stiffness due to the intermetatarsal neuroma, and (iii) moderate difficulty in a physical activity due to the intermetatarsal neuroma; or (d) a Personalized Activity Rating Scale (PARS) score of at least 4 for at least one physical activity. In certain embodiments, during the 24 hour period prior to administration of the first dose of capsaicin, the patient suffers from one or more of the following: (a) an average walking foot pain due to the intermetatarsal neuroma of at least 6 on the Numeric Pain Rating Scale (NPRS); (b) a worst neuroma foot pain due to the intermetatarsal neuroma of at least 6 on the Numeric Pain Rating Scale (NPRS); (c) a Revised Foot Function Index (FFI—R) score indicating the patient experiences at least two of the following: (i) severe pain due to the intermetatarsal neuroma, (ii) severe stiffness due to the intermetatarsal neuroma, and (iii) severe difficulty in a physical activity due to the intermetatarsal neuroma; or (d) a Personalized Activity Rating Scale (PARS) score of at least 6 for at least one physical activity. In certain embodiments, during the 24 hour period prior to administration of the first dose of capsaicin, the patient suffers from one or more of the following: (a) an average walking foot pain due to the intermetatarsal neuroma of at least 8 on the Numeric Pain Rating Scale (NPRS); (b) a worst neuroma foot pain due to the intermetatarsal neuroma of at least 8 on the Numeric Pain Rating Scale (NPRS); (c) a Revised Foot Function Index (FFI—R) score indicating the patient experiences at all of the following: (i) severe pain due to the intermetatarsal neuroma, (ii) severe stiffness due to the intermetatarsal neuroma, and (iii) severe difficulty in a physical activity due to the intermetatarsal neuroma; or (d) a Personalized Activity Rating Scale (PARS) score of at least 8 for at least one physical activity.

The methods may be further characterized according to whether the patient has a low Quality of Life score, such as a low score on a EuroQol-5 Dimensions (EQ-5D-5L) scale, due to pain or other conditions due to the intermetatarsal neuroma.

The methods may be further characterized according to whether the patient was previously able to achieve temporarily relief from the pain due to intermetatarsal neuroma using other therapies, such as an injectable steroid, an oral analgesic, or sclerosing agent. Accordingly, in certain embodiments, the method is further characterized by the feature that the patient did not achieve relief from pain due the intermetatarsal neuroma for a duration greater than 2 months following treatment using an injectable steroid, an oral analgesic, or administration of a sclerosing agent to alleviate pain due to the intermetatarsal neuroma.

The methods may be further characterized according to the age of the patient. In certain embodiments, the patient has an age in the range of about 20 to about 30 years old, about 30 to about 40 years old, about 40 to about 50 years old, about 50 to about 60 years old, or about 60) to about 70 years old, or an age greater than 70 years old.

The methods may be further characterized according to the gender of the patient, such as a male or female patient. In certain embodiments, the patient is an adult human male, or an adult human female. In certain embodiments, the patient is a transgender human.

In certain embodiments, the patient is a pediatric human.

Exemplary More Specific Embodiments

Exemplary more specific embodiments include, for example:

Embodiment No. 1: A method of attenuating transient burning sensation due to injection of capsaicin into tissue adjacent to an intermetatarsal neuroma, comprising:
  a. applying for a duration of about 15 minutes a cooling article to a human patient's skin in proximity to an intermetatarsal neuroma in need of pain relief therapy, wherein the cooling article has an exterior surface temperature in the range of from about 5° C. to about 15° C. for application to the patient's foot; then
  b. administering by injection into tissue adjacent to the intermetatarsal neuroma a pharmaceutical composition comprising a single pain-relief agent selected from the group consisting of lidocaine and a pharmaceutically acceptable salt thereof, in order to deliver a dose of lidocaine in an amount ranging from about 30 mg to about 50 mg;
  c. applying for a duration of about 30 minutes a cooling article to the human patient's skin in proximity to the intermetatarsal neuroma in need of pain relief therapy, wherein the cooling article has an exterior surface temperature in the range of from about 5° C. to about 15° C. for application to the patient's foot; then
  d. administering by injection into tissue adjacent to the intermetatarsal neuroma capsaicin in an amount of from about 100 μg to 300 μg; and then
  e. applying for a duration of at least about 30 minutes a cooling article to the patient's skin in proximity to the intermetatarsal neuroma, wherein the cooling article has an exterior surface temperature in the range of from about 5° C. to about 15° C. for application to the patient's foot;
  to thereby ameliorate nerve pain in the human patient.

Embodiment No. 2: The method of embodiment no. 1, wherein the dose of lidocaine about 40 mg.

Embodiment No. 3: The method of embodiment no. 1 or 2, wherein the cooling article covers at least 20% of the external surface of the patient's foot.

Embodiment No. 4: The method of embodiment no. 1 or 2, wherein the cooling article covers at least 30% of the external surface of the patient's foot.

Embodiment No. 5: The method of embodiment no. 1 or 2, wherein the cooling article covers at least 40% of the external surface of the patient's foot.

Embodiment No. 6: The method of embodiment no. 1 or 2, wherein the cooling article covers at least 50% of the external surface of the patient's foot.

Embodiment No. 7: The method of embodiment no. 1 or 2, wherein the cooling article covers at least 70% of the external surface of the patient's foot.

Embodiment No. 8: The method of embodiment no. 1 or 2, wherein the cooling article covers at least 80% of the external surface of the patient's foot.

Embodiment No. 9: The method of embodiment no. 1 or 2, wherein the cooling article covers at least 90% of the external surface of the patient's foot.

Embodiment No. 10: The method of any one of embodiment nos. 1-9, wherein step (c) comprises administering by injection into tissue adjacent to the intermetatarsal neuroma capsaicin in an amount of about 200 μg.

Embodiment No. 11: The method of any one of embodiment nos. 1-9, wherein step (c) comprises administering by injection into tissue adjacent to the intermetatarsal neuroma capsaicin in an amount of about 250 μg.

Embodiment No. 12: The method of any one of embodiment nos. 1-11, wherein the cooling article has an exterior surface temperature in the range of from about 6° C. to about 13° C. for application to the patient's foot.

Embodiment No. 13: The method of any one of embodiment nos. 1-11, wherein, the cooling article has an exterior surface temperature in the range of from about 7° C. to about 13° C. for application to the patient's foot.

Embodiment No. 14: The method of any one of embodiment nos. 1-11, wherein the cooling article has an exterior surface temperature in the range of from about 7° C. to about 10° C. for application to the patient's foot.

Embodiment No. 15: The method of any one of embodiment nos. 1-11, wherein the cooling article has an exterior surface temperature in the range of from about 5° C. to about 10° C. for application to the patient's foot.

Embodiment No. 16: The method of any one of embodiment nos. 1-11, wherein the cooling article has an exterior surface temperature in the range of from about 8° C. to about 10° C. for application to the patient's foot.

Embodiment No. 17: The method of any one of embodiment nos. 1-11, wherein the cooling article has an exterior surface temperature in the range of from about 6° C. to about 8° C. for application to the patient's foot.

Embodiment No. 18: The method of any one of embodiment nos. 1-11, wherein the cooling article has an exterior surface temperature in the range of from about 5° C. to about 8° C. for application to the patient's foot.

Embodiment No. 19: The method of any one of embodiment nos. 1-11, wherein the cooling article has an exterior surface temperature in the range of from about 5° C. to about 7° C. for application to the patient's foot.

Embodiment No. 20: The method of any one of embodiment nos. 1-11, wherein the cooling article has an exterior surface temperature of about 12° C. for application to the patient's foot.

Embodiment No. 21: The method of any one of embodiment nos. 1-11, wherein the cooling article has an exterior surface temperature of about 11° C. for application to the patient's foot.

Embodiment No. 22: The method of any one of embodiment nos. 1-11, wherein the cooling article has an exterior surface temperature of about 10° C. for application to the patient's foot.

Embodiment No. 23: The method of any one of embodiment nos. 1-11, wherein the cooling article has an exterior surface temperature of about 9° C. for application to the patient's foot.

Embodiment No. 24: The method of any one of embodiment nos. 1-11, wherein the cooling article has an exterior surface temperature of about 8° C. for application to the patient's foot.

Embodiment No. 25: The method of any one of embodiment nos. 1-11, wherein the cooling article has an exterior surface temperature of about 7° C. for application to the patient's foot.

Embodiment No. 26 The method of any one of embodiment nos. 1-11, wherein the cooling article has an exterior surface temperature of about 6° C. for application to the patient's foot.

Embodiment No. 27: The method of any one of embodiment nos. 1-11, wherein the cooling article has an exterior surface temperature of about 5° C. for application to the patient's foot.

Embodiment No. 28: The method of any one of embodiment nos. 1-27, wherein other than the procedures set forth in steps (a), (b), (c), (d), and (e), the method does not contain any procedure that reduces transient burning sensation experienced by the patient due to administration of capsaicin.

Embodiment No. 29: The method of any one of embodiment nos. 1-28, wherein other than the procedures set forth in steps (a), (b), (c), (d), and (e), the method does not contain any procedure that reduces pain due to the intermetatarsal neuroma.

Embodiment No. 30: The method of any one of embodiment nos. 1-29, wherein other than administration of (i) the lidocaine and (ii) the capsaicin, the patient does not receive any other pain-relief medicine.

Embodiment No. 31: The method of any one of embodiment nos. 1-30, wherein the patient experiences transient burning sensation no greater than level one on a visual analog scale ranging from zero to four, due to administering the pharmaceutical composition comprising capsaicin.

Embodiment No. 32: The method of any one of embodiment nos. 1-30, wherein the patient experiences transient burning sensation no greater than level two on a visual analog scale ranging from zero to four, due to administering the pharmaceutical composition comprising capsaicin.

Exemplary Additional Embodiments for Treating a Painful Nerve

Procedures described above for treating an intermetatarsal neuroma can be used more generally to treat a painful nerve. Exemplary embodiments for treating a painful nerve include, for example:

First Method

One aspect of the invention provides a method of ameliorating nerve pain in a human patient, wherein the method comprises:
 a. applying for a duration of about 15 minutes a cooling article to a human patient's skin in proximity to a painful nerve in need of pain relief therapy, wherein the cooling article has an exterior surface temperature in the range of from about 5° C. to about 15° C. for application to said skin; then
 b. administering by injection into tissue adjacent to the painful nerve a pharmaceutical composition comprising a single pain-relief agent selected from the group consisting of lidocaine and a pharmaceutically acceptable salt thereof, in order to deliver an effective dose of lidocaine (e.g., lidocaine in an amount ranging from about 1 mg to about 50 mg);
 c. applying for a duration of about 30 minutes a cooling article to the human patient's skin in proximity to the painful nerve in need of pain relief therapy, wherein the cooling article has an exterior surface temperature in the range of from about 5° C. to about 15° C. for application to the said skin; then
 d. administering by injection into tissue adjacent to the painful nerve capsaicin in effective amount (e.g., an amount of from about 100 µg to 300 µg); and then
 e. applying for a duration of at least about 30 minutes a cooling article to the patient's skin in proximity to the painful nerve, wherein the cooling article has an exterior surface temperature in the range of from about 5° C. to about 15° C. for application to the said skin;
 to thereby ameliorate nerve pain in the human patient.

Second Method

One aspect of the invention provides a method of attenuating transient burning sensation due to injection of capsaicin into tissue adjacent to a painful nerve in a human patient, wherein the method comprises:
 a. applying for a duration of about 15 minutes a cooling article to a human patient's skin in proximity to a painful nerve in need of pain relief therapy, wherein the cooling article has an exterior surface temperature in the range of from about 5° C. to about 15° C. for application to said skin; then
 b. administering by injection into tissue adjacent to the painful nerve a pharmaceutical composition comprising a single pain-relief agent selected from the group consisting of lidocaine and a pharmaceutically acceptable salt thereof, in order to deliver an effective dose of lidocaine (e.g., lidocaine in an amount ranging from about 1 mg to about 50 mg);
 c. applying for a duration of about 30 minutes a cooling article to the human patient's skin in proximity to the painful nerve in need of pain relief therapy, wherein the cooling article has an exterior surface temperature in the range of from about 5° C. to about 15° C. for application to said skin; then
 d. administering by injection into tissue adjacent to the painful nerve capsaicin in an effective amount (e.g., from about 100 µg to 300 µg); and then
 e. applying for a duration of at least about 30 minutes a cooling article to the patient's skin in proximity to the painful nerve, wherein the cooling article has an exterior surface temperature in the range of from about 5° C. to about 15° C. for application to said skin:
 to thereby attenuate transient burning sensation due to injection of capsaicin into tissue adjacent to a painful nerve in a human patient.

Third Method

One aspect of the invention provides a method of ameliorating nerve pain in a human patient, wherein the method comprises:
 a. applying a cooling article to a human patient's skin in proximity to a painful nerve in need of pain relief therapy; then
 b. administering by injection into tissue adjacent to the painful nerve a pharmaceutical composition comprising a single pain-relief agent selected from the group consisting of lidocaine and a pharmaceutically acceptable salt thereof, in order to deliver an effective dose of lidocaine (e.g., lidocaine in an amount ranging from about 1 mg to about 50 mg);
 c. applying a cooling article to a human patient's skin in proximity to a painful nerve in need of pain relief therapy to achieve a temperature in the range of from about 26° C. to about 33° C. for tissue in proximity to the painful nerve;
 d. administering by injection into tissue adjacent to the painful nerve capsaicin in an effective amount (e.g., from about 100 µg to 300 µg); and then
 e. applying a cooling article to the human patient's skin in proximity to the painful nerve in need of pain relief therapy;
 to thereby ameliorate nerve pain in the human patient.

Fourth Method

One aspect of the invention provides a method of attenuating transient burning sensation due to injection of capsaicin into tissue adjacent to a painful nerve, wherein the method comprises:

a. applying a cooling article to a human patient's skin in proximity to a painful nerve in need of pain relief therapy; then
b. administering by injection into tissue adjacent to the painful nerve a pharmaceutical composition comprising a single pain-relief agent selected from the group consisting of lidocaine and a pharmaceutically acceptable salt thereof, in order to deliver an effective dose of lidocaine (e.g., lidocaine in an amount ranging from about 1 mg to about 50 mg);
c. applying a cooling article to a human patient's skin in proximity to a painful nerve in need of pain relief therapy to achieve a temperature in the range of from about 26° C. to about 33° C. for tissue in proximity to the painful nerve;
d. administering by injection into tissue adjacent to the painful nerve capsaicin in an effective amount (e.g., of from about 100 µg to 300 µg); and then
e. applying a cooling article to the human patient's skin in proximity to the painful nerve in need of pain relief therapy;
to thereby attenuate transient burning sensation due to injection of capsaicin into a painful nerve or tissue in proximity to a painful nerve.

Fifth Method

One aspect of the invention provides a method of ameliorating nerve pain in a human patient, wherein the method comprises:
a. applying for a duration of at least about 10 minutes a cooling article to a human patient's skin in proximity to a painful nerve in need of pain relief therapy, wherein the cooling article has an exterior surface temperature in the range of from about 1° C. to about 15° C.; then
b. administering by injection into the painful nerve or tissue in proximity to the painful nerve a therapeutically effective amount of capsaicin; and then
c. optionally applying for a duration of at least about 10 minutes a cooling article to the patient's skin in proximity to the painful nerve, wherein the cooling article has an exterior surface temperature in the range of from about 1° C. to about 15° C.; to thereby ameliorate nerve pain in the human patient.

Sixth Method

One aspect of the invention provides a method of attenuating transient burning sensation due to injection of capsaicin into a painful nerve or tissue in proximity to a painful nerve in a human patient, wherein the method comprises:
a. applying for a duration of at least about 10 minutes a cooling article to a human patient's skin in proximity to a painful nerve in need of pain relief therapy, wherein the cooling article has an exterior surface temperature in the range of from about 1° C. to about 15° C.; then
b. administering by injection into the painful nerve or tissue in proximity to the painful nerve a therapeutically effective amount of capsaicin; and then
c. optionally applying for a duration of at least about 10 minutes a cooling article to the patient's skin in proximity to the painful nerve, wherein the cooling article has an exterior surface temperature in the range of from about 1° C. to about 15° C.; to thereby attenuate transient burning sensation due to injection of capsaicin into a painful nerve or tissue in proximity to a painful nerve.

Seventh Method

One aspect of the invention provides a method of ameliorating nerve pain in a human patient, wherein the method comprises:
a. applying a cooling article to a human patient's skin in proximity to a painful nerve in need of pain relief therapy to achieve a temperature in the range of from about 20° C. to about 33° C. for tissue in proximity to the painful nerve; then
b. administering by injection into the painful nerve or tissue in proximity to the painful nerve a therapeutically effective amount of capsaicin; and then
c. optionally applying a cooling article to the patient's skin in proximity to the painful nerve;
to thereby ameliorate nerve pain in the human patient.

Eighth Method

One aspect of the invention provides a method of attenuating transient burning sensation due to injection of capsaicin into a painful nerve or tissue in proximity to a painful nerve, wherein the method comprises:
a. applying a cooling article to a human patient's skin in proximity to a painful nerve in need of pain relief therapy to achieve a temperature in the range of from about 20° C. to about 33° C. for tissue in proximity to the painful nerve; then
b. administering by injection into the painful nerve or tissue in proximity to the painful nerve a therapeutically effective amount of capsaicin; and then
c. optionally applying a cooling article to the patient's skin in proximity to the painful nerve;
to thereby attenuate transient burning sensation due to injection of capsaicin into a painful nerve or tissue in proximity to a painful nerve.

Additional features described above in connection with treating an intermetatarsal neuroma are reiterated here.

IV. GENERAL ASPECTS OF INJECTABLE FORMULATIONS

Various injectable formulations are described in the literature and known to those of skill in the art. The injectable formulation may typically contain water and one or more additional components to render the formulation optimally suited for injection into a subject.

When administering capsaicin according to methods described herein, the capsaicin is desirably administered in the form of a pharmaceutical composition formulated for injection. In certain embodiments, the pharmaceutical composition formulated for injection is an aqueous pharmaceutical composition.

The capsaicin may be dissolved in oils, polyethylene glycol (PEG), propylene glycol (PG), and/or other solvents commonly used to prepare injectable or implantable solutions. Suitable pharmaceutically acceptable vehicles include aqueous vehicles, nonaqueous vehicles, antimicrobial agents, isotonic agents, buffers, antioxidants, suspending and dispersing agents, emulsifying agents, sequestering or chelating agents, and combinations or mixtures thereof. It is appreciated that when one or more solvents are used in the formulations of the invention, they may be combined, e.g., with a pharmaceutically acceptable buffer and may be present in the final formulation, e.g., in an amount ranging from about 10% to about 100%, more preferably from about 20% to about 100%.

Exemplary aqueous vehicles include Sodium Chloride Injection, Bacteriostatic Sodium Chloride Injection, Ringers Injection, Isotonic Dextrose Injection, Sterile Water Injection, Bacteriostatic Sterile Water Injection, Dextrose Lactated Ringers Injection and any combinations or mixtures thereof.

Exemplary nonaqueous parenteral vehicles include fixed oils of vegetable origin, cottonseed oil, corn oil, sesame oil, peanut oil, and combinations or mixtures thereof.

Exemplary antimicrobial agents in bacteriostatic or fungistatic concentrations include phenols, cresols, mercurials, benzyl alcohol, chlorobutanol, ethyl and propyl p-hydroxybenzoic acid esters, thimerosal, benzalkonium chloride, benzethonium chloride, and mixtures thereof.

Exemplary isotonic agents include sodium chloride, dextrose, and combinations or mixtures thereof.

Exemplary antioxidants include ascorbic acid, sodium bisulfate, and combinations or mixtures thereof.

Exemplary suspending and dispersing agents include sodium carboxymethylcelluose, hydroxypropyl methylcellulose, polyvinylpyrrolidone, any combinations or mixtures thereof.

Exemplary emulsifying agents include anionic emulsifying agents (e.g., sodium lauryl sulfate, sodium stearate, calcium oleate, and combinations or mixtures thereof), cationic emulsifying agents (e.g., cetrimide), and non-ionic emulsifying agents (e.g., Polysorbate 80) (Tween 80)).

Exemplary sequestering or chelating agents of metal ions include ethylenediaminetetraacetic acid (EDTA), citric acid, sorbitol, tartaric acid, phosphoric acid, and the like.

Suitable surfactants include, but are not limited to, sodium stearyl fumarate, diethanolamine cetyl sulfate, polyethylene glycol, isostearate, polyethoxylated castor oil, benzalkonium chloride, nonoxyl 10, octoxynol 9, polyoxyethylene sorbitan fatty acids (polysorbate 20, 40, 60 and 80), sodium lauryl sulfate, sorbitan esters (sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate, sorbitan tri-isostearate), lecithin pharmaceutical acceptable salts thereof and combinations thereof. When one or more surfactants are utilized in the formulations of the invention, they may be combined, e.g., with a pharmaceutically acceptable vehicle and may be present in the final formulation, e.g., in an amount ranging from about 0.1% to about 20%, more preferably from about 0.5% to about 10%. In certain other embodiments, a surfactant can preferably be combined with one or more of the pharmaceutically acceptable vehicles previously described herein so that the surfactant or buffering agent prevents the initial stinging or burning discomfort associated with capsaicinoid administration, as a wetting agent, emulsifier, solubilizer and/or antimicrobial.

Buffering agents may also be used to provide drug stability; to control the therapeutic activity of the drug substance (Ansel, Howard C., "Introduction to Pharmaceutical Dosage Forms," 4th Ed., 1985); and/or to prevent the initial stinging or burning discomfort associated with capsaicin administration. Suitable buffers include, but are not limited to, sodium bicarbonate, sodium citrate, citric acid, sodium phosphate, pharmaceutically acceptable salts thereof, and combinations thereof. When one or more buffers are utilized in the formulations of the invention, they may be combined, e.g., with a pharmaceutically acceptable vehicle and may be present in the final formulation, e.g., in an amount ranging from about 0.1% to about 20%, more preferably from about 0.5% to about 10%. In certain embodiments, the buffer is an acetate salt, phosphate salt, citrate salt; corresponding acids of the foregoing; and combinations or mixtures thereof.

In certain embodiments, the pharmaceutical vehicle utilized to deliver the injectable capsaicin may comprise about 20% PEG 300, about 10 mM histidine and about 5% sucrose in water for injection. In certain other embodiments, the pharmaceutical vehicle utilized to deliver the injectable capsaicin may comprise about 30-50% PEG 300. This may be used as such or further diluted in water for injection to achieve a larger volume.

The injectable formulation may be further characterized according to the concentration of capsaicin in the formulation. In certain embodiments, the injectable formulation contains the capsaicin at a concentration ranging from about 0.01 mg/mL to about 4 mg/mL, about 0.05 mg/mL to about 3 mg/mL, about 0.1 mg/mL to about 2 mg/mL, about 0.15 mg/mL to about 2 mg/mL, about 0.2 mg/mL to about 0.8 mg/mL, about 0.25 mg/mL to about 0.6 mg/mL, about 0.25 mg/mL to about 0.5 mg/mL, about 0.3 mg/mL to about 0.5 mg/mL, about 0.3 mg/mL to about 0.4 mg/mL, about 0.35 mg/mL to about 0.45 mg/mL, or about 0.375 mg/mL to about 0.425 mg/mL. In certain preferred embodiments, the injectable formulation contains capsaicin at a concentration ranging from about 0.05 mg/mL to about 0.15 mg/mL, or about 0.3 mg/mL to about 0.4 mg/mL. In certain other preferred embodiments, the injectable formulation contains capsaicin at a concentration of about 0.1 mg/mL.

In certain embodiments, the injectable formulation contains trans-capsaicin at a concentration ranging from about 0.01 mg/mL to about 4 mg/mL, about 0.05 mg/mL to about 3 mg/mL, about 0.1 mg/mL to about 2 mg/mL, about 0.15 mg/mL to about 2 mg/mL, about 0.2 mg/mL to about 0.8 mg/mL, about 0.25 mg/mL to about 0.6 mg/mL, about 0.25 mg/mL to about 0.5 mg/mL, about 0.3 mg/mL to about 0.5 mg/mL, about 0.3 mg/mL to about 0.4 mg/mL, about 0.35 mg/mL to about 0.45 mg/mL, or about 0.375 mg/mL to about 0.425 mg/mL. In certain preferred embodiments, the injectable formulation contains trans-capsaicin at a concentration ranging from about 0.05 mg/mL to about 0.15 mg/mL, or about 0.3 mg/mL to about 0.4 mg/mL. In certain other preferred embodiments, the injectable formulation contains trans-capsaicin at a concentration of about 0.1 mg/mL.

In certain embodiments, the injectable formulation contains the capsaicin at a concentration of about 0.1 mg/mL, 0.15 mg/mL, 0.2 mg/mL, 0.25 mg/mL, 0.3 mg/mL, 0.325 mg/mL, 0.35 mg/mL, 0.37 mg/mL, 0.38 mg/mL, 0.39 mg/mL, 0.4 mg/mL, 0.41 mg/mL, 0.42 mg/mL, 0.43 mg/mL, 0.44 mg/mL, 0.45 mg/mL, 0.475 mg/mL, 0.5 mg/mL, 0.55 mg/mL, 0.575 mg/mL, 0.6 mg/mL, 0.625 mg/mL, 0.65 mg/mL, 0.675 mg/mL, 0.7 mg/mL, 0.75 mg/mL, 0.8 mg/mL, 0.9 mg/mL, 1.0 mg/mL, 1.5 mg/mL, or 2.0 mg/mL. In certain preferred embodiments, the injectable formulation contains the capsaicin at a concentration of about 0.1 mg/mL.

The injectable formulation may be further characterized according to the solvent present to dissolve the capsaicin. In certain embodiments, the solvent in the injectable formulation is a mixture of water and polyethylene glycol (e.g., polyethylene glycol having a number-average molecular weight of about 300 g/mol). The relative amounts of water and polyethylene glycol in the injectable formulation may be characterized. For example, in certain embodiments, the injectable formulation contains a mixture of water and polyethylene glycol (e.g., polyethylene glycol having a number-average molecular weight of about 300 g/mol) as solvent, wherein upon a volume basis there is 3-6 times more water than polyethylene glycol. In certain embodiments, the injectable formulation contains a mixture of water and polyethylene glycol (e.g., polyethylene glycol having a number-average molecular weight of about 300 g/mol) as solvent, wherein upon a volume basis there is 4-5 times more water than polyethylene glycol. In certain embodiments, the polyethylene glycol has a number-average molecular weight in the range of about 250 g/mol to about 350 g/mol.

The injectable formulation may be further characterized according to the volume of injectable formulation administered to tissue proximal to the intermetatarsal neuroma. In certain embodiments, the volume of injectable formulation administered per unit dose is in the range of about 0.5 mL to about 5 mL, about 0.6 mL to about 4 mL, about 0.7 mL to about 3 mL, about 0.8 mL to about 2.5 mL, or about 1 mL to about 2 mL. In certain other embodiments, the volume of injectable formulation administered per unit dose is in the range of about 1.5 mL to about 2.5 mL. In certain other embodiments, the volume of injectable formulation administered per unit dose is about 2 mL.

The foregoing embodiments, may be combined to describe more specific injectable formulations. For example, in certain embodiments, the injectable formulation comprises trans-capsaicin at a concentration of about 0.1 mg/mL, water, and a polyethylene glycol (e.g., polyethylene glycol having a number-average molecular weight of 300 g/mol). In certain embodiments, the injectable formulation comprises trans-capsaicin at a concentration of about 0.1 mg/mL, water, and a polyethylene glycol having a number-average molecular weight of 300 g/mol), wherein upon a volume basis there is 4-5 times more water than polyethylene glycol. In certain embodiments, the injectable formulation consists essentially of trans-capsaicin at a concentration of about 0.1 mg/mL, water, and a polyethylene glycol having a number-average molecular weight of 300 g/mol, wherein upon a volume basis there is 4-5 times more water than polyethylene glycol.

V. POLYETHYLENE GLYCOL/WATER INJECTABLE FORMULATIONS

In certain embodiments, the methods described herein may administer the capsaicin in the form of a pharmaceutical composition. Such pharmaceutical composition may, in certain embodiments, further comprise water and a poly (ethylene glycol). In certain embodiments, the pharmaceutical composition comprising capsaicin consists essentially of water, capsaicin, and a poly(ethylene glycol). In certain embodiments, the poly(ethylene glycol) has a number-average molecular weight of about 300 g/mol. In certain embodiments, the poly(ethylene glycol) is present in an amount of about 30% by weight of the pharmaceutical formulation.

In certain embodiments, the pharmaceutical composition utilized to deliver capsaicin may comprise about 20% by weight PEG 300, about 10 mM histidine and about 5% sucrose in water for injection.

In certain other embodiments, the pharmaceutical composition utilized to deliver the capsaicin may comprise about 30-50% PEG 300. This may be used as such or further diluted in water for injection to achieve a larger volume.

VI. POLYETHYLENE GLYCOL ESTER/WATER INJECTABLE FORMULATIONS

Capsaisin aqueous injectable formulations containing a polyethylene glycol ester can be used in the methods described herein. A benefit of such capsaicin aqueous injectable formulations containing a polyethylene glycol ester is that they are stable to storage and can be administered directly to a patient via injection. A solubilizing agent containing a polyethylene glycol ester of a long-chain hydroxyalkanoic acid or a polyethylene glycol ester of a long-chain hydroxyalkenoic acid (such as a mixture containing a polyethylene glycol ester of 12-hydroxystearic acid, a polyethylene glycol ester of 12-((12-hydroxyoctadecanoyl)oxy) octadecanoic acid, and polyethylene glycol sold by BASF under the trade name KOLLIPHOR® HS 15) was determined to be able to solubilize greater amounts of capsaicin than other tested solubilizing agents in the aqueous medium at the desired pH range, and yet produced a formulation suitable for injection to a patient and that is sufficiently stable to storage that it may be used in the typical distribution routes for pharmaceutical agents. The above noted solubilizing agent is also superiorly compatible with capsaicin, which improves the stability of the formulation to storage. By contrast, polysorbates, such as Polysorbate 80, can have a greater propensity to form peroxides. Such peroxides can cause undesired oxidation of capsaicin, resulting in loss of capsaicin during storage of the formulation and increase in the amount and identity of impurities. The solubilizing agent specified above overcomes this deficiency of polysorbate. Additionally, the solubilizing agent noted above overcomes the adverse side effect of polysorbates, such as Polysorbate 80, of triggering release of histamine when administered to a patient.

Accordingly, one exemplary aqueous, capsaicin injectable formulation for use in the methods described herein comprises:
 a. about 0.03% (w/w) to about 0.3% (w/w) of capsaicin;
 b. about 0.1% (w/w) to about 3% (w/w) of a solubilizing agent, wherein the solubilizing agent comprises (i) a polyethylene glycol ester of a ($C_{15}$-$C_{25}$) hydroxyalkanoic acid, (ii) a polyethylene glycol ester of a ($C_{15}$-$C_{25}$) hydroxyalkenoic acid, or (iii) a polyethylene glycol ester of a ($C_{15}$-$C_{25}$) alkanoic acid substituted by a —OC(O)($C_{14}$-$C_{24}$) hydroxyalkyl group;
 c. about 0.001% (w/w) to about 2% (w/w) of an antioxidant; and
 d. at least 92% (w/w) water.

Another exemplary aqueous, capsaicin injectable formulation for use in the methods described herein comprises:
 a. about 0.01% (w/w) to about 0.5% (w/w) of capsaicin;
 b. about 0.01% (w/w) to about 5% (w/w) of a solubilizing agent, wherein the solubilizing agent comprises (i) a polyethylene glycol ester of a ($C_{15}$-$C_{25}$) hydroxyalkanoic acid, (ii) a polyethylene glycol ester of a ($C_{15}$-$C_{25}$) hydroxyalkenoic acid, or (iii) a polyethylene glycol ester of a ($C_{15}$-$C_{25}$) alkanoic acid substituted by a —OC(O)($C_{14}$-$C_{24}$) hydroxyalkyl group; and
 c. water.

Further description of exemplary components and features of the aqueous injectable formulations are described in more detail below.

Amount of Solubilizing Agent

The formulation can be further characterized according to the amount of solubilizing agent in the formulation. For example, in certain embodiments, the formulation comprises about 0.5% (w/w) to about 1.5% (w/w) of the solubilizing agent. In certain other embodiments, the formulation comprises about 0.8% (w/w) to about 1.2% (w/w) of the solubilizing agent. In certain other embodiments, the formulation comprises about 1% (w/w) of the solubilizing agent. In certain other embodiments, the formulation comprises about 1.5% (w/w) to about 2.5% (w/w) of the solubilizing agent. In certain other embodiments, the formulation comprises about 2% (w/w) of the solubilizing agent.

Identity of Solubilizing Agent

The formulation can be further characterized according to the identity of the solubilizing agent in the formulation. For example, in certain embodiments, the solubilizing agent comprises (i) a polyethylene glycol ester of a ($C_{15}$-$C_{25}$) hydroxyalkanoic acid, or (ii) a polyethylene glycol ester of a ($C_{15}$-$C_{25}$) hydroxyalkenoic acid. In certain embodiments, the solubilizing agent comprises a ($C_{14}$-$C_{24}$) hydroxyalkyl-$CO_2$-(polyethylene glycolyl)-H and ($C_{14}$-$C_{24}$) hydroxyalkyl-$CO_2$—($C_{14}$-$C_{24}$) alkylene-$CO_2$-(polyethylene glycolyl)-H. In certain embodiments, the solubilizing agent comprises a ($C_{14}$-$C_{24}$) hydroxyalkyl-$CO_2$-(polyethylene glycolyl)-H, ($C_{14}$-$C_{24}$) hydroxyalkyl-$CO_2$—($C_{14}$-$C_{24}$) alkylene-$CO_2$-(polyethylene glycolyl)-H, and polyethylene glycol. In certain embodiments, the solubilizing agent comprises (a) from about 60% (w/w) to about 80% (w/w) of a mixture of ($C_{14}$-$C_{24}$) hydroxyalkyl-$CO_2$-(polyethylene glycolyl)-H and ($C_{14}$-$C_{24}$) hydroxyalkyl-$CO_2$—($C_{14}$-$C_{24}$) alkylene-$CO_2$-(polyethylene glycolyl)-H, and (b) from about 20% (w/w) to about 40% (w/w) polyethylene glycol. In certain embodiments, the solubilizing agent comprises (a) about 70% (w/w) of a mixture of ($C_{14}$-$C_{24}$) hydroxyalkyl-$CO_2$-(polyethylene glycolyl)-H and ($C_{14}$-$C_{24}$) hydroxyalkyl-$CO_2$—($C_{14}$-$C_{24}$) alkylene-$CO_2$-(polyethylene glycolyl)-H, and (b) about 30% (w/w) polyethylene glycol. In certain embodiments, the solubilizing agent is a mixture of ($C_{14}$-$C_{24}$) hydroxyalkyl-$CO_2$-(polyethylene glycolyl)-H, ($C_{14}$-$C_{24}$) hydroxyalkyl-$CO_2$—($C_{14}$-$C_{24}$) alkylene-$CO_2$-(polyethylene glycolyl)-H, and polyethylene glycol. In certain embodiments, the solubilizing agent is a mixture of (a) from about 60% (w/w) to about 80% (w/w) of a mixture of ($C_{14}$-$C_{24}$) hydroxyalkyl-$CO_2$-(polyethylene glycolyl)-H and ($C_{14}$-$C_{24}$) hydroxyalkyl-$CO_2$—($C_{14}$-$C_{24}$) alkylene-$CO_2$-(polyethylene glycolyl)-H, and (b) from about 20% (w/w) to about 40% (w/w) polyethylene glycol. In certain embodiments, the solubilizing agent is a mixture of (a) about 70% (w/w) of a mixture of ($C_{14}$-$C_{24}$) hydroxyalkyl-$CO_2$-(polyethylene glycolyl)-H and ($C_{14}$-$C_{24}$) hydroxyalkyl-$CO_2$—($C_{14}$-$C_{24}$) alkylene-$CO_2$-(polyethylene glycolyl)-H, and (b) about 30% (w/w) polyethylene glycol.

In a more specific embodiment, the solubilizing agent comprises a ($C_{17}$) hydroxyalkyl-$CO_2$-(polyethylene glycolyl)-H and ($C_{17}$) hydroxyalkyl-$CO_2$—($C_{17}$) alkylene-$CO_2$-(polyethylene glycolyl)-H. In certain embodiments, the solubilizing agent comprises a ($C_{17}$) hydroxyalkyl-$CO_2$-(polyethylene glycolyl)-H, ($C_{17}$) hydroxyalkyl-$CO_2$—($C_{17}$) alkylene-$CO_2$-(polyethylene glycolyl)-H, and polyethylene glycol. In certain embodiments, the solubilizing agent comprises (a) from about 60% (w/w) to about 80% (w/w) of a mixture of ($C_{17}$) hydroxyalkyl-$CO_2$-(polyethylene glycolyl)-H and ($C_{17}$) hydroxyalkyl-$CO_2$—($C_{17}$) alkylene-$CO_2$-(polyethylene glycolyl)-H, and (b) from about 20% (w/w) to about 40% (w/w) polyethylene glycol. In certain embodiments, the solubilizing agent comprises (a) about 70% (w/w) of a mixture of ($C_{17}$) hydroxyalkyl-$CO_2$-(polyethylene glycolyl)-H and ($C_{17}$) hydroxyalkyl-$CO_2$—($C_{17}$) alkylene-$CO_2$-(polyethylene glycolyl)-H, and (b) about 30% (w/w) polyethylene glycol. In certain embodiments, the solubilizing agent is a mixture of (a) from about 60% (w/w) to about 80% (w/w) of a mixture of ($C_{17}$) hydroxyalkyl-$CO_2$-(polyethylene glycolyl)-H and ($C_{17}$) hydroxyalkyl-$CO_2$—($C_{17}$) alkylene-$CO_2$-(polyethylene glycolyl)-H, and (b) from about 20% (w/w) to about 40% (w/w) polyethylene glycol. In certain embodiments, the solubilizing agent is a mixture of (a) about 70% (w/w) of a mixture of ($C_{17}$) hydroxyalkyl-$CO_2$-(polyethylene glycolyl)-H and ($C_{17}$) hydroxyalkyl-$CO_2$—($C_{17}$) alkylene-$CO_2$-(polyethylene glycolyl)-H, and (b) about 30% (w/w) polyethylene glycol.

In certain embodiments, the mole ratio of (a) ($C_{14}$-$C_{24}$) hydroxyalkyl-$CO_2$-(polyethylene glycolyl)-H to (b) ($C_{14}$-$C_{24}$) hydroxyalkyl-$CO_2$—($C_{14}$-$C_{24}$) alkylene-$CO_2$-(polyethylene glycolyl)-H in the formulation is in the range of 10:1 to 1:10, 5:1 to 1:5, 2:1 to 1:2, 10:1 to 5:1, 5:1 to 2:1, 2:1 to 1:1, 1:1 to 1:2, 1:2 to 1:5, 1:5 to 1:10, or is greater than 10:1, or less than 1:1. In certain embodiments, the mole ratio of (a) ($C_{17}$) hydroxyalkyl-$CO_2$-(polyethylene glycolyl)-H to (b) ($C_{17}$) hydroxyalkyl-$CO_2$—($C_{17}$) alkylene-$CO_2$-(polyethylene glycolyl)-H in the formulation is in the range of 10:1 to 1:10, 5:1 to 1:5, 2:1 to 1:2, 10:1 to 5:1, 5:1 to 2:1, 2:1 to 1:1, 1:1 to 1:2, 1:2 to 1:5, 1:5 to 1:10, or is greater than 10:1, or less than 1:1.

In a more specific embodiment, the solubilizing agent comprises

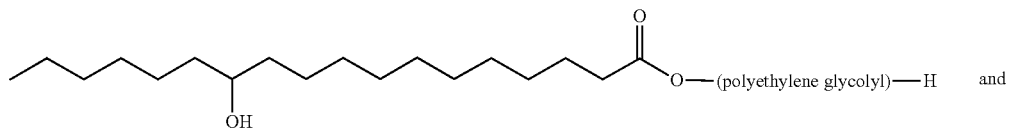

and

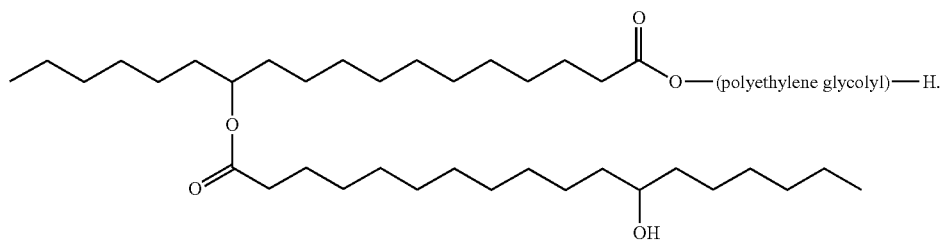

In another more specific embodiment, the solubilizing agent is a mixture of
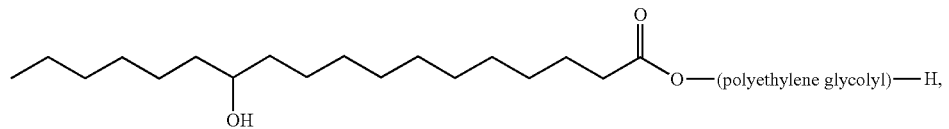
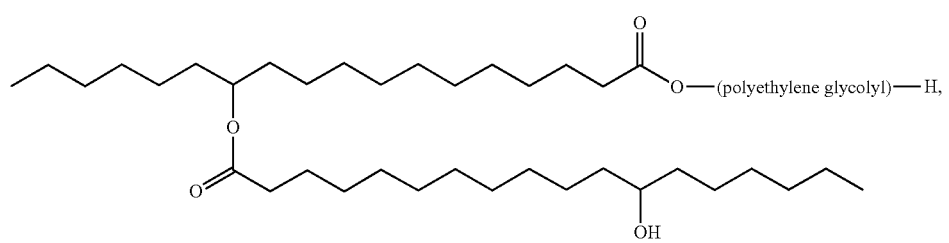
and polyethylene glycol. In certain other embodiments, the solubilizing agent comprises (a) about 70% (w/w) of a mixture of
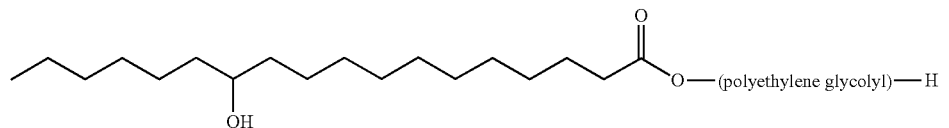
and
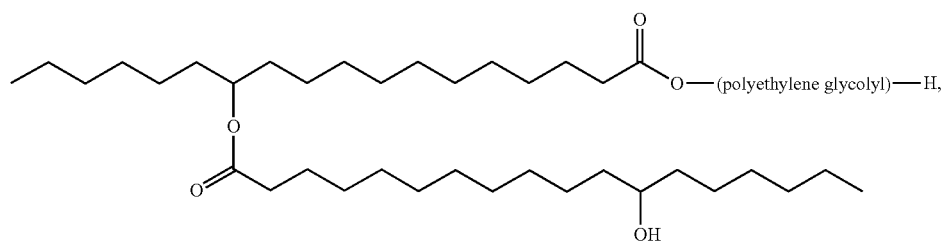
and (b) about 30% (w/w) polyethylene glycol. In certain other embodiments, the solubilizing agent is a mixture of (a) about 70% (w/w) of a mixture of
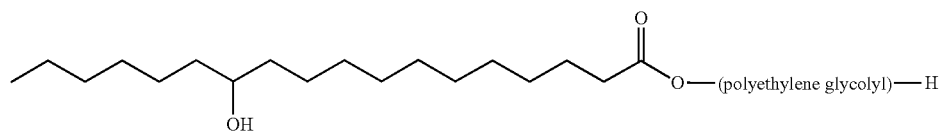

and

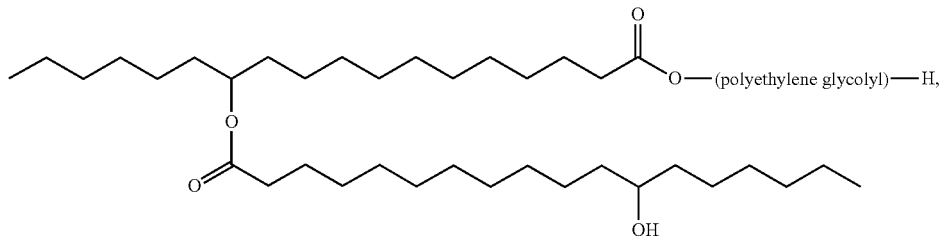

and (b) about 30% (w/w) polyethylene glycol. In certain other embodiments, the solubilizing agent comprises (a) from 68% (w/w) to 72% (w/w) of a mixture of

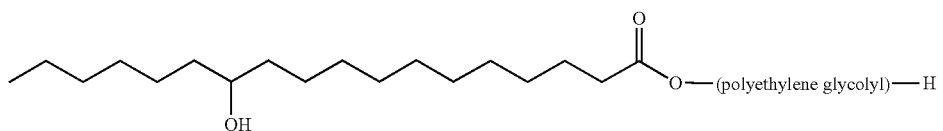

and

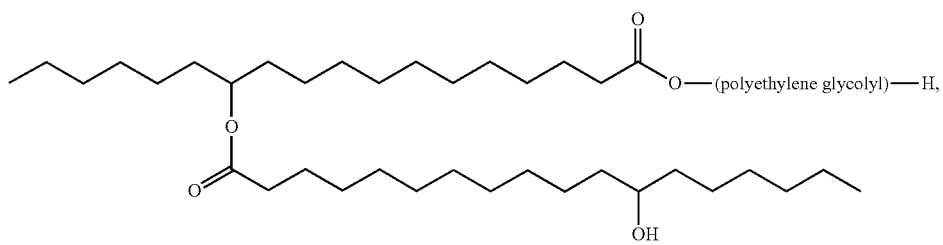

and (b) from 28% (w/w) to 32% (w/w) polyethylene glycol.

The above solubilizing agent can be further characterized according to the weight-average molecular weight of any polyethylene glycolyl component. For example, in certain embodiments, the polyethylene glycolyl has a weight-average molecular weight in the range of about 100 g/mol to about 3000 g/mol. In certain embodiments, the polyethylene glycolyl has a weight-average molecular weight in the range of about 200 g/mol to about 1500 g/mol. In certain embodiments, the polyethylene glycol has a weight-average molecular weight in the range of about 200 g/mol to about 1000 g/mol. In certain embodiments, the polyethylene glycolyl has a weight-average molecular weight in the range of about 300 g/mol to about 900 g/mol. In certain embodiments, the polyethylene glycolyl has a weight-average molecular weight in the range of about 500 g/mol to about 800 g/mol. In certain embodiments, the polyethylene glycolyl has a weight-average molecular weight in the range of about 600 g/mol to about 750 g/mol. In certain embodiments, the polyethylene glycolyl has a weight-average molecular weight in the range of about 600 g/mol to about 700 g/mol. In certain embodiments, the polyethylene glycolyl has a weight-average molecular weight of about 660 g/mol. In certain embodiments, the polyethylene glycolyl has a weight-average molecular weight in the range of about 100 g/mol to about 300 g/mol, about 300 g/mol to about 500 g/mol, about 500 g/mol to about 1000 g/mol, about 1000 g/mol to about 1500 g/mol, about 1500 g/mol to about 2000 g/mol, or about 2000 g/mol to about 2500 g/mol.

The above solubilizing agent can be further characterized according to the weight-average molecular weight of any polyethylene glycol component. For example, in certain embodiments, the polyethylene glycol has a weight-average molecular weight in the range of about 100 g/mol to about 3000 g/mol. In certain embodiments, the polyethylene glycol has a weight-average molecular weight in the range of about 200 g/mol to about 1500 g/mol. In certain embodiments, the polyethylene glycol has a weight-average molecular weight in the range of about 200 g/mol to about 1000 g/mol. In certain embodiments, the polyethylene glycol has a weight-average molecular weight in the range of about 300 g/mol to about 900 g/mol. In certain embodiments, the polyethylene glycol has a weight-average molecular weight in the range of about 500 g/mol to about 800 g/mol. In certain embodiments, the polyethylene glycol has a weight-average molecular weight in the range of about 600 g/mol to about 750 g/mol. In certain embodiments, the polyethylene glycol has a weight-average molecular weight in the range of about 600 g/mol to about 700 g/mol. In certain embodiments, the polyethylene glycol has a weight-average molecular weight of about 660 g/mol. In certain embodiments, the polyethylene glycol has a weight-average molecular weight in the range of about 100 g/mol to about 300 g/mol, about 300 g/mol to about 500 g/mol, about 500 g/mol to about 1000 g/mol, about 1000 g/mol to about 1500 g/mol, about 1500 g/mol to about 2000 g/mol, or about 2000 g/mol to about 2500 g/mol.

In yet other embodiments, any polyethylene glycol or polyethylene glycolyl each independently have a weight-average molecular weight in the range of about 100 g/mol to about 3000 g/mol. In certain embodiments, any polyethylene glycol or polyethylene glycolyl each independently have a weight-average molecular weight in the range of about 200 g/mol to about 1500 g/mol. In certain embodiments, any polyethylene glycol or polyethylene glycolyl each independently have a weight-average molecular weight in the range of about 200 g/mol to about 1000 g/mol. In certain embodiments, any polyethylene glycol or polyethylene glycolyl each independently have a weight-average molecular weight in the range of about 300 g/mol to about 900 g/mol. In certain embodiments, any polyethylene glycol or polyethylene glycolyl each independently have a weight-average molecular weight in the range of about 500 g/mol to about 800 g/mol. In certain embodiments, any polyethylene glycol or polyethylene glycolyl each independently have a weight-average molecular weight in the range of about 600 g/mol to about 750 g/mol. In certain embodiments, any polyethylene glycol or polyethylene glycolyl each independently have a weight-average molecular weight in the range of about 600 g/mol to about 700 g/mol. In certain embodiments, any polyethylene glycol or polyethylene glycolyl each independently have a weight-average molecular weight of about 660 g/mol. In certain embodiments, any polyethylene glycol or polyethylene glycolyl each independently have a weight-average molecular weight in the range of about 100 g/mol to about 300 g/mol, about 300 g/mol to about 500 g/mol, about 500 g/mol to about 1000 g/mol, about 1000 g/mol to about 1500 g/mol, about 1500 g/mol to about 2000 g/mol, or about 2000 g/mol to about 2500 g/mol.

Antioxidant

The formulation can be further characterized according to the antioxidant in the formulation. For example, in certain embodiments, the formulation comprises about 0.005% (w/w) to about 0.1% (w/w) of an antioxidant. In certain embodiments, the formulation comprises about 0.01% (w/w) of an antioxidant. In certain embodiments, the antioxidant is an organic compound. In certain embodiments, the antioxidant is a substituted phenol. In certain embodiments, the antioxidant is a phenolic antioxidant. In certain embodiments, the antioxidant is dibutylhydroxytoluene.

Chelating Agent

The formulation may optionally further comprise a chelating agent. Accordingly, in certain embodiments, the formulation further comprises a chelating agent. In certain embodiments, the formulation comprises about 0.001% (w/w) to about 0.5% (w/w) of a chelating agent. In certain embodiments, the formulation comprises about 0.01% (w/w) to about 0.05% (w/w) of a chelating agent. In certain embodiments, the formulation comprises about 0.025% (w/w) of a chelating agent.

Exemplary chelating agents include, but are not limited to, ethylenediaminetetraacetic acid (EDTA), citric acid, sorbitol, tartaric acid, phosphoric acid, salts of the foregoing, and the like. In certain embodiments, the chelating agent is an aliphatic amine compound containing at least two carboxylic acid groups. In certain embodiments, the chelating agent is ethylenediaminetetraacetic acid or a salt thereof.

In certain embodiments, the chelating agent is a metal ion chelating agent.

In certain embodiments, the combination of an antioxidant and a chelating agent (e.g., ethylenediaminetetraacetic acid or salt thereof) can increase the stability of an aqueous capsaicin formulation.

Buffer

The formulation may optionally further comprise a buffer. The buffer helps reduce changes in pH of the formulation over time and may provide improved drug stability. Exemplary buffers include, but are not limited to, sodium bicarbonate, sodium citrate, citric acid, sodium phosphate, pharmaceutically acceptable salts thereof, and combinations thereof. In certain embodiments, the buffer is an acetate salt, phosphate salt, citrate salt; corresponding acids of the foregoing; and combinations or mixtures thereof.

Accordingly, in certain embodiments, the formulation further comprises a buffer. In certain embodiments, the buffer comprises a carboxylic acid compound having a molecular weight less than 500 g/mol, a salt thereof, or a mixture thereof. In certain embodiments, the buffer comprises a $C_1$-$C_6$ alkanoic acid, a salt thereof, or a mixture thereof. In certain embodiments, the buffer comprises acetic acid, a salt of acetic acid, or a mixture thereof.

Osmolality

The formulation may be further characterized according to the osmolality of the formulation. Formulations having an osmolality at or near the osmolality of a typical bodily fluid are referred to as isotonic. Formulations having an osmolality greater than the osmolality of a typical bodily fluid are referred to as hypertonic. Formulations having an osmolality less than the osmolality of a typical bodily fluid are referred to as hypotonic.

The osmolality of the formulation may be optionally adjusted by including a tonicity modifier. Accordingly, in certain embodiments, the formulation further comprises a tonicity modifier. In certain embodiments, the formulation comprises about 0.01% (w/w) to about 5% (w/w) of a tonicity modifier. In certain embodiments, the formulation comprises about 0.1% (w/w) to about 2% (w/w) of a tonicity modifier. In certain embodiments, the formulation comprises about 0.3% (w/w) to about 0.9% (w/w) of a tonicity modifier.

In certain embodiments, the tonicity modifier is an alkali metal salt. In certain embodiments, the tonicity modifier is sodium chloride. In certain embodiments, the tonicity modifier is a monosaccharide. In certain embodiments, the tonicity modifier is dextrose.

Formulations may be characterized according to an osmolality threshold or range. For example, in certain embodiments, the formulation may have an osmolality of at least 200 mOsm/kg, 220 mOsm/kg, 240 mOsm/kg, 260 mOsm/kg, 280 mOsm/kg, 300 mOsm/kg, 325 mOsm/kg, 350 mOsm/kg, 375 mOsm/kg, 400 mOsm/kg, 425 mOsm/kg, 450 mOsm/kg, 500 mOsm/kg, 600 mOsm/kg, 700 mOsm/kg, 800 mOsm/kg, 900 mOsm/kg, or 1000 mOsm/kg. In certain embodiments, the formulation has osmolality of at least 240 mOsm/kg. In certain embodiments, the formulation has osmolality of at least 270 mOsm/kg.

In certain embodiments, the formulation has an osmolality in the range of from about 200 mOsm/kg to about 400 mOsm/kg, from about 240 mOsm/kg to about 350 mOsm/kg, from about 240 mOsm/kg to about 340 mOsm/kg, from about 270 mOsm/kg to about 340 mOsm/kg, from about 270 mOsm/kg to about 330 mOsm/kg, from about 270 mOsm/kg to about 310 mOsm/kg, from about 290 mOsm/kg to about 330 mOsm/kg, from about 280 mOsm/kg to about 300 mOsm/kg, or from about 300 mOsm/kg to about 320 mOsm/kg. In certain embodiments, the formulation has an osmolality in the range of from about 240 mOsm/kg to about 340 mOsm/kg. In certain other embodiments, the formulation has an osmolality in the range from about 270 mOsm/kg to about 330 mOsm/kg.

In certain embodiments, the formulation has osmolality of about 200 mOsm/kg, about 220 mOsm/kg, about 240 mOsm/kg, about 250 mOsm/kg, about 260 mOsm/kg, about 270 mOsm/kg, about 280 mOsm/kg, about 290 mOsm/kg, about 300 mOsm/kg, about 310 mOsm/kg, about 320 mOsm/kg, about 330 mOsm/kg, about 340 mOsm/kg, about 350 mOsm/kg, about 360 mOsm/kg, about 370 mOsm/kg, or about 380 mOsm/kg. In a preferred embodiment, the formulation has osmolality of about 290 mOsm/kg. In another preferred embodiment, the formulation has osmolality of about 310 mOsm/kg.

Amount of Water

The formulation may be further characterized according to the amount of water in the formulation. For example, in certain embodiments, the formulation comprises at least 95% (w/w) water. In certain embodiments, the formulation comprises at least 97% (w/w) water. In certain embodiments, the formulation comprises from about 95% (w/w) to about 99% (w/w) water. In certain embodiments, the formulation comprises from about 97% (w/w) to about 98% (w/w) water. In certain embodiments, the formulation comprises from about 93% (w/w) to about 96% (w/w) water.

pH of the Formulation

The formulation may be further characterized according to the pH of the formulation. For example, in certain embodiments, the formulation has a pH in the range of about 4 to about 7. In certain embodiments, the formulation has a pH in the range of about 5 to about 6. In certain embodiments, the formulation has a pH of about 5.1, 5.2, 5.3, 5.4, 5.5, 5.6, 5.7, 5.8., or 5.9. In certain embodiments, the formulation has a pH of about 5.5.

Capsaicin

Capsaicin has the chemical name N-[(4-hydroxy-3-methoxyphenyl)methyl]-8-methylnon-6-enamide, and due to the presence of a carbon-carbon double bond can exist as a mixture of cis and trans isomers. The formulations may be characterized according to the isomeric purity of the capsaicin administered to the patient. For example, in certain embodiments, the capsaicin is a mixture of cis-capsaicin and trans-capsaicin that contains at least 95% by weight trans-capsaicin. In certain embodiments, the capsaicin is a mixture of cis-capsaicin and trans-capsaicin that contains at least 97% by weight trans-capsaicin. In certain embodiments, the capsaicin is a mixture of cis-capsaicin and trans-capsaicin that contains at least 98% by weight trans-capsaicin. In certain embodiments, the capsaicin is a mixture of cis-capsaicin and trans-capsaicin that contains at least 99% by weight trans-capsaicin. In certain other embodiments, the capsaicin is a mixture of cis-capsaicin and trans-capsaicin that contains at least 95% by weight cis-capsaicin.

The isomeric purity of capsaicin may also be expressed according to the molar ratio of trans vs. cis isomer. Accordingly, in certain embodiments, the capsaicin is present as a mixture of trans and cis isomers, wherein the ratio of trans:cis isomers is at least 10:1. In certain embodiments, the ratio of trans:cis isomers is at least 15:1. In certain embodiments, the capsaicin consists essentially of the trans isomer.

The formulation may be further characterized according to the amount of capsaicin in the formulation. For example, in certain embodiments, the formulation comprises from about 0.03% (w/w) to about 0.15% (w/w) of capsaicin. In certain embodiments, the formulation comprises from about 0.03% (w/w) to about 0.07% (w/w) of capsaicin. In certain embodiments, the formulation comprises from about 0.01% (w/w) to about 0.03% (w/w) of capsaicin, 0.03% (w/w) to about 0.05% (w/w) of capsaicin, 0.05% (w/w) to about 0.07% (w/w) of capsaicin, 0.07% (w/w) to about 0.09% (w/w) of capsaicin, 0.09% (w/w) to about 0.11% (w/w) of capsaicin, or 0.11% (w/w) to about 0.13% (w/w) of capsaicin. In certain embodiments, the formulation comprises about 0.05% (w/w) of capsaicin. In certain embodiments, the formulation comprises from about 0.08% (w/w) to about 0.12% (w/w) of capsaicin. In certain embodiments, the formulation comprises from about 0.12% (w/w) to about 0.15% (w/w) of capsaicin, from about 0.15% (w/w) to about 0.18% (w/w) of capsaicin, from about 0.18% (w/w) to about 0.21% (w/w) of capsaicin, from about 0.21% (w/w) to about 0.25% (w/w) of capsaicin, or from about 0.25% (w/w) to about 0.3% (w/w) of capsaicin. In certain embodiments, the formulation comprises about 0.1% (w/w) of capsaicin.

Additional Pain-Relief Agent

The formulation may optionally contain a further pain-relief agent. For example, in certain embodiments, the formulation may further comprise a caine alkaloid. Exemplary caine alkaloids include lidocaine, dibucaine, bupivacaine, ropivacaine, etidocaine, tetracaine, procaine, chlorocaine, prilocaine, mepivacaine, xylocaine, 2-chloroprocaine, and pharmaceutically acceptable salts thereof. In certain embodiments, the formulation further comprises lidocaine, such as where the lidocaine is present in an amount of about 0.5% (w/w), 1.0% (w/w), 2.0% (w/w), 3.0% (w/w) or 4.0% (w/w) of the formulation, or in an amount ranging from about 0.5% (w/w) to about 2.0% (w/w), or about 2.0% (w/w) to about 4.0% (w/w) of the formulation.

Exemplary Formulations

In certain embodiments, the formulation is one of the formulations in Table 1 below.

TABLE 1

| No. | Formulation |
|---|---|
| 1 | An aqueous, capsaicin injectable formulation, comprising:<br>a. about 0.03% (w/w) to about 0.3% (w/w) of capsaicin;<br>b. about 0.1% (w/w) to about 3% (w/w) of a solubilizing agent, wherein the solubilizing agent comprises (i) a polyethylene glycol ester of a ($C_{15}$-$C_{25}$) hydroxyalkanoic acid, (ii) a polyethylene glycol ester of a ($C_{15}$-$C_{25}$) hydroxyalkenoic acid, or (iii) a polyethylene glycol ester of a ($C_{15}$-$C_{25}$) alkanoic acid substituted by a —OC(O)($C_{14}$-$C_{24}$) hydroxyalkyl group;<br>c. about 0.001% (w/w) to about 2% (w/w) of an antioxidant; and<br>d. at least 92% (w/w) water; and<br>having a pH in the range of about 3 to about 8. |
| 2 | An aqueous, capsaicin injectable formulation, comprising:<br>a. about 0.04% (w/w) to about 0.06% (w/w) of capsaicin;<br>b. about 0.7% (w/w) to about 1.3% (w/w) of a solubilizing agent, wherein the solubilizing agent comprises (i) a polyethylene glycol ester of a ($C_{15}$-$C_{25}$) hydroxyalkanoic acid, or (ii) a polyethylene glycol ester of a ($C_{15}$-$C_{25}$) hydroxyalkenoic acid;<br>c. about 0.001% (w/w) to about 0.1% (w/w) of an antioxidant; and<br>d. at least 92% (w/w) water; and<br>having a pH in the range of about 4 to about 7. |
| 3 | An aqueous, capsaicin injectable formulation, comprising:<br>a. about 0.04% (w/w) to about 0.06% (w/w) of trans-capsaicin;<br>b. about 0.7% (w/w) to about 1.3% (w/w) of a solubilizing agent, wherein the solubilizing agent comprises (a) from about 60% (w/w) to about 80% (w/w) of a mixture of ($C_{17}$)hydroxyalkyl-$CO_2$-(polyethylene glycolyl)-H and ($C_{17}$)hydroxyalkyl-$CO_2$-($C_{17}$) alkylene-$CO_2$-(polyethylene glycolyl)-H, and (b) from about 20% (w/w) to about 40% (w/w) polyethylene glycol; |

TABLE 1-continued

| No. | Formulation |
|---|---|
| | c. about 0.001% (w/w) to about 0.1% (w/w) of an antioxidant; and<br>d. at least 95% (w/w) water; and<br>having a pH in the range of about 4 to about 7. |
| 4 | An aqueous, capsaicin injectable formulation, comprising:<br>a. about 0.08% (w/w) to about 0.12% (w/w) of capsaicin;<br>b. about 1.8% (w/w) to about 2.2% (w/w) of a solubilizing agent, wherein the solubilizing agent comprises (i) a polyethylene glycol ester of a ($C_{15}$-$C_{25}$) hydroxyalkanoic acid, or (ii) a polyethylene glycol ester of a ($C_{15}$-$C_{25}$) hydroxyalkenoic acid;<br>c. about 0.001% (w/w) to about 0.1% (w/w) of an antioxidant; and<br>d. at least 93% (w/w) water; and<br>having a pH in the range of about 4 to about 7. |
| 5 | An aqueous, capsaicin injectable formulation, comprising:<br>a. about 0.08% (w/w) to about 0.12% (w/w) of capsaicin;<br>b. about 1.8% (w/w) to about 2.2% (w/w) of a solubilizing agent, wherein the solubilizing agent comprises (a) from about 60% (w/w) to about 80% (w/w) of a mixture of ($C_{17}$)hydroxyalkyl-$CO_2$-(polyethylene glycolyl)-H and ($C_{17}$)hydroxyalkyl-$CO_2$-($C_{17}$)alkylene-$CO_2$-(polyethylene glycolyl)-H, and (b) from about 20% (w/w) to about 40% (w/w) polyethylene glycol;<br>c. about 0.001% (w/w) to about 0.1% (w/w) of an antioxidant; and<br>d. at least 93% (w/w) water; and<br>having a pH in the range of about 4 to about 7. |

Exemplary more specific formulations are provided in Tables 2 and 3 below.

TABLE 2

| No. | Formulation |
|---|---|
| 1 | An aqueous, capsaicin injectable formulation, comprising:<br>a. about 0.04% (w/w) to about 0.06% (w/w) of capsaicin;<br>b. about 0.5% (w/w) to about 1.5% (w/w) of a solubilizing agent, wherein the solubilizing agent comprises polyethylene glycol; |

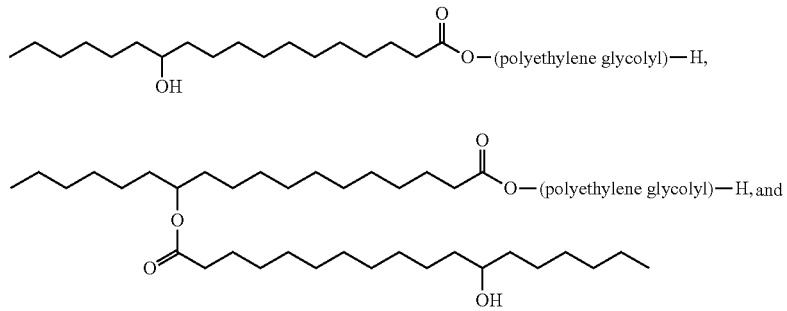

c. about 0.005% (w/w) to about 0.015% (w/w) of an antioxidant;
d. about 0.3% (w/w) to about 1% (w/w) of an alkali metal acetate;
e. about 0.01% (w/w) to about 0.05% (w/w) of a chelating agent;
f. about 0.3% (w/w) to about 0.9% (w/w) of a tonicity modifier;
g. at least 95% (w/w) water; and
having a pH in the range of about 5 to about 6.

2  An aqueous, capsaicin injectable formulation, comprising:
a. about 0.04% (w/w) to about 0.06% (w/w) of capsaicin;
b. about 0.8% (w/w) to about 1.2% (w/w) of a solubilizing agent, wherein the solubilizing agent comprises

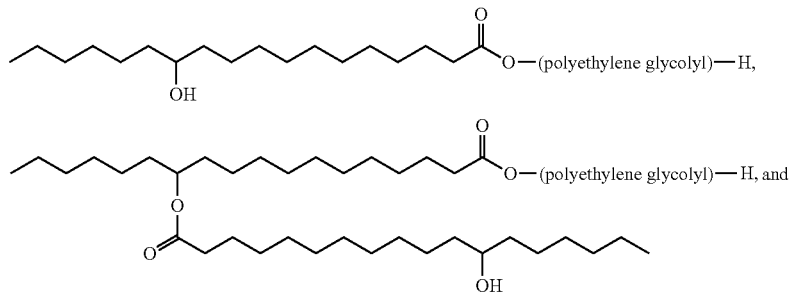

polyethylene glycol;
c. about 0.005% (w/w) to about 0.015% (w/w) of dibutylhydroxytoluene;
d. about 0.3% (w/w) to about 1% (w/w) of sodium acetate;
e. about 0.01% (w/w) to about 0.05% (w/w) of ethylenediaminetetraacetic acid or a salt thereof;
f. about 0.3% (w/w) to about 0.9% (w/w) of sodium chloride;
g. at least 95% (w/w) water; and
having a pH in the range of about 5 to about 6.

TABLE 2-continued

| No. | Formulation |
|---|---|
| 3 | An aqueous, capsaicin injectable formulation, comprising:<br>a. about 0.05% (w/w) of trans-capsaicin;<br>b. about 1% (w/w) of a solubilizing agent, wherein the solubilizing agent comprises<br>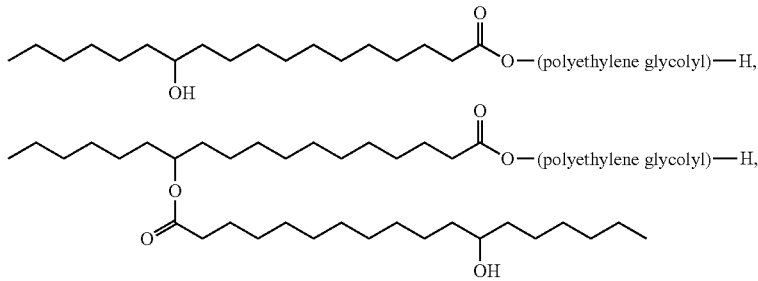<br>and polyethylene glycol;<br>c. about 0.01% (w/w) dibutylhydroxytoluene;<br>d. about 0.5% (w/w) to about 0.8% (w/w) of sodium acetate;<br>e. about 0.01% (w/w) to about 0.05% (w/w) of ethylenediaminetetraacetic acid or a salt thereof;<br>f. about 0.3% (w/w) to about 0.9% (w/w) of sodium chloride;<br>g. at least 95% (w/w) water; and<br>having a pH in the range of about 5 to about 6. |
| 4 | An aqueous, capsaicin injectable formulation, comprising:<br>a. about 0.08% (w/w) to about 0.12% (w/w) of capsaicin;<br>b. about 1.5% (w/w) to about 2.5% (w/w) of a solubilizing agent, wherein the solubilizing agent comprises<br>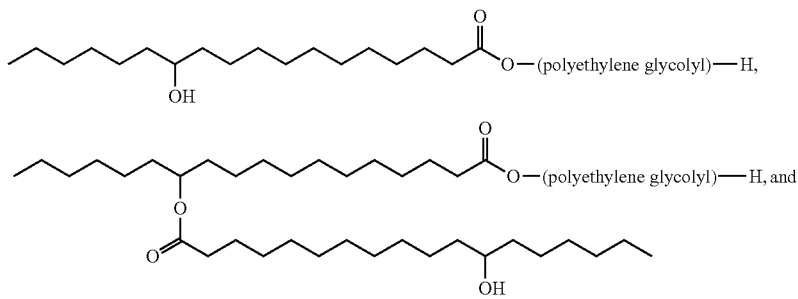<br>polyethylene glycol;<br>c. about 0.005% (w/w) to about 0.015% (w/w) of an antioxidant;<br>d. about 0.1% (w/w) to about 1% (w/w) of an alkali metal carboxylate compound;<br>e. about 0.01% (w/w) to about 0.5% (w/w) of a chelating agent;<br>f. about 2% (w/w) to about 4% (w/w) of a tonicity modifier;<br>g. at least 93% (w/w) water; and<br>having a pH in the range of about 5 to about 6. |
| 5 | An aqueous, capsaicin injectable formulation, comprising:<br>a. about 0.08% (w/w) to about 0.12% (w/w) of capsaicin;<br>b. about 1.8% (w/w) to about 2.2% (w/w) of a solubilizing agent, wherein the solubilizing agent comprises<br>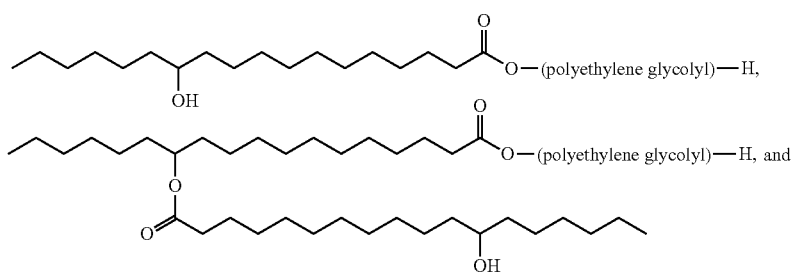<br>polyethylene glycol;<br>c. about 0.005% (w/w) to about 0.015% (w/w) of an antioxidant;<br>d. about 0.1% (w/w) to about 1% (w/w) of an alkali metal carboxylate compound; |

TABLE 2-continued

| No. | Formulation |
|---|---|
| | e. about 0.01% (w/w) to about 0.5% (w/w) of a chelating agent; |
| | f. about 2% (w/w) to about 4% (w/w) of a tonicity modifier; |
| | g. at least 93% (w/w) water; and |
| | having a pH in the range of about 5 to about 6. |
| 6 | An aqueous, capsaicin injectable formulation, comprising: |
| | a. about 0.1% (w/w) of capsaicin; |
| | b. about 2% (w/w) of a solubilizing agent, wherein the solubilizing agent comprises |

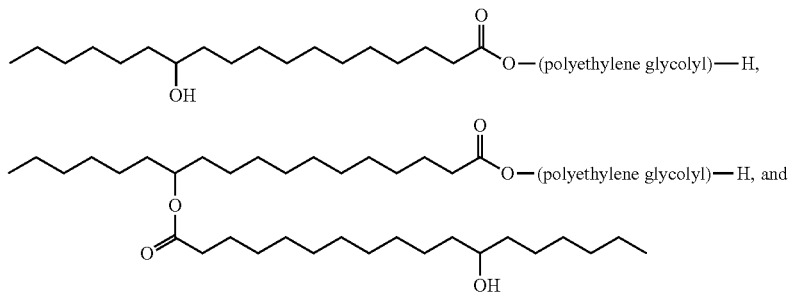

polyethylene glycol;
c. about 0.005% (w/w) to about 0.015% (w/w) of an antioxidant;
d. about 0.1% (w/w) to about 1% (w/w) of an alkali metal carboxylate compound;
e. about 0.01% (w/w) to about 0.5% (w/w) of a chelating agent;
f. about 2.5% (w/w) to about 3.5% (w/w) of a tonicity modifier;
g. at least 93% (w/w) water; and
having a pH in the range of about 5 to about 6.

TABLE 3

| No. | Formulation |
|---|---|
| 1 | An aqueous, capsaicin injectable formulation, comprising:<br>a. about 0.1% (w/w) of capsaicin;<br>b. about 2% (w/w) of a solubilizing agent, wherein the solubilizing agent comprises |

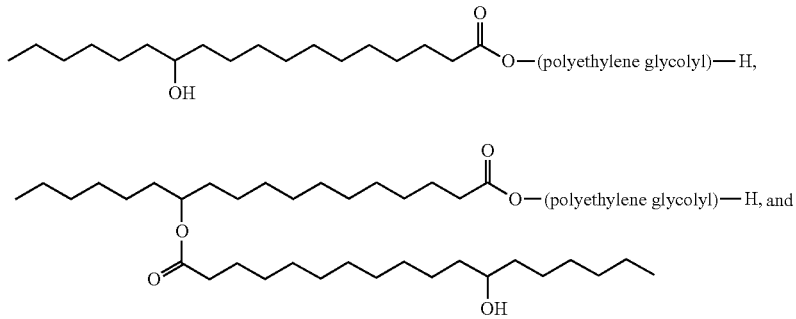

polyethylene glycol;
c. about 0.01% (w/w) of an antioxidant;
d. about 0.1% (w/w) to about 1% (w/w) of an alkali metal citrate salt;
e. about 0.1% (w/w) of a chelating agent;
f. about 3% (w/w) of a tonicity modifier; and
g. at least 93% (w/w) water.

TABLE 3-continued

| No. | Formulation |
|---|---|
| 2 | An aqueous, capsaicin injectable formulation, comprising:<br>a. about 0.1% (w/w) of capsaicin;<br>b. about 2% (w/w) of a solubilizing agent, wherein the solubilizing agent comprises<br>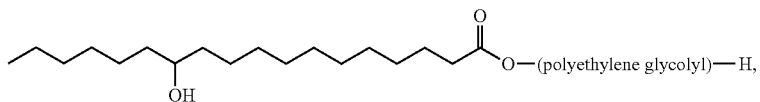<br>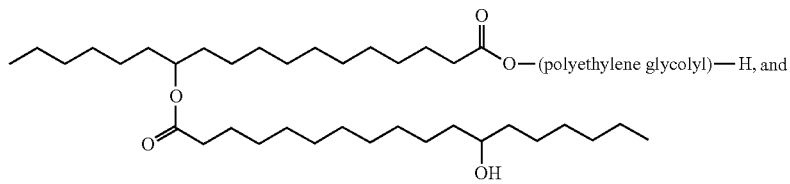<br>polyethylene glycol;<br>c. about 0.01% (w/w) of dibutylhydroxytoluene;<br>d. about 0.1% (w/w) to about 1% (w/w) of a disodium citrate salt;<br>e. about 0.1% (w/w) of ethylenediaminetetraacetic acid or a salt thereof;<br>f. about 3% (w/w) of dextrose;<br>g. at least 93% (w/w) water; and<br>having a pH in the range of about 5 to about 6. |
| 3 | An aqueous, capsaicin injectable formulation, comprising:<br>a. about 0.1% (w/w) of trans-capsaicin;<br>b. about 2% (w/w) of a solubilizing agent, wherein the solubilizing agent that comprises<br>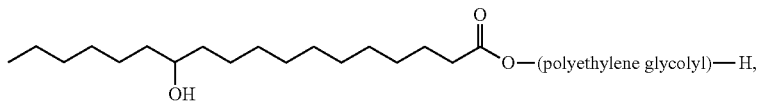<br>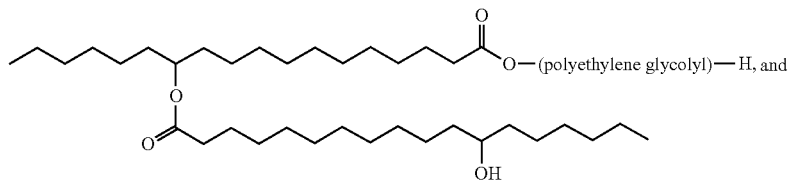<br>polyethylene glycol;<br>c. about 0.01% (w/w) of dibutylhydroxytoluene;<br>d. about 0.1% (w/w) to about 1% (w/w) of a disodium citrate salt;<br>e. about 0.1% (w/w) of ethylenediaminetetraacetic acid or a salt thereof;<br>f. about 3% (w/w) of dextrose;<br>g. at least 93% (w/w) water; and<br>having a pH in the range of about 5 to about 6. |

In yet other embodiments, the aqueous, capsaicin injectable formulation comprises (a) about 0.04% (w/w) to about 0.06% (w/w) of capsaicin; (b) about 0.5% (w/w) to about 1.5% (w/w) of a solubilizing agent, wherein the solubilizing agent comprises

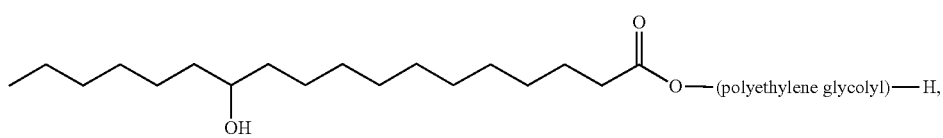

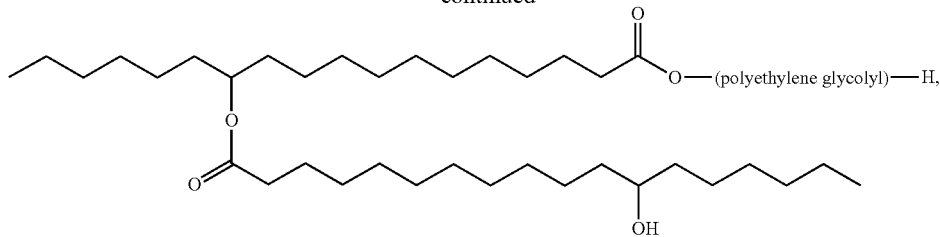

and polyethylene glycol; (c) about 0.005% (w/w) to about 0.015% (w/w) of an antioxidant; (d) about 0.2% (w/w) to about 1% (w/w) of an alkali metal acetate; (e) about 0.01% (w/w) to about 0.05% (w/w) of a chelating agent; (f) about 0.3% (w/w) to about 0.9% (w/w) of a tonicity modifier; and (g) at least 96% (w/w) water; and having a pH in the range of about 5 to about 6.

In other embodiments, the aqueous, capsaicin injectable formulation comprises (a) about 0.04% (w/w) to about 0.06% (w/w) of capsaicin; (b) about 0.8% (w/w) to about 1.2% (w/w) of a solubilizing agent, wherein the solubilizing agent comprises

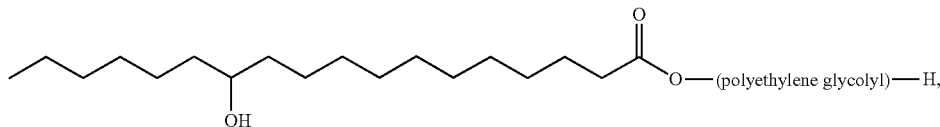

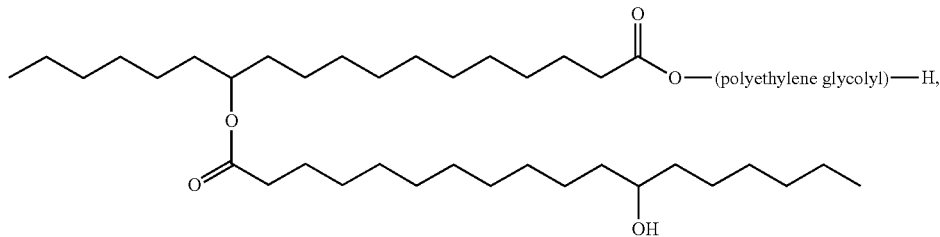

and polyethylene glycol; (c) about 0.005% (w/w) to about 0.015% (w/w) of dibutylhydroxytoluene; (d) about 0.2% (w/w) to about 1% (w/w) of sodium acetate; (e) about 0.01% (w/w) to about 0.05% (w/w) of ethylenediaminetetraacetic acid or a salt thereof; (f) about 0.3% (w/w) to about 0.9% (w/w) of sodium chloride; (g) at least 96% (w/w) water, and has a pH in the range of about 5 to about 6.

In other embodiments, the aqueous, capsaicin injectable formulation comprises
  a. about 0.04% (w/w) to about 0.06% (w/w) of capsaicin;
  b. about 0.8% (w/w) to about 1.2% (w/w) of a solubilizing agent, wherein the solubilizing agent comprises (a) about 70% (w/w) of a mixture of

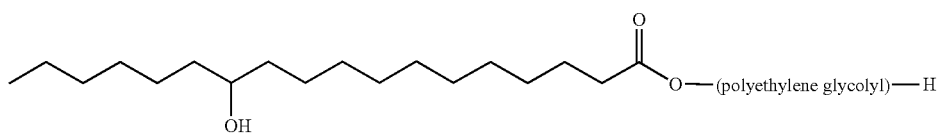

and

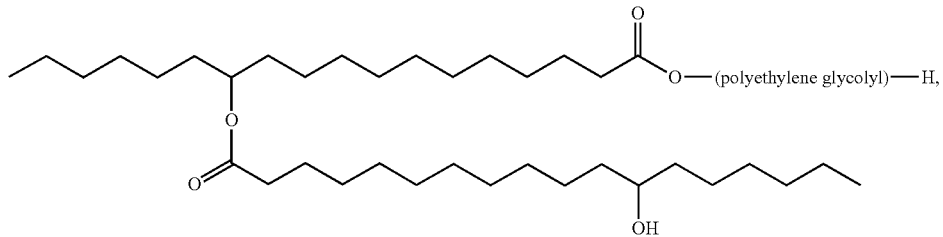

and (b) about 30% (w/w) polyethylene glycol;
c. about 0.005% (w/w) to about 0.015% (w/w) of dibutyl-hydroxytoluene;
d. about 0.2% (w/w) to about 1% (w/w) of sodium acetate;
e. about 0.01% (w/w) to about 0.05% (w/w) of ethylenediaminetetraacetic acid or a salt thereof;
f. about 0.3% (w/w) to about 0.9% (w/w) of sodium chloride;
g. at least 96% (w/w) water; and
having a pH in the range of about 5 to about 6.

In other embodiments, the aqueous, capsaicin injectable formulation comprises
h. about 0.04% (w/w) to about 0.06% (w/w) of capsaicin;
i. about 0.8% (w/w) to about 1.2% (w/w) of a solubilizing agent, wherein the solubilizing agent is a mixture of (a) about 70% (w/w) of a mixture of

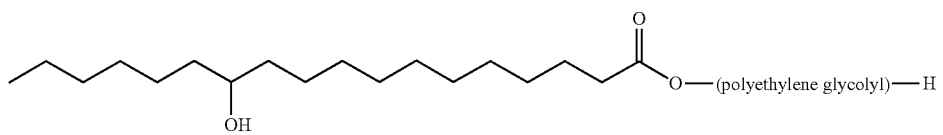

and

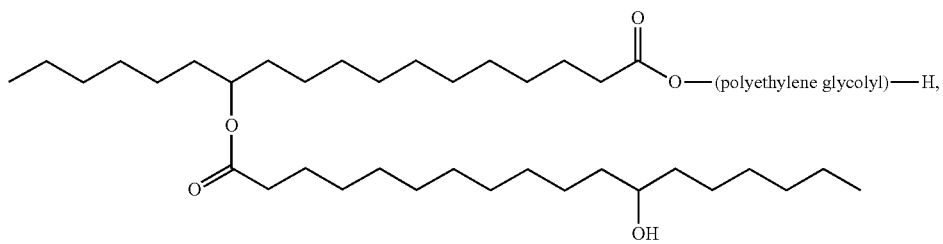

and (b) about 30% (w/w) polyethylene glycol;
j. about 0.005% (w/w) to about 0.015% (w/w) of dibutyl-hydroxytoluene;
k. about 0.2% (w/w) to about 1% (w/w) of sodium acetate;
l. about 0.01% (w/w) to about 0.05% (w/w) of ethylene-diaminetetraacetic acid or a salt thereof;
m. about 0.3% (w/w) to about 0.9% (w/w) of sodium chloride;
n. at least 96% (w/w) water; and
having a pH in the range of about 5 to about 6.

In other embodiments, the aqueous, capsaicin injectable formulation comprises
a. about 0.05% (w/w) of capsaicin;
b. about 1% (w/w) of a solubilizing agent, wherein the solubilizing agent comprises

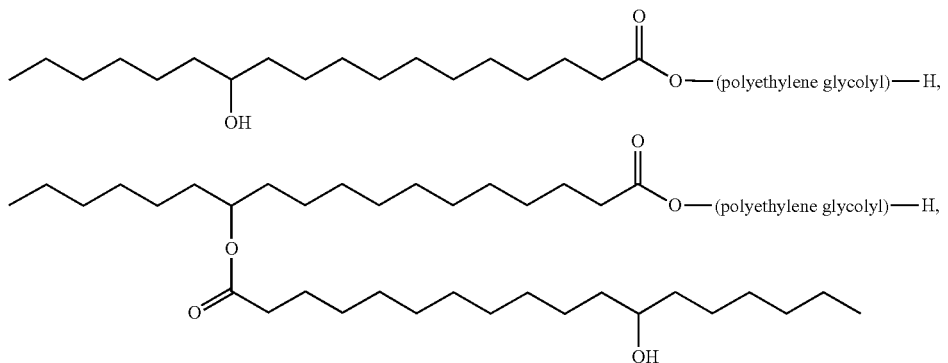

and polyethylene glycol;
c. about 0.005% (w/w) to about 0.015% (w/w) of dibutyl-hydroxytoluene;
d. about 0.2% (w/w) to about 1% (w/w) of sodium acetate;
e. about 0.01% (w/w) to about 0.05% (w/w) of ethylene-diaminetetraacetic acid or a salt thereof;
f. about 0.3% (w/w) to about 0.9% (w/w) of sodium chloride;
g. at least 96% (w/w) water; and
having a pH of about 5.5.

In other embodiments, the aqueous, capsaicin injectable formulation comprises
a. about 0.05% (w/w) of capsaicin;
b. about 1% (w/w) of a solubilizing agent, wherein the solubilizing agent is a mixture

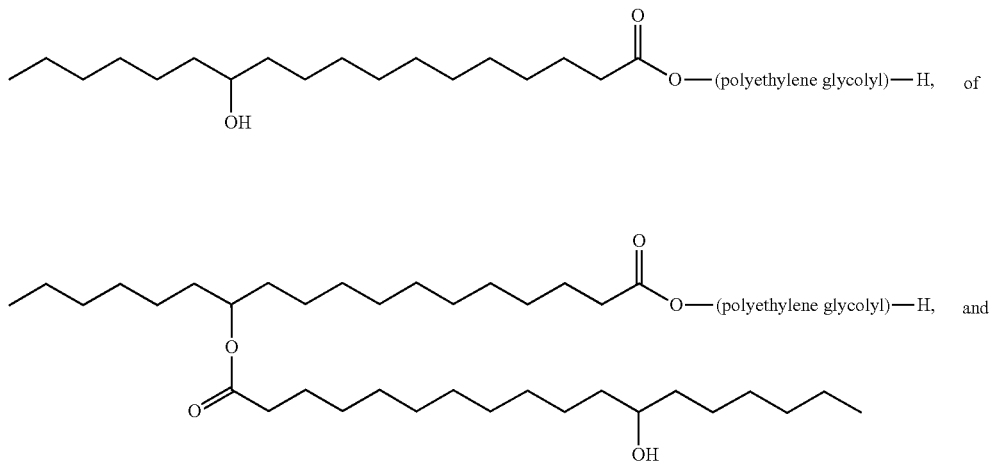

polyethylene glycol;
c. about 0.005% (w/w) to about 0.015% (w/w) of dibutylhydroxytoluene;
d. about 0.2% (w/w) to about 1% (w/w) of sodium acetate;
e. about 0.01% (w/w) to about 0.05% (w/w) of ethylenediaminetetraacetic acid or a salt thereof;
f. about 0.3% (w/w) to about 0.9% (w/w) of sodium chloride;
g. at least 96% (w/w) water; and
having a pH of about 5.5.

Each of the foregoing formulations may be further characterized according to the weight-average molecular weight of the polyethylene glycol component(s). Accordingly, in certain embodiments, the polyethylene glycol has a weight-average molecular weight in the range of about 200 g/mol to about 1500 g/mol. In certain embodiments, the polyethylene glycol has a weight-average molecular weight in the range of about 200 g/mol to about 1000 g/mol. In certain embodiments, the polyethylene glycol has a weight-average molecular weight in the range of about 300 g/mol to about 900 g/mol. In certain embodiments, the polyethylene glycol has a weight-average molecular weight in the range of about 500 g/mol to about 800 g/mol. In certain embodiments, the polyethylene glycol has a weight-average molecular weight in the range of about 600 g/mol to about 700 g/mol. In certain embodiments, the polyethylene glycol has a weight-average molecular weight in the range of about 100 g/mol to about 300 g/mol, about 300 g/mol to about 500 g/mol, about 500 g/mol to about 1000 g/mol, about 1000 g/mol to about 1500 g/mol, about 1500 g/mol to about 2000 g/mol, or about 2000 g/mol to about 2500 g/mol.

Exemplary more specific formulations are provided in Tables 4 and 5 below.

TABLE 4

| No. | Formulation |
|---|---|
| 1 | An aqueous, capsaicin injectable formulation, comprising:<br>a. about 0.05% (w/w) of trans-capsaicin;<br>b. about 1% (w/w) of a solubilizing agent, wherein the solubilizing agent is a mixture of<br>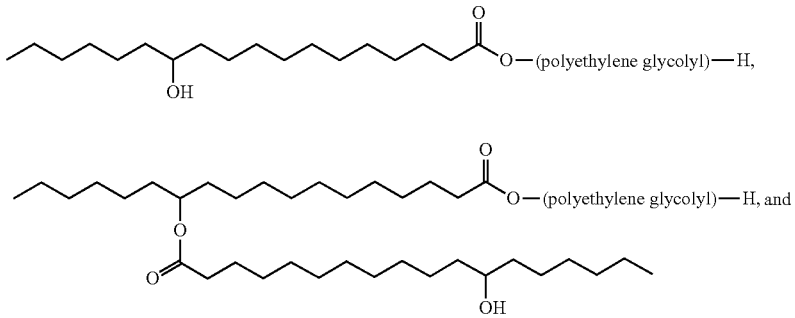<br>polyethylene glycol; wherein the polyethylene glycolyl has a weight average molecular weight of about 660 g/mol;<br>c. about 0.01% (w/w) dibutylhydroxytoluene;<br>d. about 0.68% (w/w) of sodium acetate or a mixture of sodium acetate and acetic acid;<br>e. about 0.025% (w/w) of ethylenediaminetetraacetic acid or a salt thereof;<br>f. about 0.6% (w/w) of sodium chloride;<br>g. at least 97% (w/w) water; and<br>having a pH of about 5.5. |
| 2 | An aqueous, capsaicin injectable formulation, comprising:<br>a. 0.05% (w/w) of trans-capsaicin;<br>b. 1% (w/w) of a solubilizing agent, wherein the solubilizing agent is a mixture of<br>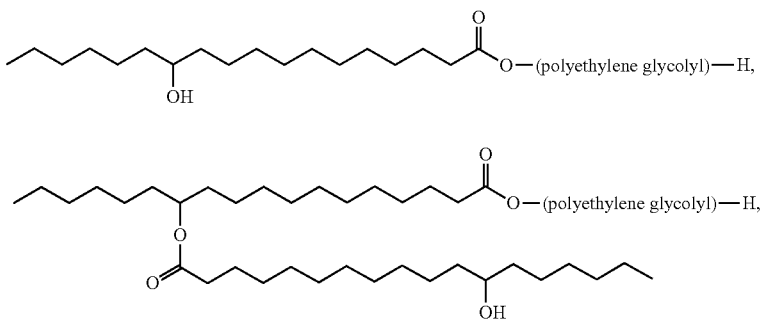<br>and polyethylene glycol; wherein the polyethylene glycolyl has a weight average molecular weight of about 660 g/mol;<br>c. 0.01% (w/w) dibutylhydroxytoluene;<br>d. 0.68% (w/w) of sodium acetate or a mixture of sodium acetate and acetic acid; |

TABLE 4-continued

| No. | Formulation |
|---|---|
| | e. 0.025% (w/w) of ethylenediaminetetraacetic acid or a salt thereof; |
| | f. 0.6% (w/w) of sodium chloride; |
| | g. at least 97% (w/w) water; and |
| | having a pH of 5.5. |
| 3 | An aqueous, capsaicin injectable formulation, comprising: |
| | a. about 0.05% (w/w) of trans-capsaicin; |
| | b. about 1% (w/w) of a solubilizing agent, wherein the solubilizing agent is a mixture of |

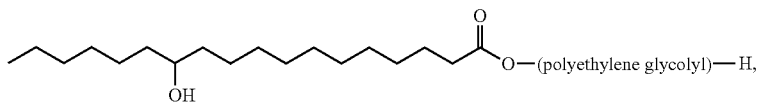

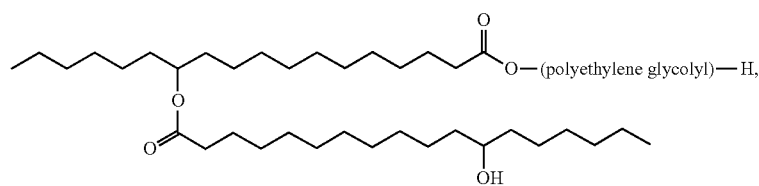

and polyethylene glycol; wherein the polyethylene glycolyl has a weight average molecular weight of about 660 g/mol;
c. about 0.01% (w/w) dibutylhydroxytoluene;
d. about 0.34% (w/w) of sodium acetate or a mixture of sodium acetate and acetic acid;
e. about 0.025% (w/w) of ethylenediaminetetraacetic acid or a salt thereof;
f. about 0.75% (w/w) of sodium chloride;
g. at least 97% (w/w) water; and
having a pH of about 5.5.

4 An aqueous, capsaicin injectable formulation, comprising:
a. 0.05% (w/w) of trans-capsaicin;
b. 1% (w/w) of a solubilizing agent, wherein the solubilizing agent is a mixture of

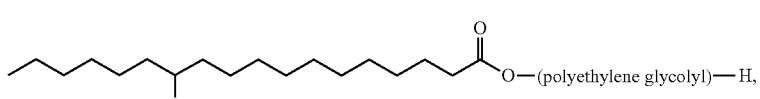

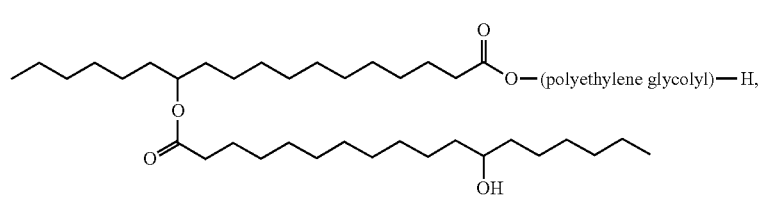

and polyethylene glycol; wherein the polyethylene glycolyl has a weight average molecular weight of about 660 g/mol;
c. 0.01% (w/w) dibutylhydroxytoluene;
d. 0.34% (w/w) of sodium acetate or a mixture of sodium acetate and acetic acid;
e. 0.025% (w/w) of ethylenediaminetetraacetic acid or a salt thereof;
f. 0.75% (w/w) of sodium chloride;
g. at least 97% (w/w) water; and
having a pH of 5.5.

TABLE 5

| No. | Formulation |
|---|---|
| 1 | An aqueous, capsaicin injectable formulation, comprising:<br>a. about 0.05% (w/w) of trans-capsaicin;<br>b. about 1% (w/w) of a solubilizing agent, wherein the solubilizing agent is a mixture of<br>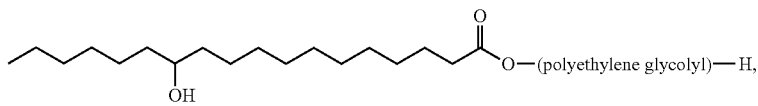<br>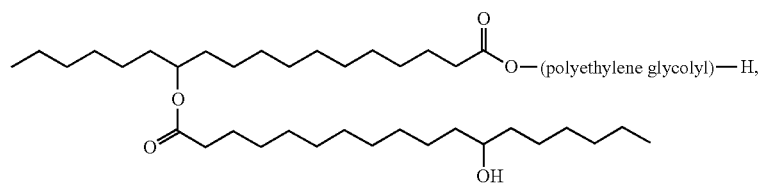<br>and polyethylene glycol; wherein the polyethylene glycolyl has a weight average molecular weight of about 660 g/mol;<br>c. about 0.01% (w/w) dibutylhydroxytoluene;<br>d. about 0.22% (w/w) of sodium citrate or a mixture of sodium citrate and citric acid;<br>e. about 0.025% (w/w) of ethylenediaminetetraacetic acid or a salt thereof;<br>f. about 0.8% (w/w) of sodium chloride;<br>g. at least 97% (w/w) water; and<br>having a pH of about 5.5. |
| 2 | An aqueous, capsaicin injectable formulation, comprising:<br>a. 0.05% (w/w) of trans-capsaicin;<br>b. 1% (w/w) of a solubilizing agent, wherein the solubilizing agent is a mixture of<br>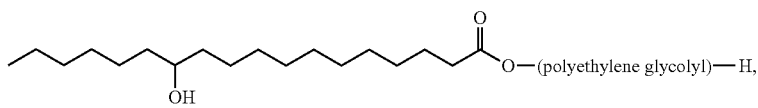<br>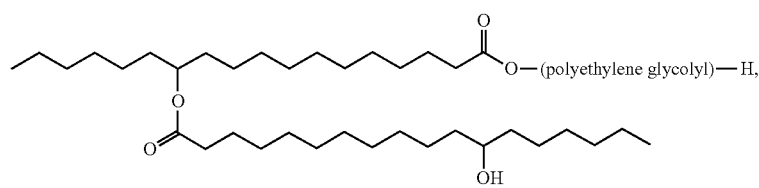<br>and polyethylene glycol; wherein the polyethylene glycolyl has a weight average molecular weight of about 660 g/mol;<br>c. 0.01% (w/w) dibutylhydroxytoluene;<br>d. 0.22% (w/w) of sodium citrate or a mixture of sodium citrate and citric acid;<br>e. 0.025% (w/w) of ethylenediaminetetraacetic acid or a salt thereof;<br>f. 0.8% (w/w) of sodium chloride;<br>g. at least 97% (w/w) water; and<br>having a pH of 5.5. |

TABLE 5-continued

No. Formulation

3  An aqueous, capsaicin injectable formulation, comprising:
   a. about 1% (w/w) of trans-capsaicin;
   b. about 2% (w/w) of a solubilizing agent, wherein the solubilizing
   agent is a mixture of

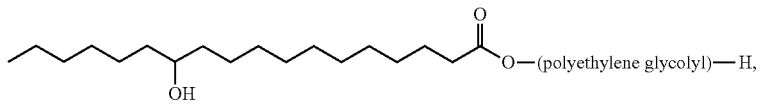

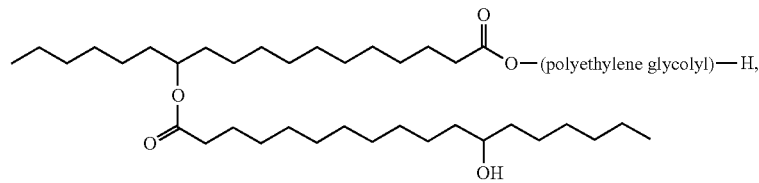

and polyethylene glycol; wherein the polyethylene glycolyl has a
   weight average molecular weight of about 660 g/mol;
   about 0.01% (w/w) dibutylhydroxytoluene;
   d. about 20 mM of sodium citrate or a mixture of sodium citrate and
   citric acid;
   e. about 0.1% (w/w) of ethylenediaminetetraacetic acid or a salt
   thereof;
   f. about 3.15% (w/w) of dextrose;
   g. at least 93% (w/w) water; and
   having a pH of about 5 to about 6.
4  An aqueous, capsaicin injectable formulation, comprising:
   a. 1% (w/w) of trans-capsaicin;
   b. 2% (w/w) of a solubilizing agent, wherein the solubilizing agent is
   a mixture of

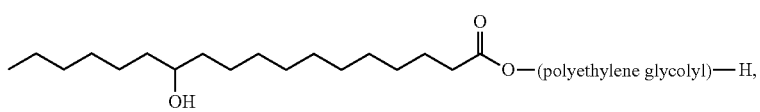

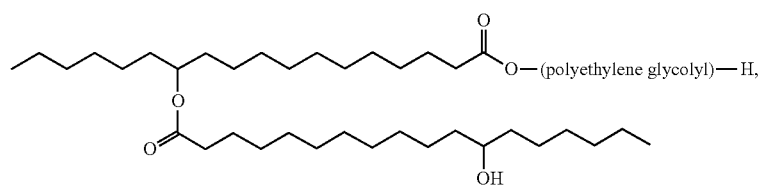

and polyethylene glycol; wherein the polyethylene glycolyl has a
   weight average molecular weight of about 660 g/mol;
   c. 0.01% (w/w) dibutylhydroxytoluene;
   d. 20 mM of sodium citrate or a mixture of sodium citrate and citric
   acid;
   e. 0.1% (w/w) of ethylenediaminetetraacetic acid or a salt thereof;
   f. 3.15% (w/w) of dextrose;
   g. at least 93% (w/w) water; and
   having a pH of about 5 to about 6.

In certain embodiments, the formulation is one of the formulations described in Tables 1-5 above, wherein the formulation has an osmolality in the range of from about 240 mOsm/kg to about 340 mOsm/kg. In certain embodiments, the formulation is one of the formulations described in Tables 1-5 above, wherein the formulation has an osmolality in the range from about 270 mOsm/kg to about 330 mOsm/kg.

Stability of the Aqueous Capsaicin Injectable Formulations

A formulation containing capsaicin can be further characterized according to the stability of the formulation upon storage. For example, in certain embodiments, the formulation is characterized by the feature that less than 1% of the capsaicin degrades upon storage at 25° C. for 24 weeks. In certain other embodiments, less than 0.5% of the capsaicin degrades upon storage at 25° C. for 24 weeks. In certain other embodiments, less than 0.1% of the capsaicin degrades upon storage at 25° C. for 24 weeks. In certain other embodiments, less than 1% of the capsaicin degrades upon storage at 40° C. for 24 weeks. In certain other embodiments, less than 0.5% of the capsaicin degrades upon storage at 40° C. for 24 weeks.

Amount of Capsaicin-Dimer in an Aqueous Capsaicin Injectable Formulations

A formulation containing capsaicin can be further characterized according to the amount of any impurities in the formulation, such as the amount of capsaicin-dimer having the following formula:

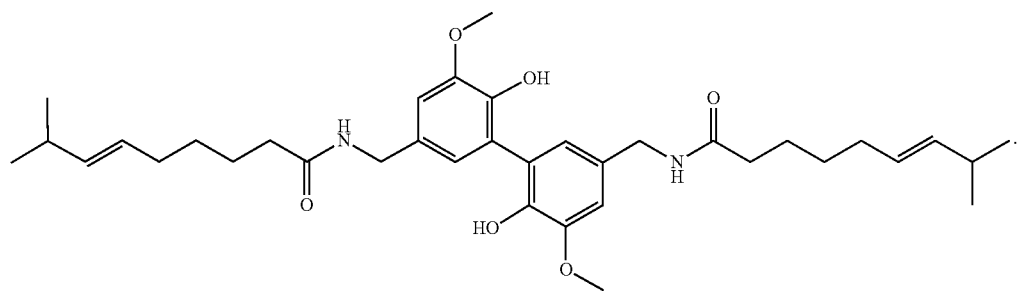 [SMILES: COc1cc(CNC(=O)CCCC/C=C/C(C)C)cc(-c2cc(CNC(=O)CCCC/C=C/C(C)C)cc(OC)c2O)c1O]

Accordingly, in certain embodiments, the formulation is characterized by the feature that it contains less than 3% (w/w) of capsaicin-dimer having the following structure:

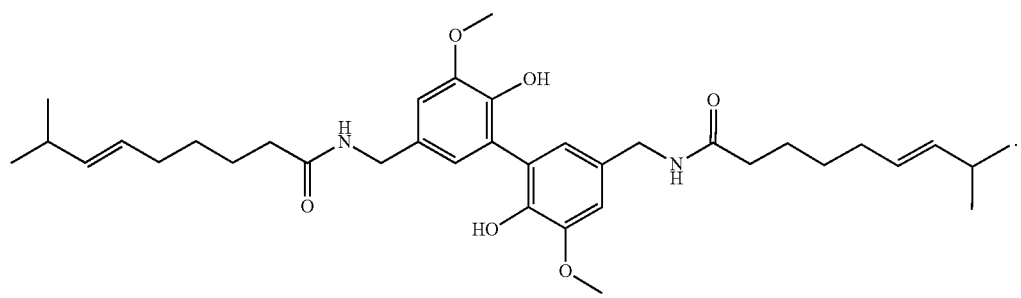 [SMILES: COc1cc(CNC(=O)CCCC/C=C/C(C)C)cc(-c2cc(CNC(=O)CCCC/C=C/C(C)C)cc(OC)c2O)c1O]

In certain other embodiments, the formulation contains less than 2% (w/w) of the capsaicin-dimer. In certain other embodiments, the formulation contains less than 1% (w/w) of the capsaicin-dimer. In certain other embodiments, the formulation contains less than 0.6% (w/w) of the capsaicin-dimer.

In certain other embodiments, upon storage at 25° C. for 12 weeks, the formulation contains less than 3% (w/w) of capsaicin-dimer having the following structure:

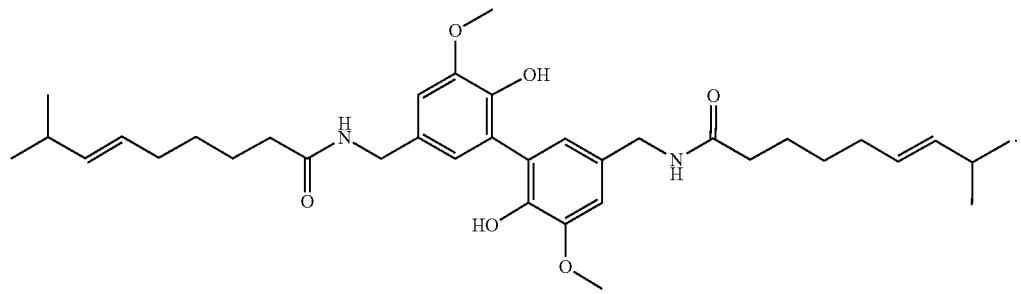 [SMILES: COc1cc(CNC(=O)CCCC/C=C/C(C)C)cc(-c2cc(CNC(=O)CCCC/C=C/C(C)C)cc(OC)c2O)c1O]

In certain other embodiments, upon storage at 25° C. for 12 weeks, the formulation contains less than 2% (w/w) of capsaicin-dimer. In certain other embodiments, upon storage at 25° C. for 24 weeks, the formulation contains less than 1% (w/w) of the capsaicin-dimer. In certain other embodiments, upon storage at 25° C. for 24 weeks, the formulation contains less than 0.6% (w/w) of the capsaicin-dimer.

Amount of Substituted 1,1'-Biphenyl Compound in an Aqueous Capsaicin Injectable Formulations A formulation containing capsaicin can be further characterized according to the amount of substituted 1,1'-biphenyl compound having the following structure:

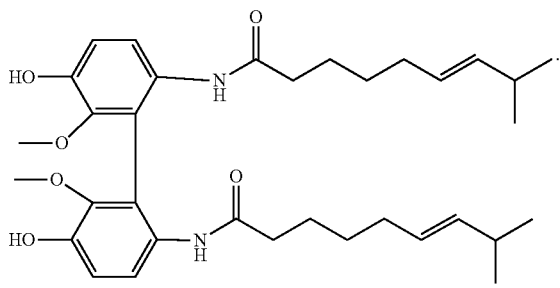 [SMILES: COc1c(O)ccc(NC(=O)CCCC/C=C/C(C)C)c1-c1c(NC(=O)CCCC/C=C/C(C)C)ccc(O)c1OC]

In certain embodiments, the formulation contains less than 2% (w/w) of the substituted 1,1'-biphenyl compound. In certain embodiments, the formulation contains less than 1% (w/w) of the substituted 1,1'-biphenyl compound.

In certain other embodiments, upon storage at 25° C. for 12 weeks, the formulation contains less than 3% (w/w) of the aforementioned substituted 1,1'-biphenyl compound. In certain other embodiments, upon storage at 25° C. for 12 weeks, the formulation contains less than 2% (w/w) of the substituted 1,1'-biphenyl compound. In certain other embodiments, upon storage at 25° C. for 24 weeks, the formulation contains less than 1% (w/w) of the substituted 1,1'-biphenyl compound. In certain other embodiments, upon storage at 25° C. for 24 weeks, the formulation contains less than 0.6% (w/w) of substituted 1,1'-biphenyl compound.

Amount of Optional Other Components in the Injectable Formulations

Formulations herein can be further characterized according to the amount of optional other components. For example, in certain embodiments, the formulation contains less than 0.1% (w/w) of any polysorbate (e.g., polysorable 20 or polysorbate 80). In certain embodiments, the formulation does not contain any polysorbate. In certain embodiments, the formulation contains less than 0.1% (w/w) of any polysorbate, cyclodextrin, or alcohol. In certain embodiments, the formulation does not contain any polysorbate, cyclodextrin, or alcohol.

In yet other embodiments, other than said solubilizing agent, the formulation contains less than 0.1% (w/w) of any polymer, oligomer-containing agent, or agent that improves the solubility of capsaicin. In yet other embodiments, other than said solubilizing agent, the formulation does not contain any polymer, oligomer-containing agent, or agent that improves the solubility of capsaicin. In yet other embodiments, the formulation contains less than 0.1% (w/w) of any cyclodextrin, cellulose, alcohol (e.g., menthol), or hyaluronic acid. In yet other embodiments, the formulation does not contain any cyclodextrin, cellulose, alcohol (e.g., menthol), or hyaluronic acid.

In certain embodiments, the formulation contains less than 0.1% (w/w) of any phospholipid, polysaccharide, protein polymer, cellulose, sorbitan ester, or histidine. In certain embodiments, the formulation does not contain of any phospholipid, polysaccharide, protein polymer, cellulose, sorbitan ester, or histidine. In certain embodiments, the formulation contains less than 0.1% (w/w) of any polyvinylpyrrolidone polymer. In certain embodiments, the formulation does not contain any polyvinylpyrrolidone polymer.

In certain embodiments, the formulation contains less than 0.5% (w/w) of any polyalkylene glycol (e.g., polyethylene glycol) polymer. In certain embodiments, the formulation contains less than 0.3% (w/w), 0.25% (w/w), 0.2% (w/w), 0.15% (w/w), 0.1% (w/w), 0.05% (w/w) 0.01% (w/w) of any polyalkylene glycol (e.g., polyethylene glycol) polymer.

In certain embodiments, the formulation contains less than 0.5% (w/w) of any surfactant. In certain embodiments, the formulation contains less than 0.3% (w/w), 0.25% (w/w), 0.2% (w/w), 0.15% (w/w), 0.1% (w/w), 0.05% (w/w) 0.01% (w/w) of any surfactant. In certain embodiments, but for any component of the formulation named in the description of the formulation that would qualify as a surfactant, the formulation does not contain any other agent that is a surfactant.

EXAMPLES

The invention now being generally described, will be more readily understood by reference to the following examples, which are included merely for purposes of illustration of certain aspects and embodiments of the present invention, and is not intended to limit the invention.

Example 1—Intra-Articular Injection of Capsaicin to Treat Osteoarthritic Knee Joint Pain in Human Patients Human patients experiencing osteoarthritic knee joint pain received either placebo, a 0.5 mg intra-articular injection of capsaicin into the osteoarthritic knee joint, or a 1.0 mg intra-articular injection of capsaicin into the osteoarthritic knee joint. Transient burning sensation due to administration of capsaicin was attenuated by administering capsaicin according to the following procedure: (i) applying for a duration of about 15 minutes a cooling article to an exterior surface of a human patient's knee presenting with osteoarthritic knee joint pain, wherein the cooling article was a Breg cooling wrap cooled by circulating ice-cold water, (ii) administering by injection into the intra-articular space of the joint of the knee a 15 mL aliquot of a 2% w/w lidocaine solution in saline, (iii) applying for a duration of about 30 minutes a cooling article to an exterior surface of the knee, wherein the cooling article was a Breg cooling wrap cooled by circulating ice-cold water, (iv) administering by injection into the intra-articular space of the joint of the knee a 4 mL aliquot of a solution containing water, polyethylene glycol having a number-average molecular weight of about 300 g/mol, and for patients receiving capsaicin a dose of capsaicin in an amount of 0.5 mg or 1.0 mg, and (v) applying a cooling article to an exterior surface of the knee for a duration of at least about 30 minutes (and up to 60) minutes upon patient request), wherein the cooling article was a Breg cooling wrap cooled by circulating ice-cold water. Further description of experimental procedures and results are provided below:

Experimental Procedures

Human patients aged 45-80 years with chronic knee osteoarthritis, stable moderate to severe pain, and intolerability to analgesics were randomized to receive a single intra-articular injection of placebo into the osteoarthritic knee, a single intra-articular injection of a 0.5 mg dose of capsaicin into the osteoarthritic knee, or a single intra-articular injection of a 1.0 mg dose of capsaicin into the osteoarthritic knee.

The test article (i.e., placebo or capsaicin) was administered according to the following procedure: (i) applying for a duration of about 15 minutes a cooling article to an exterior surface of a human patient's knee presenting with osteoarthritic knee joint pain, wherein the cooling article was a Breg cooling wrap cooled by circulating ice-cold water, (ii) administering by injection into the intra-articular space of the joint of the knee a 15 mL aliquot of a 2% w/w lidocaine solution in saline, (iii) applying for a duration of about 30 minutes a cooling article to an exterior surface of the knee, wherein the cooling article was a Breg cooling wrap cooled by circulating ice-cold water, (iv) administering by injection into the intra-articular space of the joint of the knee a 4 mL aliquot of a solution containing water, polyethylene glycol having a number-average molecular weight of about 300 g/mol, and for patients receiving capsaicin a dose of capsaicin in an amount of 0.5 mg or 1.0 mg, and (v) applying a cooling article to an exterior surface of the knee for a duration of at least about 30 minutes (and up to 60 minutes upon patient request), wherein the cooling article was a Breg cooling wrap cooled by circulating ice-cold water.

Safety assessments included treatment-emergent adverse events (TEAEs), serious AEs (SAEs), laboratory abnormalities, and procedural pain ratings (none, mild, moderate, moderately severe, severe). The procedure pain ratings characterize the extent of transient burning sensation experienced by patients due to administration of capsaicin.

Patients completed Patient Global Impression of Change (PGIC; change vs baseline in index knee on 7-point scale; 1=very much improved; 7=very much worse, with scores of 1 or 2 indicating significant improvement) and Patient-specific Functional Scale (PSFS; rate≤3 important activities difficult to perform due to index knee pain on 0-10 scale; 0-able to perform; 10=unable to perform) at scheduled visits. Odds ratios for PGIC scores were calculated with chi-square tests. Changes in Western Ontario and McMaster Universities Osteoarthritis Index (WOMAC) B stiffness subscale and WOMAC C function subscale through week 24 were also assessed. PSFS, WOMAC B, and WOMAC C scores were evaluated using a mixed model for repeated measures. Statistical tests were 2-sided (alpha, P=0.10).

Results—Safety

The safety population included 175 patients (placebo, n=70; capsaicin at 0.5 mg dose, n=34; and capsaicin at 1.0 mg dose, n=71). TEAEs were reported by 21 (30%), 16 (47%), and 21 (30%) patients in the placebo, capsaicin 0.5 mg dose, and capsaicin 1.0 mg dose groups, respectively, and were mild (19%, 29%, 20%) or moderate (11%, 18%, 9.9%) in severity. The most common TEAEs with capsaicin, regardless of dose, were arthralgia (7.6% vs 5.7% placebo) and upper respiratory tract infection (4.8% vs 4.3%). One SAE (shoulder pain from osteoarthritis) in the capsaicin 0.5 mg dose group was not considered treatment related. Few laboratory abnormalities were observed, with most being mild and associated with comorbidities.

Most patients had moderate pain at rest before injection of capsaicin (or placebo). At 2 hours after injection of capsaicin (or placebo), most patients in all groups reported no (50%) or mild (39%) pain.

Incidence of TEAEs was 30% for placebo, 47% for capsaicin at a 0.5 mg dose, and 30% for capsaicin at a 1.0 mg dose, with most mild or moderate in severity and unrelated to treatment. The most common TEAE with the capsaicin 1.0 mg dose was arthralgia (placebo, 5.7%; capsaicin 1.0 mg dose, 7.0%). The following table lists the most commonly reported TEAE through 24 weeks of treatment.

TABLE

Most Commonly Reported TEAEs Through 24 Weeks of Treatment

| TEAE, n (%) | Placebo (n = 70) | Capsaicin 0.5 mg Dose (n = 34) | Capsaicin 1.0 mg Dose (n = 71) | Capsaicin at Either 0.5 mg or 1.0 Dose (n = 105) |
|---|---|---|---|---|
| All TEAEs | 21 (30) | 16 (47) | 21 (30) | 37 (35) |
| Arthralgia | 4 (5.7) | 3 (8.8) | 5 (7.0) | 8 (7.6) |
| Upper respiratory tract infection | 3 (4.3) | 2 (5.9) | 3 (4.2) | 5 (4.8) |
| Influenza | 3 (4.3) | 1 (2.9) | 2 (2.8) | 3 (2.9) |
| Nasopharyngitis | 2 (2.9) | 1 (2.9) | 2 (2.8) | 3 (2.9) |
| Joint effusion | 0 | 3 (8.8) | 0 | 3 (2.9) |
| Hepatic enzyme increased | 0 | 2 (5.9) | 1 (1.4) | 3 (2.9) |

The results demonstrate that a single injection of capsaicin at a 1.0 mg dose was well tolerated with a safety profile generally comparable to placebo for up to 24 weeks.

Results—Efficacy in Treating Osteoarthritic Knee Joint Pain

Efficacy was evaluated in 172 patients (placebo, n=69; capsaicin at 0.5 mg dose, n=33; and capsaicin at 1.0 mg dose, n=70). Based on PGIC, patients receiving a 1.0 mg dose of capsaicin had a greater than two-fold likelihood of having "significant improvement" (ratings of "very much improved" or "much improved") at weeks 4, 8, and 12 compared with placebo. At week 4, greater proportions of patients reported "significant improvement" in the index knee with the 0.5 mg dose capsaicin (58%; P=0.18) or 1.0 mg dose of capsaicin (64%; P=0.01) versus placebo (44%); similar findings were observed at weeks 12 and 24.

On PSFS, a 1.0 mg dose of capsaicin significantly improved patients' ability to perform activities versus placebo at weeks 4-16. A 1.0 mg dose of capsaicin significantly improved WOMAC B score (least squares mean difference [LSMD]: −2.1; P=0.007) and WOMAC C score (LSMD: −14.8; P=0.02) versus placebo through week 16. Tabulated results are provided in the following Table.

TABLE

Effect of Capsaicin Injection vs Placebo on Patient Global Impression of Change (PGIC) and Patient-specific Functional Scale (PSFS) Through 24 Weeks of Treatment

| Week No. | PGIC: Odds Ratio vs Placebo (P value)[a] | | PSFS: LSMD versus Placebo (P value) | |
|---|---|---|---|---|
| | Capsaicin at 0.5 mg Dose | Capsaicin at 1.0 mg Dose | Capsaicin at 0.5 mg Dose | Capsaicin at 1.0 mg Dose |
| 4 | 1.76 (P = 0.18) | 2.34 (P = 0.01) | 0.01 (P = 0.98) | −1.4 (P = 0.0006) |
| 8 | 1.89 (P = 0.14) | 2.50 (P = 0.008) | −0.03 (P = 0.96) | −0.9 (P = 0.03) |
| 12 | 2.75 (P = 0.03) | 2.40 (P = 0.01) | −0.4 (P = 0.40) | −1.1 (P = 0.007) |

TABLE-continued

Effect of Capsaicin Injection vs Placebo on Patient Global Impression of Change (PGIC) and Patient-specific Functional Scale (PSFS) Through 24 Weeks of Treatment

| | PGIC: Odds Ratio vs Placebo (P value)[a] | | PSFS: LSMD versus Placebo (P value) | |
|---|---|---|---|---|
| Week No. | Capsaicin at 0.5 mg Dose | Capsaicin at 1.0 mg Dose | Capsaicin at 0.5 mg Dose | Capsaicin at 1.0 mg Dose |
| 16 | 2.37 (P = 0.05) | 1.85 (P = 0.07) | −0.5 (P = 0.35) | −0.9 (P = 0.04) |
| 24 | 1.68 (P = 0.23) | 1.64 (P = 0.15) | −0.05 (P = 0.93) | −0.5 (P = 0.27) |

[a]Odds Ratio (OR) for significant improvement (scores of 1 [very much improved] or 2 [much improved] on PGIC). LSMD, least squares mean difference; OR, odds ratio. Prespecified alpha for significance set at 0.1.

The results demonstrate that a single injection of capsaicin at a 1.0 mg dose produced statistically significant improvements in physical function for 12-16 weeks and numerically greater improvements at 24 weeks versus placebo in patients with moderate to severe osteoarthritis knee pain.

Example 2—Sequential Injection of Capsaicin with Cooling and Lidocaine Local Anesthetic to Achieve Long Duration Relief from Pain Associated with an Intermetatarsal Neuroma Patients experiencing pain due to an intermetatarsal neuroma are to be treated by administering up to four doses of trans-capsaicin, at 200 µg of capsaicin per dose, by injecting trans-capsaicin into the area of the neuroma (but not inserting the medical instrument performing the injection into the intermetatarsal neuroma itself). Following the first dose of trans-capsaicin, any subsequent dose of trans-capsaicin is to be administered no sooner than 3 months following the prior dose of trans-capsaicin. Further description of experimental procedures and methods for analysis of pain relief are provided below.

Patients to Be Treated

Patients to be treated are those having previously received trans-capsaicin for relief of pain due to an intermetatarsal neuroma. Patients may receive trans-capsaicin injection in the current study under the following conditions:
1. If the previous injection with trans-capsaicin occurred at least 6 months previously, and the average (walking) neuroma pain has been ≥2 for 2 consecutive interactive web response system (IWRS) or interactive voice response system (IVRS) assessments, or
2. If the previous injection with trans-capsaicin occurred ≥3, but <6 months previously and the patient reports an average (walking) neuroma pain of ≥4 for 2 consecutive IWRS/IVRS assessments.

Administration of trans-Capsaicin trans-Capsaicin is to be injected in the amount of 200 µg per dose by ultrasound-guided needle placement into the area of the neuroma. The dose of trans-capsaicin is injected as a 2 mL solution containing trans-capsaicin at a concentration of 100 µg/mL. Local anesthesia will be performed with up to 4 mL of 1% lidocaine (without epinephrine) injected adjacent to the neuroma 30 minutes prior to injection of trans-capsaicin. Adjunct use of cooling will be applied for 15 minutes before 1% lidocaine injection; after lidocaine injection cooling will be put back on for 30 minutes prior to trans-capsaicin injection. Cooling will be removed for trans-capsaicin injection and then reapplied immediately following the injection for a minimum of 30 minutes and up to 1 hour.

If procedure pain is adequately controlled by the above protocol, subsequent injections will be performed similarly. If the above protocol does not adequately control procedure pain, subsequent trans-capsaicin injections may add an ankle block using an injection of 1% lidocaine such that the posterior tibial nerve at the level of the ankle and the branches of the superficial peroneal nerve on the dorsum of the foot are blocked to achieve a complete sensory blockade in the affected space both dorsal and plantar to the neuroma.

trans-Capsaicin is supplied as a 2 mg/mL solution in PEG-300 (poly ethylene glycol having a number-average molecular weight of approximately 300 g/mol) and must be diluted prior to injection, trans-Capsaicin will be diluted with sterile water and PEG-300 such that the final solution for injection contains 30% PEG-300 at a final concentration of 100 µg/mL trans-capsaicin.

Study Periods and Visits

Patients are to participate in a Screening/Enrollment visit, Monthly Monitoring visits and phone calls (in alternating months), up to 4 Treatment Cycles which will consist of 4 visits each, and a Week 52/End of Treatment visit. Each Treatment Cycle will be comprised of the following 4 visits: Treatment Visit 1/Treatment Day 1, Treatment Visit 2/Week 1 Phone Call, Treatment Visit 3/Week 2 Clinic visit, and Treatment Visit 4/Week 4 Clinic visit. A Treatment Cycle will begin on the day a subject is scheduled to receive an injection of trans-capsaicin.

Subjects will be eligible to receive additional treatment with trans-capsaicin 200 µg starting at the Enrollment Visit through Week 48 of the study. During this time, if subjects meet the requirements for receiving an injection of trans-capsaicin for their neuroma pain, then they will begin a new Treatment Cycle as described above. Subjects may receive a maximum of 4 treatments with a minimum of 3 months between each dose.

Screening/Enrollment Visit

The following procedures will be performed at Screening:
1. Written informed consent.
2. Eligibility criteria.
3. Enrollment.
4. Medical history.
5. Complete physical examination (excluding a genito-urinary exam) including weight and height.
6. 12-lead electrocardiogram (ECG).
7. Clinical laboratory tests: chemistry, hematology, urinalysis.
8. Urine drug screen.
9. Urine pregnancy test for females of childbearing potential.
10. Vital signs.
11. Training and instruction on assessment of neuroma foot pain (NPRS) during the previous 24 hours and weekly use of the IWRS/IVRS System (NPRS scores and use of rescue medication).
12. Neuroma foot pain at study visit (average walking pain and worst pain over last 24 hours) using NPRS.
13. Foot function assessment.
14. Quality of Life (QoL) assessment.
15. Concomitant medications and therapies. During the study, all medications and non-drug therapies (including rescue medication) be recorded.

Monthly Monitoring: Telephone Calls and Site Visits

All subjects will record their neuroma foot pain scores and use of rescue medication weekly via IWRS/IVRS system from home throughout the study.

Subjects will be monitored during the course of the study by telephone calls and clinic visits performed on alternating months (i.e., phone call at Month 1, clinic visit at Month 2, phone call at Month 3, etc.). In each monitoring call the subject will be asked assessments.

The first telephone call will take place 4 weeks following the Enrollment/Screening visit and 4 weeks after the Treatment Visit 4/Treatment Week 4 of each Treatment Cycle. The first clinic visit will occur 1 month after the first telephone call.

When subjects have eligible pain as noted above, and receive study treatment, they will complete Treatment Cycle Visits 1 to 4 and then enter post-treatment monitoring. Subjects will receive post-treatment telephone calls every other month and will also return to the clinic during alternating months (every other month).

Monthly Telephone Calls

During telephone calls, the following assessments will be completed:
1. Adverse events.
2. Concomitant medications and therapies. Details of all medications and non-drug therapies (including rescue medication) will be recorded at this time.
3. Review IWRS/IVRS System compliance with subject, and instruct subject to continue weekly entries (NPRS scores and use of rescue medication). Conduct subject retraining if non-compliant.

Monthly Site Visits

During in-clinic study visits, the following assessments will be completed:
1. Vital signs.
2. Sensory and motor examination of both feet.
3. Review IWRS/IVRS System entries and compliance with subject, and instruct subject to continue weekly entries (NPRS scores and use of rescue medication). Conduct subject retraining if non-compliant.
4. Neuroma foot pain at study visit (average walking pain and worst pain over last 24 hours) using NPRS.
5. Neuroma foot pain: PGIC from the subject's most recent assessment.
6. Foot function assessment.
7. QoL assessment.
8. Adverse events.
9. Concomitant medications and therapies. Use of all medications and non-drug therapies (including rescue medication) must be recorded.

Treatment Cycles (1-4)

Subjects will continue to record neuroma foot pain and use of rescue medication by IWRS/IVRS System at home throughout each Treatment Cycle.

Treatment Visit 1 / Treatment Day 1

Pre-Injection Assessments

The following procedures will be performed pre-dose on Treatment Day 1 of each Treatment Cycle:
1. Complete physical examination (excluding a genitourinary exam) including weight.
2. Collection of blood for PK analysis (PK consented population only).
3. Clinical laboratory tests: chemistry, hematology, urinalysis.
4. Urine drug screen.
5. Urine pregnancy test.
6. Vital signs.
7. Sensory and motor examination of both feet.
8. Review IWRS/IVRS System entries and compliance with subject, and instruct subject to continue weekly entries (NPRS scores and use of rescue medication). Conduct subject retraining if non-compliant.
9. Neuroma foot pain rating at study visit (average walking pain and worst pain over last 24 hours) using NPRS.
10. Procedure pain (Baseline, pre-dose): Subjects will rate their current pain for the affected foot (NPRS; 0-10) at rest.
11. Foot function assessment.
12. QoL assessment.
13. Adverse events.
14. Concomitant medications and therapies. During the study, all medications and non-drug therapies (including rescue medication) be recorded.

Treatment Day 1 Injection and Post-Injection Assessments trans-Capsaicin injection will be performed using ultrasound-guided needle placement, with use of adjunct cooling. The following procedures should be performed for each injection:
i. Injection related pain will not be categorized as an adverse event, as pain post injection is assessed several times post injection.
ii. Adjunct use of cooling will be applied for 15 minutes prior to 1% lidocaine injection.
iii. Cooling device is removed for lidocaine injection, immediately followed by reapplying the cooling device for 10 minutes.
   Subject will rate his/her current pain at rest 10 minutes (+2 minutes) after lidocaine injection iv. Replace adjunct cooling for 20 minutes.
v. At 30 minutes after lidocaine administration, remove the cooling device.
vi. Inject trans-capsaicin into the area of the affected foot's neuroma.
vii. Immediately after trans-capsaicin injection apply cooling (for a minimum of 30 minutes and up to 1 hour).

The following procedures will be performed post-injection on Treatment Day 1 of each Treatment Cycle. Note that injection related pain will not be captured as adverse events, as pain post injection is assessed several times post injection.
1. Subject will rate his/her current pain at rest 30 minutes (+5 minutes) after trans-capsaicin injection.
2. Adjunct cooling should be removed to assess pain and reapplied immediately after assessment of pain is recorded.
3. At 1 hour post trans-capsaicin injection:
   If adjunct cooling is still being used, cooling should be removed for assessment, adjunct cooling should no longer be used after 1 hour post trans-capsaicin injection.
   Subject will rate his/her current pain at rest 1 hour after trans-capsaicin injection (±10 minutes).
   Injection site assessment (erythema, edema): at 1 hour post-injection. Evaluated separately by the investigator or a trained designee using a categorical scale of "none, mild, moderate or severe". Significant bruising or other clinically significant injection site reactions (other than erythema and edema) must be recorded as AEs.
4. At 2 hours post trans-capsaicin injection:
   Subject will rate his/her current pain at rest 2 hours after trans-capsaicin injection (±10 minutes).

Injection site assessment (erythema, edema): at 2 hour post-injection.
5. Collection of blood at 0.25, 0.5, 1, 1.5, 2, 4, 8, 10, and 12 h post-dose, for PK analysis (PK consented population only) and first treatment cycle only; if any subjects in the PK population receive further treatment with trans-capsaicin, blood samples will be drawn pre-dose and at 2 h post-dose for calculation of the trans-capsaicin plasma concentrations.
6. Vital signs will be collected at discharge (approximately 2 hours post-injection, or 12 hours post-injection for the PK population).
7. When leaving the clinic, subjects should be instructed not to take a warm or hot bath or shower or expose the injected foot to heat within 24 hours after the injection.

Treatment Visit 2 Week 1, Telephone Call

The study staff will telephone the subject at Week 1 (Visit 2) for the following assessments:
1. Adverse events.
2. Concomitant medications and therapies. Use of all medications and non-drug therapies (including rescue medication) must be recorded.

Treatment Visit 3 Week 2, Site Visit

Subjects will return to the clinic at Visit 3 (Week 2) for the following assessments:
1. Vital signs.
2. Sensory and motor examination of both feet.
3. Injection site assessment (erythema, edema).
4. Review IWRS/IVRS System entries and compliance with subject, and instruct subject to continue weekly entries (NPRS scores and use of rescue medication). Conduct subject re-training if non-compliant.
5. Neuroma foot pain at study visit (average walking pain and worst pain over last 24 hours) using NPRS.
6. Neuroma foot pain: PGIC from the subject's most recent assessment.
7. Foot function assessment.
8. QoL assessment.
9. Adverse events.
10. Concomitant medications and therapies. Use of all medications and non-drug therapies (including rescue medication) must be recorded.

Treatment Visit 4 (Treatment Cycles 1-4, Week 4, Site Visit)

Subjects will return to the clinic at Visit 4 (Week 4) for the following assessments:
1. Vital signs.
2. Sensory and motor examination of both feet.
3. Injection site assessment (erythema, edema).
4. Review IWRS/IVRS System entries and compliance with subject, and instruct subject to continue weekly entries (NPRS scores and use of rescue medication). Conduct subject retraining if non-compliant.
5. Neuroma foot pain at study visit (average walking pain and worst pain over last 24 hours) using NPRS.
6. Neuroma foot pain: PGIC from the subject's most recent injection.
7. Foot function assessment.
8. QoL assessment.
9. Adverse events.
10. Concomitant medications and therapies. Use of all medications and non-drug therapies (including rescue medication) must be recorded.

Final Visit (Week 52) or Early Termination Visit

At Week 52 or upon early termination, subjects will return to the clinic for the following assessments:
1. Complete physical examination (excluding a genitourinary exam) including weight.
2. 12-lead ECG
3. Clinical laboratory tests: chemistry, hematology, urinalysis.
4. Urine drug screen.
5. Urine pregnancy test for females of childbearing potential.
6. Vital signs.
7. Sensory and motor examination. Assessed for both feet.
8. Neuroma foot pain rating at study visit (average walking pain and worst pain over last 24 hours) using NPRS.
9. Neuroma foot pain: PGIC from the subject's most recent assessment.
10. Foot function assessment.
11. QoL assessment.
12. Adverse events.
13. Concomitant medications and therapies. During the study, use of all medications and non-drug therapies (including rescue medication) must be recorded.

A subject who receives their last dose at Week 48 will complete both the Week 4 Treatment Cycle assessments and all additional Final Visit assessments at the same visit.

Assessment of Pain Relief

The following tests are to be used in evaluating relief from pain due to the intermetatarsal neuroma;

Average Walking and Worst Neuroma Foot Pain

Subjects will use an IWRS/IVRS System at bedtime to record on a weekly basis their average foot pain score with walking during the previous 24 hours. Neuroma foot pain with walking will be evaluated using a 0 to 10 NPRS (0="no pain" and 10="worst possible pain"). Subjects will also record their worst neuroma foot pain over the previous 24 hours using the NPRS.

Neuroma Foot Pain Assessed at Study Visits

Subjects will rate their average neuroma foot pain score with walking during the previous 24 hours at each study visit. Neuroma foot pain will be evaluated using the NPRS. Subjects will also record their worst neuroma foot pain over the previous 24 hours using the NPRS.

Foot Function Assessments

To evaluate any functional changes, at scheduled in-clinic study visits, subjects will complete the FFI—R.

Patient Global Impression of Change

Subjects will rate change in neuroma foot pain as compared to the most recent assessment in each treatment cycle using the PGIC at each scheduled in-clinic study visit, according to the Schedule of Events.

Need for Oral Rescue Medication to Treat Morton's Neuroma Pain

Subjects may only take oral OTC pain medications or prescription medication such as celecoxib (up to 200 mg twice daily) etc., as rescue medication for their neuroma foot pain. The number of days that the subject used rescue medication in the previous week will be recorded weekly by the subject in the IWRS/IVRS System. Additional rescue medication details will be collected at study visits and follow-up telephone calls in the source documents and eCRF, recorded as concomitant medications.

Quality of Life

Quality of life will be assessed using a EQ-5D-5L scale at scheduled in-clinic study visits.

Example 3—Administration of Two Doses of Capsaicin with Cooling and Lidocaine Local Anesthetic to Achieve Long Duration Relief from Pain Associated with an Intermetatarsal Neuroma Twenty-seven adult, human patients experiencing pain due to an intermetatarsal neuroma were treated by administering a first dose of trans-capsaicin (200 µg of trans-capsaicin) and then, after at least 11 weeks, administered a second dose of trans-capsaicin (200 µg of trans-capsaicin). Patients rated their average walking pain due to the intermetatarsal neuroma on a Numeric Pain Rating Scale (NPRS), where pain is characterized by the patient on a scale of zero to ten (with zero being "no pain", and ten being "worst possible pain"). Patients rated their average walking pain due to the intermetatarsal neuroma on (i) just prior to receiving the injection of trans-capsaicin and (ii) four (4) weeks after receiving each injection of trans-capsaicin. Patients reported a reduction in average walking pain due to the intermetatarsal neuroma when measured at four weeks after injection of trans-capsaicin for each administration of trans-capsaicin. Further description of experimental procedures and results are provided below.

Part I—Experimental Procedures trans-Capsaicin was administered to twenty-seven (27) adult, human patients experiencing pain due to an intermetatarsal neuroma according to the procedures described below. Prior to administering the first dose of trans-capsaicin in this study, patients reported an average walking pain due to the intermetatarsal neuroma of at least four on the Numeric Pain Rating Scale (NPRS). Patients received two doses of trans-capsaicin.
Administration of trans-Capsaicin
trans-Capsaicin was injected in the amount of 200 µg per dose by ultrasound-guided needle placement into the area of the neuroma (but not inserting the needle into the intermetatarsal neuroma itself). The dose of trans-capsaicin was injected as a 2 mL solution containing trans-capsaicin at a concentration of 100 µg/mL. Local anesthesia was performed with up to 4 mL of 1% lidocaine (without epinephrine) injected adjacent to the neuroma 30 minutes prior to injection of trans-capsaicin. Adjunct use of cooling was applied before 1% lidocaine injection; after lidocaine injection cooling was put back on for 30 minutes prior to trans-capsaicin injection. Cooling was removed for trans-capsaicin injection and then reapplied immediately following the injection.

trans-Capsaicin was supplied as a 2 mg/mL solution in PEG-300 (poly ethylene glycol having a number-average molecular weight of approximately 300 g/mol) and was diluted prior to injection with sterile water such that the final solution for injection contained 30% PEG-300 at a final concentration of 100 g/mL trans-capsaicin.

The second dose of trans-capsaicin was administered to patients at a time ranging from 83 days to 196 days after administration of the first dose of trans-capsaicin in this study. The mean time period between administration of the first dose of trans-capsaicin and the second dose of trans-capsaicin in this study was 116 days.
Evaluation of Pain Due to the Intermetatarsal Neuroma
Pain due to the intermetatarsal neuroma was evaluated by having patients rate their average walking pain due to the intermetatarsal neuroma on a Numeric Pain Rating Scale (NPRS), where pain is characterized by the patient on a scale of zero to ten (with zero being "no pain", and ten being "worst possible pain"). Patients rated their average walking pain due to the intermetatarsal neuroma on (i) just prior to receiving the injection of trans-capsaicin and (ii) four (4) weeks after receiving each injection of trans-capsaicin.

Part II—Results

There was a 1.6 point reduction in patients reported average walking pain due to the intermetatarsal neuroma measured at four weeks after injection of the first dose of trans-capsaicin compared to patients reported average walking pain prior to receiving the first dose of trans-capsaicin. There was a 2.3 point reduction in patients' reported average walking pain due to the intermetatarsal neuroma measured at four weeks after injection of the second dose of trans-capsaicin compared to patients' reported average walking pain just prior to receiving the second dose of trans-capsaicin. The results show that repeat injection of trans-capsaicin is effective in ameliorating pain due to an intermetatarsal neuroma.

Example 4—Capsaicin Aqueous Formulations Containing a Solubilizing Agent

Multiple aqueous formulations were prepared and analyzed to determine the amount of dissolved capsaicin. The formulations contained different solubilizing agents to increase the amount of capsaicin dissolved in the aqueous medium. The experimental procedures and results are described below.

Part I—Analysis of Capsaicin Solubility in Multiple Aqueous Formulations

Aqueous formulations were prepared containing capsaicin and a solubilizing agent selected from Tween 20, Tween 80, Kolliphor ELP, Kolliphor HS 15, Kollidon 12 PF, and Kollidon 17 PF as further defined below. Experimental procedures and results are described below:

Experimental Procedures

The equilibrium solubility of capsaicin was determined in a series of aqueous solutions. Six different types of vehicles were prepared at three different concentrations each. Tween 20 solutions were prepared at a range of 0.2% to 10% (w/v). Tween 80 solutions were prepared at a range of 0.2% to 1.0% (w/v). Kolliphor ELP and Kolliphor HS 15 solutions were both prepared at a range of 5% to 20% (w/v). Kollidon 12 PF solutions were prepared at a range of 2.5% to 10% (w/v). Kollidon 17 PF solutions were prepared at a range of 0.5% to 2.0% (w/v).

For each test solution, quantities of 20-30 mg of capsaicin were added to a micro centrifuge tubes. A volume of 1.5 mL of the appropriate test vehicle was added to each to create a suspension. The capped tubes were mixed on a laboratory rotator at ambient temperature. At approximately 48 hours after sample preparation, the tubes were removed from the rotator and centrifuged to separate the solid phase from the solution. An aliquot of the supernatant was withdrawn from each sample and diluted as necessary for HPLC analysis to determine the solution concentration of the capsaicin. The pH of the supernatant was measured 48 hours after preparation and the appearance of solid and supernatant were noted.

As reported in the literature, Tween 20 is also known as Polysorbate 20, which has the chemical name polyoxyethylene (20) sorbitan monolaurate. Tween 80 is also known as Polysorbate 80, which has the chemical name polyoxyethylene (20) sorbitan monooleate. Kolliphor ELP has CAS Registry No. 61791-12-6, and is a composition sold by BASF under the chemical name polyoxyl-35-castor oil and marketed by BASF as Kolliphor™ ELP; the composition is made by reacting castor oil with ethylene oxide in a molar ratio of 1:35. The Kolliphor HS 15 has CAS Registry No. 70142-34-6, and is a mixture containing about (a) about 70% (w/w) of a mixture of

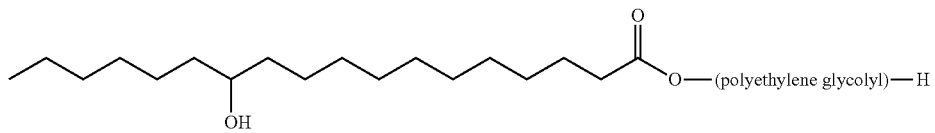

and

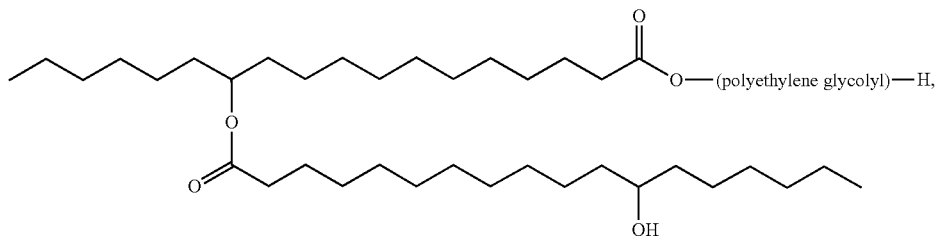

and (b) about 30% (w/w) polyethylene glycol; where the polyethylene glycolyl has a weight-average molecular weight of about 660 g/mol; which is sold and marketed by BASF as Kolliphor® HS 15. Kollidon 12 PF is a polyvinylpyrrolidone having a weight-average molecular weight in the range of 2,000 to 3,000 g/mol, sold by BASF under the name Kollidon® 12 PF. Kollidon 17 PF is a polyvinylpyrrolidone having a weight-average molecular weight in the range of 7,000 to 11,000 g/mol, sold by BASF under the name Kollidon® 17 PF.

Results

Results from the above analysis are presented in Table 1. For all test solutions except those containing Kollidon 12 PF or Kollidon17 PF, the observed concentration of capsaicin increased concordant with increasing surfactant concentration. With the exception of Kollidon 12 PF and Kollidon 17 PF, at least one test solution from each of different solubilizing agents reached the minimum target concentration of capsaicin of 1 mg/mL capsaicin. Both Kollidon 12 PF and Kollidon 17 PF solutions, at all strengths, failed to reach the minimum target concentration of 1 mg/mL capsaicin. The highest concentrations of capsaicin were observed in the 20% strength Kolliphor ELP {c(Capsaicin)=13.0 mg/mL} and 20% Kolliphor HS 15 {c(Capsaicin)=12.2 mg/mL} solutions.

The observed pH-values in the supernatants of the test solutions ranged from pH=3.88 to pH=7.27. Appearances of both the liquid supernatant and the remaining solid were observed to be clear and as at initial solution preparation. For all samples that had remaining solid, the solid appeared white and had the no notable difference from its starting consistency.

After centrifugation of the sample containing 20% Kolliphor ELP no solid residue could be detected, which signifies that the equilibrium solubility for Capsaicin in this vehicle was not reached and is greater than the observed c(Capsaicin)=13.0 mg/mL. For the 20% Kolliphor HS vehicle, the amount of pelleted solid from centrifugation was at the limit of detection.

TABLE 1

| Sample (amount in weight percent) | Observed [Capsaicin] (mg/mL) | pH (at 48 hr) | appearance pellet | appearance supernatant |
|---|---|---|---|---|
| Tween 20 (0.2%) | 0.146 | 6.78 | white | clear |
| Tween 20 (2%) | 1.11 | 6.16 | white | clear |
| Tween 20 (10%) | 5.39 | 6.03 | white | clear |
| Tween 80 (0.2%) | 0.233 | 6.45 | white | clear |
| Tween 80 (0.5%) | 0.245 | 7.27 | white | clear |
| Tween 80 (1.0%) | 1.00 | 7.03 | white | clear |
| Kolliphor ELP (5%) | 4.20 | 5.61 | white | clear |
| Kolliphor ELP (10%) | 8.14 | 5.21 | white | clear |
| Kolliphor ELP (20%) | 13.0 | 4.70 | none | clear |
| Kolliphor HS 15 (5%) | 3.81 | 6.65 | white | clear |
| Kolliphor HS 15 (10%) | 7.18 | 6.97 | white | clear |
| Kolliphor HS 15 (20%) | 12.2 | 7.01 | white | clear |
| Kollidon 12 (2.5%) | 0.276 | 4.22 | white | clear |
| Kollidon 12 (5%) | 0.624 | 4.00 | white | clear |
| Kollidon 12 (10%) | 0.378 | 3.88 | white | clear |
| Kollidon 17 (0.5%) | 0.150 | 5.75 | white | clear |
| Kollidon 17 (1.0%) | 0.247 | 4.66 | white | clear |
| Kollidon 17 (2.0%) | 0.199 | 4.20 | white | clear |

Part II—Capsaicin Solubility in Cyclodextrin Solutions

Aqueous formulations were prepared containing capsaicin and a solubilizing agent selected from hydroxypropyl-β-cyclodextrin and captisol (i.e., sodium sulfobutyl ethers β-cyclodextrin). Experimental procedures and results are described below.

Experimental Procedures

For each cyclodextrin solution, quantities of about 20-30 mg of capsaicin were suspended in 1.5 mL of the respective cyclodextrin solution. The capped tubes were mixed on a laboratory rotator at ambient temperature. At approximately 48 hours after sample preparation, the tubes were removed from the rotator and centrifuged to separate the solid phase from the solution. An aliquot of the supernatant was withdrawn from each sample and diluted as necessary for HPLC analysis to determine the solution concentration of the capsaicin, which was quantitated relative to the reference standard. The pH of the supernatant was measured and the appearance of both the supernatant and the solid were noted at 48 hours.

Results

Results from the above analysis are presented in Table 2. For both cyclodextrins tested, at all solution strengths, at least 2 mg/mL capsaicin was observed. Hydroxypropyl-β-cyclodextrin had slightly higher concentrations of capsaicin than captisol for all solution strengths. The pH of the solutions ranged from 7.00 to 7.94. The liquid portion of each sample was clear and appeared unchanged from its original state. The solid portion of each sample was white, granular, and appeared as it did prior to the addition of the cyclodextrin solution. The 25% solutions of both cyclodextrins had very little remaining solid.

TABLE 2

| Sample | Peak area (mAU) | Observed [Capsaicin], mg/mL | appearance pellet | appearance supernatant | pH (at 48 hr) |
|---|---|---|---|---|---|
| 5% Hydroxypropyl-β-cyclodextrin | 4247905 | 2.39 | White | clear | 7.32 |
| 10% Hydroxypropyl-β-cyclodextrin | 7891725 | 4.45 | White | clear | 7.44 |
| 25% Hydroxypropyl-β-cyclodextrin | 20541037 | 11.6 | White | clear | 7.00 |
| 5% Captisol | 3734548 | 2.10 | White | clear | 7.94 |
| 10% Captisol | 6561988 | 3.70 | White | clear | 7.65 |
| 25% Captisol | 14660216 | 8.26 | White | clear | 7.23 |

Part III—Capsaicin Solubility in Additional Aqueous Solutions

Aqueous formulations were prepared containing capsaicin and an additive. The solubility of capsaicin was also analyzed in deionized water. Experimental procedures and results are described below.

Experimental Procedures

For each of the six solutions, quantities of about 20-30 mg of capsaicin were added to each of six micro centrifuge tubes. A volume of 1.5 mL of the appropriate solution was added to each to create a suspension. The capped tubes were mixed on a laboratory rotator at ambient temperature. At approximately 7 days after sample preparation, the tubes were removed from the rotator and centrifuged to separate the solid phase from the solution. An aliquot of the supernatant was withdrawn from each sample and diluted as necessary for HPLC analysis to determine the solution concentration of the capsaicin, which was quantitated relative to the reference standard. The pH-values of the supernatant were measured and the appearance of both the supernatant and the pelleted solid were noted.

Results

Results from the above analysis are presented in Table 3. The lowest concentration of the capsaicin was observed in deionized water with c(Capsaicin)=7.6 µg/mL while solubilization of capsaicin in aqueous 2.5% glycerol resulted in the highest observed concentration of capsaicin with c(Capsaicin)=38 µg/mL.

TABLE 3

| Sample | Peak area (mAU) | Observed [Capsaicin], mg/mL | appearance pellet | appearance supernatant | pH (at 7 days) |
|---|---|---|---|---|---|
| Water | 135565 | 0.008 | White | clear | 4.53 |
| 5% mannitol | 381253 | 0.021 | White | clear | 5.53 |
| 5% mannitol, 0.1M pH 5 Citrate | 513817 | 0.020 | White | clear | 4.73 |
| 5% mannitol, 0.1M pH 6 Citrate | 378148 | 0.021 | White | clear | 5.86 |
| 5% mannitol, 0.1M pH 5 Acetate | 484164 | 0.027 | White | clear | 5.25 |
| 2.5% glycerol in water | 682320 | 0.038 | White | clear | 6.47 |

Example 5—Preparation of Additional Exemplary Capsaicin Aqueous Formulations Three additional exemplary stable aqueous capsaicin injectable formulations were prepared. Experimental procedures and results are provided below.

Part I—Preparation of First Exemplary Additional Formulation

The formulation listed in the table below was prepared by the following procedure:
(a) Place 900 ml of water in a vessel;
(b) Add 6.80 grams of sodium acetate to the vessel containing water;
(c) Adjust solution pH to 5.5 by adding 1N HCl;
(d) Add 10.0 grams of Kolliphor HS 15 to the solution [the Kolliphor HS 15 has CAS Registry No 70142-34-6, and is a mixture containing (a) about 70% (w/w) of a mixture of

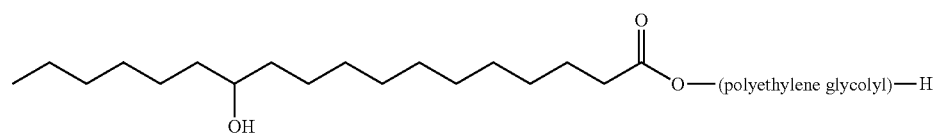

and

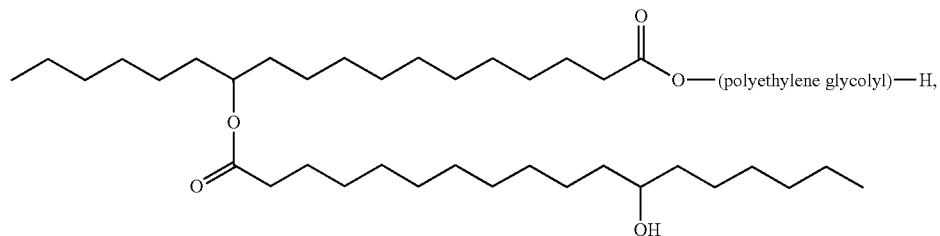

and (b) about 30% (w/w) polyethylene glycol; where the polyethylene glycolyl has a weight-average molecular weight of about 660 g/mol; which is sold and marketed by BASF as Kolliphor® HS 15];
(e) Add 0.10 grams of dibutylhydroxytoluene to the solution, and let the solution age for at least 2 hours;
(f) Add 0.25 grams of ethylenediaminetetraacetic acid tetrasodium salt to the solution;
(g) Add 0.50 grams of capsaicin to the solution, and age the solution until capsaicin dissolves;
(h) Add 6.0 grams of NaCl to the solution;
(i) Adjust pH of the solution to pH=5.5 by adding 1N HCl or 1N NaOH as needed;
(j) qs, with water so the volume of the solution reaches 1 liter, and
(k) Sterile filter the solution.

---

Formulation

An aqueous, capsaicin injectable formulation, comprising:

a. 0.05% (w/w) of trans-capsaicin;

b. 1% (w/w) of a solubilizing agent, wherein the solubilizing agent is a mixture of

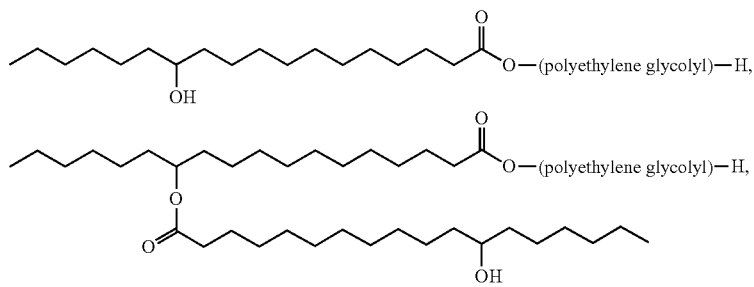

and polyethylene glycol; wherein the polyethylene glycolyl has a weight average molecular weight of about 660 g/mol;

c. 0.01% (w/w) dibutylhydroxytoluene;

d. 0.68% (w/w) of sodium acetate or a mixture of sodium acetate and acetic acid;

e. 0.025% (w/w) of ethylenediaminetetraacetic acid or a salt thereof;

f. 0.6% (w/w) of sodium chloride;

g. qs. with water (i.e., least 97.6% (w/w)); and having a pH of 5.5.

Part II—Preparation of Second Exemplary Additional Formulation

The formulation listed in the table below was prepared by the following procedure:
(a) Place 900 mL of water in a vessel;
(b) Add 3.40 grams of sodium acetate to the vessel containing water;
(c) Adjust solution pH to 5.5 by adding 1N HCl;
(d) Add 10.0 grams of Kolliphor HS 15 to the solution [the Kolliphor HS 15 has CAS Registry No 70142-34-6, and is a mixture containing (a) about 70% (w/w) of a mixture of

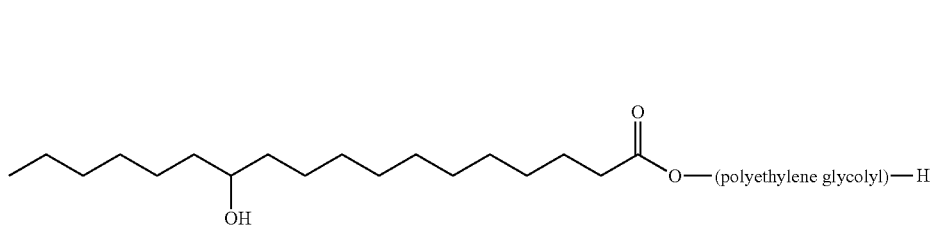

and

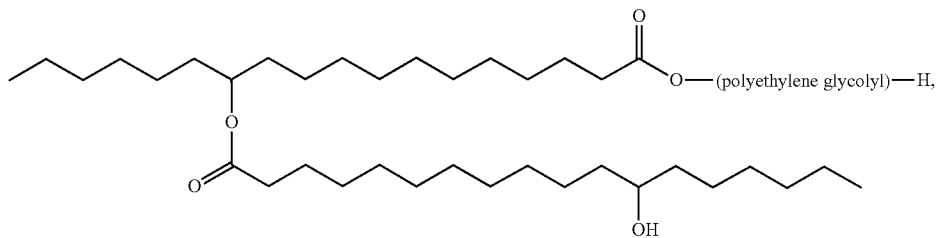

and (b) about 30% (w/w) polyethylene glycol; where the polyethylene glycolyl has a weight-average molecular weight of about 660 g/mol; which is sold and marketed by BASF as Kolliphor® HS 15];
(e) Add 0.10 grams of dibutylhydroxytoluene to the solution, and let the solution age for at least 2 hours; and
(f) Add 0.25 grams of ethylenediaminetetraacetic acid tetrasodium salt to the solution;
(g) Add 0.50 grams of capsaicin to the solution, and age the solution until capsaicin dissolves;
(h) Add 7.5 grams of NaCl to the solution;
(i) Adjust pH of the solution to pH=5.5 by adding 1N HCl or 1N NaOH as needed;
(j) qs, with water so the volume of the solution reaches 1 liter; and
(k) Sterile filter the solution.

| Formulation |
|---|
| An aqueous, capsaicin injectable formulation, comprising:<br>a. 0.05% (w/w) of trans-capsaicin;<br>b. 1% (w/w) of a solubilizing agent, wherein the solubilizing agent is a mixture of<br>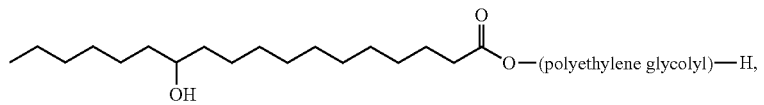<br>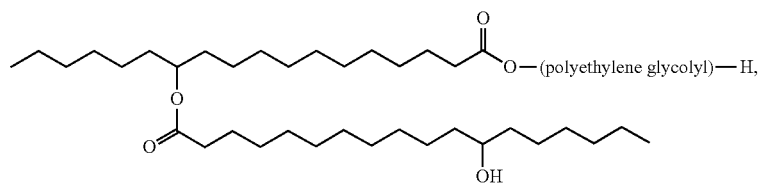<br>and polyethylene glycol; wherein the polyethylene glycolyl has a weight average molecular weight of about 660 g/mol;<br>c. 0.01% (w/w) dibutylhydroxytoluene;<br>d. 0.34% (w/w) of sodium acetate or a mixture of sodium acetate and acetic acid;<br>e. 0.025% (w/w) of ethylenediaminetetraacetic acid or a salt thereof;<br>f. 0.75% (w/w) of sodium chloride;<br>g. qs. with water (i.e., least 97.8% (w/w)); and<br>having a pH of 5.5. |

Part III—Preparation of Third Exemplary Additional Formulation

The formulation listed in the table below was prepared by the following procedure:
(a) Place 900 mL of water in a vessel;
(b) Add 2.2 grams of trisodium citrate dihydrate to the vessel containing water;
(c) Adjust solution pH to 5.5 by adding 1N HCl;
(d) Add 10.0 grams of Kolliphor HS 15 to the solution [the Kolliphor HS 15 has CAS Registry No 70142-34-6, and is a mixture containing (a) about 70% (w/w) of a mixture of

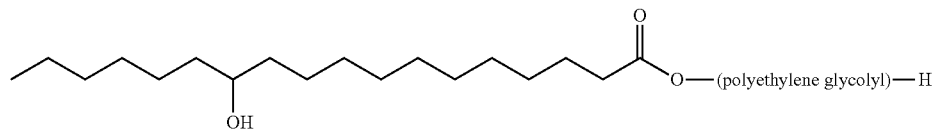

and

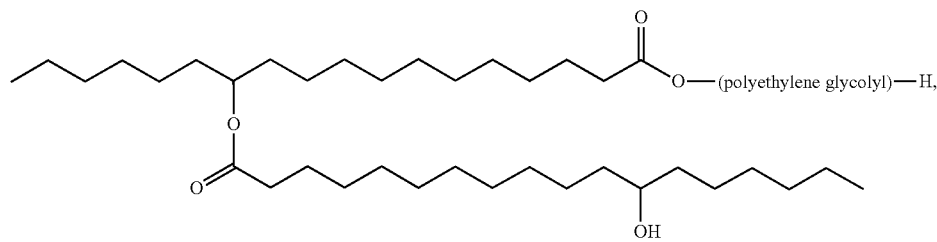

and (b) about 30% (w/w) polyethylene glycol; where the polyethylene glycolyl has a weight-average molecular weight of about 660 g/mol; which is sold and marketed by BASF as Kolliphor® HS 15];

(e) Add 0.10 grams of dibutylhydroxytoluene to the solution, and let the solution age for at least 2 hours;

(f) Add 0.25 grams of ethylenediaminetetraacetic acid tetrasodium salt to the solution;

(g) Add 0.50 grams of capsaicin to the solution, and age the solution until capsaicin dissolves;

(h) Add 8.0 grams of NaCl to the solution;

(i) Adjust pH of the solution to pH=5.5 by adding 1N HCl or 1N NaOH as needed;

(j) qs, with water so the volume of the solution reaches 1 liter, and (k) Sterile filter the solution.

| Formulation |
|---|
| An aqueous, capsaicin injectable formulation, comprising:<br>a. 0.05% (w/w) of trans-capsaicin;<br>b. 1% (w/w) of a solubilizing agent, wherein the solubilizing agent is a mixture of<br>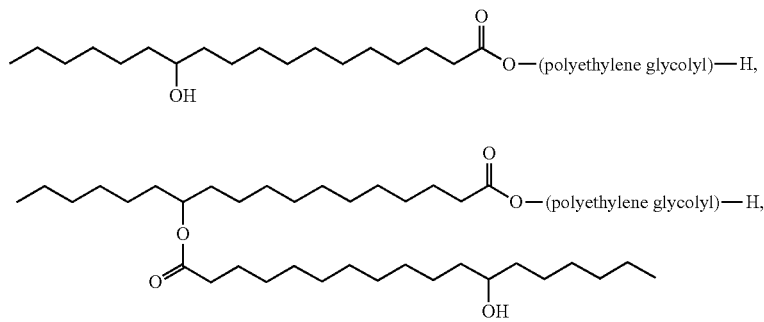<br>and polyethylene glycol; wherein the polyethylene glycolyl has a weight average molecular weight of about 660 g/mol;<br>c. 0.01% (w/w) dibutylhydroxytoluene;<br>d. 0.22% (w/w) of sodium citrate or a mixture of sodium citrate and citric acid;<br>e. 0.025% (w/w) of ethylenediaminetetraacetic acid or a salt thereof;<br>f. 0.8% (w/w) of sodium chloride;<br>g. qs. with water (i.e., 97.9% (w/w) water); and<br>having a pH of 5.5. |

Example 6—Preparation of Additional Exemplary Capsaicin Aqueous Formulations

The exemplary aqueous capsaicin formulations listed in Table 1 below were prepared. The abbreviation BHT refers to dibutylhydroxytoluene. The abbreviation "EDTA" refers to ethylenediaminetetraacetic acid. The Kolliphor HS-15 has CAS Registry No 70142-34-6, and is a mixture containing (a) about 70% (w/w) of a mixture of

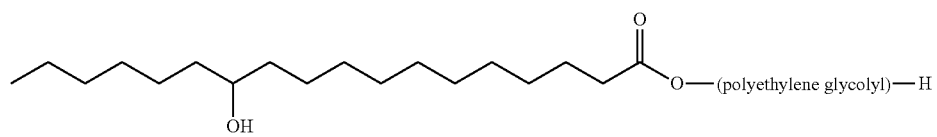

and

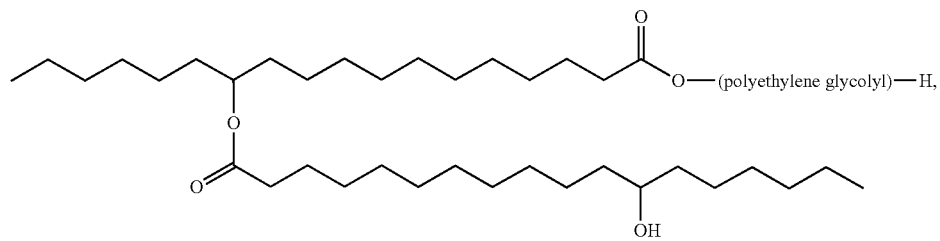

and (b) about 30% (w/w) polyethylene glycol; where the polyethylene glycolyl has a weight-average molecular weight of about 660 g/mol; which is sold and marketed by BASF as Kolliphor® HS 15.

TABLE 1

| Solution 1A: | Solution 1P: |
|---|---|
| 1 mg/ml Capsaicin<br>2% Kolliphor HS-15<br>20 mM citrate buffer<br>0.1% disodium EDTA<br>0.01% BHT<br>0.625% NaCl | 2% Kolliphor HS-15<br>20 mM citrate buffer<br>0.1% disodium EDTA<br>0.01% BHT<br>0.625% NaCl |
| Solution 2A: | Solution 3A: |
| 2 mg/ml Capsaicin<br>4% Kolliphor HS-15<br>20 mM citrate buffer<br>0.1% disodium EDTA<br>0.01% BHT<br>0.625% NaCl | 1 mg/ml Capsaicin<br>2% Kolliphor HS-15<br>0.1% disodium EDTA<br>0.01% BHT<br>3.15% Dextrose |
| Solution 3P: | Solution 4A: |
| 2% Kolliphor HS-15<br>20 mM citrate buffer<br>0.1% disodium EDTA<br>0.01% BHT<br>3.15% Dextrose | 2 mg/ml Capsaicin<br>4% Kolliphor HS-15<br>20 mM citrate buffer<br>0.1% disodium EDTA<br>0.01% BHT<br>3.15% Dextrose |

Example 7—Analysis of Human Knee Temperature During Cooling

Human patients were subjected to cooling of the knee joint using two different cooling methodologies. A temperature probe was placed into the intraarticular space of the patient's knee joint to measure intraarticular temperature of the knee joint. A temperature probe was also placed on the skin in the area to be cooled in order to measure skin temperature in the area to be cooled. The first cooling methodology tested was a Breg Knee WrapOn Polar Pad (as illustrated in FIG. 1) that utilizes circulating ice-water to achieve cooling. The second cooling methodology tested was ice-pack cooling, in which the patient's knee was wrapped with a stockinette and then the ice pack was positioned on top of the stockinette so that the ice pack is positioned over the patient's patella; the ice pack is then secured in place using an elasticated bandage. The ice pack was a LEADSTAR pain relief reusable cold therapy ice pack (size=6 inches). Temperature measurements were recorded over time. Experimental procedures and results are provided below.

Part I—Experimental Procedures

Five healthy human patients were recruited for this study evaluating cooling of the knee joint using two different cooling methodologies. The first cooling methodology tested was a Breg Knee WrapOn Polar Pad (as illustrated in FIG. 1) that utilizes circulating ice-water to achieve cooling, where the pad is placed on skin surrounding the knee. The second cooling methodology tested was ice-pack cooling, in which the patient's knee was wrapped with a stockinette and then the ice pack was positioned on top of the stockinette so that the ice pack (having a surface for application to the patient, wherein said surface has a diameter of approximately six inches) is positioned over the patient's patella; the ice pack is then secured in place using an elasticated bandage. To reduce any potential bias from order effects, three of the subjects received the Breg Knee WrapOn Polar Pad on their left knee and ice-pack cooling on their right knee, while the other two subjects received ice-pack cooling on their left knee and the Breg Knee WrapOn Polar Pad on their right knee. Temperatures within the knee joint were obtained from the recording device at no less than 5 minute intervals (+/−2 min) from the time of placement of the probes until the probes are removed.

Prior to cooling of the knee joint, under sterile conditions, an intraarticular temperature probe was positioned in each knee and an additional temperature probe was placed on the surface of the knee near to the site of injection. At the discretion of the physician performing the procedure, in order to reduce discomfort for the patient, the protocol authorized the physician to instill a volume of 1-2 cc of 2% w/w lidocaine (without epinephrine) into the skin and subcutaneous tissue of the knee at the site of intra-articular probe insertion. Temperature measurements were carried out on the left knee first for three patients, while temperature measurements were carried out on the right knee first for two patients. After obtaining baseline knee intraarticular and skin temperature, the cooling regimen was applied for 15 minutes, followed by intraarticular injection of 2% w/w lidocaine (without epinephrine). Cooling was continued for up to a maximum total of 120 minutes. The probe was removed within approximately 30 minutes after removal of the cooling and the subject was allowed some rest and then the analogous procedure was performed on the patient's right knee for three patients, and the left knee for the other two patients. There was a maximum of four hours between the end of cooling on the left knee and start of cooling on the right knee.

Patients that participated in the study passed the following screening criteria and meet the patient inclusion and exclusion criteria are set forth below. As part of patient screening, patients received an intradermal injection of 100 μL (100 μg) capsaicin into the non-dominant volar forearm. To be eligible to enter the study, patients were able to tolerate the capsaicin injection. Screening patients rated the pain from capsaicin injection at 5, 10, 20, and 30 minutes after injection using a 0-10 Numerical Pain Rating Scale, where "0" equals no pain and "10" equals worst possible pain.

Inclusion Criteria

1. Patient is male or female.
2. Patient is aged between 18 and 45 years, inclusive.
3. Patient has signed and dated an ethics approved informed consent form (ICF).
4. Patient's Body Mass Index (BMI) is between 18 and 32 kg/m2, inclusive and patient's weight is greater than or equal to 50 kg.
5. Patients must be in good health, in the opinion of the Investigator, as determined by a medical history, physical examination, clinical laboratory tests, vital signs and 12 lead electrocardiogram (ECG).
6. Patients must be able to communicate well with the Investigator, understand and comply with the requirements of the study.
7. Patients must be able to tolerate the capsaicin injection given at screening.

Exclusion Criteria

1. Patient has had a clinically significant illness that has not completely resolved in the four weeks before screening.
2. Patient has a history of neurological disorder which may impact the perception of pain or impairs the patient's ability to fully participate in the trial.
3. Patient has used analgesic medications in the 2 days prior to dosing for cohorts 2 to 4, except for paracetamol, as needed.
4. Patient has used topical medications applied to the knee for osteoarthritis pain (including capsaicin, lidocaine, prescription or OTC medications) from 90 days prior to screening through to dosing.
5. Patient has been injected with corticosteroids in the knee 90 days prior to screening through to dosing.
6. Patient uses any prescription or non-prescription medications, including herbal and dietary supplements (including St. John's wort) within 14 days prior to the first dose of study medication. By exception, the patient may take acetaminophen (≤2 grams/day) for up to 48 hours prior to any dose of study medication.
7. Patient has a significant history of drug/solvent abuse or a positive drugs of abuse (DOA) test at screening.
8. Patient has a history of alcohol abuse or currently drinks more than 28 units per week.
9. Patient is, in the opinion of the Investigator, not suitable to participate in the study.
10. Patient has participated in any clinical study with an investigational drug/device within 3 months (or five half-lives if this longer than 3 months) prior to the first day of dosing.
11. Patient has a positive Human Immunodeficiency Virus (HIV), Hepatitis B or Hepatitis C screen.
12. Patient has lost or donated 500 mL or more of blood within the 3 months prior to screen, or intends to donate blood during the study.
13. Patient with known intolerance to capsaicin, hot peppers or any excipient in the investigational medicinal product (i.e., capsaicin formulation for injection) or lidocaine.
14. Pregnant or breastfeeding females.
15. History of allergic reaction to the planned local anesthesia/analgesic regimens, ethylenediaminetetraacetic acid (EDTA), Kolliphor HS 15, butylated hydroxytoluene (BHT), or capsaicin.
16. Patient has any active skin disorders, skin trauma, significant scarring or skin disease on either forearm, or a significant history of trauma or skin disease in either arm.
17. Any other severe acute or chronic medical or psychiatric condition, or laboratory abnormality, that may increase the risk associated with a) study participation b) Investigational product administration c) may interfere with the interpretation of study results and, in the judgment of the investigator, in discussion with the Sponsor, would make the patient inappropriate for entry into this study.

Patients rated pain from the procedure using a Numerical Pain Rating Scale (NPRS) (0-10) at the following time points:

At pre-cooling after placement of the temperature probes.

At rest, 5 minutes prior to intra-articular lidocaine (without epinephrine) injection.

At rest, 10 minutes after intra-articular injection of 2% w/w lidocaine (without epinephrine).

Ratings will continue at 10-minute intervals until removal of the temperature probes. The 10 minute intervals will allow for a +/−2-minute variance in timing.

Part II—Results

The experimental procedure was completed successfully for four healthy human patients. For the fifth patient subjected to the experimental procedure, there was a deviation from protocol due to early removal of a temperature probe. Therefore, experimental results are provided below for the four healthy human patients upon which the experimental procedure was completed successfully.

Figure 2:
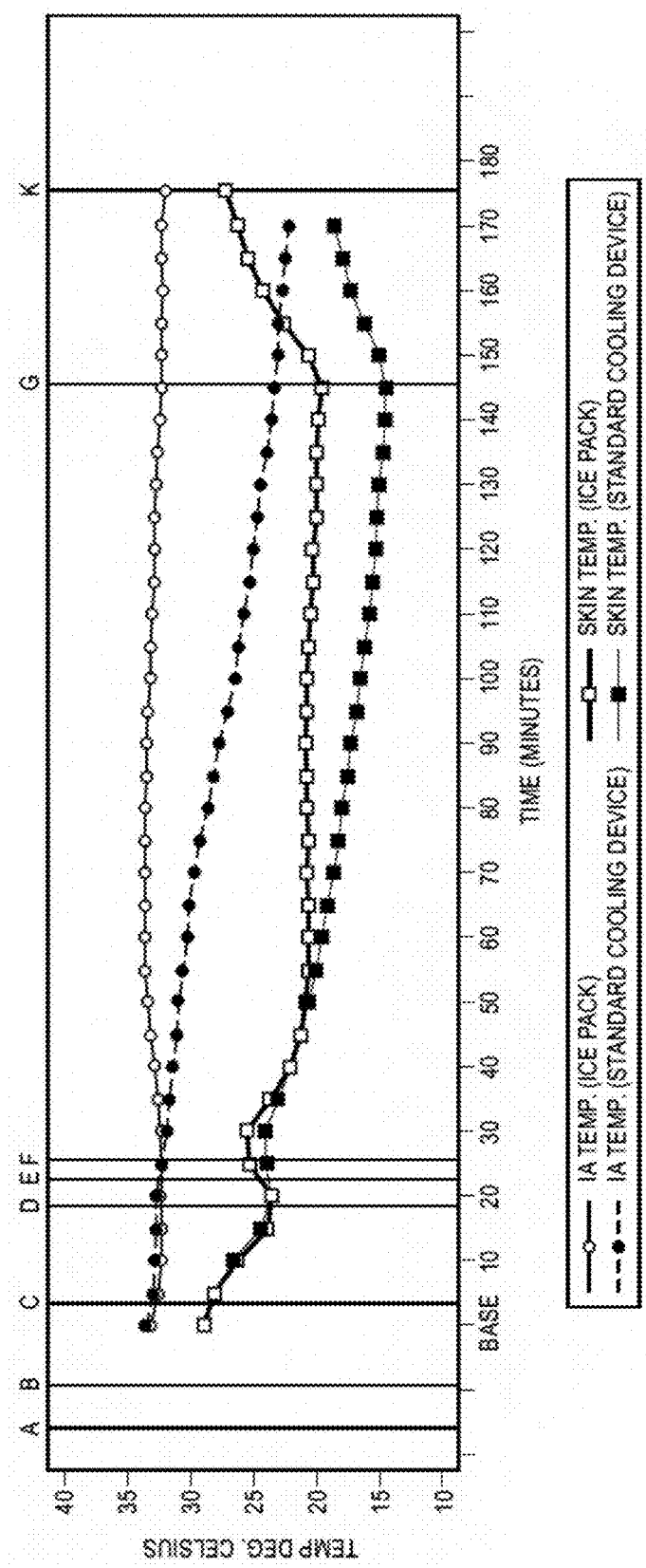
FIG. 2 is a graph showing mean intraarticular (IA) temperature and mean skin temperature over time using the following cooling devices: (i) a Breg Knee WrapOn Polar Pad or (ii) Ice Pack, as further described in Example 7. The "Standard Cooling Device" was a Breg Knee WrapOn Polar Pad. The following designations apply to the graph: A is the time at which any temperature reading of the temperature probe was made prior to insertion into the intraarticular space of the patient's knee; B is the time which the temperature probe was inserted into the intraarticular space of the patient's knee; C is time at which the cooling device was applied to the patient's knee; D is the time at which the cooling device was removed from the patient's knee; E is the time at which a solution of 2% w/w lidocaine was administered to the patient's knee by intraarticular injection; F is the time at which the cooling device was reapplied to the patient's knee; G is the time at which the cooling device was removed from the patient's knee; K is the time at which the temperature probe was removed from the patient's knee.

Mean temperature values for intraarticular temperature in the knee joint recorded over time are presented in FIG. 2, along with skin temperature values recorded over time. Data show that the Breg Knee WrapOn Polar Pad resulted in lower intraarticular temperature for the patient's knee joint after about 30 minutes of cooling, compared to ice-pack cooling.

Figure 3:
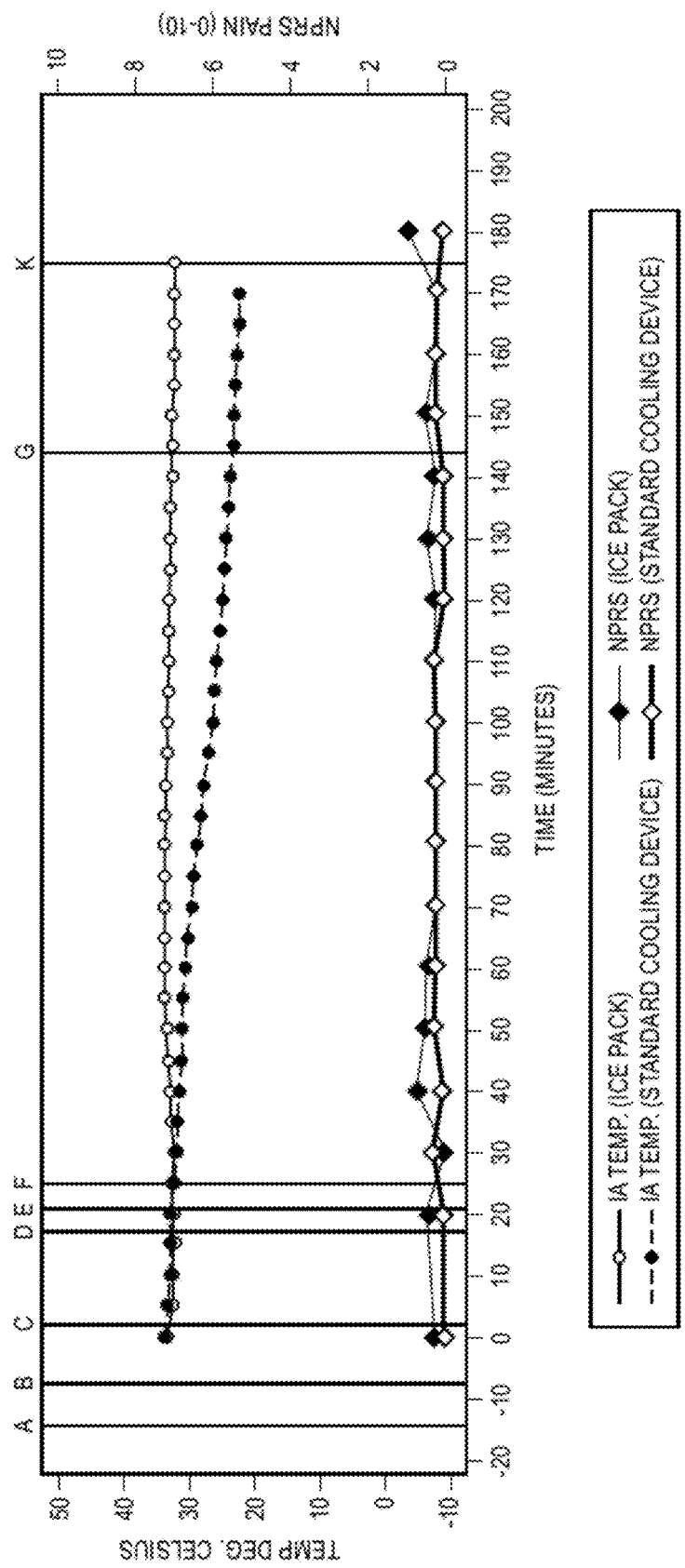
FIG. 3 is a graph showing mean intraarticular (IA) temperature and mean NPRS Pain scores over time using the following cooling devices: (i) a Breg Knee WrapOn Polar Pad or (ii) Ice Pack, as further described in Example 7. The "Standard Cooling Device" was a Breg Knee WrapOn Polar Pad. The following designations apply to the graph: A is the time at which any temperature reading of the temperature probe was made prior to insertion into the intraarticular space of the patient's knee; B is the time which the temperature probe was inserted into the intraarticular space of the patient's knee; C is time at which the cooling device was applied to the patient's knee; D is the time at which the cooling device was removed from the patient's knee; E is the time at which a solution of 2% w/w lidocaine was administered to the patient's knee by intraarticular injection; F is the time at which the cooling device was reapplied to the patient's knee; G is the time at which the cooling device was removed from the patient's knee; K is the time at which the temperature probe was removed from the patient's knee.

FIG. 3 provides mean temperature values for intraarticular temperature in the knee joint recorded over time, along with NPRS pain values recorded over time.

Tabulated mean temperature values along with mean NPRS Pain scores recorded in the study are provided in Table 1 below.

TABLE 1

Tabulated mean temperature values along with mean NPRS Pain scores recorded in the study are provided in Table 1 below.

| Cooling Method | Baseline | 5 min | 10 min | 15 min | 20 min |
|---|---|---|---|---|---|
| *IA Temperature* | | | | | |
| Ice Pack | 33.2 (+/− 1.1) | 32.6 (+/− 1.2) | 32.4 (+/− 1.2) | 32.4 (+/− 1.0) | 32.6 (+/− 0.9) |
| Standard Cooling Device | 33.6 (+/− 0.8) | 33.1 (+/− 0.6) | 32.9 (+/− 0.8) | 32.8 (+/− 1.1) | 32.8 (+/− 1.1) |
| *Skin Temperature* | | | | | |
| Ice Pack | 29.0 (+/− 1.0) | 28.1 (+/− 1.2) | 26.3 (+/− 1.3) | 23.9 (+/− 1.3) | 23.6 (+/− 1.0) |
| Standard Cooling Device | 28.9 (+/− 1.1) | 28.1 (+/− 0.6) | 26.7 (+/− 0.4) | 24.6 (+/− 0.4) | 23.5 (+/− 1.2) |
| *Knee Pain (NPRS)* | | | | | |
| Ice Pack | 0.3 (+/− 0.5) | | | | 0.5 (+/− 1.0) |
| Standard Cooling Device | 0.0 (+/− 0.0) | | | | 0.0 (+/− 0.0) |

| Cooling Method | 25 min | 30 min | 35 min | 40 min | 45 min |
|---|---|---|---|---|---|
| *IA Temperature* | | | | | |
| Ice Pack | 32.4 (+/− 0.8) | 32.3 (+/− 0.6) | 32.7 (+/− 0.5) | 32.9 (+/− 0.8) | 33.2 (+/− 0.7) |
| Standard Cooling Device | 32.3 (+/− 0.8) | 31.9 (+/− 1.1) | 31.7 (+/− 1.0) | 31.4 (+/− 0.9) | 31.2 (+/− 0.9) |
| *Skin Temperature* | | | | | |
| Ice Pack | 25.3 (+/− 0.7) | 25.6 (+/− 1.1) | 23.7 (+/− 2.4) | 22.1 (+/− 2.1) | 21.2 (+/− 1.9) |
| Standard Cooling Device | 24.0 (+/− 1.8) | 24.2 (+/− 1.2) | 23.1 (+/− 2.3) | 22.1 (+/− 2.7) | 21.2 (+/− 2.7) |
| *Knee Pain (NPRS)* | | | | | |
| Ice Pack | | 0.0 (+/− 0.0) | | 0.8 (+/− 1.5) | |
| Standard Cooling Device | | 0.3 (+/− 0.6) | | 0.0 (+/− 0.0) | |

| Cooling Method | 50 min | 55 min | 60 min | 65 min | 70 min |
|---|---|---|---|---|---|
| *IA Temperature* | | | | | |
| Ice Pack | 33.4 (+/− 0.6) | 33.6 (+/− 0.5) | 33.7 (+/− 0.4) | 33.7 (+/− 0.5) | 33.7 (+/− 0.6) |
| Standard Cooling Device | 31.0 (+/− 0.8) | 30.7 (+/− 0.8) | 30.4 (+/− 0.9) | 30.1 (+/− 1.0) | 29.7 (+/− 1.2) |
| *Skin Temperature* | | | | | |
| Ice Pack | 20.9 (+/− 2.3) | 20.7 (+/− 2.7) | 20.6 (+/− 3.1) | 20.7 (+/− 3.3) | 20.8 (+/− 3.6) |
| Standard Cooling Device | 20.6 (+/− 2.8) | 20.0 (+/− 2.8) | 19.5 (+/− 2.6) | 19.2 (+/− 2.7) | 18.7 (+/− 2.7) |
| *Knee Pain (NPRS)* | | | | | |
| Ice Pack | 0.5 (+/− 1.0) | | 0.5 (+/− 1.0) | | 0.3 (+/− 0.5) |
| Standard Cooling Device | 0.3 (+/− 0.5) | | 0.3 (+/− 0.5) | | 0.3 (+/− 0.5) |

| Cooling Method | 75 min | 80 min | 85 min | 90 min | 95 min |
|---|---|---|---|---|---|
| *IA Temperature* | | | | | |
| Ice Pack | 33.6 (+/− 0.7) | 33.6 (+/− 0.9) | 33.5 (+/− 1.0) | 33.5 (+/− 1.1) | 33.4 (+/− 1.3) |
| Standard Cooling Device | 29.2 (+/− 1.4) | 28.8 (+/− 1.4) | 28.3 (+/− 1.5) | 27.8 (+/− 1.5) | 27.1 (+/− 1.2) |
| *Skin Temperature* | | | | | |
| Ice Pack | 20.8 (+/− 3.9) | 20.8 (+/− 4.1) | 20.8 (+/− 4.1) | 20.8 (+/− 4.1) | 20.8 (+/− 4.1) |
| Standard Cooling Device | 18.3 (+/− 2.5) | 17.9 (+/− 2.4) | 17.5 (+/− 2.3) | 17.2 (+/− 2.2) | 16.8 (+/− 2.1) |
| *Knee Pain (NPRS)* | | | | | |
| Ice Pack | | 0.3 (+/− 0.5) | | 0.3 (+/− 0.5) | |
| Standard Cooling Device | | 0.3 (+/− 0.5) | | 0.3 (+/− 0.5) | |

TABLE 1-continued

Tabulated mean temperature values along with mean NPRS Pain scores recorded in the study are provided in Table 1 below.

| Cooling Method | 100 min | 105 min | 110 min | 115 min | 120 min |
|---|---|---|---|---|---|
| *IA Temperature* | | | | | |
| Ice Pack | 33.2 (+/− 1.4) | 33.2 (+/− 1.4) | 33.1 (+/− 1.4) | 33.0 (+/− 1.5) | 33.0 (+/− 1.5) |
| Standard Cooling Device | 26.5 (+/− 1.0) | 26.1 (+/− 1.2) | 25.7 (+/− 1.6) | 25.3 (+/− 1.5) | 25.1 (+/− 1.6) |
| *Skin Temperature* | | | | | |
| Ice Pack | 20.7 (+/− 4.2) | 20.6 (+/− 4.3) | 20.4 (+/− 4.4) | 20.4 (+/− 4.6) | 20.3 (+/− 4.7) |
| Standard Cooling Device | 16.5 (+/− 2.1) | 16.2 (+/− 2.0) | 15.8 (+/− 1.9) | 15.5 (+/− 1.9) | 15.3 (+/− 1.8) |
| *Knee Pain (NPRS)* | | | | | |
| Ice Pack | 0.3 (+/− 0.5) | | 0.3 (+/− 0.5) | | 0.3 (+/− 0.5) |
| Standard Cooling Device | 0.3 (+/− 0.5) | | 0.3 (+/− 0.5) | | 0.0 (+/− 0.0) |

| Cooling Method | 125 min | 130 min | 135 min | 140 min | 145 min |
|---|---|---|---|---|---|
| *IA Temperature* | | | | | |
| Ice Pack | 32.9 (+/− 1.4) | 32.8 (+/− 1.4) | 32.7 (+/− 1.3) | 32.5 (+/− 1.3) | 32.4 (+/− 1.2) |
| Standard Cooling Device | 24.7 (+/− 1.7) | 24.4 (+/− 1.8) | 24.1 (+/− 1.8) | 23.7 (+/− 1.8) | 23.3 (+/− 1.7) |
| *Skin Temperature* | | | | | |
| Ice Pack | 20.1 (+/− 4.5) | 20.0 (+/− 4.4) | 20.1 (+/− 4.6) | 19.9 (+/− 4.4) | 19.6 (+/− 4.0) |
| Standard Cooling Device | 15.2 (+/− 1.7) | 15.0 (+/− 1.5) | 14.8 (+/− 1.4) | 14.7 (+/− 1.3) | 14.6 (+/− 1.3) |
| *Knee Pain (NPRS)* | | | | | |
| Ice Pack | | 0.5 (+/− 1.0) | | 0.3 (+/− 0.5) | |
| Standard Cooling Device | | 0.0 (+/− 0.0) | | 0.0 (+/− 0.0) | |

| Cooling Method | 150 min | 155 min | 160 min | 165 min | 170 min |
|---|---|---|---|---|---|
| *IA Temperature* | | | | | |
| Ice Pack | 32.4 (+/− 1.1) | 32.3 (+/− 1.1) | 32.2 (+/− 1.2) | 32.3 (+/− 1.2) | 32.3 (+/− 1.3) |
| Standard Cooling Device | 23.2 (+/− 1.4) | 23.0 (+/− 1.1) | 22.8 (+/− 1.1) | 22.5 (+/− 1.1) | 22.3 (+/− 1.3) |
| *Skin Temperature* | | | | | |
| Ice Pack | 20.7 (+/− 4.4) | 22.5 (+/− 4.7) | 24.2 (+/− 4.2) | 25.4 (+/− 3.7) | 26.3 (+/− 3.5) |
| Standard Cooling Device | 15.1 (+/− 1.2) | 16.2 (+/− 1.5) | 17.3 (+/− 1.5) | 18.0 (+/− 1.4) | 18.7 (+/− 1.2) |
| *Knee Pain (NPRS)* | | | | | |
| Ice Pack | 0.5 (+/− 1.0) | | 0.3 (+/− 0.5) | | 0.3 (+/− 0.5) |
| Standard Cooling Device | 0.3 (+/− 0.5) | | 0.3 (+/− 0.5) | | 0.3 (+/− 0.5) |

| Cooling Method | 175 min | 180 min |
|---|---|---|
| *LA Temperature* | | |
| Ice Pack | | 32.1 |
| Standard Cooling Device | | |
| *Skin Temperature* | | |
| Ice Pack | | 27.1 |
| Standard Cooling Device | | |
| *Knee Pain (NPRS)* | | |
| Ice Pack | | 1.0 |
| Standard Cooling Device | | 0.0 |

Example 8—Analysis of Procedure Pain Due to Intraarticular Administration of Capsaicin Human patients experiencing osteoarthritic knee joint pain were subjected to two different protocols for intraarticular administration of trans-capsaicin. Temporary pain expected due to administration of capsaicin was analyzed, along with the intraarticular temperature of the knee joint and the temperature of the patient's skin in the area to be cooled.

One of the protocols utilized a Breg Knee WrapOn Polar Pad (as illustrated in FIG. 1) that utilizes circulating ice-water to achieve cooling, where the pad is placed on skin surrounding the knee in order to cool the knee joint. The other protocol utilized ice-pack cooling, in which the patient's knee was wrapped with a stockinette and then the ice pack was positioned on top of the stockinette so that the ice pack is positioned over the patient's patella to thereby cool the knee joint. The ice pack was a LEADSTAR pain relief reusable cold therapy ice pack (size=6 inches). A temperature probe was placed into the intraarticular space of the patient's knee joint to measure intraarticular temperature of the knee joint. A temperature probe was also placed on the skin in the area to be cooled in order to measure skin temperature in the area to be cooled.

Experimental procedures and results are provided below

Part I—Experimental Procedures

Five human patients suffering from moderate to severe painful bilateral knee osteoarthritis were recruited for this study evaluating the impact that cooling protocol has on the magnitude of temporary pain experienced by the patient due to administration of capsaicin. Patients had an average "pain with walking over the past 24 hours" for each knee in the range of 4-9 (inclusive) on a 0-10 numerical pain rating scale where "0" equals no pain and "10" equals worst possible pain (NPRS). Patients that participated in the study passed the following screening criteria and meet the patient inclusion and exclusion criteria are set forth below. As part of patient screening, patients received an intradermal injection of 100 µL (100 µg) capsaicin into the non-dominant volar forearm. To be eligible to enter the study, patients were able to tolerate the capsaicin injection. Screening patients rated the pain from capsaicin injection at 5, 10, 20, and 30 minutes after injection using a 0-10 Numerical Pain Rating Scale, where "0" equals no pain and "10" equals worst possible pain.

Inclusion Criteria
1. Patient is male or female.
2. Patient is aged between 45 and 75 years, inclusive.
3. Patient has signed and dated an ethics approved informed consent form (ICF).
4 Patient's Body Mass Index (BMI) is between 18 and 32 kg/m2, inclusive and patient's weight is greater than or equal to 50 kg.
5. Patient has a diagnosis of bilateral moderate to severe painful knee osteoarthritis (patients will be required to have a score on Pain with walking in the previous 24 hours, of 4 to 9, inclusive (Numeric Pain Rating Scale 0-10). The condition must be chronic with a history of painful arthritis for at least 3 months prior to entry into the study.
6. All patients must otherwise be in good health, in the opinion of the Investigator, as determined by a medical history, physical examination, clinical laboratory tests, vital signs and 12 lead electrocardiogram (ECG).
7. Patients must be able to communicate well with the Investigator, understand and comply with the requirements of the study.
8. Patients have had previous bilateral AP radiographs (or CT/MRI scan) of the knees which demonstrate osteoarthritis in both knee joints within the prior 36 months.
9 Patient must be able to tolerate the capsaicin injection given at screening.

Exclusion Criteria
1 Patient has had a clinically significant illness, other than osteoarthritis, that has not completely resolved in the four weeks before screening.
2. Patient has a history of neurological disorder which may impact the perception of pain or impairs the patient's ability to fully participate in the trial.
3. Patient has used analgesic medications in the 2 days prior to dosing, except for paracetamol, as needed.
4. Patient has used topical medications applied to the knee for osteoarthritis pain (including capsaicin, lidocaine, prescription or OTC medications) from 90 days prior to screening through to dosing.
5. Patient has been injected with corticosteroids in the knee 90 days prior to screening through to dosing.
6. Patient currently uses opioids for any condition other than osteoarthritis knee pain (maximum dose 15 mg hydrocodone, or equivalent, per day prescribed by a physician).
7. Patient has physical/occupational/chiropractic therapy for the lower extremities or acupuncture for the lower extremities 30 days prior to screening or during the period to dosing.
8. Patient has had joint replacement surgery at any time, or open surgery of the knee in the past 12 months prior to screening, or prior arthroscopic surgery of the knee within 6 months prior to screening.
9. Patient has a history of a bleeding diathesis, or is using anti-coagulant drugs, excluding low dose aspirin.
10. Patient has a significant history of drug/solvent abuse or a positive drugs of abuse (DOA) test at screening. Prescribed opioids, as noted in exclusion, 6 are permitted.
11. Patient has a history of alcohol abuse or currently drinks more than 28 units per week.
12. Patient is, in the opinion of the Investigator, not suitable to participate in the study.
13. Patient has participated in any clinical study with an investigational drug/device within 3 months (or five half-lives if this longer than 3 months) prior to the first day of dosing.
14. Patient has a positive Human Immunodeficiency Virus (HIV), Hepatitis B or Hepatitis C screen.
15. Patient has lost or donated 500 mL or more of blood within the 3 months prior to screen, or intends to donate blood during the study.
16. Patient with active chronic pain conditions other than knee osteoarthritis, including periarticular pain about the knee.
17. Patient with known intolerance to capsaicin, hot peppers or any excipient in the investigational medicinal product or lidocaine.
18. Pregnant or breastfeeding females.
19. History of allergic reaction to the planned local anesthesia/analgesic regimens, ethylenediaminetetraacetic acid (EDTA), Kolliphor HS 15, butylated hydroxytoluene (BHT), or capsaicin.

20. Patient has any active skin disorders, skin trauma, significant scarring or skin disease on either forearm, or a significant history of trauma or skin disease in either arm.
21. Any other severe acute or chronic medical or psychiatric condition, or laboratory abnormality, that may increase the risk associated with a) study participation b) Investigational product administration c) may interfere with the interpretation of study results and, in the judgment of the investigator, in discussion with the Sponsor, would make the patient inappropriate for entry into this study.

The following therapies were prohibited both prior to and during the study (i.e., prohibiting therapies):

Injection of corticosteroids in the index knee from 90 days prior to Screening through study completion.

Topical medications applied to the index knee for osteoarthritis pain (including capsaicin, lidocaine, prescription, or OTC medications) from 90 days prior to Screening through study completion.

Current use of opioids for any condition other than for osteoarthritis of the index knee (maximum dose of 15 mg of hydrocodone [or equivalent] per day as background medication is allowed at entry if prescribed by a physician).

Regular use of anticoagulant blood thinners.

Use of an investigational medication within 30 days prior to Screening, or 5 PK or PD half-lives (whichever is longer), or scheduled to receive such an agent while participating in the study.

Physical/occupational/chiropractic or acupuncture therapy for the lower extremities within 30 days of Screening, or need for such therapy during the course of the study.

Joint replacement surgery of the index knee at any time, or open surgery of the index knee in the past 12 months prior to Screening, or prior arthroscopic surgery of the index knee within 6 months of Screening.

Surgery, or other invasive procedures, or intraarticular injections (other than the study drug) while participating in the study.

The patient was excluded from study participation if they had taken any medication prior to randomization that would indicate that the patient has a serious or unstable illness, is not in good general health, or has a condition that would contraindicate study participation. If a patient received an excluded therapy after enrolment, continuation in the study was at the discretion of the sponsor/investigator/medical monitor. Patients were not to take a hot bath or shower, or expose the injected knee to external heat within 12 hours after the injection.

One of the protocols utilized a Breg Knee WrapOn Polar Pad (as illustrated in FIG. 1) that utilizes circulating ice-water to achieve cooling, where the pad is placed on skin surrounding the knee in order to cool the knee joint. The other protocol utilized ice-pack cooling, in which the patient's knee was wrapped with a stockinette and then the ice pack was positioned on top of the stockinette so that the ice pack (having a surface for application to the patient, wherein said surface has a diameter of approximately six inches) is positioned over the patient's patella to thereby cool the knee joint. A temperature probe was placed into the intraarticular space of the patient's knee joint to measure intraarticular temperature of the knee joint. At the discretion of the physician performing the procedure, in order to reduce discomfort for the patient, the protocol authorized the physician to instill a volume of 1-2 cc of 2% w/w lidocaine (without epinephrine) into the skin and subcutaneous tissue of the knee at the site of intra-articular probe insertion. A temperature probe was also placed on the skin in the area to be cooled in order to measure skin temperature in the area to be cooled.

One the first day of the study, patients were randomized so that (i) three patients receiving cooling of the knee joint using the Breg Knee WrapOn Polar Pad and (ii) two patients will receive ice-pack cooling over the patella as set forth above. Patients were subjected to the following procedure:

Placement of intraarticular temperature probe and skin temperature probe. At the discretion of the physician performing the procedure, in order to reduce discomfort for the patient, the protocol authorized the physician to instill a volume of 1-2 cc of 2% w/w lidocaine (without epinephrine) into the skin and subcutaneous tissue of the knee at the site of intra-articular probe insertion.

Cooling using the designated technique was performed for 15 minutes (+/−2 minutes).

Cooling apparatus was removed from the patient's knee.

Intraarticular injection of lidocaine 2% w/w (without epinephrine) 15 mL solution into the patient's knee joint.

Cooling using the designated technique was performed for 30 minutes (+/−2 minutes).

Intraarticular injection of the investigational medicinal product (IMP) was performed to deliver trans-capsaicin in the amount of 1 mg. The IMP was provided as a pre-filled syringe containing 2 mL of fluid containing trans-capsaicin at a concentration of 0.5 mg/mL.

Knee joint was flexed and extended five times over 1 minute to ensure appropriate distribution of IMP.

Cooling using the designated technique was performed for 60 minutes (up to a maximum total of 120 minutes).

The temperature probe was removed approximately 30 minutes after removal of the cooling apparatus.

Temperatures within the knee and on the skin in the region undergoing cooling were obtained from the recording device at no less than 5 minute intervals (+/−2 min) from the time of placement of the probes until the probes were removed.

Pain due to injection of trans-capsaicin was assessed on a Numerical Pain Rating scale (0-10) for 75 minutes after injection of trans-capsaicin. A verbal NPRS was used to assess procedure pain during the study. Patients were asked to indicate the severity of any pain experienced on a scale of 0 to 10 (NPRS; 0 corresponds to no pain and 10 corresponds to the worst pain imaginable). Patients were instructed to consider procedure pain separately from their baseline osteoarthritis pain. Pain was assessed on a Numerical Pain Rating scale (0-10) according the following schedule:

At pre-cooling after placement of the temperature probes.
At rest, prior to intra-articular lidocaine injection.
At rest, 10 minutes after intra-articular lidocaine injection.
At rest prior to injection of trans-capsaicin.
Ratings will continue at 10 minute intervals beginning 10 minutes after the injection of trans-capsaicin until removal of the temperature probe.
The 10 minute intervals allow for a +/−2-minute variance in timing.

Patients were permitted to leave the clinic when they could ambulate independently, but no sooner than 1 hour after removal of the temperature probe.

Patients returned to the clinic 7±2 days later to have the procedure performed on their right knee.

Part II—Results

The experimental procedure was completed successfully for four human patients. For the fifth patient subjected to the experimental procedure, there was a deviation from protocol. For this reason, experimental results are provided below separately for (i) the four human patients for which the experimental procedure was completed successfully, and (ii) all five human patients.

Figure 4:
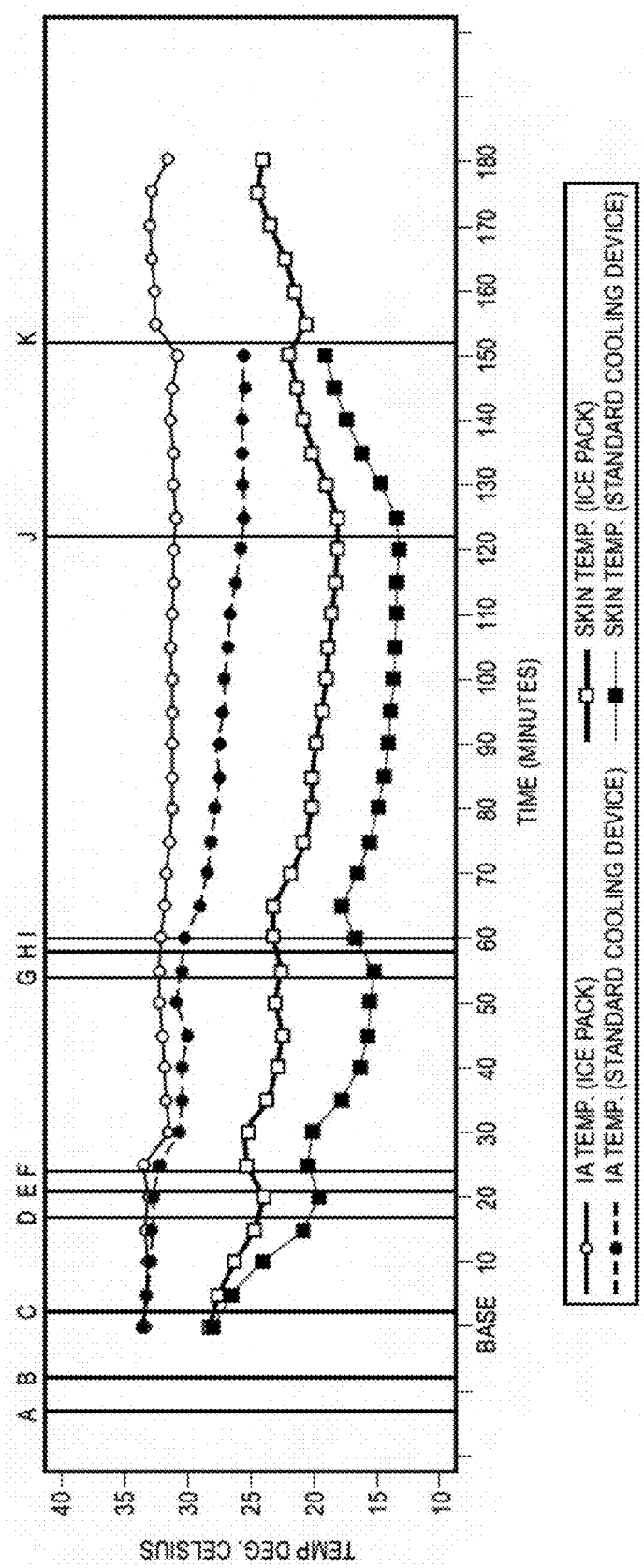
FIG. 4 is a graph showing mean intraarticular (IA) temperature and mean skin temperature over time using the following cooling devices: (i) a Breg Knee WrapOn Polar Pad or (ii) Ice Pack, as further described in Example 8. The "Standard Cooling Device" was a Breg Knee WrapOn Polar Pad. The following designations apply to the graph: A is the time at which any temperature reading of the temperature probe was made prior to insertion into the intraarticular space of the patient's knee; B is the time which the temperature probe was inserted into the intraarticular space of the patient's knee; C is time at which the cooling device was applied to the patient's knee; D is the time at which the cooling device was removed from the patient's knee; E is the time at which a solution of 2% w/w lidocaine was administered to the patient's knee by intraarticular injection; F is the time at which the cooling device was reapplied to the patient's knee; G is the time at which the cooling device was removed from the patient's knee; H is the time that transcapsaicin was administered by intraarticular injection; I is the time at which the cooling device was reapplied to the patient's knee; J is the time at which the cooling device was removed from the patient's knee; K is the time at which the temperature probe was removed from the patient's knee.
Figure 5:
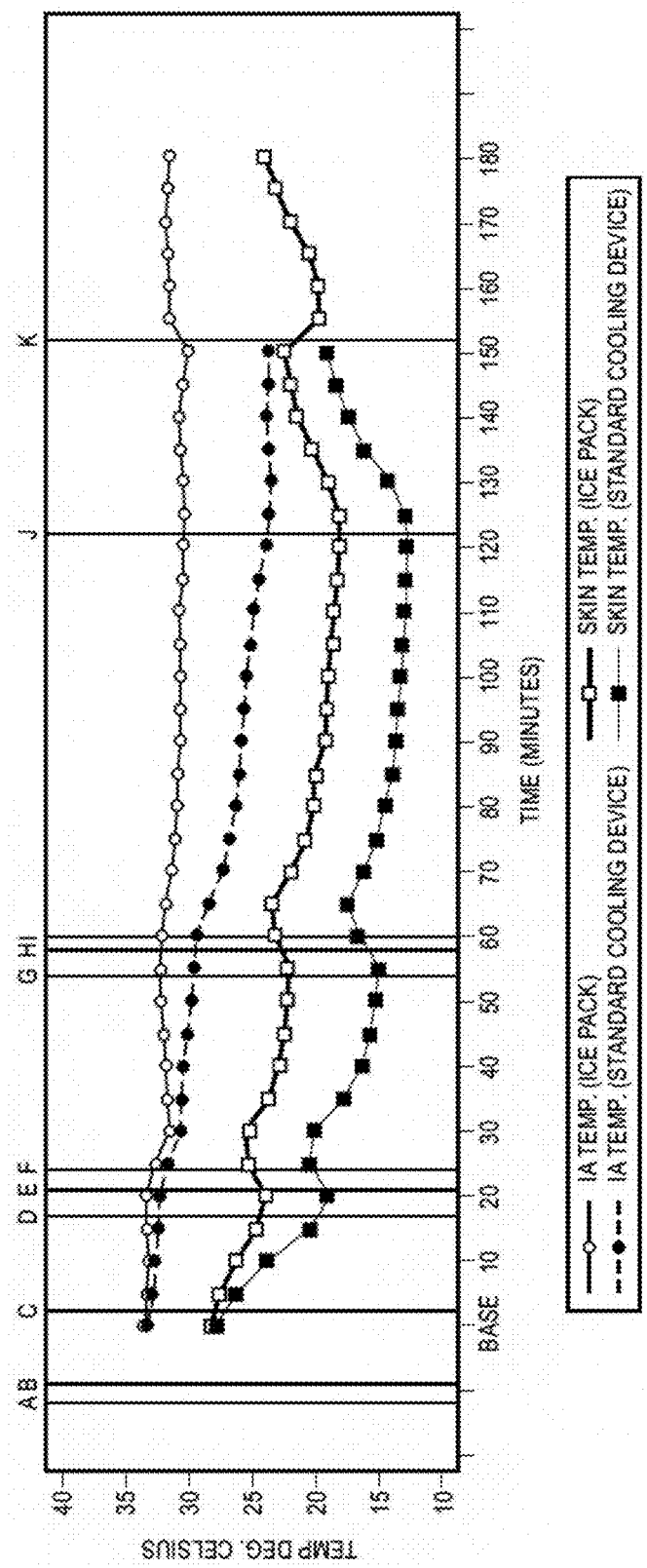
FIG. 5 is a graph showing mean intraarticular (IA) temperature and mean skin temperature over time using the following cooling devices: (i) a Breg Knee WrapOn Polar Pad or (ii) Ice Pack, as further described in Example 8. The "Standard Cooling Device" was a Breg Knee WrapOn Polar Pad. The following designations apply to the graph: A is the time at which any temperature reading of the temperature probe was made prior to insertion into the intraarticular space of the patient's knee; B is the time which the temperature probe was inserted into the intraarticular space of the patient's knee; C is time at which the cooling device was applied to the patient's knee; D is the time at which the cooling device was removed from the patient's knee; E is the time at which a solution of 2% w/w lidocaine was administered to the patient's knee by intraarticular injection; F is the time at which the cooling device was reapplied to the patient's knee; G is the time at which the cooling device was removed from the patient's knee; H is the time that trans-capsaicin was administered by intraarticular injection; I is the time at which the cooling device was reapplied to the patient's knee; J is the time at which the cooling device was removed from the patient's knee; K is the time at which the temperature probe was removed from the patient's knee.

Mean values for intraarticular temperature in the knee joint recorded over time are presented in FIG. 4, along with mean values for skin temperature recorded over time, for the four human patients for which the experimental procedure was completed successfully. Mean values for intraarticular temperature in the knee joint recorded over time are presented in FIG. 5, along with mean values for skin temperature recorded over time, for all five human patients.

Figure 6:
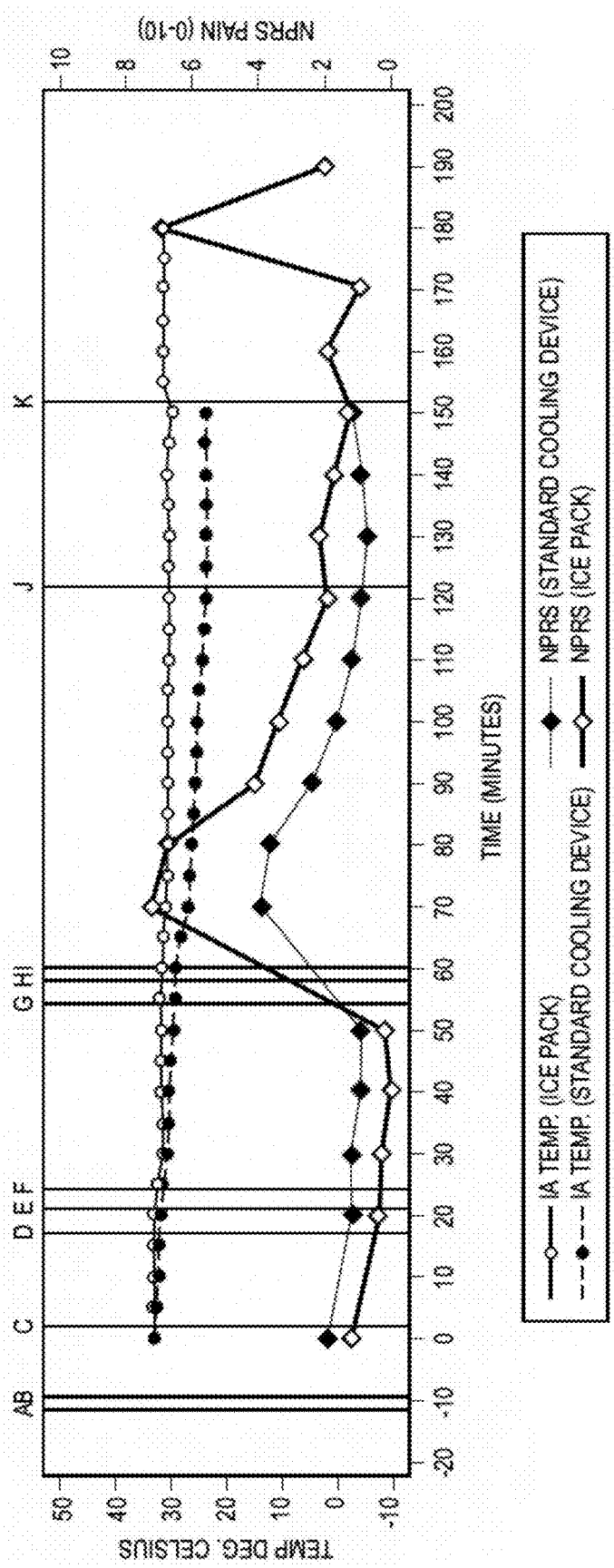
FIG. 6 is a graph showing mean intraarticular (IA) temperature and mean NPRS Pain scores over time using the following cooling devices: (i) a Breg Knee WrapOn Polar Pad or (ii) Ice Pack, as further described in Example 8. The "Standard Cooling Device" was a Breg Knee WrapOn Polar Pad. The following designations apply to the graph: A is the time at which any temperature reading of the temperature probe was made prior to insertion into the intraarticular space of the patient's knee; B is the time which the temperature probe was inserted into the intraarticular space of the patient's knee; C is time at which the cooling device was applied to the patient's knee; D is the time at which the cooling device was removed from the patient's knee; E is the time at which a solution of 2% w/w lidocaine was administered to the patient's knee by intraarticular injection; F is the time at which the cooling device was reapplied to the patient's knee; G is the time at which the cooling device was removed from the patient's knee; H is the time that trans-capsaicin was administered by intraarticular injection; I is the time at which the cooling device was reapplied to the patient's knee; J is the time at which the cooling device was removed from the patient's knee; K is the time at which the temperature probe was removed from the patient's knee.
Figure 7:
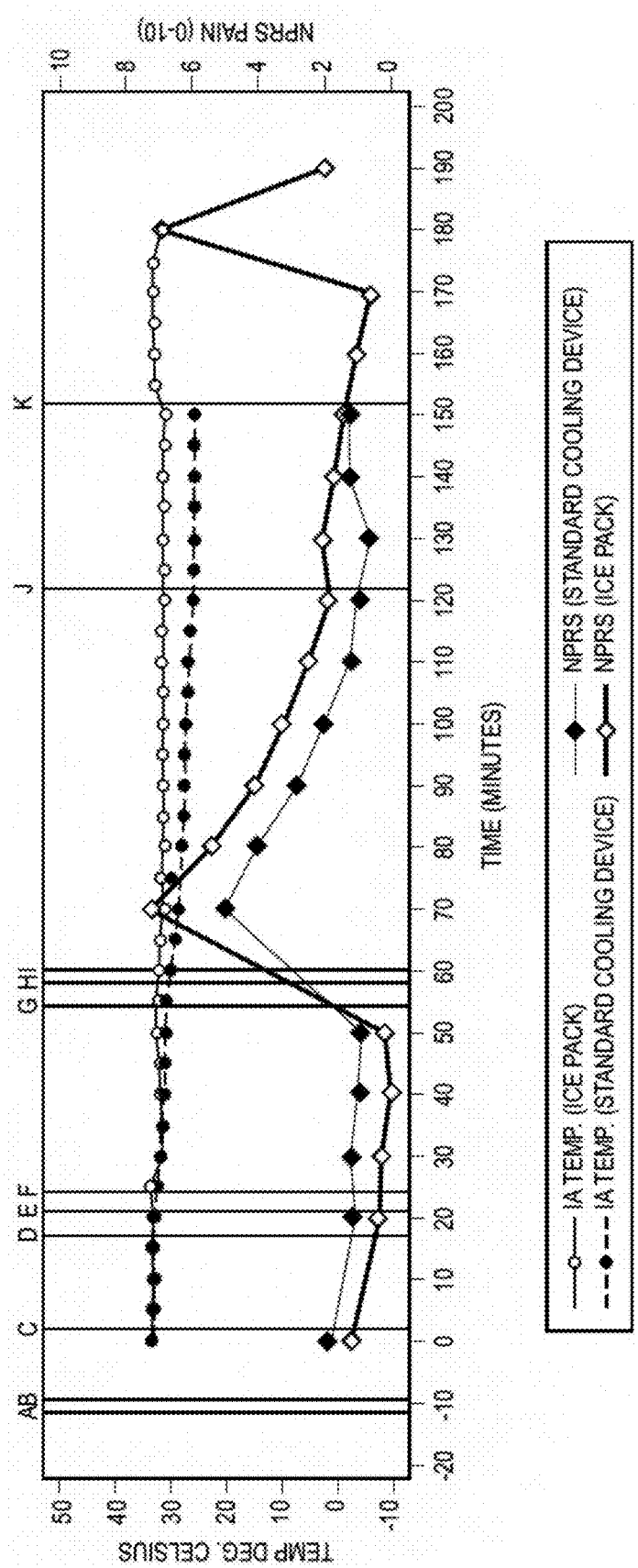
FIG. 7 is a graph showing mean intraarticular (IA) temperature and mean NPRS Pain scores over time using the following cooling devices: (i) a Breg Knee WrapOn Polar Pad or (ii) Ice Pack, as further described in Example 8. The "Standard Cooling Device" was a Breg Knee WrapOn Polar Pad. The following designations apply to the graph: A is the time at which any temperature reading of the temperature probe was made prior to insertion into the intraarticular space of the patient's knee; B is the time which the temperature probe was inserted into the intraarticular space of the patient's knee; C is time at which the cooling device was applied to the patient's knee; D is the time at which the cooling device was removed from the patient's knee; E is the time at which a solution of 2% w/w lidocaine was administered to the patient's knee by intraarticular injection; F is the time at which the cooling device was reapplied to the patient's knee; G is the time at which the cooling device was removed from the patient's knee; H is the time that trans-capsaicin was administered by intraarticular injection; I is the time at which the cooling device was reapplied to the patient's knee; J is the time at which the cooling device was removed from the patient's knee; K is the time at which the temperature probe was removed from the patient's knee.

Mean NPRS Pain scores recorded over time are presented in FIG. 6, along with mean values for intraarticular temperature in the knee joint, for the four human patients for which the experimental procedure was completed successfully. Mean NPRS Pain scores recorded over time are presented in FIG. 7, along with mean values for intraarticular temperature in the knee joint, for all five four human patients.

For the four human patients for which the experimental procedure was completed successfully, tabulated mean temperature values along with mean NPRS Pain scores recorded in the study are provided in Table 1 below. Table 2 below provides tabulated mean temperature values along with mean NPRS Pain scores recorded in the study for all five human patients.

The data show that the Breg Knee WrapOn Polar Pad resulted in lower intraarticular temperature for the patient's knee joint after about 30 minutes of cooling, compared to ice-pack cooling. Additionally, pain due to capsaicin injection was less when Breg Knee WrapOn Polar Pad cooling was used, compared to ice-pack cooling.

Tabulated mean temperature values along with mean NPRS Pain scores recorded in the study are provided in Table 1 below.

TABLE 1

| Cooling Method | Baseline | 5 min | 10 min | 15 min | 20 min |
|---|---|---|---|---|---|
| IA Temperature | | | | | |
| Ice Pack | 33.4 (+/− 1.6) | 33.2 (+/− 1.3) | 33.2 (+/− 1.2) | 33.3 (+/− 1.2) | 33.4 (+/− 1.0) |
| Standard Cooling Device | 33.2 (+/− 0.8) | 32.8 (+/− 0.8) | 32.6 (+/− 0.9) | 32.4 (+/− 1.2) | 32.4 (+/− 1.4) |
| Skin Temperature | | | | | |
| Ice Pack | 28.1 (+/− 1.2) | 27.4 (+/− 1.2) | 26.2 (+/− 1.3) | 24.5 (+/− 1.7) | 24.0 (+/− 1.7) |
| Standard Cooling Device | 27.6 (+/− 0.4) | 26.2 (+/− 0.6) | 23.7 (+/− 0.5) | 20.4 (+/− 0.8) | 19.1 (+/− 1.0) |
| Knee Pain (NPRS) | | | | | |
| Ice Pack | 1.3 (+/− 2.5) | | | | 0.5 (+/− 0.6) |
| Standard Cooling Device | 2.0 (+/− 2.7) | | | | 1.3 (+/− 1.9) |

| Cooling Method | 25 min | 30 min | 35 min | 40 min | 45 min |
|---|---|---|---|---|---|
| IA Temperature | | | | | |
| Ice Pack | 32.5 (+/− 0.8) | 31.4 (+/− 0.8) | 31.7 (+/− 1.1) | 31.9 (+/− 1.2) | 32.0 (+/− 1.2) |
| Standard Cooling Device | 31.7 (+/− 1.3) | 30.8 (+/− 1.5) | 30.6 (+/− 1.9) | 30.4 (+/− 1.9) | 30.1 (+/− 1.9) |
| Skin Temperature | | | | | |
| Ice Pack | 25.1 (+/− 1.5) | 25.4 (+/− 0.9) | 23.9 (+/− 1.0) | 23.0 (+/− 1.6) | 22.5 (+/− 2.0) |
| Standard Cooling Device | 20.3 (+/− 0.9) | 20.1 (+/− 1.0) | 17.9 (+/− 1.4) | 16.6 (+/− 1.6) | 15.7 (+/− 1.7) |
| Knee Pain (NPRS) | | | | | |
| Ice Pack | | 0.3 (+/− 0.6) | | 0.0 | |
| Standard Cooling Device | | 1.3 (+/− 1.3) | | | |

| Cooling Method | 50 min | 55 min | 60 min | 65 min | 70 min |
|---|---|---|---|---|---|
| IA Temperature | | | | | |
| Ice Pack | 32.0 (+/− 1.2) | 32.1 (+/− 1.2) | 32.0 (+/− 0.5) | 31.6 (+/− 0.8) | 31.3 (+/− 2.2) |
| Standard Cooling Device | 29.8 (+/− 2.0) | 29.7 (+/− 2.0) | 29.5 (+/− 1.6) | 28.4 (+/− 1.0) | 27.2 (+/− 0.9) |
| Skin Temperature | | | | | |
| Ice Pack | 22.2 (+/− 2.3) | 22.1 (+/− 2.6) | 23.3 (+/− 2.4) | 23.7 (+/− 2.3) | 22.1 (+/− 2.8) |
| Standard Cooling Device | 15.1 (+/− 1.7) | 14.8 (+/− 1.6) | 16.3 (+/− 1.2) | 17.4 (+/− 1.0) | 16.2 (+/− 1.1) |
| Knee Pain (NPRS) | | | | | |
| Ice Pack | 0.3 (+/− 0.5) | | | | 7.3 (+/− 1.9) |
| Standard Cooling Device | 1.0 (+/− 0.8) | | | | 4.0 (+/− 2.2) |

TABLE 1-continued

| Cooling Method | 75 min | 80 min | 85 min | 90 min | 95 min |
|---|---|---|---|---|---|
| *IA Temperature* | | | | | |
| Ice Pack | 31.0 (+/− 2.7) | 30.9 (+/− 3.1) | 30.9 (+/− 3.1) | 30.8 (+/− 3.3) | 30.8 (+/− 3.3) |
| Standard Cooling Device | 26.8 (+/− 0.9) | 26.4 (+/− 0.8) | 26.1 (+/− 1.0) | 25.9 (+/− 1.3) | 25.7 (+/− 1.5) |
| *Skin Temperature* | | | | | |
| Ice Pack | 20.9 (+/− 3.2) | 20.4 (+/− 3.6) | 19.9 (+/− 4.0) | 19.1 (+/− 4.5) | 19.0 (+/− 4.5) |
| Standard Cooling Device | 15.1 (+/− 1.2) | 14.5 (+/− 1.2) | 14.1 (+/− 1.2) | 13.8 (+/− 1.1) | 13.5 (+/− 1.1) |
| *Knee Pain (NPRS)* | | | | | |
| Ice Pack | | 6.8 (+/− 2.5) | | 4.3 (+/− 1.7) | |
| Standard Cooling Device | | 3.8 (+/− 1.5) | | 2.5 (+/− 1.7) | |

| Cooling Method | 100 min | 105 min | 110 min | 115 min | 120 min |
|---|---|---|---|---|---|
| *IA Temperature* | | | | | |
| Ice Pack | 30.8 (+/− 3.3) | 30.8 (+/− 3.4) | 30.7 (+/− 3.6) | 30.6 (+/− 3.7) | 30.5 (+/− 3.8) |
| Standard Cooling Device | 25.4 (+/− 1.6) | 25.1 (+/− 1.7) | 24.8 (+/− 1.8) | 24.4 (+/− 1.7) | 23.9 (+/− 1.7) |
| *Skin Temperature* | | | | | |
| Ice Pack | 18.8 (+/− 4.5) | 18.6 (+/− 4.6) | 18.4 (+/− 4.6) | 18.2 (+/− 4.4) | 18.0 (+/− 4.3) |
| Standard Cooling Device | 13.3 (+/− 1.0) | 13.1 (+/− 1.0) | 13.0 (+/− 0.9) | 12.9 (+/− 0.9) | 12.8 (+/− 0.9) |
| *Knee Pain (NPRS)* | | | | | |
| Ice Pack | 3.5 (+/− 1.7) | | 2.8 (+/− 2.2) | | 2.0 (+/− 1.4) |
| Standard Cooling Device | 1.8 (+/− 1.5) | | 1.3 (+/− 1.0) | | 1.0 (+/− 0.8) |

| Cooling Method | 125 min | 130 min | 135 min | 140 min | 145 min |
|---|---|---|---|---|---|
| *IA Temperature* | | | | | |
| Ice Pack | 30.5 (+/− 3.8) | 30.6 (+/− 3.4) | 30.8 (+/− 3.0) | 30.9 (+/− 2.7) | 30.6 (+/− 3.1) |
| Standard Cooling Device | 23.7 (+/− 1.7) | 23.6 (+/− 1.9) | 23.7 (+/− 2.0) | 23.8 (+/− 2.2) | 23.7 (+/− 2.5) |
| *Skin Temperature* | | | | | |
| Ice Pack | 18.1 (+/− 4.1) | 19.1 (+/− 3.4) | 20.5 (+/− 2.7) | 21.4 (+/− 2.5) | 22.1 (+/− 2.6) |
| Standard Cooling Device | 13.1 (+/− 1.2) | 14.3 (+/− 1.3) | 16.1 (+/− 1.2) | 17.4 (+/− 1.0) | 18.4 (+/− 1.0) |
| *Knee Pain (NPRS)* | | | | | |
| Ice Pack | | 2.3 (+/− 1.0) | | 1.8 (+/− 1.3) | |
| Standard Cooling Device | | 0.8 (+/− 0.5) | | 1.0 (+/− 0.8) | |

| Cooling Method | 150 min | 155 min | 160 min | 165 min | 170 min |
|---|---|---|---|---|---|
| *IA Temperature* | | | | | |
| Ice Pack | 30.2 (+/− 3.9) | 31.7 | 31.6 | 31.7 | 31.7 |
| Standard Cooling Device | 23.7 (+/− 2.6) | | | | |
| *Skin Temperature* | | | | | |
| Ice Pack | 22.7 (+/− 2.7) | 19.8 | 19.7 | 20.4 | 22.0 |
| Standard Cooling Device | 19.1 (+/− 1.0) | | | | |
| *Knee Pain (NPRS)* | | | | | |
| Ice Pack | 1.3 (+/− 1.0) | | 2.0 | | 1.0 |
| Standard Cooling Device | 1.3 (+/− 1.3) | | | | |

TABLE 1-continued

| Cooling Method | 175 min | 180 min | 190 min |
|---|---|---|---|
| *IA Temperature* | | | |
| Ice Pack | 31.7 | 31.6 | |
| Standard Cooling Device | | | |
| *Skin Temperature* | | | |
| Ice Pack | 23.3 | 24.2 | |
| Standard Cooling Device | | | |
| *Knee Pain (NPRS)* | | | |
| Ice Pack | | 7.0 | 2.0 |
| Standard Cooling Device | | | |

TABLE 2

| Cooling Method | Baseline | 5 min | 10 min | 15 min | 20 min |
|---|---|---|---|---|---|
| *IA Temperature* | | | | | |
| Ice Pack | 33.5 (+/− 1.4) | 33.4 (+/− 1.2) | 33.3 (+/− 1.1) | 33.4 (+/− 1.1) | 33.3 (+/− 0.9) |
| Standard Cooling Device | 33.6 (+/− 1.2) | 33.3 (+/− 1.3) | 33.1 (+/− 1.5) | 33.0 (+/− 1.7) | 32.9 (+/− 1.7) |
| *Skin Temperature* | | | | | |
| Ice Pack | 28.3 (+/− 1.2) | 27.7 (+/− 1.3) | 26.5 (+/− 1.3) | 24.8 (+/− 1.5) | 24.2 (+/− 1.6) |
| Standard Cooling Device | 28.0 (+/− 1.0) | 26.7 (+/− 1.1) | 24.2 (+/− 1.2) | 20.9 (+/− 1.4) | 19.5 (+/− 1.4) |
| *Knee Pain (NPRS)* | | | | | |
| Ice Pack | 1.0 (+/− 2.2) | | | | 0.4 (+/− 0.5) |
| Standard Cooling Device | 1.8 (+/− 2.4) | | | | 1.0 (+/− 1.7) |

| Cooling Method | 25 min | 30 min | 35 min | 40 min | 45 min |
|---|---|---|---|---|---|
| *IA Temperature* | | | | | |
| Ice Pack | 33.5 (+/− 2.4) | 31.4 (+/− 0.8) | 31.7 (+/− 1.1) | 31.9 (+/− 1.2) | 32.0 (+/− 1.2) |
| Standard Cooling Device | 32.2 (+/− 1.7) | 31.5 (+/− 2.1) | 31.5 (+/− 2.5) | 31.3 (+/− 2.6) | 31.1 (+/− 2.7) |
| *Skin Temperature* | | | | | |
| Ice Pack | 25.3 (+/− 1.3) | 25.4 (+/− 0.9) | 23.9 (+/− 1.0) | 23.0 (+/− 1.6) | 22.5 (+/− 2.0) |
| Standard Cooling Device | 20.7 (+/− 1.2) | 20.6 (+/− 1.4) | 18.5 (+/− 1.8) | 17.1 (+/− 1.9) | 16.2 (+/− 1.9) |
| *Knee Pain (NPRS)* | | | | | |
| Ice Pack | | 0.3 (+/− 0.5) | | 0.0 | |
| Standard Cooling Device | | 1.2 (+/− 1.1) | | | |

| Cooling Method | 50 min | 55 min | 60 min | 65 min | 70 min |
|---|---|---|---|---|---|
| *IA Temperature* | | | | | |
| Ice Pack | 32.4 (+/− 1.3) | 32.4 (+/− 1.2) | 32.3 (+/− 0.7) | 32.0 (+/− 1.0) | 31.7 (+/− 2.1) |
| Standard Cooling Device | 30.8 (+/− 2.8) | 30.6 (+/− 2.7) | 30.1 (+/− 2.0) | 29.2 (+/− 2.2) | 28.6 (+/− 3.1) |
| *Skin Temperature* | | | | | |
| Ice Pack | 23.3 (+/− 3.1) | 22.6 (+/− 2.5) | 23.3 (+/− 2.1) | 23.4 (+/− 2.1) | 21.9 (+/− 2.4) |
| Standard Cooling Device | 15.6 (+/− 1.9) | 15.3 (+/− 1.7) | 16.8 (+/− 1.4) | 17.8 (+/− 1.3) | 16.7 (+/− 1.4) |
| *Knee Pain (NPRS)* | | | | | |
| Ice Pack | 0.3 (+/− 0.5) | | | | 7.3 (+/− 1.9) |
| Standard Cooling Device | 0.8 (+/− 0.8) | | | | 5.0 (+/− 2.9) |

TABLE 2-continued

| Cooling Method | 75 min | 80 min | 85 min | 90 min | 95 min |
|---|---|---|---|---|---|
| IA Temperature | | | | | |
| Ice Pack | 31.4 (+/− 2.5) | 31.3 (+/− 2.8) | 31.3 (+/− 2.8) | 31.3 (+/− 3.0) | 31.3 (+/− 3.1) |
| Standard Cooling Device | 28.3 (+/− 3.3) | 27.9 (+/− 3.5) | 27.7 (+/− 3.7) | 27.5 (+/− 3.9) | 27.4 (+/− 4.0) |
| Skin Temperature | | | | | |
| Ice Pack | 20.9 (+/− 2.8) | 20.4 (+/− 3.1) | 20.3 (+/− 3.5) | 19.8 (+/− 4.2) | 19.4 (+/− 4.1) |
| Standard Cooling Device | 15.7 (+/− 1.6) | 15.1 (+/− 1.6) | 14.6 (+/− 1.6) | 14.3 (+/− 1.6) | 14.1 (+/− 1.6) |
| Knee Pain (NPRS) | | | | | |
| Ice Pack | | 5.4 (+/− 3.7) | | 4.0 (+/− 1.6) | |
| Standard Cooling Device | | 4.0 (+/− 1.4) | | 2.8 (+/− 1.6) | |

| Cooling Method | 100 min | 105 min | 110 min | 115 min | 120 min |
|---|---|---|---|---|---|
| IA Temperature | | | | | |
| Ice Pack | 31.4 (+/− 3.1) | 31.3 (+/− 3.2) | 31.3 (+/− 3.4) | 31.2 (+/− 3.5) | 31.1 (+/− 3.6) |
| Standard Cooling Device | 27.2 (+/− 4.2) | 26.9 (+/− 4.3) | 26.7 (+/− 4.5) | 26.3 (+/− 4.6) | 25.9 (+/− 4.8) |
| Skin Temperature | | | | | |
| Ice Pack | 19.1 (+/− 4.0) | 18.9 (+/− 4.0) | 18.7 (+/− 4.0) | 18.5 (+/− 3.9) | 18.3 (+/− 3.8) |
| Standard Cooling Device | 13.9 (+/− 1.6) | 13.7 (+/− 1.6) | 13.6 (+/− 1.6) | 13.5 (+/− 1.6) | 13.4 (+/− 1.6) |
| Knee Pain (NPRS) | | | | | |
| Ice Pack | 3.2 (+/− 1.6) | | 2.4 (+/− 2.1) | | 1.8 (+/− 1.3) |
| Standard Cooling Device | 2.0 (+/− 1.4) | | 1.2 (+/− 0.8) | | 1.0 (+/− 0.7) |

| Cooling Method | 125 min | 130 min | 135 min | 140 min | 145 min |
|---|---|---|---|---|---|
| IA Temperature | | | | | |
| Ice Pack | 31.1 (+/− 3.6) | 31.2 (+/− 3.3) | 31.3 (+/− 2.9) | 31.4 (+/− 2.7) | 31.3 (+/− 3.1) |
| Standard Cooling Device | 25.7 (+/− 4.9) | 25.7 (+/− 5.0) | 25.7 (+/− 4.9) | 25.8 (+/− 4.8) | 25.7 (+/− 4.9) |
| Skin Temperature | | | | | |
| Ice Pack | 18.3 (+/− 3.6) | 19.1 (+/− 2.9) | 20.2 (+/− 2.4) | 21.0 (+/− 2.4) | 21.5 (+/− 2.6) |
| Standard Cooling Device | 13.6 (+/− 1.6) | 14.7 (+/− 1.4) | 16.3 (+/− 1.2) | 17.6 (+/− 1.0) | 18.6 (+/− 1.0) |
| Knee Pain (NPRS) | | | | | |
| Ice Pack | | 2.0 (+/− 1.0) | | 1.8 (+/− 1.1) | |
| Standard Cooling Device | | 0.6 (+/− 0.5) | | 1.2 (+/− 0.8) | |

| Cooling Method | 150 min | 155 min | 160 min | 165 min | 170 min |
|---|---|---|---|---|---|
| IA Temperature | | | | | |
| Ice Pack | 30.9 (+/− 3.8) | 32.7 (+/− 1.4) | 32.7 (+/− 1.6) | 32.9 (+/− 1.7) | 33.0 (+/− 1.8) |
| Standard Cooling Device | 25.6 (+/− 4.9) | | | | |
| Skin Temperature | | | | | |
| Ice Pack | 22.1 (+/− 2.6) | 20.8 (+/− 1.5) | 21.6 (+/− 2.7) | 22.4 (+/− 2.9) | 23.6 (+/− 2.3) |
| Standard Cooling Device | 19.3 (+/− 1.0) | | | | |
| Knee Pain (NPRS) | | | | | |
| Ice Pack | 1.4 (+/− 0.9) | | 1.0 (+/− 1.4) | | 0.5 (+/− 0.7) |
| Standard Cooling Device | 1.2 (+/− 1.1) | | | | |

TABLE 2-continued

| Cooling Method | 175 min | 180 min | 190 min |
|---|---|---|---|
| *IA Temperature* | | | |
| Ice Pack | 33.0 (+/− 1.9) | 31.6 | |
| Standard Cooling Device | | | |
| *Skin Temperature* | | | |
| Ice Pack | 24.6 (+/− 1.8) | 24.2 | |
| Standard Cooling Device | | | |
| *Knee Pain (NPRS)* | | | |
| Ice Pack | | 7.0 | 2.0 |
| Standard Cooling Device | | | |

Example 9—Analysis of Procedure Pain Due to Intraarticular Administration of Capsaicin Human patients experiencing osteoarthritic knee joint pain were subjected to two different protocols for intraarticular administration of trans-capsaicin. Temporary pain expected due to administration of capsaicin was analyzed, along with the intraarticular temperature of the knee joint and the temperature of the patient's skin in the area to be cooled.

One of the protocols utilized a Breg Knee WrapOn Polar Pad (as illustrated in FIG. 1) that utilizes circulating ice-water to achieve cooling, where the pad is placed on skin surrounding the knee in order to cool the knee joint. The other protocol utilized an Elasto-Gel All Purpose Therapy Wrap measuring 6 inches by 24 inches in size, in order to cool the knee joint. A temperature probe was placed into the intraarticular space of the patient's knee joint to measure intraarticular temperature of the knee joint. A temperature probe was also placed on the skin in the area to be cooled in order to measure skin temperature in the area to be cooled. Experimental procedures and results are provided below

Part I—Experimental Procedures

Experimental procedure used was the same as described in Example 8 herein, except that an Elasto-Gel All Purpose Therapy Wrap measuring 6 inches by 24 inches in size was used to cool the knee joint, in lieu of the ice pack. The Elasto-Gel All Purpose Therapy Wrap was removed from a freezer (approximately 0° F.) just prior to use.

Part II—Results

The experimental procedure was completed successfully for four human patients. For the fifth patient subjected to the experimental procedure, there was a deviation from protocol. For this reason, experimental results are provided below separately for (i) the four human patients for which the experimental procedure was completed successfully and (ii) all five human patients.

Figure 8:
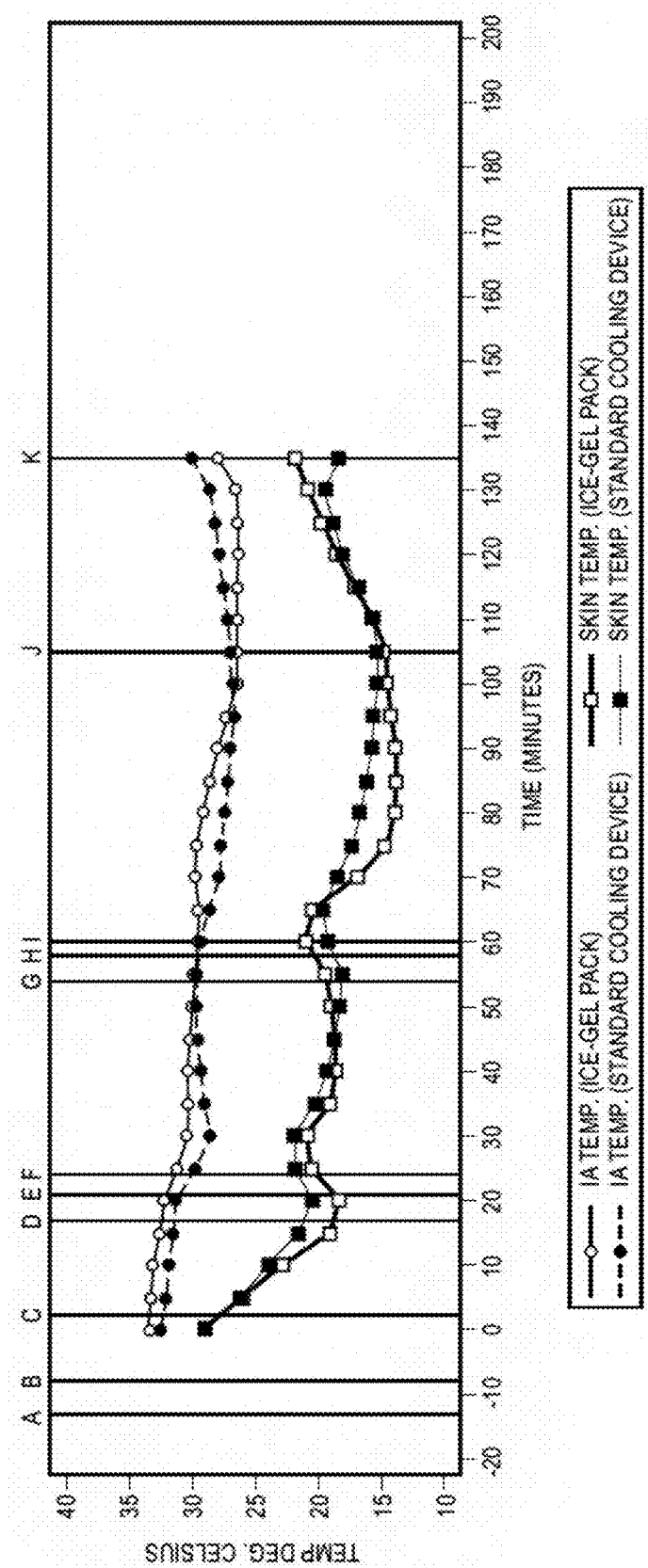
FIG. 8 is a graph showing mean intraarticular (IA) temperature and mean skin temperature over time using the following cooling devices: (i) a Breg Knee WrapOn Polar Pad or (ii) Elasto-Gel All Purpose Therapy Wrap, as further described in Example 9. The "Standard Cooling Device" was a Breg Knee WrapOn Polar Pad. The "Ice-Gel Pack" was an Elasto-Gel All Purpose Therapy Wrap. The following designations apply to the graph: A is the time at which any temperature reading of the temperature probe was made prior to insertion into the intraarticular space of the patient's knee; B is the time which the temperature probe was inserted into the intraarticular space of the patient's knee; C is time at which the cooling device was applied to the patient's knee; D is the time at which the cooling device was removed from the patient's knee; E is the time at which a solution of 2% w/w lidocaine was administered to the patient's knee by intraarticular injection; F is the time at which the cooling device was reapplied to the patient's knee; G is the time at which the cooling device was removed from the patient's knee; H is the time that trans-capsaicin was administered by intraarticular injection; I is the time at which the cooling device was reapplied to the patient's knee; J is the time at which the cooling device was removed from the patient's knee; K is the time at which the temperature probe was removed from the patient's knee.
Figure 9:
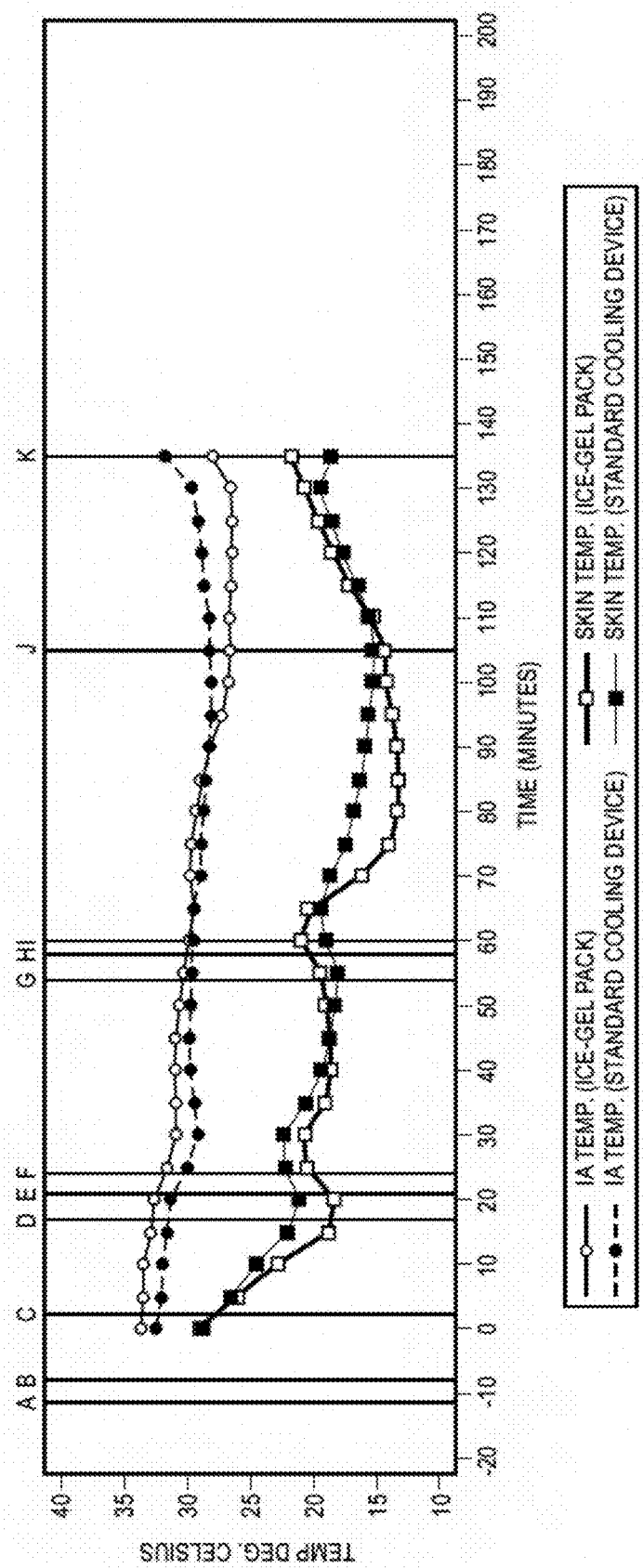
FIG. 9 is a graph showing mean intraarticular (IA) temperature and mean skin temperature over time using the following cooling devices: (i) a Breg Knee WrapOn Polar Pad or (ii) Elasto-Gel All Purpose Therapy Wrap, as further described in Example 9. The "Standard Cooling Device" was a Breg Knee WrapOn Polar Pad. The "Ice-Gel Pack" was an Elasto-Gel All Purpose Therapy Wrap. The following designations apply to the graph: A is the time at which any temperature reading of the temperature probe was made prior to insertion into the intraarticular space of the patient's knee; B is the time which the temperature probe was inserted into the intraarticular space of the patient's knee; C is time at which the cooling device was applied to the patient's knee; D is the time at which the cooling device was removed from the patient's knee; E is the time at which a solution of 2% w/w lidocaine was administered to the patient's knee by intraarticular injection; F is the time at which the cooling device was reapplied to the patient's knee; G is the time at which the cooling device was removed from the patient's knee; H is the time that trans-capsaicin was administered by intraarticular injection; I is the time at which the cooling device was reapplied to the patient's knee; J is the time at which the cooling device was removed from the patient's knee; K is the time at which the temperature probe was removed from the patient's knee.

Mean values for intraarticular temperature in the knee joint recorded over time are presented in FIG. 8, along with mean values for skin temperature recorded over time, for the four human patients for which the experimental procedure was completed successfully. Mean values for intraarticular temperature in the knee joint recorded over time are presented in FIG. 9, along with mean values for skin temperature recorded over time, for all five human patients.

Figure 10:
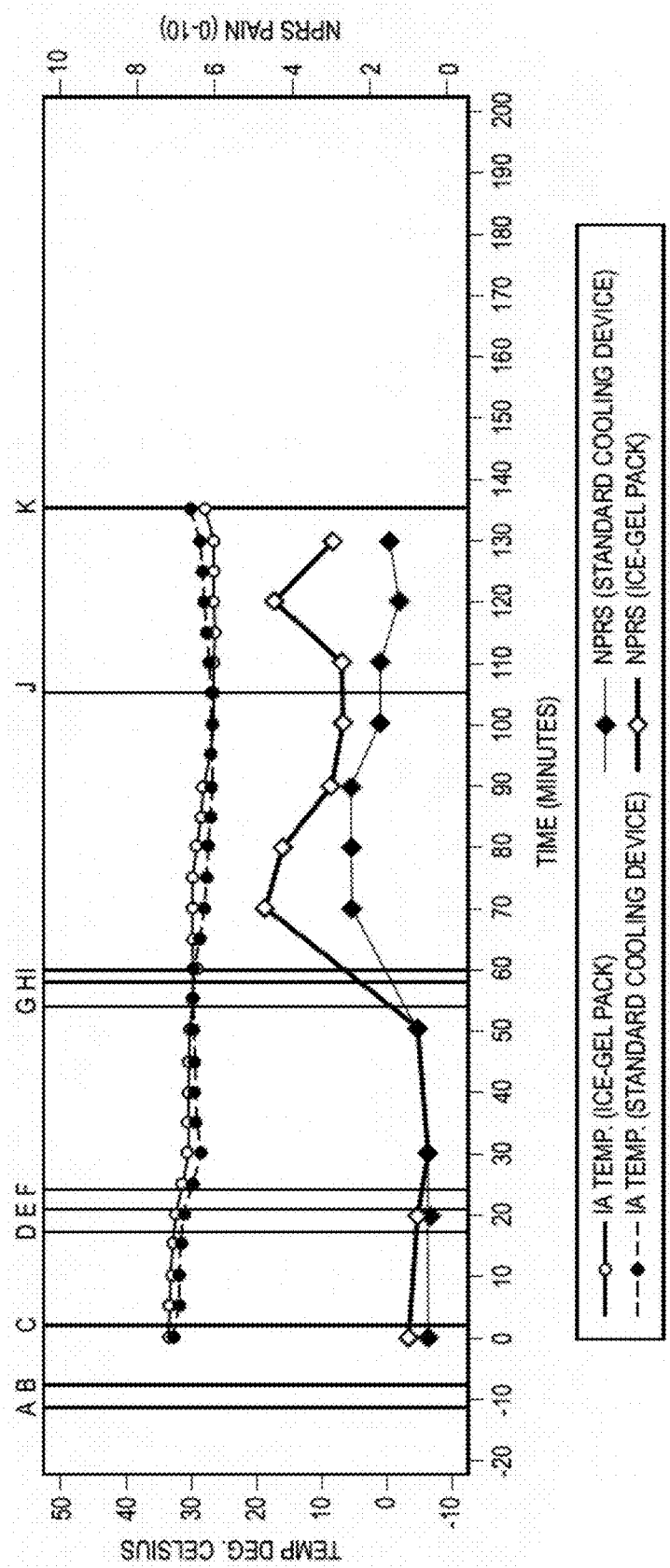
FIG. 10 is a graph showing mean intraarticular (IA) temperature and mean NPRS Pain scores over time using the following cooling devices: (i) a Breg Knee WrapOn Polar Pad or (ii) Elasto-Gel All Purpose Therapy Wrap, as further described in Example 9. The "Standard Cooling Device" was a Breg Knee WrapOn Polar Pad. The "Ice-Gel Pack" was an Elasto-Gel All Purpose Therapy Wrap. The following designations apply to the graph: A is the time at which any temperature reading of the temperature probe was made prior to insertion into the intraarticular space of the patient's knee; B is the time which the temperature probe was inserted into the intraarticular space of the patient's knee; C is time at which the cooling device was applied to the patient's knee; D is the time at which the cooling device was removed from the patient's knee; E is the time at which a solution of 2% w/w lidocaine was administered to the patient's knee by intraarticular injection; F is the time at which the cooling device was reapplied to the patient's knee; G is the time at which the cooling device was removed from the patient's knee; H is the time that trans-capsaicin was administered by intraarticular injection; I is the time at which the cooling device was reapplied to the patient's knee; J is the time at which the cooling device was removed from the patient's knee; K is the time at which the temperature probe was removed from the patient's knee.
Figure 11:
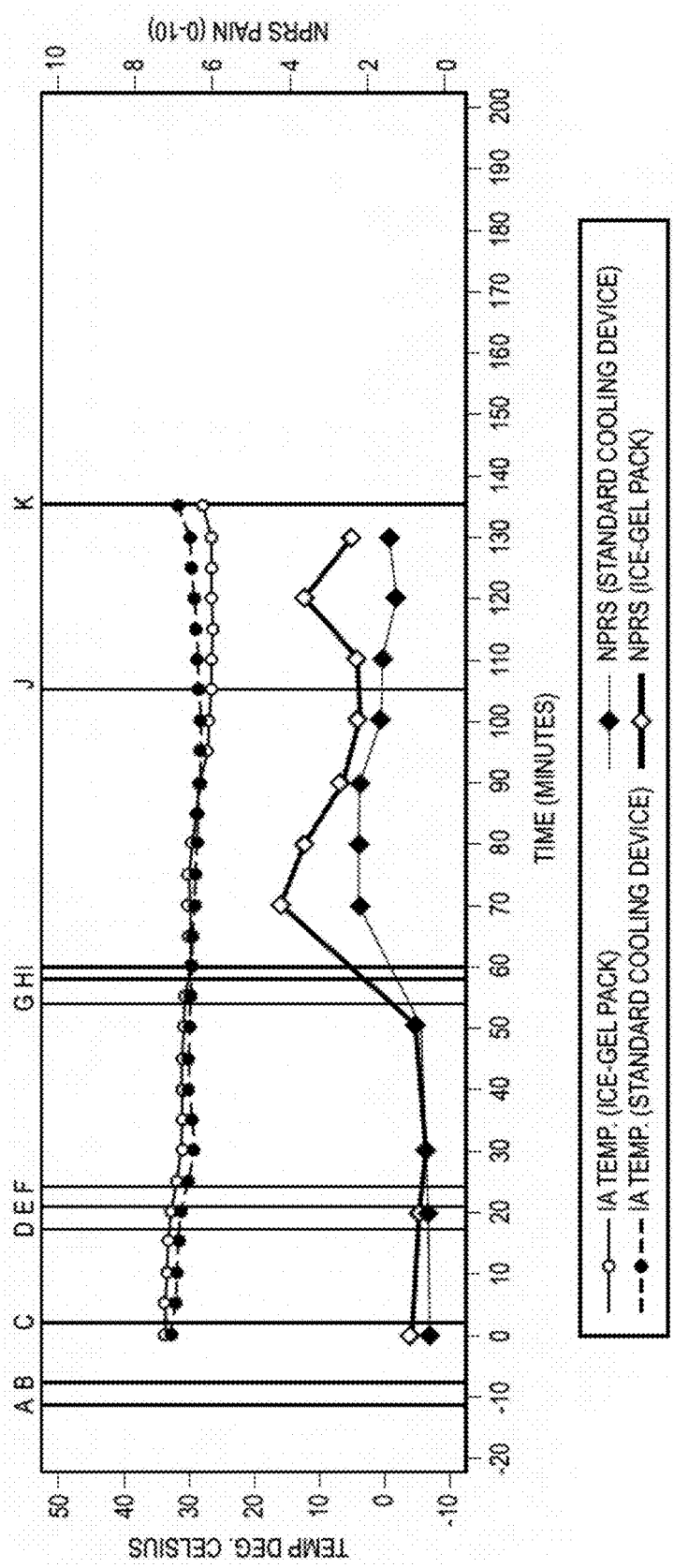
FIG. 11 is a graph showing mean intraarticular (IA) temperature and mean NPRS Pain scores over time using the following cooling devices: (i) a Breg Knee WrapOn Polar Pad or (ii) Elasto-Gel All Purpose Therapy Wrap, as further described in Example 9. The "Standard Cooling Device" was a Breg Knee WrapOn Polar Pad. The "Ice-Gel Pack" was an Elasto-Gel All Purpose Therapy Wrap. The following designations apply to the graph: A is the time at which any temperature reading of the temperature probe was made prior to insertion into the intraarticular space of the patient's knee; B is the time which the temperature probe was inserted into the intraarticular space of the patient's knee; C is time at which the cooling device was applied to the patient's knee; D is the time at which the cooling device was removed from the patient's knee; E is the time at which a solution of 2% w/w lidocaine was administered to the patient's knee by intraarticular injection; F is the time at which the cooling device was reapplied to the patient's knee; G is the time at which the cooling device was removed from the patient's knee; H is the time that trans-capsaicin was administered by intraarticular injection; I is the time at which the cooling device was reapplied to the patient's knee; J is the time at which the cooling device was removed from the patient's knee; K is the time at which the temperature probe was removed from the patient's knee.

Mean NPRS Pain scores recorded over time are presented in FIG. 10, along with mean values for intraarticular temperature in the knee joint, for the four human patients for which the experimental procedure was completed successfully. Mean NPRS Pain scores recorded over time are presented in FIG. 11, along with mean values for intraarticular temperature in the knee joint, for all five four human patients.

For the four human patients for which the experimental procedure was completed successfully, tabulated mean temperature values along with mean NPRS Pain scores recorded in the study are provided in Table 1 below. Table 2 below provides tabulated mean temperature values along with mean NPRS Pain scores recorded in the study for all five human patients.

TABLE 1

| Cooling Method | Baseline | 5 min | 10 min | 15 min | 20 min |
|---|---|---|---|---|---|
| *IA Temperature* | | | | | |
| Ice-Gel Pack | 33.6 (+/− 0.9) | 33.3 (+/− 1.0) | 33.1 (+/− 1.1) | 32.7 (+/− 1.2) | 32.2 (+/− 1.4) |
| Standard Cooling Device | 32.6 (+/− 0.4) | 32.1 (+/− 0.5) | 31.9 (+/− 0.6) | 31.7 (+/− 0.6) | 31.3 (+/− 0.9) |
| *Skin Temperature* | | | | | |
| Ice-Gel Pack | 29.0 (+/− 0.9) | 26.2 (+/− 2.3) | 22.9 (+/− 2.5) | 19.1 (+/− 2.9) | 18.6 (+/− 2.9) |
| Standard Cooling Device | 28.9 (+/− 1.5) | 26.5 (+/− 2.2) | 24.2 (+/− 2.7) | 21.6 (+/− 3.4) | 20.6 (+/− 3.6) |

TABLE 1-continued

| | Knee Pain (NPRS) | | | | |
|---|---|---|---|---|---|
| Ice-Gel Pack | 1.0 (+/− 0.8) | | | | 0.8 (+/− 0.5) |
| Standard Cooling Device | 0.5 (+/− 0.6) | | | | 0.5 (+/− 0.6) |

| Cooling Method | 25 min | 30 min | 35 min | 40 min | 45 min |
|---|---|---|---|---|---|
| | IA Temperature | | | | |
| Ice-Gel Pack | 31.3 (+/− 1.4) | 30.5 (+/− 1.4) | 30.4 (+/− 1.6) | 30.4 (+/− 1.7) | 30.3 (+/− 2.1) |
| Standard Cooling Device | 29.8 (+/− 1.7) | 28.6 (+/− 2.1) | 29.1 (+/− 1.6) | 29.5 (+/− 1.6) | 29.7 (+/− 1.7) |
| | Skin Temperature | | | | |
| Ice-Gel Pack | 20.7 (+/− 2.5) | 21.0 (+/− 1.9) | 19.1 (+/− 2.1) | 18.7 (+/− 2.3) | 18.8 (+/− 2.4) |
| Standard Cooling Device | 21.9 (+/− 3.1) | 22.1 (+/− 2.7) | 20.3 (+/− 3.1) | 19.4 (+/− 3.3) | 18.9 (+/− 3.3) |
| | Knee Pain (NPRS) | | | | |
| Ice-Gel Pack | | 0.5 (+/− 0.6) | | | |
| Standard Cooling Device | | 0.5 (+/− 0.6) | | | |

| Cooling Method | 50 min | 55 min | 60 min | 65 min | 70 min |
|---|---|---|---|---|---|
| | IA Temperature | | | | |
| Ice-Gel Pack | 30.1 (+/− 2.5) | 29.8 (+/− 2.7) | 29.6 (+/− 2.4) | 29.6 (+/− 1.9) | 29.8 (+/− 1.7) |
| Standard Cooling Device | 29.7 (+/− 1.9) | 29.7 (+/− 2.1) | 29.5 (+/− 2.0) | 28.7 (+/− 2.1) | 28.0 (+/− 2.6) |
| | Skin Temperature | | | | |
| Ice-Gel Pack | 19.2 (+/− 2.6) | 19.6 (+/− 2.7) | 21.2 (+/− 2.7) | 20.6 (+/− 2.5) | 16.9 (+/− 2.3) |
| Standard Cooling Device | 18.5 (+/− 3.3) | 18.2 (+/− 3.4) | 19.3 (+/− 3.4) | 19.9 (+/− 3.6) | 18.7 (+/− 3.5) |
| | Knee Pain (NPRS) | | | | |
| Ice-Gel Pack | 0.8 (+/− 1.0) | | | | 4.8 (+/− 3.2) |
| Standard Cooling Device | 0.8 (+/− 1.0) | | | | 2.5 (+/− 3.7) |

| Cooling Method | 75 min | 80 min | 85 min | 90 min | 95 min |
|---|---|---|---|---|---|
| | IA Temperature | | | | |
| Ice-Gel Pack | 29.7 (+/− 1.5) | 29.3 (+/− 1.6) | 28.7 (+/− 2.0) | 28.0 (+/− 2.5) | 27.1 (+/− 3.3) |
| Standard Cooling Device | 27.8 (+/− 2.7) | 27.5 (+/− 2.8) | 27.2 (+/− 3.1) | 27.0 (+/− 3.5) | 26.8 (+/− 4.0) |
| | Skin Temperature | | | | |
| Ice-Gel Pack | 14.8 (+/− 2.3) | 14.2 (+/− 2.5) | 14.0 (+/− 2.8) | 14.1 (+/− 3.0) | 14.5 (+/− 3.4) |
| Standard Cooling Device | 17.6 (+/− 3.0) | 16.9 (+/− 2.7) | 16.4 (+/− 2.4) | 16.0 (+/− 2.1) | 15.7 (+/− 2.0) |
| | Knee Pain (NPRS) | | | | |
| Ice-Gel Pack | | 4.3 (+/− 3.0) | | 3.0 (+/− 1.8) | |
| Standard Cooling Device | | 2.5 (+/− 3.0) | | 2.5 (+/− 2.4) | |

| Cooling Method | 100 min | 105 min | 110 min | 115 min | 120 min |
|---|---|---|---|---|---|
| | IA Temperature | | | | |
| Ice-Gel Pack | 26.7 (+/− 3.3) | 26.6 (+/− 3.4) | 26.6 (+/− 3.3) | 26.6 (+/− 3.2) | 26.5 (+/− 3.0) |
| Standard Cooling Device | 26.9 (+/− 3.9) | 27.0 (+/− 3.9) | 27.2 (+/− 3.8) | 27.6 (+/− 3.3) | 27.9 (+/− 3.1) |
| | Skin Temperature | | | | |
| Ice-Gel Pack | 14.7 (+/− 3.5) | 14.9 (+/− 3.3) | 15.9 (+/− 3.3) | 17.4 (+/− 3.5) | 18.7 (+/− 4.0) |
| Standard Cooling Device | 15.6 (+/− 2.1) | 15.4 (+/− 2.1) | 15.9 (+/− 2.0) | 17.0 (+/− 2.1) | 18.1 (+/− 2.4) |
| | Knee Pain (NPRS) | | | | |
| Ice-Gel Pack | 2.8 (+/− 1.5) | | 2.8 (+/− 2.1) | | 4.5 (+/− 3.3) |
| Standard Cooling Device | 1.8 (+/− 1.5) | | 1.8 (+/− 1.5) | | 1.3 (+/− 1.3) |

TABLE 1-continued

| Cooling Method | 125 min | 130 min | 135 min |
|---|---|---|---|
| IA Temperature | | | |
| Ice-Gel Pack | 26.5 (+/− 2.7) | 26.6 (+/− 2.7) | 28.1 (+/− 2.0) |
| Standard Cooling Device | 28.3 (+/− 3.0) | 28.6 (+/− 2.8) | 30.2 |
| Skin Temperature | | | |
| Ice-Gel Pack | 19.9 (+/− 4.6) | 20.9 (+/− 4.9) | 22.0 (+/− 5.9) |
| Standard Cooling Device | 19.1 (+/− 2.7) | 19.8 (+/− 2.8) | 18.4 |
| Knee Pain (NPRS) | | | |
| Ice-Gel Pack | | 3.0 (+/− 1.4) | |
| Standard Cooling Device | | 1.5 (+/− 1.0) | |

TABLE 2

| Cooling Method | Baseline | 5 min | 10 min | 15 min | 20 min |
|---|---|---|---|---|---|
| IA Temperature | | | | | |
| Ice-Gel Pack | 33.7 (+/− 0.8) | 33.5 (+/− 0.9) | 33.3 (+/− 1.0) | 33.0 (+/− 1.3) | 32.6 (+/− 1.5) |
| Standard Cooling Device | 32.5 (+/− 0.4) | 32.1 (+/− 0.5) | 31.9 (+/− 0.5) | 31.6 (+/− 0.6) | 31.3 (+/− 0.8) |
| Skin Temperature | | | | | |
| Ice-Gel Pack | 28.8 (+/− 0.9) | 26.1 (+/− 2.0) | 22.7 (+/− 2.2) | 18.9 (+/− 2.5) | 18.3 (+/− 2.6) |
| Standard Cooling Device | 28.7 (+/− 1.3) | 26.6 (+/− 1.9) | 24.5 (+/− 2.4) | 22.1 (+/− 3.1) | 21.1 (+/− 3.4) |
| Knee Pain (NPRS) | | | | | |
| Ice-Gel Pack | 0.8 (+/− 0.8) | | | | 0.6 (+/− 0.5) |
| Standard Cooling Device | 0.4 (+/− 0.5) | | | | 0.4 (+/− 0.5) |

| Cooling Method | 25 min | 30 min | 35 min | 40 min | 45 min |
|---|---|---|---|---|---|
| IA Temperature | | | | | |
| Ice-Gel Pack | 31.7 (+/− 1.5) | 30.9 (+/− 1.5) | 30.9 (+/− 1.8) | 31.0 (+/− 2.0) | 30.8 (+/− 2.2) |
| Standard Cooling Device | 30.0 (+/− 1.5) | 29.1 (+/− 2.1) | 29.5 (+/− 1.6) | 29.7 (+/− 1.5) | 29.8 (+/− 1.5) |
| Skin Temperature | | | | | |
| Ice-Gel Pack | 20.4 (+/− 2.2) | 20.8 (+/− 1.7) | 19.1 (+/− 1.8) | 18.7 (+/− 2.0) | 18.8 (+/− 2.1) |
| Standard Cooling Device | 22.4 (+/− 2.9) | 22.4 (+/− 2.4) | 20.4 (+/− 2.7) | 19.3 (+/− 2.9) | 18.7 (+/− 2.9) |
| Knee Pain (NPRS) | | | | | |
| Ice-Gel Pack | | 0.4 (+/− 0.5) | | | |
| Standard Cooling Device | | 0.4 (+/− 0.5) | | | |

| Cooling Method | 50 min | 55 min | 60 min | 65 min | 70 min |
|---|---|---|---|---|---|
| IA Temperature | | | | | |
| Ice-Gel Pack | 30.6 (+/− 2.5) | 30.3 (+/− 2.6) | 29.9 (+/− 2.2) | 29.6 (+/− 1.7) | 29.7 (+/− 1.5) |
| Standard Cooling Device | 29.8 (+/− 1.6) | 29.6 (+/− 1.8) | 29.6 (+/− 1.8) | 29.6 (+/− 2.7) | 29.0 (+/− 3.3) |
| Skin Temperature | | | | | |
| Ice-Gel Pack | 19.2 (+/− 2.2) | 19.6 (+/− 2.3) | 21.0 (+/− 2.3) | 20.1 (+/− 2.4) | 16.2 (+/− 2.5) |
| Standard Cooling Device | 18.2 (+/− 2.9) | 17.9 (+/− 3.1) | 19.0 (+/− 3.0) | 19.6 (+/− 3.2) | 18.5 (+/− 3.1) |
| Knee Pain (NPRS) | | | | | |
| Ice-Gel Pack | 0.6 (+/− 0.9) | | | | 4.2 (+/− 3.0) |
| Standard Cooling Device | 0.6 (+/− 0.9) | | | | 2.2 (+/− 3.3) |

TABLE 2-continued

| Cooling Method | 75 min | 80 min | 85 min | 90 min | 95 min |
|---|---|---|---|---|---|
| *IA Temperature* | | | | | |
| Ice-Gel Pack | 29.7 (+/− 1.3) | 29.3 (+/− 1.4) | 28.8 (+/− 1.8) | 28.2 (+/− 2.3) | 27.2 (+/− 2.9) |
| Standard Cooling Device | 28.9 (+/− 3.5) | 28.7 (+/− 3.6) | 28.5 (+/− 3.8) | 28.3 (+/− 4.2) | 28.1 (+/− 4.5) |
| *Skin Temperature* | | | | | |
| Ice-Gel Pack | 14.1 (+/− 2.5) | 13.5 (+/− 2.7) | 13.3 (+/− 2.9) | 13.4 (+/− 3.0) | 13.9 (+/− 3.3) |
| Standard Cooling Device | 17.5 (+/− 2.6) | 16.7 (+/− 2.3) | 16.3 (+/− 2.1) | 15.9 (+/− 1.9) | 15.6 (+/− 1.8) |
| *Knee Pain (NPRS)* | | | | | |
| Ice-Gel Pack | | 3.6 (+/− 3.0) | | 2.6 (+/− 1.8) | |
| Standard Cooling Device | | 2.2 (+/− 2.7) | | 2.2 (+/− 2.2) | |

| Cooling Method | 100 min | 105 min | 110 min | 115 min | 120 min |
|---|---|---|---|---|---|
| *IA Temperature* | | | | | |
| Ice-Gel Pack | 26.8 (+/− 2.9) | 26.7 (+/− 2.9) | 26.6 (+/− 2.9) | 26.6 (+/− 2.8) | 26.4 (+/− 2.6) |
| Standard Cooling Device | 28.1 (+/− 4.4) | 28.2 (+/− 4.3) | 28.3 (+/− 4.2) | 28.6 (+/− 3.7) | 28.8 (+/− 3.4) |
| *Skin Temperature* | | | | | |
| Ice-Gel Pack | 14.1 (+/− 3.4) | 14.3 (+/− 3.2) | 15.4 (+/− 3.1) | 17.0 (+/− 3.1) | 18.4 (+/− 3.6) |
| Standard Cooling Device | 15.4 (+/− 1.8) | 15.2 (+/− 1.9) | 15.6 (+/− 1.8) | 16.6 (+/− 2.1) | 17.7 (+/− 2.3) |
| *Knee Pain (NPRS)* | | | | | |
| Ice-Gel Pack | 2.2 (+/− 1.8) | | 2.2 (+/− 2.2) | | 3.6 (+/− 3.5) |
| Standard Cooling Device | 1.6 (+/− 1.3) | | 1.6 (+/− 1.3) | | 1.2 (+/− 1.1) |

| Cooling Method | 125 min | 130 min | 135 min |
|---|---|---|---|
| *IA Temperature* | | | |
| Ice-Gel Pack | 26.4 (+/− 2.4) | 26.6 (+/− 2.4) | 28.1 (+/− 2.0) |
| Standard Cooling Device | 29.2 (+/− 3.3) | 29.5 (+/− 3.2) | 31.7 (+/− 2.1) |
| *Skin Temperature* | | | |
| Ice-Gel Pack | 19.6 (+/− 4.0) | 20.6 (+/− 4.3) | 22.0 (+/− 5.9) |
| Standard Cooling Device | 18.7 (+/− 2.5) | 19.5 (+/− 2.6) | 18.6 (+/− 0.3) |
| *Knee Pain (NPRS)* | | | |
| Ice-Gel Pack | | 2.4 (+/− 1.8) | |
| Standard Cooling Device | | 1.4 (+/− 0.9) | |

Example 10—Analysis of Procedure Pain Due to Intraarticular Administration of Capsaicin Human patients experiencing osteoarthritic knee joint pain were subjected to two different protocols for intraarticular administration of trans-capsaicin. Temporary pain expected due to administration of capsaicin was analyzed, along with the intraarticular temperature of the knee joint and the temperature of the patient's skin in the area to be cooled.

One of the protocols utilized a Breg Knee WrapOn Polar Pad (as illustrated in FIG. 1) that utilizes circulating ice-water to achieve cooling, where the pad is placed on skin surrounding the knee in order to cool the knee joint. The other protocol utilized an Elasto-Gel All Purpose Therapy Wrap measuring 6 inches by 24 inches in size to cool the knee joint. The Elasto-Gel All Purpose Therapy Wrap was removed from a freezer (approximately 0° F.) just prior to use. A temperature probe was placed into the intraarticular space of the patient's knee joint to measure intraarticular temperature of the knee joint. A temperature probe was also placed on the skin in the area to be cooled in order to measure skin temperature in the area to be cooled.

Experimental procedures and results are provided below

Part I—Experimental Procedures

Five human patients suffering from moderate to severe painful bilateral knee osteoarthritis were recruited for this study evaluating the impact that cooling protocol has on the magnitude of temporary pain experienced by the patient due to administration of capsaicin. Patients had an average "pain with walking over the past 24 hours" for each knee in the range of 4-9 (inclusive) on a 0-10 numerical pain rating scale where "0" equals no pain and "10" equals worst possible pain (NPRS). Patients that participated in the study passed the following screening criteria and meet the patient inclusion and exclusion criteria are set forth below. As part of patient screening, patients received an intradermal injection of 100 µL (100 µg) capsaicin into the non-dominant volar forearm. To be eligible to enter the study, patients were able to tolerate the capsaicin injection. Screening subjects rated the pain from capsaicin injection at 5, 10, 20, and 30 minutes after injection using a 0-10 Numerical Pain Rating Scale, where "0" equals no pain and "10" equals worst possible pain.

Inclusion Criteria
1. Patient is male or female.
2. Patient is aged between 45 and 75 years, inclusive.
3. Patient has signed and dated an ethics approved informed consent form (ICF).
4. Patient's Body Mass Index (BMI) is between 18 and 32 kg/m2, inclusive and patient's weight is greater than or equal to 50 kg.
5. Patient has a diagnosis of bilateral moderate to severe painful knee osteoarthritis (patients will be required to have a score on Pain with walking in the previous 24 hours, of 4 to 9, inclusive (Numeric Pain Rating Scale 0-10). The condition must be chronic with a history of painful arthritis for at least 3 months prior to entry into the study.
6. All patients must otherwise be in good health, in the opinion of the Investigator, as determined by a medical history, physical examination, clinical laboratory tests, vital signs and 12 lead electrocardiogram (ECG).
7. Patients must be able to communicate well with the Investigator, understand and comply with the requirements of the study.
8. Patients have had previous bilateral AP radiographs (or CT/MRI scan) of the knees which demonstrate osteoarthritis in both knee joints within the prior 36 months.
9. Patient must be able to tolerate the capsaicin injection given at screening.

Exclusion Criteria
1. Patient has had a clinically significant illness, other than osteoarthritis, that has not completely resolved in the four weeks before screening.
2. Patient has a history of neurological disorder which may impact the perception of pain or impairs the patient's ability to fully participate in the trial.
3. Patient has used analgesic medications in the 2 days prior to dosing, except for paracetamol, as needed.
4. Patient has used topical medications applied to the knee for osteoarthritis pain (including capsaicin, lidocaine, prescription or OTC medications) from 90 days prior to screening through to dosing.
5. Patient has been injected with corticosteroids in the knee 90 days prior to screening through to dosing.
6. Patient currently uses opioids for any condition other than osteoarthritis knee pain (maximum dose 15 mg hydrocodone, or equivalent, per day prescribed by a physician).
7. Patient has physical/occupational/chiropractic therapy for the lower extremities or acupuncture for the lower extremities 30 days prior to screening or during the period to dosing.
8. Patient has had joint replacement surgery at any time, or open surgery of the knee in the past 12 months prior to screening, or prior arthroscopic surgery of the knee within 6 months prior to screening.
9. Patient has a history of a bleeding diathesis, or is using anti-coagulant drugs, excluding low dose aspirin.
10. Patient has a significant history of drug/solvent abuse or a positive drugs of abuse (DOA) test at screening. Prescribed opioids, as noted in exclusion, 6 are permitted.
11. Patient has a history of alcohol abuse or currently drinks more than 28 units per week.
12. Patient is, in the opinion of the Investigator, not suitable to participate in the study.
13. Patient has participated in any clinical study with an investigational drug/device within 3 months (or five half-lives if this longer than 3 months) prior to the first day of dosing.
14. Patient has a positive Human Immunodeficiency Virus (HIV), Hepatitis B or Hepatitis C screen.
15. Patient has lost or donated 500 mL or more of blood within the 3 months prior to screen, or intends to donate blood during the study.
16. Patient with active chronic pain conditions other than knee osteoarthritis, including periarticular pain about the knee.
17. Patient with known intolerance to capsaicin, hot peppers or any excipient in the investigational medicinal product or lidocaine.
18. Pregnant or breastfeeding females.
19. History of allergic reaction to the planned local anesthesia/analgesic regimens, ethylenediaminetetraacetic acid (EDTA), Kolliphor HS 15, butylated hydroxytoluene (BHT), or capsaicin.
20. Patient has any active skin disorders, skin trauma, significant scarring or skin disease on either forearm, or a significant history of trauma or skin disease in either arm.
21. Any other severe acute or chronic medical or psychiatric condition, or laboratory abnormality, that may increase the risk associated with a) study participation b) Investigational product administration c) may interfere with the interpretation of study results and, in the judgment of the investigator, in discussion with the Sponsor, would make the patient inappropriate for entry into this study.

The following therapies were prohibited both prior to and during the study (i.e., prohibiting therapies):

Injection of corticosteroids in the index knee from 90 days prior to Screening through study completion.

Topical medications applied to the index knee for osteoarthritis pain (including capsaicin, lidocaine, prescription, or OTC medications) from 90 days prior to Screening through study completion.

Current use of opioids for any condition other than for osteoarthritis of the index knee (maximum dose of 15 mg of hydrocodone [or equivalent] per day as background medication is allowed at entry if prescribed by a physician).

Regular use of anticoagulant blood thinners.

Use of an investigational medication within 30 days prior to Screening, or 5 PK or PD half-lives (whichever is longer), or scheduled to receive such an agent while participating in the study.

Physical/occupational/chiropractic or acupuncture therapy for the lower extremities within 30 days of Screening, or need for such therapy during the course of the study.

Joint replacement surgery of the index knee at any time, or open surgery of the index knee in the past 12 months prior to Screening, or prior arthroscopic surgery of the index knee within 6 months of Screening.

Surgery, or other invasive procedures, or intraarticular injections (other than the study drug) while participating in the study.

The patient was excluded from study participation if they had taken any medication prior to randomization that would indicate that the patient has a serious or unstable illness, is not in good general health, or has a condition that would contraindicate study participation. If a patient received an excluded therapy after enrolment, continuation in the study was at the discretion of the sponsor/investigator/medical monitor. Patients were not to take a hot bath or shower, or expose the injected knee to external heat within 12 hours after the injection.

One of the protocols utilized a Breg Knee WrapOn Polar Pad (as illustrated in FIG. 1) that utilizes circulating ice-water to achieve cooling, where the pad is placed on skin surrounding the knee in order to cool the knee joint. The other protocol utilized an Elasto-Gel All Purpose Therapy Wrap measuring 6 inches by 24 inches, whereby the wrap is placed around the knee joint in order to cool the knee joint. The Elasto-Gel All Purpose Therapy Wrap was removed from a freezer (approximately 0° F.) just prior to use. A temperature probe was placed into the intraarticular space of the patient's knee joint to measure intraarticular temperature of the knee joint. At the discretion of the physician performing the procedure, in order to reduce discomfort for the patient, the protocol authorized the physician to instill a volume of 1-2 cc of 2% w/w lidocaine (without epinephrine) into the skin and subcutaneous tissue of the knee at the site of intra-articular probe insertion. A temperature probe was also placed on the skin in the area to be cooled in order to measure skin temperature in the area to be cooled.

One the first day of the study, patients were randomized so that (i) three patients received cooling of the knee joint using the Breg Knee WrapOn Polar Pad and (ii) two patients received Elasto-Gel All Purpose Therapy Wrap as set forth above. Patients receiving cooling of the knee joint using the Breg Knee WrapOn Polar Pad were subjected to the following procedure:

Placement of intraarticular temperature probe and skin temperature probe. At the discretion of the physician performing the procedure, in order to reduce discomfort for the patient, the protocol authorized the physician to instill a volume of 1-2 cc of 2% w/w lidocaine (without epinephrine) into the skin and subcutaneous tissue of the knee at the site of intra-articular probe insertion.

Cooling using the designated technique was performed for 30 minutes (+/−2 minutes).

Cooling apparatus was removed from the patient's knee.

Intraarticular injection of lidocaine 2% w/w (without epinephrine) 15 mL solution into the patient's knee joint.

Intraarticular injection of the investigational medicinal product (IMP) was performed to deliver trans-capsaicin in the amount of 1 mg. The trans-capsaicin was injected, using the same needle as the lidocaine 2% w/w (without epinephrine), 3 minutes after the intra-articular injection of lidocaine 2% w/w (without epinephrine). The IMP was provided as a pre-filled syringe containing 2 mL of fluid containing trans-capsaicin at a concentration of 0.5 mg/mL.

Knee joint was flexed and extended five times over 1 minute to ensure appropriate distribution of IMP.

Cooling using the designated technique was performed for 10 minutes.

The temperature probe was removed approximately 20 minutes after removal of the cooling apparatus.

Patients receiving cooling of the knee joint using the Elasto-Gel All Purpose Therapy Wrap were subjected to the following procedure:

Placement of intraarticular temperature probe and skin temperature probe. At the discretion of the physician performing the procedure, in order to reduce discomfort for the patient, the protocol authorized the physician to instill a volume of 1-2 cc of 2% w/w lidocaine (without epinephrine) into the skin and subcutaneous tissue of the knee at the site of intra-articular probe insertion.

Cooling using the designated technique was performed for 30 minutes (+/−2 minutes).

Cooling apparatus was removed from the patient's knee.

Intraarticular injection of lidocaine 2% w/w (without epinephrine) 15 mL solution into the patient's knee joint.

Intraarticular injection of the investigational medicinal product (IMP) was performed to deliver trans-capsaicin in the amount of 1 mg. The trans-capsaicin was injected, using the same needle as the lidocaine 2% w/w (without epinephrine), 3 minutes after the intra-articular injection of lidocaine 2% w/w (without epinephrine). The IMP was provided as a pre-filled syringe containing 2 mL of fluid containing trans-capsaicin at a concentration of 0.5 mg/mL.

Knee joint was flexed and extended five times over 1 minute to ensure appropriate distribution of IMP.

The temperature probe was removed approximately 30 minutes after removal of the cooling apparatus.

Temperatures within the knee and on the skin in the region undergoing cooling were obtained from the recording device at no less than 5 minute intervals (+/−2 min) from the time of placement of the probes until the probes were removed.

Pain due to injection of trans-capsaicin was assessed on a Numerical Pain Rating scale (0-10) for 75 minutes after injection of trans-capsaicin. A verbal NPRS was used to assess procedure pain during the study. Patients were asked to indicate the severity of any pain experienced on a scale of 0 to 10 (NPRS; 0 corresponds to no pain and 10 corresponds to the worst pain imaginable). Patients were instructed to consider procedure pain separately from their baseline osteoarthritis pain. Pain was assessed on a Numerical Pain Rating scale (0-10) according the following schedule:

At pre-cooling after placement of the temperature probes.
At rest, prior to intra-articular lidocaine injection.
At rest, 10 minutes after intra-articular lidocaine injection.
At rest prior to injection of trans-capsaicin.
Ratings will continue at 10 minute intervals beginning 10 minutes after the injection of trans-capsaicin until removal of the temperature probe.
The 10 minute intervals will allow for a +/−2-minute variance in timing.

Patients were permitted to leave the clinic when they could ambulate independently, but no sooner than 1 hour after removal of the temperature probe.

Patients returned to the clinic 7±2 days later to have the procedure performed on their right knee.

Part II—Results

The experimental procedure was completed successfully for four human patients. For the fifth patient subjected to the experimental procedure, there was a deviation from protocol. Experimental results are provided below for the four human patients for which the experimental procedure was completed successfully.

Figure 12:
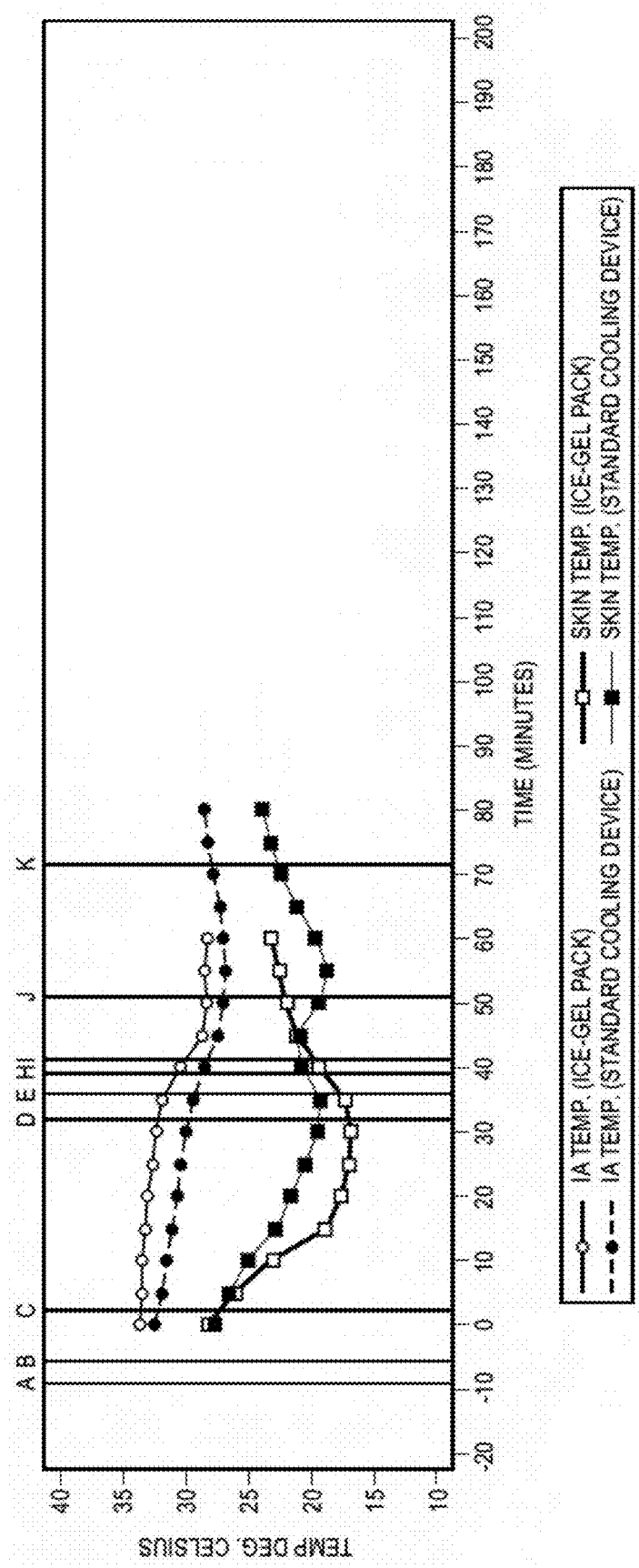
FIG. 12 is a graph showing mean intraarticular (IA) temperature and mean skin temperature over time using the following cooling devices: (i) a Breg Knee WrapOn Polar Pad or (ii) Elasto-Gel All Purpose Therapy Wrap, as further described in Example 10. The "Standard Cooling Device" was a Breg Knee WrapOn Polar Pad. The "Ice-Gel Pack" was an Elasto-Gel All Purpose Therapy Wrap. The following designations apply to the graph: A is the time at which any temperature reading of the temperature probe was made prior to insertion into the intraarticular space of the patient's knee; B is the time which the temperature probe was inserted into the intraarticular space of the patient's knee; C is time at which the cooling device was applied to the patient's knee; D is the time at which the cooling device was removed from the patient's knee; E is the time at which a solution of 2% w/w lidocaine was administered to the patient's knee by intraarticular injection; F is the time at which the cooling device was reapplied to the patient's knee; G is the time at which the cooling device was removed from the patient's knee; H is the time that trans-capsaicin was administered by intraarticular injection; I is the time at which the cooling device was reapplied to the patient's knee; J is the time at which the cooling device was removed from the patient's knee; K is the time at which the temperature probe was removed from the patient's knee.
Figure 13:
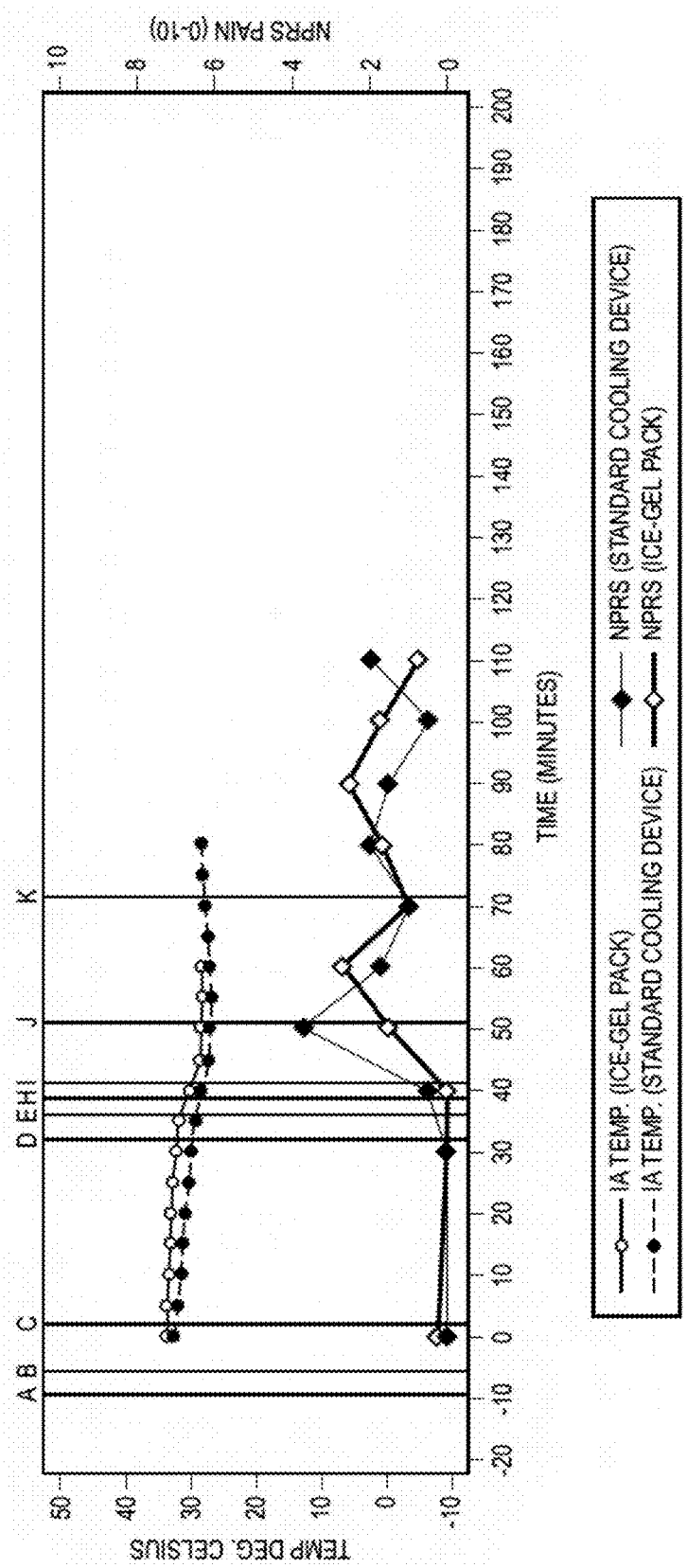
FIG. 13 is a graph showing mean intraarticular (IA) temperature and mean NPRS Pain scores over time using the following cooling devices: (i) a Breg Knee WrapOn Polar Pad or (ii) Elasto-Gel All Purpose Therapy Wrap, as further described in Example 10. The "Standard Cooling Device" was a Breg Knee WrapOn Polar Pad. The "Ice-Gel Pack" was an Elasto-Gel All Purpose Therapy Wrap. The following designations apply to the graph: A is the time at which any temperature reading of the temperature probe was made prior to insertion into the intraarticular space of the patient's knee; B is the time which the temperature probe was inserted into the intraarticular space of the patient's knee; C is time at which the cooling device was applied to the patient's knee; D is the time at which the cooling device was removed from the patient's knee; E is the time at which a solution of 2% w/w lidocaine was administered to the patient's knee by intraarticular injection; F is the time at which the cooling device was reapplied to the patient's knee; G is the time at which the cooling device was removed from the patient's knee; H is the time that trans-capsaicin was administered by intraarticular injection; I is the time at which the cooling device was reapplied to the patient's knee; J is the time at which the cooling device was removed from the patient's knee; K is the time at which the temperature probe was removed from the patient's knee.

Mean values for intraarticular temperature in the knee joint recorded over time are presented in FIG. 12, along with mean values for skin temperature recorded over time. Mean NPRS Pain scores recorded over time are presented in FIG. 13, along with mean values for intraarticular temperature in the knee joint. Tabulated mean temperature values along with mean NPRS Pain scores recorded in the study are provided in Table 1 below.

TABLE 1

| Cooling Method | Baseline | 5 min | 10 min | 15 min | 20 min |
|---|---|---|---|---|---|
| *IA Temperature* | | | | | |
| Ice-Gel Pack | 33.8 (+/− 1.7) | 33.5 (+/− 2.0) | 33.4 (+/− 2.2) | 33.2 (+/− 2.4) | 33.0 (+/− 2.7) |
| Standard Cooling Device | 32.5 (+/− 2.6) | 31.9 (+/− 2.8) | 31.5 (+/− 2.9) | 31.2 (+/− 3.1) | 30.8 (+/− 3.4) |
| *Skin Temperature* | | | | | |
| Ice-Gel Pack | 28.4 (+/− 0.9) | 26.5 (+/− 1.0) | 23.2 (+/− 1.1) | 19.2 (+/− 1.1) | 17.7 (+/− 1.4) |
| Standard Cooling Device | 27.7 (+/− 0.9) | 26.7 (+/− 1.0) | 25.0 (+/− 1.2) | 22.9 (+/− 1.4) | 21.7 (+/− 1.3) |
| *Knee Pain (NPRS)* | | | | | |
| Ice-Gel Pack | 0.3 (+/− 0.5) | | | | |
| Standard Cooling Device | 0.0 (+/− 0.0) | | | | |

| Cooling Method | 25 min | 30 min | 35 min | 40 min | 45 min |
|---|---|---|---|---|---|
| *IA Temperature* | | | | | |
| Ice-Gel Pack | 32.7 (+/− 3.0) | 32.3 (+/− 3.3) | 31.8 (+/−3.1) | 30.4 (+/− 2.5) | 28.7 (+/− 2.7) |
| Standard Cooling Device | 30.4 (+/− 3.6) | 29.9 (+/− 3.7) | 29.3 (+/− 3.8) | 28.5 (+/− 3.6) | 27.5 (+/− 3.5) |
| *Skin Temperature* | | | | | |
| Ice-Gel Pack | 17.1 (+/− 1.8) | 16.9 (+/− 2.1) | 17.4 (+/− 2.2) | 19.5 (+/− 1.9) | 21.4 (+/− 1.5) |
| Standard Cooling Device | 20.6 (+/− 1.3) | 19.7 (+/− 1.3) | 19.4 (+/− 1.1) | 20.7 (+/− 0.8) | 21.2 (+/− 0.9) |
| *Knee Pain (NPRS)* | | | | | |
| Ice-Gel Pack | | 0.0 (+/− 0.0) | | 0.0 (+/− 0.0) | |
| Standard Cooling Device | | 0.0 (+/− 0.0) | | 0.5 (+/− 1.0) | |

| Cooling Method | 50 min | 55 min | 60 min | 65 min | 70 min |
|---|---|---|---|---|---|
| *IA Temperature* | | | | | |
| Ice-Gel Pack | 28.4 (+/− 3.3) | 28.5 (+/− 3.5) | 28.4 (+/− 3.5) | | |
| Standard Cooling Device | 27.1 (+/− 4.3) | 27.0 (+/− 4.8) | 27.1 (+/− 4.5) | 27.3 (+/− 3.8) | 28.0 (+/− 3.2) |
| *Skin Temperature* | | | | | |
| Ice-Gel Pack | 22.0 (+/− 1.4) | 22.6 (+/− 1.5) | 23.3 (+/− 1.6) | | |
| Standard Cooling Device | 19.5 (+/− 1.2) | 18.7 (+/− 1.2) | 19.6 (+/− 1.0) | 21.2 (+/− 1.2) | 22.5 (+/− 1.6) |
| *Knee Pain (NPRS)* | | | | | |
| Ice-Gel Pack | 1.5 (+/− 2.4) | | 2.8 (+/− 3.1) | | 1.0 (+/− 0.8) |
| Standard Cooling Device | 3.8 (+/− 2.9) | | 1.8 (+/− 2.4) | | 1.0 (+/− 2.0) |

| Cooling Method | 75 min | 80 min | 90 min | 100 min | 110 min |
|---|---|---|---|---|---|
| *IA Temperature* | | | | | |
| Ice-Gel Pack | | | | | |
| Standard Cooling Device | 28.3 (+/− 3.3) | 28.5 (+/− 3.3) | | | |
| *Skin Temperature* | | | | | |
| Ice-Gel Pack | | | | | |
| Standard Cooling Device | 23.2 (+/− 2.2) | 23.9 (+/− 2.7) | | | |
| *Knee Pain (NPRS)* | | | | | |
| Ice-Gel Pack | | 1.8 (+/− 2.9) | 2.5 (+/− 2.9) | 1.8 (+/− 2.9) | 0.8 (+/− 1.5) |
| Standard Cooling Device | | 2.0 (+/− 4.0) | 1.5 (+/− 2.4) | 0.5 (+/− 1.0) | 2.0 (+/− 4.0) |

Example 11—Temperature Profile Analysis of Cooling Apparatus

Figure 14:
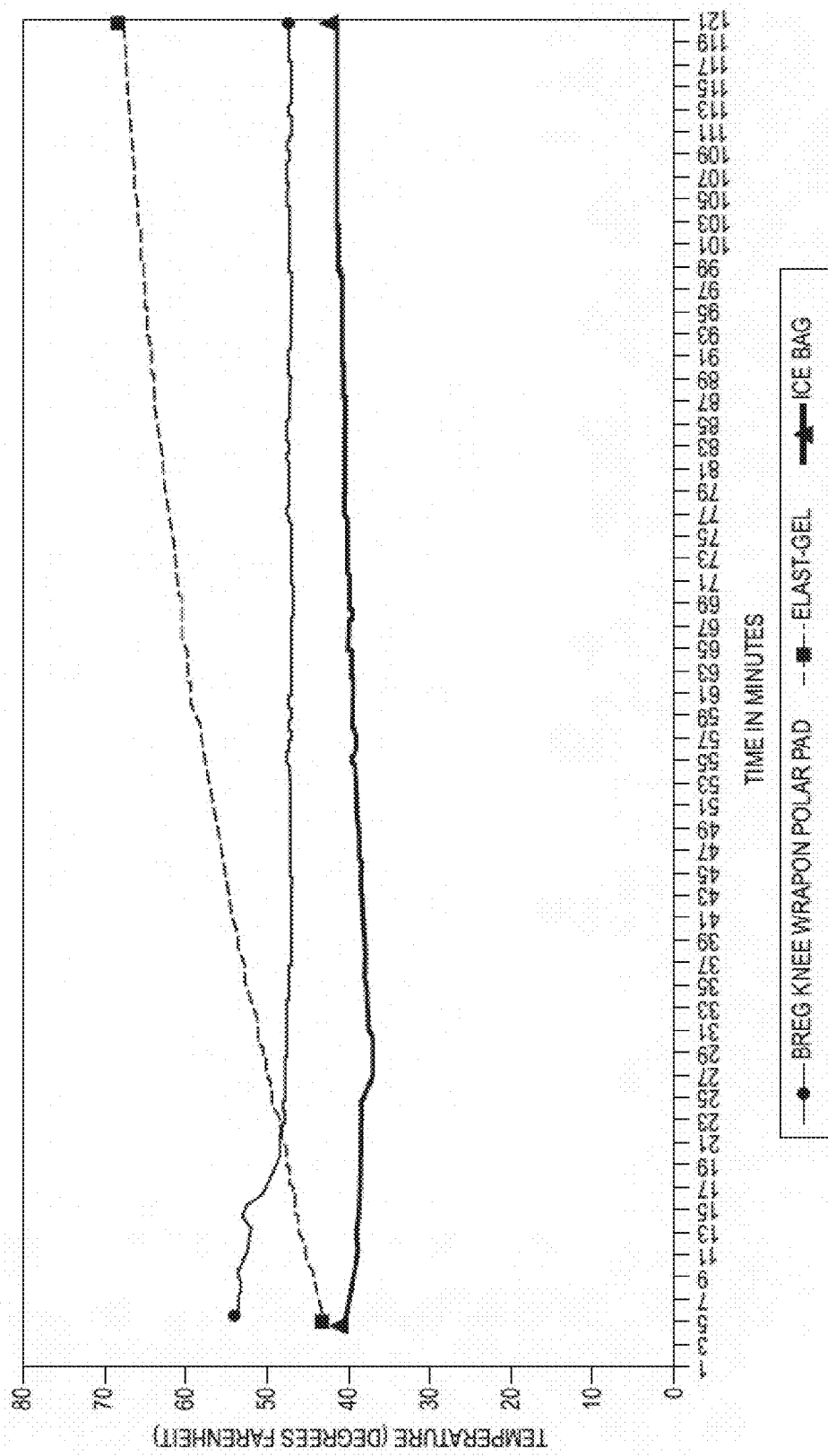
FIG. 14 is a graph showing temperature profiles recorded for Breg Knee WrapOn Polar Pad, Elasto-gel cooling device, and ice-pack, as further described in Example 11.

The temperature of the cooling surface of the following cooling devices was measured over time: (i) Breg Knee WrapOn Polar Pad (as illustrated in FIG. 1) that utilizes circulating ice-water to achieve cooling, (ii) an Elasto-Gel All Purpose Therapy Wrap measuring 6 inches by 24 inches in size, which was removed from a freezer immediately prior to use, and (iii) an ice-pack wrapped in a stockinet of thickness analogous to that used when an ice pack is used to provide cooling a human patient's knee (in which the patient's knee is wrapped in a stockinet to avoid direct contact between the ice pack and the patient's skin). Temperature values recorded as a function of time are presented in Table 1 below. Temperature values are also displayed graphically in FIG. 14. The first temperature value in Table 1 was taken 5 minutes after the start of the experiment in order to allow equilibration of the cooling surface temperature from initiation of the experiment. Temperature values provided for the Breg Knee WrapOn Polar Pad are the average temperature observed for the first cooling pad and the second cooling pad of the device. The Elasto-Gel All Purpose Therapy Wrap and the ice-pack were removed from a freezer (approximately 0° F.) just prior to use.

TABLE 1

| | Temperature of Cooling Surface (° F.) | | |
|---|---|---|---|
| Time (min) | Breg Knee WrapOn Polar Pad | Elasto-Gel | Ice Pack Wrapped in Stockinet |
| 5 | 53.6 | 42.9 | 40.6 |
| 6 | 53.4 | 43.2 | 40.1 |
| 7 | 53.25 | 43.7 | 39.9 |
| 8 | 53 | 43.9 | 39.5 |
| 9 | 53.25 | 44.2 | 39.2 |
| 10 | 52.6 | 44.9 | 39.1 |
| 11 | 52.25 | 45.1 | 38.8 |
| 12 | 52.05 | 45.5 | 38.8 |
| 13 | 51.85 | 45.9 | 38.8 |
| 14 | 52.75 | 46.1 | 38.6 |
| 15 | 52.45 | 46.4 | 38.6 |
| 16 | 50.4 | 46.6 | 38.4 |
| 17 | 49.95 | 47 | 38.4 |
| 18 | 49.1 | 47.2 | 38.4 |
| 19 | 48.4 | 47.4 | 38.4 |
| 20 | 48.15 | 47.6 | 38.4 |
| 21 | 48.1 | 48 | 38.4 |
| 22 | 47.8 | 48.1 | 38.3 |
| 23 | 47.75 | 48.4 | 38.3 |
| 24 | 47.9 | 49.1 | 38.3 |
| 25 | 47.6 | 49.2 | 37.9 |
| 26 | 47.6 | 49.4 | 37.5 |
| 27 | 47.6 | 49.8 | 36.8 |
| 28 | 47.55 | 50.1 | 36.8 |
| 29 | 47.45 | 50.3 | 36.8 |
| 30 | 47.45 | 50.7 | 37 |
| 31 | 47.35 | 50.9 | 37.2 |
| 32 | 47.35 | 51.2 | 37.2 |
| 33 | 47.25 | 51.6 | 37.4 |
| 34 | 47.15 | 51.9 | 37.5 |
| 35 | 47.2 | 52.5 | 37.6 |
| 36 | 47.15 | 52.5 | 37.8 |
| 37 | 47.05 | 52.8 | 37.7 |
| 38 | 47 | 53.2 | 37.7 |
| 39 | 47 | 53.4 | 37.9 |
| 40 | 47.05 | 53.7 | 38.1 |
| 41 | 47.05 | 54.1 | 38.1 |
| 42 | 47.05 | 54.3 | 38.3 |
| 43 | 47.05 | 54.6 | 38.4 |
| 44 | 46.9 | 54.8 | 38.3 |
| 45 | 47.05 | 55 | 38.3 |
| 46 | 47.05 | 55.2 | 38.4 |
| 47 | 47.05 | 55.5 | 38.5 |
| 48 | 47 | 55.7 | 38.6 |
| 49 | 47.05 | 56.1 | 38.6 |
| 50 | 47.05 | 56.3 | 38.8 |
| 51 | 47.05 | 56.4 | 38.8 |
| 52 | 47.05 | 56.8 | 38.8 |
| 53 | 47.15 | 57.1 | 39 |
| 54 | 47.15 | 57.2 | 39 |
| 55 | 47.25 | 57.5 | 39.2 |
| 56 | 47.1 | 57.7 | 39 |
| 57 | 47.05 | 57.9 | 39 |
| 58 | 47.1 | 58.1 | 39.2 |
| 59 | 47.05 | 58.6 | 39.2 |
| 60 | 47.15 | 59 | 39.3 |
| 61 | 47.05 | 59 | 39.3 |
| 62 | 47.05 | 59.3 | 39.3 |
| 63 | 47.05 | 59.5 | 39.5 |
| 64 | 46.95 | 59.7 | 39.5 |
| 65 | 47.05 | 59.9 | 39.7 |
| 66 | 47.05 | 60.2 | 39.7 |
| 67 | 47.05 | 60.2 | 39.7 |
| 68 | 46.85 | 60.2 | 39.5 |
| 69 | 46.85 | 60.4 | 39.7 |
| 70 | 46.9 | 60.6 | 39.7 |
| 71 | 46.95 | 60.8 | 39.7 |
| 72 | 46.95 | 60.9 | 39.9 |
| 73 | 46.95 | 61.1 | 39.9 |
| 74 | 46.95 | 61.3 | 39.9 |
| 75 | 47.05 | 61.5 | 39.9 |
| 76 | 47.05 | 61.7 | 39.9 |
| 77 | 47.25 | 61.8 | 40.1 |
| 78 | 47.15 | 62 | 40.1 |
| 79 | 47.15 | 62.2 | 40.1 |
| 80 | 47.15 | 62.4 | 40.2 |
| 81 | 47.2 | 62.4 | 40.2 |
| 82 | 47.25 | 62.7 | 40.2 |
| 83 | 47.15 | 62.9 | 40.2 |
| 84 | 47.25 | 63.1 | 40.2 |
| 85 | 47.25 | 63.3 | 40.2 |
| 86 | 47.2 | 63.5 | 40.2 |
| 87 | 47.1 | 63.6 | 40.2 |
| 88 | 47.05 | 63.6 | 40.4 |
| 89 | 47.05 | 63.8 | 40.4 |
| 90 | 47.1 | 64 | 40.4 |
| 91 | 47.1 | 64 | 40.6 |
| 92 | 47 | 64.2 | 40.6 |
| 93 | 47 | 64.4 | 40.6 |
| 94 | 47 | 64.5 | 40.6 |
| 95 | 47.05 | 64.5 | 40.6 |
| 96 | 47 | 64.7 | 40.6 |
| 97 | 46.95 | 64.7 | 40.6 |
| 98 | 47.05 | 65.1 | 40.6 |
| 99 | 47.15 | 65.1 | 40.8 |
| 100 | 47.15 | 65.3 | 40.8 |
| 101 | 47.15 | 65.4 | 40.8 |
| 102 | 47.15 | 65.4 | 40.8 |
| 103 | 47.15 | 65.6 | 41 |
| 104 | 47.15 | 65.6 | 41 |
| 105 | 47.25 | 65.7 | 41 |
| 106 | 47.15 | 66 | 41 |
| 107 | 47.25 | 66 | 41 |
| 108 | 47.25 | 66.2 | 41 |
| 109 | 47.2 | 66.3 | 41 |
| 110 | 47.25 | 66.3 | 41 |
| 111 | 47.05 | 66.5 | 41 |
| 112 | 47.05 | 66.7 | 41 |
| 113 | 47.15 | 66.7 | 41 |
| 114 | 47.05 | 66.8 | 41 |
| 115 | 47.05 | 66.9 | 41 |
| 116 | 47.05 | 67.1 | 41 |
| 117 | 46.95 | 67.1 | 41 |
| 118 | 47.15 | 67.1 | 41 |
| 119 | 47.15 | 67.2 | 41 |

TABLE 1-continued

| | Temperature of Cooling Surface (° F.) | | |
|---|---|---|---|
| Time (min) | Breg Knee WrapOn Polar Pad | Elasto-Gel | Ice Pack Wrapped in Stockinet |
| 120 | 47.15 | 67.4 | 41.1 |
| 121 | 47.15 | 67.4 | 41.1 |

Example 12-Intra-Articular Injection of Capsaicin to Treat Osteoarthritic Knee Joint Pain in Human Patients Human patients experiencing chronic, moderate to severe osteoarthritic knee joint pain may be treated for such pain by intra-articular injection of a 1.0 mg dose of trans-capsaicin into the osteoarthritic knee joint according to the clinical protocol described below. The investigational medicinal product (IMP) in this protocol is a 1.0 mg dose of trans-capsaicin provided as a pre-filled syringe containing 2.0 mL of solution containing trans-capsaicin (concentration of trans-capsaicin in the solution is 0.5 mg/mL). Patients are selected for treatment according to the patient selection criteria described below, and then treated according to the treatment procedure described below.

Patients Selection

Patients are selected according to the criteria set forth below. For this clinical study, the study population will contain three types of patients, with a targeted minimum of 150 patients of each type:
1. Patients with unilateral or bilateral osteoarthritis of the knee, with one knee (the index knee) with moderate to severe pain (Kellgren-Lawrence [KL] grade 1-4) and the other knee (the contralateral knee) with no to mild pain. These patients will receive an injection in the index knee only.
2. Patients with bilateral osteoarthritis of the knees, with both knees having moderate to severe pain (KL grade 1-4, with worse pain in the index knee). These patients will receive an injection in each knee (1 week apart).
3. Patients who have unilateral osteoarthritis of the knee, with one knee with moderate to severe pain (the index knee [KL grades 1-4]) and previous PJR or TJR in the other knee (the contralateral knee). These patients will receive an injection in the index knee only.

Patients must satisfy the inclusion criteria set for the below, and also not have any of the exclusion criteria set forth below.

Inclusion Criteria:
1. Male or female patients between 40 and 95 years of age (inclusive).
2. Confirmation of osteoarthritis of the knee: radiography of both knees using standard standing films (scored by the investigator) or using the fixed flexion method, taken during the Pre-screening Visit. The index knee must show evidence of chronic osteoarthritis with a K-L grade of 1, 2, 3 or 4. Patients who were screen failures for clinical study CNTX-4975i-OA 301 or 304 may be considered for this trial if the K-L grade of the index knee is 1-4, inclusive.
3. Confirmation of osteoarthritis of the index knee: American College of Rheumatology (ACR) diagnostic criteria.
4. For patients for monoarticular knee injection, the index knee must have moderate to severe pain at screening associated with osteoarthritis, which must be stable for a minimum of 6 months prior to Screening, as assessed by the investigator. These patients may have:
    a) unilateral or bilateral osteoarthritis, with the index knee having moderate to severe pain, and the contralateral knee having none to mild pain, or
    b) unilateral or bilateral osteoarthritis, with the index knee having moderate to severe pain and the other knee having had a partial (PJR) or total joint replacement (TJR) within 5 years of the screening visit. The knee with the PJR/TJR is not to be injected with trans-capsaicin.
   For patients for bilateral knee injection, the index knee must have moderate to severe pain at screening associated with osteoarthritis, and greater pain in the index knee than in the contralateral knee. Their pain must be stable for a minimum of 6 months prior to Screening, as assessed by the investigator.
   For qualifying knee pain with walking, patients will use a numeric pain rating scale (NPRS) (0-10:0=no pain, 10=worst pain ever) to rate their knee pain with walking (both knees, regardless if the knee is natural or PJR/TJR).
5. BMI≤45 kg/m².
6. Patients must have failed 2 or more prior therapies. Failure is deemed to be inadequate relief in the opinion of the investigator. A therapy may be deemed to have been inadequate because of one or more of the following: 1) unacceptable adverse events (AEs); 2) initial failure to achieve clinically adequate pain relief; 3) initial pain relief that was not maintained; or 4) medical condition resulting in contraindication to the standard of care appropriate to the severity of the index knee osteoarthritis pain. "Therapies" include, but are not limited to, each of the following: nonsteroidal anti-inflammatory drugs (NSAIDs) (including topical), opioids, duloxetine, other systemic therapy, intraarticular corticosteroids, intraarticular viscosupplements, physical therapy, bracing, and orthotics.
7. Females not of childbearing potential, defined as postmenopausal for at least 1 year, or surgically sterile (bilateral tubal ligation, bilateral oophorectomy, or hysterectomy), or practicing one of the following medically acceptable methods of birth control throughout the study period:
   Hormonal methods such as oral, implantable, injectable, or transdermal contraceptives for a minimum of 1 full cycle (based on the patient's usual menstrual cycle period) before IMP administration
   Total abstinence from sexual intercourse since the last menses before IMP administration
   Intrauterine device
   Double barrier method (condoms, sponge, diaphragm, with spermicidal jellies or cream)
8. Able to speak, read, and understand the language of the study used for the informed consent.
9. Willing and able to:
    a) understand the study requirements,
    b) abide by the study restrictions and requirements,
    c) complete the study procedures,
    d) be compliant and independently (i.e., without assistance) record responses on the efficacy during clinic visits
    e) independently communicate meaningfully with the study personnel.
10. Signed informed consent form approved by the institutional review board (IRB).

11. Patients may come into the study with their choice of knee osteoarthritis analgesic. The current pain medication must be identified as that taken only for pain in the knee osteoarthritis or pain in the PJR/TJR, and not for another pain indication. The patients will complete a daily paper diary of their background knee analgesic medications during the screening period and throughout the trial.

Exclusion Criteria:
1. Joint replacement surgery of the index knee at any time, or open surgery of the index knee in the past 24 months. Joint replacement of the contralateral knee is permitted for patients who will not receive an injection in the contralateral knee.
2. Prior arthroscopic surgery of the index knee within 6 months of screening.
3. Any painful conditions of the index knee due to joint disease other than osteoarthritis. For example, radicular or referred pain involving the index knee or from joint disease other than osteoarthritis involving the index knee, such as, but not restricted to, inflammatory diseases, e.g., rheumatoid arthritis, psoriatic arthritis, chondromalacia patellae, metabolic diseases, gout/pseudogout, hemochromatosis, acromegaly, etc.
4. Periarticular pain from any cause, including referred pain, bursitis, tendonitis, soft tissue tenderness, or subacute/acute pain from injury.
5. Other chronic pain anywhere in the body that requires the use of analgesic medications, including, but not limited to, local painful areas, myofascial pain syndromes, fibromyalgia, genetic, metabolic abnormalities, hematologic, or neuropathic pain.
6. Instability of the index or contralateral knee (e.g., cruciate ligament tear or rupture, significant protruding meniscus, substantial ligamentous laxity, unstable partial or total joint replacement).
7. Misalignment (>10 degrees *varus* or valgus) of the index knee on standing.
8. Documented history of neuropathic arthropathy or finding of bony fragmentation in the index knee with imaging (radiographic, computed tomography, or magnetic resonance imaging).
9. Physical/occupational/chiropractic therapy for the lower extremities or acupuncture for the lower extremities within 30 days of Screening, or need for such therapy during the study.
10. Plans to have surgery, other invasive procedures, or intraarticular injections for either knee (other than the IMP) while participating in the study.
11. Has used topical capsaicin on the index knee within 60 days of Screening, or at any time during the trial.
12. Current use of opioids for any condition other than for osteoarthritis of the index knee (maximum dose of 15 mg of hydrocodone [or equivalent] per day).
13. Corticosteroid injection into the index or contralateral knee within 90 days of Screening.
14. Received intraarticular viscosupplementation (e.g., Synvisc®, Hyalgan®) within 90 days of Screening.
15. History of allergic reaction to the planned local anesthesia/analgesic regimens, ethylenediaminetetraacetic acid (EDTA), Kolliphor HS 15, butylated hydroxytoluene (BHT), or capsaicin.
16. Presence of any medical condition or unstable health status that, in the judgment of the investigator, might adversely impact the safety of the patient, or the conduct of the study, or negatively affect the resulting data, including chronic conditions that are likely to alter the rate of healing or are likely to result in safety complications unrelated to the study medication, or significantly compromise key organ systems. For any question regarding eligibility, it is strongly recommended that the investigator discuss the patient with the medical monitor.
17. Is pregnant or is breast feeding.
18. Has a malignancy, a history of malignancy, or has received treatment for malignancy at any time, with exception of resected and cured basal cell carcinoma and squamous cell carcinoma of the skin.
19. Regular use of anticoagulant blood thinners (except low-dose aspirin, Dabigatran 150 mg once daily [qd], Enoxaparin 40 mg qd, Rivaroxaban 10 mg qd, or Apixaban 2.5 mg twice daily [bid], or clopidogrel 75 mg qd, which are allowed).
20. Active cutaneous disease at the anticipated site of IMP injection that would prevent the safe administration of IMP.
21. Ulcer or open wound anywhere on the index knee.
22. Specific laboratory abnormalities:
   Hemoglobin<11.0 g/dL
   White blood cells (WBC)<$2.5 \times 10^9$/L
   Neutrophils<$1.5 \times 10^9$/L
   Platelets<$100 \times 10^9$/L
   Aspartate transaminase (AST) or alanine transaminase (ALT)>2× upper limit of normal
   Creatinine>1.6 mg/dL
   Glucose (fasting)>250 mg/dL
   HgbA1c>9.
23. Clinically significant abnormal laboratory result at the Screening Visit (in the opinion of the investigator), or significant organ disease that would put the patient at undue risk or affect the ability of the patient to participate in the trial. For any question regarding eligibility, it is strongly recommended that the investigator discusses the patient with the medical monitor.
24. Use of an investigational medication within 30 days of Screening or 5 pharmacokinetic or pharmacodynamic half-lives (whichever is longer), or scheduled to receive such an agent while participating in the current study.
25. Prior participation in a study involving intra-articular administration of capsaicin.
26. Has any of the following characteristics:
   Active or historic substance use disorder within the previous year, as defined by the Diagnostic and Statistical Manual for Mental Health Disorders, fifth edition.
   Test is positive upon urine drug screen for a substance of abuse (prescribed opioids acceptable).
   Has a history, at any time, or currently, of suicidal ideation, suicide attempt, or increased risk of suicide.
   Has an unacceptable level of depression or anxiety as measured by the Hospital Anxiety and Depression Scale (HADS)
   Has unacceptable chronic pain as measured by the Fibromyalgia Symptom Scale Score (FSS)
   Has a positive pregnancy test at the Screening or Treatment Visit.
   Has ongoing litigation for workers' compensation.
   Has any condition, or is taking any medication, that would be contraindicated for study participation.

Treatment Procedure

Patients meeting the selection criteria described above are to be treated for their chronic, moderate to severe osteoarthritic knee joint pain according to the procedure set forth below. The procedure is based on a clinical study protocol, where the overall maximum duration of the study is expected to be approximately 10 weeks. The sequence and maximum duration of the study periods will be as follows:

Screening Period up to 15 days.
Treatment Period (open-label): 1 day per knee treated, maximum 2 days.
Post-treatment period: 8 weeks from the first trans-capsaicin.

The maximum IMP treatment for each patient is 2 days. The maximum study duration for each patient is approximately 10 weeks.

All patients will receive a single intraarticular injection of a 1.0 mg dose of trans-capsaicin into the index knee; patients with bilateral osteoarthritis will receive an injection of said capsaicin in both knees (injections will be separated by 1 week). Patients will continue to be followed for 8 weeks.

Pre-Medication

All patients are required to be administered an intraarticular injection of 15 ml of lidocaine [without epinephrine] (1% or 2% w/w, depending on the assigned injection regimen) to ensure 1) the local targeted concentration of trans-capsaicin in the joint, 2) distension of the joint capsule to improve access of trans-capsaicin to the joint space, and 3) to provide some analgesia for efficacy and tolerability. The full 15 mL of lidocaine solution [without epinephrine] and the full 2 mL of IMP must be injected into the knee joint as directed. The 5 flexion-extension moves of the knee after intra-articular injection of the IMP is injected into the knee also improve access of trans-capsaicin to the entire joint space.

Prior to the required injection of intraarticular lidocaine, the investigator may, at his or her discretion, pre-medicate patients with an oral dose of an opioid or nonsteroidal anti-inflammatory drug (NSAID). The skin at the point of the subsequent injection(s) may also be infiltrated with 1-2 mL of lidocaine and/or another topical analgesic such as ethyl chloride spray. It is recommended not to use more than two methods of local analgesia about the knee.

Injection of trans-Capsaicin

Each site will be randomly assigned one of the following five joint treatment regimens to be employed for all patients at that site:

1. Breg Cooling Control Group:
   a. The use of ultrasound for intra-articular injections (IA) is recommended, but not required. If not using ultrasound guided injection, then with a clinical intraarticular injection, joint fluid must be identified within the needle hub before injection of 2% w/w lidocaine (without epinephrine) and the IMP.
   b. Controlled joint cooling wrap with an ice water pump system (Breg Cooler) will be applied 15 minutes prior to intraarticular injection of the full 15 mL 2% w/w lidocaine (without epinephrine) into the joint using standard aseptic technique.
   c. Inject intraarticularly the full 15 ml of 2% w/w lidocaine (without epinephrine) into the joint using appropriate antiseptic technique.
   d. Controlled cooling will be resumed for a further 30 minutes after the intraarticular injection of the full 15 mL 2% w/w lidocaine (without epinephrine) into the joint.
   e. The cooling device will then be removed and investigational medicinal product (IMP) intraarticular injection will be administered.
   f. The knee joint will be passively flexed and extended 5 times over 1 minute to facilitate distribution of the IMP within the index knee.
   g. Then controlled cooling will be reapplied for a minimum of 30 minutes, and up to 90 minutes, as needed, after IMP injection, depending on the patient's comfort. The cooling may be discontinued after a minimum of 30 minutes after intraarticular IMP injection, if the patient has a pain level that is acceptable for the patient and investigator (0-4 scale; none, mild, moderate, moderately severe and severe).
   h. The pain level on discontinuing the cooling, with the duration of cooling, must be entered into the CRF. If the cooling must be reapplied, the time and pain level must be recorded in the CRF, and timing of subsequent pain assessments should be on the standard time lines in the CRF.

2. Gel Pack Cooling Group
   a. The use of ultrasound for intra-articular injections (IA) is recommended, but not required. If not using ultra-

| Group | Cooling Device | Cooling prior to lidocaine administration Lidocaine % Cooling after administration of lidocaine | Needle | Cooling After Administration of IMP |
| --- | --- | --- | --- | --- |
| 1. Breg Cooling Control Group | Breg ice water pump | 15 mins 2% w/w lidocaine 30 mins | separate needles for lidocaine and study drug | 30 to 90 mins as needed |
| 2. Gel Pack Cooling Group | Elasto-Gel | 40 mins 2% w/w lidocaine 10 mins | separate needles for lidocaine and study drug | 10 to 90 mins as needed |
| 3. Shortened Gel Pack Cooling Group | Elasto-Gel | 30 mins 2% w/w lidocaine 10 mins | separate needles for lidocaine and study drug | 10 to 90 mins as needed |
| 4. Single Needle Injection Gel Pak Cooling Group- 2% w/w Lidocaine | Elasto-Gel | 45 mins 2% w/w lidocaine no cooling | single needle for the lidocaine and study drug administrations | up to 90 mins as needed |
| 5. Single Needle Injection Gel Pack Cooling Group-1% w/w Lidocaine | Elasto-Gel | 45 mins 1% w/w lidocaine no cooling | single needle for the lidocaine and study drug administrations | up to 90 mins as needed | sound guided injection, then with a clinical intraarticular injection, joint fluid must be identified within the needle hub before injection of 2% w/w lidocaine (without epinephrine) and the IMP.
b. Gel pack cooling applied for 40 minutes to the knee using the gel pack over a stockinette or light-weight pants. This may be outside of the exam room, but at the investigator's discretion, may be done in the exam room. If done outside the exam room, patient may be moved to the exam room+/−5 minutes of the 40-minute cooling (with gel pack remaining on the knee).
c. Inject intraarticularly the full 15 mL 2% w/w lidocaine (without epinephrine) into the joint using appropriate antiseptic technique.
d. Gel pack cooling is applied for 10 minutes to the knee using the gel pack over a stockinette or light-weight pants.
e. The gel pack will then be removed and IMP intraarticular injection will be administered using appropriate antiseptic technique.
f. The knee joint will be passively flexed and extended 5 times over 1 minute to facilitate distribution of the IMP within the index knee.
g. Then gel pack cooling will be reapplied for a minimum of 10 minutes, and up to 90 minutes, as needed, after IMP injection, depending on the patient's comfort. The cooling may be discontinued after a minimum of 10 minutes after intraarticular IMP injection. If the patient has a pain level that is acceptable for the patient and investigator (0-4 scale; none, mild, moderate, moderately severe and severe).
h. The pain level on discontinuing the cooling, with the duration of cooling, must be entered into the CRF. If the cooling must be reapplied, the time and pain level must be recorded in the CRF, and timing of subsequent pain assessments should be on the standard time lines in the CRF.

3. Shortened Gel Pack Cooling Group:
a. The use of ultrasound for intra-articular injections (IA) is recommended, but not required. If not using ultrasound guided injection, then with a clinical intraarticular injection, joint fluid must be identified within the needle hub before injection of 2% w/w lidocaine (without epinephrine) and the IMP.
b. Gel pack cooling applied for 30 minutes to the knee using the gel pack over a stockinette or light-weight pants. This may be outside of the exam room, but at the investigator's discretion, may be done in the exam room. If done outside the exam room, patient may be moved to the exam room+/−5 minutes of the 30-minute cooling (with gel pack remaining on the knee).
c. Inject intraarticularly the full 15 mL 2% w/w lidocaine (without epinephrine) into the joint using appropriate antiseptic technique.
d. Gel pack cooling is applied for 5 minutes to the knee using the gel pack over a stockinette or light-weight pants.
e. The gel pack will then be removed and IMP intraarticular injection will be administered.
f. The knee joint will be passively flexed and extended 5 times over 1 minute to facilitate distribution of the IMP within the index knee.
g. Then gel pack cooling may be reapplied for up to 90 minutes, as needed, after IMP injection, depending on the patient's comfort. The patient may remain in the exam room, or be moved to a more comfortable area with the gel pack. The gel pack may be discontinued after intraarticular IMP injection if the patient has a pain level that is acceptable for the patient and investigator (0-4 scale; none, mild, moderate, moderately severe and severe).
h. The pain level on discontinuing the cooling, with the duration of cooling, must be entered into the CRF. If the cooling must be reapplied, the time and pain level must be recorded in the CRF, and timing of subsequent pain assessments should be on the standard time lines in the CRF.

4. Single Needle Injection Gel Pack Cooling Group-2% w/w IA Lidocaine
a. The use of ultrasound for intra-articular injections (IA) is recommended, but not required. If not using ultrasound guided injection, then with a clinical intraarticular injection, joint fluid must be identified within the needle hub before injection of 2% w/w lidocaine (without epinephrine) or the IMP.
b. Gel pack cooling applied for 40 minutes to the knee using the gel pack over a stockinette or light-weight pants. This may be outside of the exam room, but at the investigator's discretion, may be done in the exam room. If done outside the exam room, patient may be moved to the exam room+/−5 minutes of the 45-minute cooling (with gel pack remaining on the knee).
c. Inject intraarticularly the full 15 mL 2% w/w lidocaine (without epinephrine) into the joint using appropriate antiseptic technique.
d. After the 2% w/w lidocaine intraarticular injection, the IMP intraarticular injection, using the same needle, will be injected into the joint using appropriate antiseptic technique after 3 minutes of the 2% w/w lidocaine (without epinephrine).
e. The knee joint will be passively flexed and extended 5 times over 1 minute to facilitate distribution of the IMP within the index knee.
f. Then gel pack cooling may be reapplied for up to 90 minutes, as needed, after IMP injection, depending on the patient's comfort. The patient may remain in the exam room, or be moved to a more comfortable area with the gel pack. The gel pack may be discontinued after a minimum of 10 minutes after intraarticular IMP injection if the patient has a pain level that is acceptable for the patient and investigator (0-4 scale; none, mild, moderate, moderately severe and severe).
g. The pain level on discontinuing the cooling, with the duration of cooling, must be entered into the CRF. If the cooling must be reapplied, the time and pain level must be recorded in the CRF, and timing of subsequent pain assessments should be on the standard time lines in the CRF.

5. Single Needle Injection Gel Pack Cooling Group-1% w/w IA Lidocaine
a. The use of ultrasound for intra-articular injections (IA) is recommended, but not required. If not using ultrasound guided injection, then with a clinical intraarticular injection, joint fluid must be identified within the needle hub before injection of 1% w/w lidocaine (without epinephrine) or the IMP.
b. Gel pack cooling applied for 40 minutes to the knee using the gel pack over a stockinette or light-weight pants. This may be outside of the exam room, but at the investigator's discretion, may be done in the exam room. If done outside the exam room, patient may be moved to the exam room+/−5 minutes of the 40-minute cooling (with gel pack remaining on the knee).

c. Inject intraarticularly the full 15 mL 1% w/w lidocaine (without epinephrine) into the joint using appropriate antiseptic technique.
d. After the 1% w/w lidocaine intraarticular injection, the IMP intraarticular injection, using the same needle, will be injected into the joint using appropriate antiseptic technique after 3 minutes of the 2% w/w lidocaine (without epinephrine).
e. The knee joint will be passively flexed and extended 5 times over 1 minute to facilitate distribution of the IMP within the index knee.
f. Then gel pack cooling may be reapplied for up to 90 minutes, as needed, after IMP injection, depending on the patient's comfort. The patient may remain in the exam room, or be moved to a more comfortable area with the gel pack. The gel pack may be discontinued after intraarticular IMP injection if the patient has a pain level that is acceptable for the patient and investigator (0-4 scale; none, mild, moderate, moderately severe and severe).
g. The pain level on discontinuing the cooling, with the duration of cooling, must be entered into the CRF. If the cooling must be reapplied, the time and pain level must be recorded in the CRF, and timing of subsequent pain assessments should be on the standard time lines in the CRF.

Patients should not take a hot bath or shower, or expose the injected knee to external heat, within 12 hours after the injection.

Study staff will call patients to assess osteoarthritis pain, adverse events, and the use of rescue medication, on Day 3 post-injection (for bilateral knee injections, calls will occur 3 days after each injection). Patients will return to the clinic at Weeks 4 and 8 for study assessments.

Efficacy will be assessed on the osteoarthritis index knee(s) using a numeric pain rating scale (NPRS); the Knee Injury and Osteoarthritis Outcome Score (KOOS), which includes subscales for pain, other symptoms, activities of daily living, sports and recreation, and quality of life; a Joint Replacement Questionnaire; a Patient Satisfaction Questionnaire; an Investigator Satisfaction Questionnaire; and rescue medication use. Pain with walking will also be collected and assessed for the contralateral knee.

For patients with bilateral knee injections, the contralateral knee will also be assessed using the same scales as the index knee, and the effect of bilateral knee injections will be combined as a composite score to examine the overall benefit.

Safety will be assessed by injection site assessments (erythema and edema), assessment of procedure pain, adverse events (AEs), physical examination findings, vital sign measurements, 12-lead electrocardiograms (ECGs), clinical laboratory test results, and sensory testing.

Evaluation Criteria

Evaluation criterial include a primary efficacy endpoint, second efficacy endpoints, and exploratory efficacy endpoints.

Primary Efficacy Endpoint:

The primary endpoint is assessment of the clinically acceptable trans-capsaicin treatment regimen, with the Breg Cooling Control Group as the standard, using three outcomes in a combined assessment performed on the index knee of 1) NPRS pain after trans-capsaicin injection, 2) patient satisfaction with the treatment regimen (SS), and 3) investigator satisfaction with the treatment regimen (IS). For the procedure to be considered clinically acceptable, it must be no more than 30% worse than the Breg Cooling Control Group.

Secondary Efficacy Endpoints:
Assessment of the primary combined outcome using the contralateral knee for the patients who received bilateral injections and the index knee for all other patients.
Assessment of the primary combined outcome for each patient type.
Assessment of the primary combined outcome using the contralateral knee for the patients who received bilateral injections.
Percent of OMERACT-OARSI responders at Week 8 for patients with a single trans-capsaicin joint injection (index knee, moderate to severe pain index knee, pain not >3 for contralateral knee).
Percent of OMERACT-OARSI responders at Week 8 for patients with a bilateral knee injection of trans-capsaicin joint injection (index knee, moderate to severe pain index knee, both knees meeting OMERACT-OARSI responder criteria).
Percent of OMERACT-OARSI responders at Week 8 for patients with a single trans-capsaicin joint injection (index knee, moderate to severe pain index knee, non-index knee with PJR/TJR).
For each of the three types of patients, number of patients who have ≥30%, ≥50%, ≥70%, or ≥90% improvement AUC on the 5 subscales of the KOOS through Week 8 using the average of both knees;
Pain
Other Symptoms
Activities of Daily Living
Sports and Recreation
Quality of Life
Assess the patient satisfaction of treatment with trans-capsaicin intra-articular injection for each of the three types of patients, and all patients in the trial.
For patients with a PJR/TJR, assess their satisfaction with the trans-capsaicin intra-articular injection versus their satisfaction with their knee with a PJR/TJR Exploratory Efficacy Endpoints:
Exploratory efficacy endpoints in patients treated with 1.0 mg of trans-capsaicin, include:
Likelihood of the need for joint replacement surgery, based on KOOS subscales and patient satisfaction outcomes, from Baseline through Week 8.
Patient satisfaction with the treatment of the index knee over through Week 8 of the trial (7 point Likert Scale where 1=Completely dissatisfied and 7=Completely satisfied)
The effect of patient characteristics (including K-L grade, sex, BMI, age, unilateral/bilateral knee OA, bilateral knee osteoarthritis treatment, and history of contralateral PJR/TJR) on the analgesic efficacy of trans-capsaicin, using the KOOS subscales at each study visit through Week 8.
Frequency of use of background analgesic medication for pain in the injected knee(s) throughout the study period.
Assessment of the primary combined outcome using the average of both knees for the patients who received bilateral injections.
Safety endpoints in patients treated with trans-capsaicin;
AEs
Vital signs
Clinical laboratory evaluations (hematology, chemistry, and urinalysis)

12-lead electrocardiograms (ECG).

Physical examination (including the presence or absence of an effusion in the index knee, periarticular pain/tenderness)

Concomitant medications and therapies

Degree of procedure pain (not recorded as AEs)

Local physical findings after injection of the index knee

Injection site assessment of erythema and edema

Sensory testing

Statistical Analysis

Statistical analysis of the results may be performed according to the following procedure. The primary analysis will compare the 3 measure, equally-weighted, combined score (NPRS, patient tolerability, and patient satisfaction), assessed on the index knee, for each experimental injection procedure with the Breg Cooling Control Group. Ratios of the mean values of test/control will have 95% confidence intervals constructed for each injection procedure versus the Breg Cooling Control Group. For the procedure to be considered clinically acceptable, it must be no more than 30% worse than the Breg Cooling Control Group. If the lower limit of the 95% confidence interval for a particular procedure is greater than 0.7, the experimental procedure will be deemed clinically acceptable. This analysis will be performed on the ITT population.

Sensitivity analyses that weight the three components of the combined score unequally will also be performed, using the ITT population. Each component of the combined score will be standardized to a scale of 0-10 before being combined into a single value for analysis.

All other continuous secondary and exploratory efficacy endpoints are summarized using descriptive statistics by patient type, experimental injection procedure, and week/visit, as appropriate, and analyzed using an MMRM analysis or by analysis of covariance, as appropriate. Categorical endpoints will be compared between treatments using Pearson's chi-square or Fisher's exact test, as appropriate.

Safety analyses may be conducted using data from the safety population.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:

1. A method of ameliorating joint pain in a human patient, comprising:
    a. optionally applying a cooling article to a human patient's skin in proximity to a joint in need of pain relief therapy; then
    b. optionally administering a local anesthetic agent into said joint; then
    c. applying a cooling article to the patient's skin in proximity to said joint to achieve a temperature in the range of from 28° C. to 30° C. for tissue or fluid in the interior of the joint; then
    d. administering by injection into said joint a pharmaceutical composition comprising capsaicin in order to deliver a dose of capsaicin in an amount of 1 mg; and then the joint is flexed 5 times; and then
    e. optionally applying a cooling article to the patient's skin in proximity to said joint; to thereby ameliorate joint pain in the human patient,
        wherein the joint pain is osteoarthritic joint pain, the joint is a knee joint, and
        the following additional step is performed between steps (c) and (d): administering into said joint a pharmaceutical composition comprising a single pain-relief local anesthetic agent selected from the group consisting of lidocaine and a pharmaceutically acceptable salt thereof, in order to deliver a dose of lidocaine in an amount ranging from about 0.1 g to about 0.5 g;
        wherein the patient does not receive any pain-relief medicine other than (i) the local anesthetic agent recited in step (b) and in said additional step between steps (c) and (d) and (ii) capsaicin.

2. The method of claim 1, wherein the method does not contain step (a).

3. The method of claim 2, wherein the method does not contain step (b).

4. The method of claim 3, wherein step (c) comprises applying a cooling article to the patient's skin in proximity to the joint to achieve a temperature of 28° C. for tissue or fluid in the interior of the joint.

5. The method of claim 3, wherein step (c) comprises applying a cooling article to the patient's skin in proximity to the joint to achieve a temperature of 29° C. for tissue or fluid in the interior of the joint.

6. The method of claim 3, wherein step (c) comprises applying a cooling article to the patient's skin in proximity to the joint to achieve a temperature of 30° C. for tissue or fluid in the interior of the joint.

7. The method of claim 3, wherein the cooling article has an exterior surface temperature in the range of from about 5° C. to about 15° C. for application to the human patient's skin in proximity to said joint.

8. The method of claim 3, wherein the cooling article has an exterior surface temperature in the range of from about 8° C. to about 10° C. for application to the human patient's skin in proximity to said joint.

9. The method of claim 3, wherein the cooling article has an exterior surface temperature of about 9° C. for application to the human patient's skin in proximity to said joint.

10. The method of claim 7, wherein step (c) comprises applying for a duration of about 30 minutes the cooling article to an exterior surface of said joint.

11. The method of claim 7, wherein the dose of lidocaine is about 0.3 g.

12. The method of claim 7, wherein the dose of lidocaine is about 0.15 g.

13. The method of claim 7, wherein the patient experiences transient burning sensation no greater than level two on a visual analog scale ranging from zero to four, due to administering the pharmaceutical composition comprising capsaicin.

14. The method of claim 7, wherein transient burning sensation is evaluated at about 30 minutes after administration of the pharmaceutical composition comprising capsaicin, and said transient burning sensation is no greater than level one on a visual analog scale ranging from zero to four, due to administering the pharmaceutical composition comprising capsaicin.

15. A method of ameliorating joint pain in a human patient, comprising:
   a. optionally applying a cooling article to a human patient's skin in proximity to a joint in need of pain relief therapy; then
   b. optionally administering a local anesthetic agent into said joint; then
   c. applying a cooling article to the patient's skin in proximity to said joint to achieve a temperature in the range of from 28° C. to 30° C. for tissue or fluid in the interior of the joint; then
   d. administering by injection into said joint a pharmaceutical composition comprising capsaicin in order to deliver a dose of capsaicin in an amount of 1 mg; and then the joint is flexed 5 times; and then
   e. optionally applying a cooling article to the patient's skin in proximity to said joint; to thereby ameliorate joint pain in the human patient,
      wherein the joint pain is osteoarthritic joint pain, the joint is a knee joint, and
      the following additional step is performed between steps (c) and (d): administering into said joint a pharmaceutical composition comprising a single pain-relief local anesthetic agent selected from the group consisting of lidocaine and a pharmaceutically acceptable salt thereof, in order to deliver a dose of lidocaine in an amount ranging from about 0.1 g to about 0.5 g;
      wherein the pharmaceutical composition comprising capsaicin does not contain hyaluronic acid.

16. The method of claim 15, wherein the method does not contain step (a).

17. The method of claim 16, wherein the method does not contain step (b).

18. The method of claim 17, wherein step (c) comprises applying a cooling article to the patient's skin in proximity to the joint to achieve a temperature of 28° C. for tissue or fluid in the interior of the joint.

19. The method of claim 17, wherein step (c) comprises applying a cooling article to the patient's skin in proximity to the joint to achieve a temperature of 29° C. for tissue or fluid in the interior of the joint.

20. The method of claim 17, wherein step (c) comprises applying a cooling article to the patient's skin in proximity to the joint to achieve a temperature of 30° C. for tissue or fluid in the interior of the joint.

21. The method of claim 17, wherein the cooling article has an exterior surface temperature in the range of from about 5° C. to about 15° C. for application to the human patient's skin in proximity to said joint.

22. The method of claim 17, wherein the cooling article has an exterior surface temperature in the range of from about 8° C. to about 10° C. for application to the human patient's skin in proximity to said joint.

23. The method of claim 17, wherein the cooling article has an exterior surface temperature of about 9° C. for application to the human patient's skin in proximity to said joint.

24. The method of claim 21, wherein step (c) comprises applying for a duration of about 30 minutes the cooling article to an exterior surface of said joint.

25. The method of claim 21, wherein the dose of lidocaine is about 0.3 g.

26. The method of claim 21, wherein the dose of lidocaine is about 0.15 g.

27. The method of claim 21, wherein the patient experiences transient burning sensation no greater than level two on a visual analog scale ranging from zero to four, due to administering the pharmaceutical composition comprising capsaicin.

28. The method of claim 21, wherein transient burning sensation is evaluated at about 30 minutes after administration of the pharmaceutical composition comprising capsaicin, and said transient burning sensation is no greater than level one on a visual analog scale ranging from zero to four, due to administering the pharmaceutical composition comprising capsaicin.

29. The method of claim 15, wherein the pharmaceutical composition comprising capsaicin has a volume of about 2 mL.

* * * * *